US008476261B2

(12) United States Patent
Cociorva et al.

(10) Patent No.: US 8,476,261 B2

(45) Date of Patent: Jul. 2, 2013

(54) SPIROCYCLIC AMINOQUINOLONES AS GSK-3 INHIBITORS

(75) Inventors: Oana Cociorva, San Diego, CA (US); Yasumichi Fukuda, Shimotsuga-gun (JP); Yasushi Kohno, Shimotsuga-gun (JP); Bei Li, San Diego, CA (US); Kyoko Okada, Shimotsuga-gun (JP); Ayako Nakamura, Shimotsuga-gun (JP); Masahiro Nomura, Shimotsuga-gun (JP); Shigeki Seto, Shimotsuga-gun (JP); Anna Katrin Szardenings, Torrance, CA (US); Kazuhiro Yumoto, Shimotsuga-gun (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 227 days.

(21) Appl. No.: 12/678,120

(22) PCT Filed: Sep. 12, 2008

(86) PCT No.: PCT/US2008/010700

§ 371 (c)(1), (2), (4) Date: Aug. 24, 2010

(87) PCT Pub. No.: WO2009/035684

PCT Pub. Date: Mar. 19, 2009

(65) Prior Publication Data

US 2011/0034436 A1 Feb. 10, 2011

Related U.S. Application Data

(60) Provisional application No. 60/993,545, filed on Sep. 12, 2007.

(51) Int. Cl.
*A61K 31/5386* (2006.01)

(52) U.S. Cl.
USPC .......... 514/230.5; 544/71

(58) Field of Classification Search
USPC .......... 544/71
See application file for complete search history.

(56) References Cited

U.S. PATENT DOCUMENTS

| | | | |
|---|---|---|---|
| 3,536,809 | A | 8/1971 | Bennett et al. |
| 3,598,123 | A | 8/1971 | Zaffaroni et al. |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,044,126 | A | 8/1977 | Cook et al. |
| 4,328,245 | A | 5/1982 | Yu et al. |
| 4,364,923 | A | 12/1982 | Cook et al. |
| 4,409,239 | A | 10/1983 | Yu |
| 4,410,545 | A | 10/1983 | Yu et al. |
| 4,414,209 | A | 11/1983 | Cook et al. |
| 4,762,831 | A | 8/1988 | Grohe et al. |
| 4,847,375 | A | 7/1989 | Grohe et al. |
| 4,990,508 | A | 2/1991 | Narita et al. |
| 5,033,252 | A | 7/1991 | Carter |
| 5,052,558 | A | 10/1991 | Carter |
| 5,059,595 | A | 10/1991 | Le Grazie |
| 5,073,543 | A | 12/1991 | Marshall et al. |
| 5,120,548 | A | 6/1992 | McClelland et al. |
| 5,153,203 | A | 10/1992 | Yatsunami et al. |
| 5,190,923 | A | 3/1993 | Vincent et al. |
| 5,323,907 | A | 6/1994 | Kalvelage |
| 5,354,556 | A | 10/1994 | Sparks et al. |
| 5,387,748 | A | 2/1995 | Demuth, Jr. et al. |
| 5,430,152 | A | 7/1995 | Saukaitis et al. |
| 5,519,016 | A | 5/1996 | Kimura et al. |
| 5,591,767 | A | 1/1997 | Mohr et al. |
| 5,612,059 | A | 3/1997 | Cardinal et al. |
| 5,639,476 | A | 6/1997 | Oshlack et al. |
| 5,639,480 | A | 6/1997 | Bodmer et al. |

(Continued)

FOREIGN PATENT DOCUMENTS

| | | |
|---|---|---|
| CN | 1181381 | 11/1997 |
| CN | 1491944 A | 4/2004 |

(Continued)

OTHER PUBLICATIONS

Chu, et al., J. Heterocyclic Chem., 24, 453, 1987.
Dax, et al., J. Org. Chem., 57, 744, 1992.
Hayakawa, et al., Chem. Pharm. Bull., 32, 4907, 1984.
Ishikawa et al., Chem. Pharm. Bull., 37, 2103, 1989.
Ishikawa et al., Chem. Pharm. Bull., 38, 2459, 1990.
Okada, et al., J. Heterocyclic Chem., 28, 1067, 1991.
Parikh et al., J. Heterocyclic Chem., 25, 1567, 1988.
Asakawa et al., Horm, Metab. Re. 33 (9): 544-558, 2001.
Augeri, et al., J. Heterocyclic Chem., 27, 1509, 1990.
Yoshida et al., Synlett, 2003, 2139.

(Continued)

*Primary Examiner* — Brian McDowell
(74) *Attorney, Agent, or Firm* — Jones Day

(57) ABSTRACT

Provided herein are spirocyclic aminoquinolones of formula I and compositions containing the compounds. The compounds and compositions provided herein are useful in the prevention, amelioration or treatment of GSK-3 inhibitors mediated diseases. In Formula (I): $X^1$ is O or $NR^8$; A is bond or substituted or unsubstituted $C_1$-$C_2$ alkylene, wherein the substituents when present are selected from one to four $Q^2$ groups; where $Q^2$ is alkyl or haloalkyl; p is 0 or 1; and q is an integer of 0 to 2.

(I)

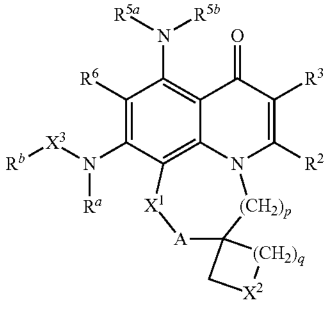

27 Claims, No Drawings

U.S. PATENT DOCUMENTS

| | | | |
|---|---|---|---|
| 5,674,533 | A | 10/1997 | Santus et al. |
| 5,698,220 | A | 12/1997 | Cardinal et al. |
| 5,709,874 | A | 1/1998 | Hanson et al. |
| 5,733,566 | A | 3/1998 | Lewis |
| 5,739,108 | A | 4/1998 | Mitchell |
| 5,759,542 | A | 6/1998 | Gurewich |
| 5,798,119 | A | 8/1998 | Herbig et al. |
| 5,840,674 | A | 11/1998 | Yatvin et al. |
| 5,891,474 | A | 4/1999 | Busetti et al. |
| 5,900,252 | A | 5/1999 | Calanchi et al. |
| 5,922,356 | A | 7/1999 | Koseki et al. |
| 5,972,366 | A | 10/1999 | Haynes et al. |
| 5,972,891 | A | 10/1999 | Kamei et al. |
| 5,980,945 | A | 11/1999 | Ruiz |
| 5,985,307 | A | 11/1999 | Hanson et al. |
| 5,993,855 | A | 11/1999 | Yoshimoto et al. |
| 6,004,534 | A | 12/1999 | Langer et al. |
| 6,039,975 | A | 3/2000 | Shah et al. |
| 6,045,830 | A | 4/2000 | Igari et al. |
| 6,048,736 | A | 4/2000 | Kosak |
| 6,060,082 | A | 5/2000 | Chen et al. |
| 6,071,495 | A | 6/2000 | Unger et al. |
| 6,087,324 | A | 7/2000 | Igari et al. |
| 6,113,943 | A | 9/2000 | Okada et al. |
| 6,120,751 | A | 9/2000 | Unger |
| 6,131,570 | A | 10/2000 | Schuster et al. |
| 6,139,865 | A | 10/2000 | Friend et al. |
| 6,197,350 | B1 | 3/2001 | Yamagata et al. |
| 6,221,633 | B1 | 4/2001 | Ertl et al. |
| 6,221,897 | B1 | 4/2001 | Frick et al. |
| 6,245,744 | B1 | 6/2001 | Frick et al. |
| 6,248,363 | B1 | 6/2001 | Patel et al. |
| 6,253,872 | B1 | 7/2001 | Neumann |
| 6,264,970 | B1 | 7/2001 | Hata et al. |
| 6,267,981 | B1 | 7/2001 | Okamoto et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,342,512 | B1 | 1/2002 | Kirsch et al. |
| 6,350,458 | B1 | 2/2002 | Modi |
| 6,376,461 | B1 | 4/2002 | Igari et al. |
| 6,419,961 | B1 | 7/2002 | Igari et al. |
| 6,589,548 | B1 | 7/2003 | Oh et al. |
| 6,613,358 | B2 | 9/2003 | Randolph et al. |
| 6,699,500 | B2 | 3/2004 | Okada et al. |
| 6,740,634 | B1 | 5/2004 | Saikawa et al. |
| 6,825,353 | B2 | 11/2004 | Saito et al. |
| 6,967,205 | B1 | 11/2005 | Abdul-Rahman |
| 2004/0132764 | A1 | 7/2004 | Locher |
| 2005/0054663 | A1 | 3/2005 | Bennett et al. |
| 2005/0182085 | A1 | 8/2005 | Defossa et al. |
| 2007/0254866 | A1 | 11/2007 | Cociorva et al. |
| 2010/0234367 | A1 | 9/2010 | Nomura et al. |
| 2011/0034436 | A1 | 2/2011 | Cociorva et al. |

FOREIGN PATENT DOCUMENTS

| | | | |
|---|---|---|---|
| EP | 0265230 | A1 | 4/1988 |
| EP | 0390215 | A2 | 10/1990 |
| EP | 0462884 | A1 | 6/1993 |
| EP | 0945435 | A1 | 9/1999 |
| EP | 1486488 | A1 | 12/2004 |
| EP | 1650192 | A1 | 4/2006 |
| ES | 0206819 | A6 | 5/1992 |
| JP | S591489 | A | 1/1984 |
| JP | 62198685 | A | 2/1986 |
| JP | S6253987 | A | 5/1986 |
| JP | S62167769 | A | 1/1987 |
| JP | S62252772 | A | 4/1987 |
| JP | S63264439 | A | 1/1988 |
| JP | S63132891 | A | 6/1988 |
| JP | 03133983 | A | 10/1989 |
| JP | H1268679 | A | 10/1989 |
| JP | H525162 | A | 2/1993 |
| WO | WO9726265 | A1 | 7/1997 |
| WO | WO9741097 | A2 | 11/1997 |
| WO | WO9808871 | A1 | 3/1998 |
| WO | WO9903861 | A1 | 1/1999 |
| WO | WO9915525 | A1 | 4/1999 |
| WO | WO9965897 | A1 | 12/1999 |
| WO | WO0038675 | A1 | 7/2000 |
| WO | WO0040569 | A1 | 7/2000 |
| WO | WO0063208 | A1 | 10/2000 |
| WO | WO0066585 | A1 | 11/2000 |
| WO | WO0071549 | A1 | 11/2000 |
| WO | WO0078312 | A1 | 12/2000 |
| WO | WO0109111 | A1 | 2/2001 |
| WO | WO0183451 | A1 | 11/2001 |
| WO | WO0185695 | A1 | 11/2001 |
| WO | WO0191752 | A1 | 12/2001 |
| WO | WO0204462 | A1 | 1/2002 |
| WO | WO0209758 | A2 | 2/2002 |
| WO | WO0217918 | A2 | 3/2002 |
| WO | WO02092571 | A1 | 11/2002 |
| WO | WO2004019932 | A1 | 3/2004 |
| WO | WO2004089930 | | 10/2004 |
| WO | WO2004096221 | A2 | 11/2004 |
| WO | WO2005007111 | A2 | 1/2005 |

OTHER PUBLICATIONS

Coghlan, et al., Chemistry & Biology 7(10):793-03, 2000.
Cohen, et al., Nature Reviews, Drug Discovery, vol. 3, No. 6, 479-487, 2004.
Haq, et al., J. Cell. Biol. 151(1):117-29, 2000.
Kim, et al., Curr. Opin. Genetics & Dev. 10:508-14, 2000.
Lee, et al., Drugs of the Future 26(9):873-81, 2001.
Salvador, et al., Expert Opinion on Pharmacotherapy 2(10):1615-22, 2001.
Santus and Baker, J. Controlled Release, 35, 1-21, 1995.
Verma, et al., Drug Development and Industrial Pharmacy, 26, 695-708, 2000.
Verma, et al., J. Controlled Release, 79, 7-27, 2002.
Atarashi, et al., Chem. Pharm. Bull. 35(5):1896-902, 1987.
Atarashi, et al., J. Heterocyclic Chem., 28, 329, 1991.
Buchwald, et al., Surgery 88(4):507-16, 1980.
Calas, et al., Eur. J. Med. Chem. 26:279-290, 1991.
Doyle, et al., J. Org. Chem. 42(14): 2426-31, 1977.
Egawa, et al., Chem. Pharm. Bull., 34, 4098, 1986.
Fujita, et al., Chem. Pharm. Bull. 44(5):987-90, 1996.
Golub, et al., J. Med. Chem 49: 6443, 2006.
Todo et al., Chem. Pharm. Bull. 42(12) 2569-2574, 1994.
Havlicek, et. al., J. Med. Chem. 40:408-12, 1997.
Kaiho, et al., J. Med. Chem., 32, 351, 1989.
Kawatsura, et al., Tetrahedron, 63, 4172, 2007.
Kiely, et al., J. Heterocyclic Chem. 26(6):1675-81, 1989.
Kiely, et al., J. Med. Chem. 31:2004-2008, 1988.
Kobayashi, et al., Org. Lett., 7, 1319, 2005.
Kobayashi, et al., Org. Lett., 7, 183, 2005.
Koga, et al., J. Med. Chem., 23, 1358, 1980.
Kondo, et al., J. Med. Chem. 31:221-25, 1988.
Langer, Science 249(4976):1527-33, 1990.
Mitscher, et al., J. Med. Chem., 30, 2283, 1987.
Miyamoto, et al., J. Med. Chem. 33:1645-56, 1990.
Scholmerich et al., Der Internist, No. 4, 533-543, 2001.
Remuzon, et al., J. Med. Chem., 34, 29, 1991.
Saloutin, et al., J. Fluoerine Chem. 65:37-41, 1993.
Saudek, et al., N. Engl. J. Med. 321(9):574-79, 1989.
Sbardella, et al., IL Farmaco 59:463-71, 2004.
Sefton, Crc Crit. Rev. Biomed. Eng. 14(3):201-40, 1987.
Shibamori, et al., Chem. Pharm. Bull. 38(9):2390-96, 1990.
Singh, R., et al., Eur. J. Med. Chem., 33:697-03, 1998.
Wentland, et al., J. Med. Chem. 31:1694-1697, 1988.
Wentland, et al, Bioorg. Med. Chem Lett. 3 (8) 1711-1716, 1993.
U.S.P.T.O. non-Final Office Action dated Oct. 16, 2008 for U.S. Appl. No. 11/718,000, filed Mar. 13, 2007.
U.S.P.T.O. Final Office Action dated May 14, 2009 for U.S. Appl. No. 11/718,000, filed Mar. 13, 2007.
U.S.P.T.O. non-Final Office Action dated Dec. 9, 2009 for U.S. Appl. No. 11/718,000, filed Mar. 13, 2007.
U.S.P.T.O. non-Final Office Action dated Jul. 7, 2010 for U.S. Appl. No. 11/718,000, filed Mar. 13, 2007.

U.S.P.T.O. Notice of Allowance Jan. 24, 2011 for U.S. Appl. No. 11/718,000, filed Jan. 13, 2007.
U.S.P.T.O. Supplemental Notice of Allowance Feb. 8, 2011 for U.S. Appl. No. 11/718,000, filed Jan. 13, 2007.
U.S.P.T.O. Notice of Allowance Jul. 20, 2011 for U.S. Appl. No. 11/718,000, filed Jan. 13, 2007.
U.S.P.T.O. non-Final Office Action dated Nov. 2, 2010 for U.S. Appl. No. 12/721,454, filed Mar. 10, 2010.
U.S.P.T.O. Notice of Allowance Apr. 8, 2011 for U.S. Appl. No. 12/721,454, filed Mar. 10, 2010.
U.S.P.T.O. Notice of Allowance Jul. 14, 2011 for U.S. Appl. No. 12/721,454, filed Mar. 10, 2010.

SPIROCYCLIC AMINOQUINOLONES AS GSK-3 INHIBITORS

PRIORITY CLAIM

This application is the national phase entry pursuant to 35 U.S.C. §371 of International Application No. PCT/US2008/010700, filed Sep. 12, 2008, which claims priority to U.S. provisional application Ser. No. 60/993,545 filed Sep. 12, 2007 to Cociorva et al. The disclosures of the above referenced applications are incorporated by reference in their entireties.

FIELD

Compounds, compositions and methods for treating GSK-3 mediated diseases are provided. The compounds provided herein are spirocyclic aminoquinolones that are GSK-3 inhibitors.

BACKGROUND

Glycogen synthase kinase-3 (GSK-3) is a serine/threonine protein kinase having α and β isoforms that are each encoded by distinct genes [Coghlan et al., *Chemistry & Biology,* 7, 793-803 (2000); and Kim and Kimmel, *Curr. Opinion Genetics Dev.,* 10, 508-514 (2000)]. GSK-3 has been implicated in various diseases including diabetes, Alzheimer's disease, CNS disorders such as manic depressive disorder and neurodegenerative diseases, and cardiomyocete hypertrophy [see, e.g., WO 99/65897; WO 00/38675; and Haq et al., *J. Cell Biol.* (2000) 151, 117]. These diseases may be caused by, or may result in, the abnormal operation of certain cell signaling pathways in which GSK-3 plays a role.

GSK-3 has been found to phosphorylate and modulate the activity of a number of regulatory proteins. These include glycogen synthase, which is the rate-limiting enzyme required for glycogen synthesis, the microtubule-associated protein Tau, the gene transcription factor β-catenin, the translation initiation factor e1F-2B, as well as ATP citrate lyase, axin, heat shock factor-1, c-Jun, c-myc, c-myb, CREB, and CEPB α. These diverse targets implicate GSK-3 in many aspects of cellular metabolism, proliferation, differentiation and development.

Small molecule inhibitors of GSK-3 have recently been reported [WO 99/65897 (Chiron) and WO 00/38675 (SmithKline Beecham)], however, there is a continued need to find more effective therapeutic agents to treat GSK-3 mediated diseases.

SUMMARY

Provided herein are compounds represented by the Formula (1):

(1)

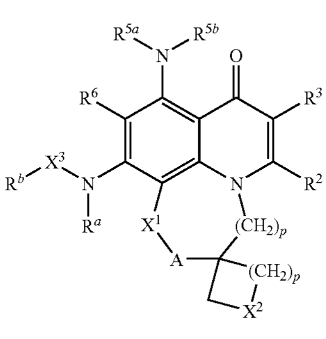

or a pharmaceutically acceptable derivative thereof, wherein $R^2$ is hydrogen or lower alkyl;

$R^3$ is hydrogen, CN, $C(O)R^{3a}$, C(NH)NHOH or 5-tetrazolyl;

$R^{3a}$ is OH, alkoxy or $NHR^{3b}$;

$R^{3b}$ is hydrogen, $NH_2$, OH or lower alkyl;

$R^{5a}$ and $R^{5b}$ are each independently hydrogen, lower alkyl or aralkyl which is optionally substituted with one to three substituents, each independently selected from $Q^0$ groups;

wherein $Q^0$ is halo, cyano, nitro, $NH_2$, alkyl or alkoxy;

$R^6$ is halo;

in each instance, independently, $R^a$ and $X^3$ are selected from (i) or (ii) as follows:

(i) $R^a$ is hydrogen or lower alkyl; and $X^3$ is substituted or unsubstituted $C_1$-$C_3$ alkylene, substituted or unsubstituted 3-6 membered cycloalkylene or substituted or unsubstituted 3-6 membered heterocyclylene, wherein the substituents when present are selected from one to four $Q^2$ groups; or (ii) $R^a$ and $X^3$ together with the nitrogen atom to which they are bonded, may form a 5 to 7 membered saturated or unsaturated ring optionally containing one or more O or S atoms, or one or more additional N atoms, in the ring;

$R^b$ is $—(CHR^{7a})_nR^7$, $—NR^{7b}R^7$, $—OR^7$, $—S(O)_rR^7$, $—NR^{7b}COY^1R^7$ or $—Y^2CONR^{7b}R^7$;

$Y^1$ is bond, O or $NR^{7b}$;

$Y^2$ is bond or O;

n is 0 or 1;

r is an integer of 0 to 2;

$R^7$ is alkyl, aryl, cycloalkyl, heterocyclyl, heteroaryl, fused heterocyclylaryl, or fused arylheterocyclyl, where $R^7$ is optionally substituted with one to five substituents, each independently selected from $Q^1$ groups;

$R^{7a}$ is hydrogen alkyl, aryl, cycloalkyl, heterocyclyl, heteroaryl, fused heterocyclylaryl, or fused arylheterocyclyl, where $R^{7a}$ is optionally substituted with one to five substituents, each independently selected from $Q^1$ groups;

$R^{7b}$ is hydrogen, alkyl, aryl, heteroaryl, aralkyl, heteroaralkyl, or fused heterocyclylaryl, where $R^{7b}$ is optionally substituted with one to five substituents, each independently selected from $Q^1$ groups;

where $Q^1$ is halo, hydroxy, oxo, thioxo, cyano, nitro, azido, mercapto, formyl, hydroxycarbonyl, hydroxycarbonylalkyl, alkyl, haloalkyl, alkenyl, alkynyl, cycloalkyl, heterocyclyl, aryl, heteroaryl, aralkyl, heteroaralkyl, alkoxy, haloalkoxy, cycloalkoxy, heterocyclyloxy, aryloxy, heteroaryloxy, aralkyloxy, heretoaralkyloxy, alkylcarbonyl, arylcarbonyl, heteroarylcarbonyl, alkoxycarbonyl, aryloxycarbonyl, aralkyloxycarbonyl, unsubstituted or substituted aminocarbonyl, alkylcarbonyloxy, arylcarbonyloxy, aralkylcarbonyloxy, alkoxycarbonyloxy, aryloxycarbonyloxy, aralkyloxycarbonyloxy, unsubstituted or substituted aminocarbonyloxy, unsubstituted or substituted amino, alkylthio, cycloalkylthio, arylthio, heteroarylthio, aralkylthio, heteroaralkylthio, alkylsulfinyl, cycloalkylsulfinyl, arylsulfinyl, heteroarylsulfinyl, aralkylsulfinyl, heteroaralkylsulfinyl, alkylsulfonyl, cycloalkylsulfonyl, arylsulfonyl, heteroarylsulfonyl, aralkylsulfonyl, heteroaralkylsulfony, alkoxysulfonyl, aryloxysulfonyl, unsubstituted or substituted aminosulfonyl or hydroxysulfonyl;

$X^1$ is O or $NR^8$;

$R^8$ is hydrogen or lower alkyl;

$X^2$ is $CH_2$, O, $NR^1$ or S;

$R^1$ is hydrogen or lower alkyl;

A is bond or substituted or unsubstituted $C_1$-$C_2$ alkylene, wherein the substituents when present are selected from one to four $Q^2$ groups;

wherein $Q^2$ is alkyl or haloalkyl;

p is 0 or 1;

q is an integer of 0 to 2.

Also provided herein are pharmaceutical compositions containing a compound of Formula (1) and a pharmaceutically acceptable carrier.

Also provided herein are methods for treating, preventing, or ameliorating one or more symptoms of GSK-3 mediated diseases by administering the compounds and compositions provided herein.

DETAILED DESCRIPTION OF EMBODIMENTS

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

As used herein, the nomenclature alkyl, alkoxy, carbonyl, etc. is used as is generally understood by those of skill in this art.

As used herein, alkyl carbon chains, if not specified, contain from 1 to 20 carbons, 1 to 16 carbons or 1 to 6 carbons and are straight or branched. In certain embodiments, alkyl carbon chains contain from 1 to 6 carbons. Exemplary alkyl groups herein include, but are not limited to, methyl, ethyl, propyl, isopropyl, isobutyl, n-butyl, sec-butyl, tert-butyl, isopentyl, neopentyl, tert-pentyl, isohexyl. As used herein, lower alkyl refers to carbon chains having from about 1 carbons up to about 6 carbons.

As used herein, alkenyl carbon chains, if not specified, contain from 2 to 20 carbons, 2 to 16 carbons or 2 to 6 carbons and are straight or branched. In certain embodiments, alkenyl carbon chains contain from 2 to 6 carbons. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. The alkenyl carbon chains of 2 to 6 carbons, in certain embodiments, contain 1 to 2 double bonds. Exemplary alkenyl groups herein include, but are not limited to, vinyl, 1-propenyl, 2-propenyl, isopropenyl, 1-butenyl, 2-butenyl, 3-butenyl, 1,3-butadienyl. As used herein, lower alkenyl refer to carbon chains having from about 2 carbons up to about 6 carbons.

As used herein, alkynyl carbon chains, if not specified, contain from 2 to 20 carbons, 2 to 16 carbons or 2 to 6 carbons and are straight or branched. In certain embodiments, alkynyl carbon chains contain from 2 to 6 carbons. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Alkynyl carbon chains of from 2 to 6 carbons, in certain embodiments, contain 1 to 2 triple bonds. Exemplary alkynyl groups herein include, but are not limited to, ethynyl, 1-propynyl and 2-propynyl. As used herein, lower alkynyl refer to carbon chains having from about 2 carbons up to about 6 carbons.

As used herein, "alkoxy" contain from 1 to 20 carbons, 1 to 16 carbons or 1 to 6 carbons and are straight or branched. In certain embodiments, alkoxy carbon chains contain from 1 to 6 carbons. Exemplary alkoxy groups herein include, but are not limited to, methoxy, ethoxy, propoxy, isopropoxy, isobutoxy, n-butoxy, sec-butoxy, tert-butoxy, isopentoxy, neopentoxy, tert-pentoxy and isohexyloxy.

As used herein, "aralkyl" refers to an alkyl group in which one of the hydrogen atoms of the alkyl is replaced by an aryl.

As used herein, "halo", "halogen" or "halide" refers to F, Cl, Br or I.

As used herein, "aryl" refers to aromatic monocyclic or multicyclic groups containing from 6 to 19 carbon atoms. Aryl groups include, but are not limited to groups such as fluorenyl, substituted fluorenyl, phenyl, substituted phenyl, naphthyl and substituted naphthyl.

As used herein, "cycloalkyl" refers to a saturated mono- or multicyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, aminocarbonyl, alkoxycarbonyl, guanidino, or the nitrogen may be quaternized to form an ammonium group where the substituents are selected as above.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, N-methylpyrrolyl, quinolinyl and isoquinolinyl.

As used herein, "fused heterocyclylaryl" refers to aryl which was fused with a heterocyclyl group. In one embodiment, fused heterocyclylaryls are those wherein heterocyclyl contains about 5 to about 6 ring atoms and the aryl thereof is phenyl. A fused heterocyclylaryl may be bonded through any atom of the ring system. Representative fused heterocyclylaryl groups include 1,3-benzodioxolan-4-yl, 1,3-benzodioxolan-5-yl, 1,3-benzodioxolan-6-yl, 1,3-benzodioxolan-7-yl, 4-indolinyl, 5-indolinyl, 6-indolinyl and 7-indolinyl.

As used herein, "fused arylheterocyclyl" refers to fused heterocyclyl which was fused to an aryl group. In one embodiment, fused arylheterocyclyls are those wherein the aryl thereof is phenyl and the heterocyclyl contains about 5 to about 6 ring atoms. A fused arylheterocyclyl may be bonded through any atom of the ring system. Representative fused arylheterocyclyl groups include 1-indolinyl, 2-indolinyl, 3-indolinyl, 1,2,3,4-tetrahydroqunolin-1-yl, 1,2,3,4-tetrahydroqunolin-2-yl, 1,2,3,4-tetrahydroqunolin-3-yl and 1,2,3,4-tetrahydroqunolin-4-yl.

As used herein, "haloalkyl" refers to an alkyl group in which one or more of the hydrogen atoms are replaced by halogen. "Lower haloalkyl" refers to a lower alkyl group in which one or more of the hydrogen atoms are replaced by halogen. Such groups include, but are not limited to, chloromethyl, trifluoromethyl and 1-chloro-2-fluoroethyl.

As used herein, "heteroaralkyl" refers to an alkyl group in which one of the hydrogen atoms are replaced by heteroaryl.

As used herein, "haloalkoxy" refers to RO— in which R is a haloalkyl group.

As used herein, "cycloalkoxy" refers to RO— in which R is a cycloalkyl group.

As used herein, "aryloxy" refers to RO— in which R is an aryl.

As used herein, "heteroaryloxy" refers to RO— in which R is a heteroaryl.

As used herein, "heterocyclyloxy" refers to RO— in which R is a heterocyclyl.

As used herein, "aralkyloxy" refers to RO— in which R is an aralkyl.

As used herein, "heteroaralkyloxy" refers to RO— in which R is a heteroaralkyl.

As used herein, "alkylcarbonyl" refers to RCO— in which R is an alkyl group.

As used herein, "arylcarbonyl" refers to RCO— in which R is an aryl.

As used herein, "heteroarylcarbonyl" refers to RCO— in which R is a heteroaryl.

As used herein, "alkoxycarbonyl" refers to RCO— in which R is an alkoxy group.

As used herein, "aryloxycarbonyl" refers to RCO— in which R is an aryloxy.

As used herein, "aralkyloxycarbonyl" refers to RCO— in which R is an aralkyloxy.

As used herein, "unsubstituted or substituted aminocarbonyl" refers to —C(O)NR'R in which R' and R are independently hydrogen, alkyl aryl, heteroaryl, aralkyl or heteroaralkyl.

As used herein, "alkylcarbonyloxy" refers to —OC(O)R in which R is alkyl.

As used herein, "arylcarbonyloxy" refers to —OC(O)R in which R is aryl.

As used herein, "aralkylcarbonyloxy" refers to —OC(O)R in which R is aralkyl.

As used herein, "alkoxycarbonyloxy" refers to —OC(O)O R in which R is alkyl.

As used herein, "aryloxycarbonyloxy" refers to —OC(O)O R in which R is aryl.

As used herein, "aralkyloxycarbonyloxy" refers to —OC(O)O R in which R is aralkyl.

As used herein, "unsubstituted or substituted aminocarbonyloxy" refers to —OC(O)NR'R in which R and R are independently hydrogen, alkyl aryl, heteroaryl, aralkyl or heteroaralkyl.

As used herein, "unsubstituted or substituted amino" refers to —NR'R in which R' and R are independently hydrogen, alkyl, aryl, heteroaryl, aralkyl, heteroaralkyl, alkylcarbonyl, arylcarbonyl, heteroarylcarbonyl, alkoxycarbonyl, aryloxycarbonyl, aralkyloxycarbonyl, unsubstituted or substituted aminocarbonyl, alkylsulfonyl, cycloalkylsulfonyl, arylsulfonyl, heteroarylsulfonyl, aralkylsulfonyl, or heteroaralkylsulfonyl.

As used herein, "alkylthio" refers to —SR in which R is alkyl.

As used herein, "cycloalkylthio" refers to —SR in which R is cycloalkyl.

As used herein, "arylthio" refers to —SR in which R is aryl.

As used herein, "heteroarylthio" refers to —SR in which R is heteroaryl.

As used herein, "aralkylthio" refers to —SR in which R is aralkyl.

As used herein, "heteroaralkylthio" refers to —SR in which R is heteroaralkyl.

As used herein, "alkylsulfinyl" refers to —S(O)R in which R is alkyl.

As used herein, "cycloalkylsulfinyl" refers to —S(O)R in which R is cycloalkyl.

As used herein, "arylsulfinyl" refers to —S(O)R in which R is aryl.

As used herein, "heteroarylsulfinyl" refers to —S(O)R in which R is heteroaryl.

As used herein, "aralkylsulfinyl" refers to —S(O)R in which R is aralkyl.

As used herein, "heteroaralkylsulfinyl" refers to —S(O)R in which R is heteroaralkyl.

As used herein, "alkylsulfonyl" refers to —$S(O)_2R$ in which R is alkyl.

As used herein, "cycloalkylsulfonyl" refers to —$S(O)_2R$ in which R is cycloalkyl.

As used herein, "arylsulfonyl" refers to —$S(O)_2R$ in which R is aryl.

As used herein, "heteroarylsulfonyl" refers to —$S(O)_2R$ in which R is heteroaryl.

As used herein, "aralkylsulfonyl" refers to —$S(O)_2R$ in which R is aralkyl.

As used herein, "heteroaralkylsulfonyl" refers to —$S(O)_2R$ in which R is heteroaralkyl.

As used herein, "alkoxysulfonyl" refers to —$S(O)_2R$ in which R is alkoxy.

As used herein, "unsubstituted or substituted aminosulfonyl" refers to —$S(O)_2N$ R'R in which R' and R are independently hydrogen, alkyl aryl, heteroaryl, aralkyl or heteroaralkyl.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and inorganic salts, such as but not limited to, sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, mesylates, and fumarates. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C═C(OR) where R is hydrogen, alkyl, alkenyl, alkynyl, aryl, aralkyl and cycloalkyl. Pharmaceutically acceptable enol esters include, but are not limited to, derivatives of formula C═C(OC(O)R) where R is hydrogen, alkyl, alkenyl, alkynyl, aryl, aralkyl and cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures.

As used herein, substantially pure means sufficiently homogeneous to appear free of readily detectable impurities as determined by standard methods of analysis, such as thin layer chromatography (TLC), gel electrophoresis, high performance liquid chromatography (HPLC), nuclear magnetic resonance (NMR), and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, the $IC_{50}$ refers to an amount, concentration or dosage of a particular test compound that achieves a 50% inhibition of a maximal response in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, treatment means any manner in which one or more of the symptoms of a disease or disorder are ameliorated or otherwise beneficially altered. Treatment also encompasses any pharmaceutical use of the compositions herein, such as use for treating diabetes.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, the terms "preventing" means guard against the recurrence of the specified disease or disorder in a patient who has already suffered from the disease or disorder, and/or lengthening the time that a patient who has suffered from the disease or disorder remains in remission.

The terms "GSK-3 mediated disease, or "GSK-3 mediated condition", as used herein, mean any disease or other deleterious condition or state in which GSK-3 is known to play a role. Such diseases or conditions include, without limitation, diabetes, conditions associated with diabetes, chronic neurodegenerative conditions including dementias such as Alzheimer's disease, Parkinson's disease, progressive supranuclear palsy, subacute sclerosing panencephalitis parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis, neurotraumatic diseases such as acute stroke, epilepsy, mood disorders such as depression, schizophrenia and bipolar disorders, rheumatoid arthritis, inflammatory bowel disease, ulceractive colitis, Crohn's disease, sepsis, pancreatic cancer, ovarian cancer and osteoporosis.

B. Compounds

Provided herein are compounds of Formula (1):

(I)

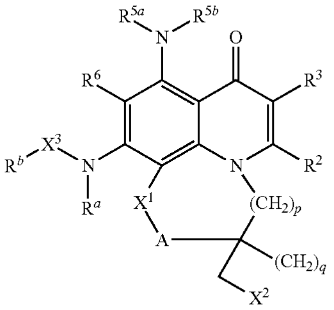

or a pharmaceutically acceptable derivative thereof, wherein $R^2$ is hydrogen or lower alkyl;

$R^3$ is hydrogen, CN, $C(O)R^{3a}$, C(NH)NHOH or 5-tetrazolyl;

$R^{3a}$ is OH, alkoxy or $NHR^{3b}$;

$R^{3b}$ is hydrogen, $NH_2$, OH or lower alkyl;

$R^{5a}$ and $R^{5b}$ are each independently hydrogen, lower alkyl or aralkyl which is optionally substituted with one to three substituents, each independently selected from $Q^0$ groups;

wherein $Q^0$ is halo, cyano, nitro, $NH_2$, alkyl or alkoxy;

$R^6$ is halo;

in each instance, independently, $R^a$ and $X^3$ are selected from (i) or (ii) as follows:

(i) $R^a$ is hydrogen or lower alkyl; and $X^3$ is substituted or unsubstituted $C_1$-$C_3$ alkylene, substituted or unsubstituted 3-6 membered cycloalkylene or substituted or unsubstituted 3-6 membered heterocyclylene, wherein the substituents when present are selected from one to four $Q^2$ groups; or (ii) $R^a$ and $X^3$ together with the nitrogen atom to which they are bonded, may form a 5 to 7 membered saturated or unsaturated ring optionally containing one or more O or S atoms, or one or more additional N atoms, in the ring;

$R^b$ is —$(CHR^{7a})_nR^7$, —$NR^{7b}R^7$, —$OR^7$, —$S(O)_lR^7$, —$NR^{7b}COY^1R^7$ or —$Y^2CONR^{7b}R^7$;

$Y^1$ is bond, O or $NR^{7b}$;

$Y^2$ is bond or O;

n is 0 or 1;

l is an integer of 0 to 2;

$R^7$ is alkyl, aryl, cycloalkyl, heterocyclyl, heteroaryl, fused heterocyclylaryl, or fused arylheterocyclyl, where $R^7$ is optionally substituted with one to five substituents, each independently selected from $Q^1$ groups;

$R^{7a}$ is hydrogen alkyl, aryl, cycloalkyl, heterocyclyl, heteroaryl, fused heterocyclylaryl, or fused arylheterocyclyl, where $R^{7a}$ is optionally substituted with one to five substituents, each independently selected from $Q^1$ groups;

$R^{7b}$ is hydrogen, alkyl, aryl, heteroaryl, aralkyl, heteroaralkyl, or fused heterocyclylaryl, where $R^{7b}$ is optionally substituted with one to five substituents, each independently selected from $Q^1$ groups;

wherein $Q^1$ is halo, hydroxy, oxo, thioxo, cyano, nitro, azido, mercapto, formyl, hydroxycarbonyl, hydroxycarbonylalkyl, alkyl, haloalkyl, alkenyl, alkynyl, cycloalkyl, heterocyclyl, aryl, heteroaryl, aralkyl, heteroaralkyl, alkoxy, haloalkoxy, cycloalkoxy, heterocyclyloxy, aryloxy, heteroaryloxy, aralkyloxy, heretoaralkyloxy, alkylcarbonyl, arylcarbonyl, heteroarylcarbonyl, alkoxycarbonyl, aryloxycarbonyl, aralkyloxycarbonyl, unsubstituted or substituted aminocarbonyl, alkylcarbonyloxy, arylcarbonyloxy, aralkylcarbonyloxy, alkoxycarbonyloxy, aryloxycarbonyloxy, aralkyloxycarbonyloxy, unsubstituted or substituted aminocarbonyloxy, unsubstituted or substituted amino, alkylthio, cycloalkylthio, arylthio, heteroarylthio, aralkylthio, heteroaralkylthio, alkylsulfinyl, cycloalkylsulfinyl, arylsulfinyl, heteroarylsulfinyl, aralkylsulfinyl, heteroaralkylsulfinyl, alkylsulfonyl, cycloalkylsulfonyl, arylsulfonyl, heteroarylsulfonyl, aralkylsulfonyl, heteroaralkylsulfonyl, alkoxysulfonyl, aryloxysulfonyl, unsubstituted or substituted aminosulfonyl or hydroxysulfonyl;

$X^1$ is O or $NR^8$;

$R^8$ is hydrogen or lower alkyl;

$X^2$ is $CH_2$, O, $NR^1$ or S;

$R^1$ is hydrogen or lower alkyl;

A is bond or substituted or unsubstituted $C_1$-$C_2$ alkylene, wherein the substituents when present are selected from one to four $Q^2$ groups;

wherein $Q^2$ is alkyl or haloalkyl;

p is 0 or 1; and q is an integer of 0 to 2.

In one embodiment, $R^{5a}$ and $R^{5b}$ are each hydrogen.

In one embodiment, $R^2$ is hydrogen.

In another embodiment, $X^1$ is O.

In another embodiment, $Y^1$ is bond.

In another embodiment, $R^3$ is CN.

In another embodiment, $R^3$ is $C(O)R^{3a}$.

In another embodiment, $R^3$ is C(NH)NHOH.

In another embodiment, $R^3$ is 5-tetrazolyl.

In one embodiment, $R^{3a}$ is OH.

In one embodiment, $X^1$ is O and $R^2$ is hydrogen.

In another embodiment, $R^a$ is hydrogen.

In one embodiment, $X^3$ is substituted or unsubstituted $C_1$-$C_3$ alkylene, wherein the substituents when present are selected from one to four $Q^2$ groups, where $Q^2$ is alkyl or haloalkyl.

In another embodiment, A is substituted or unsubstituted $C_1$-$C_2$ alkylene.

In another embodiment, A is substituted with from one to four $Q^2$ groups, wherein $Q^2$ is alkyl or haloalkyl; and p is 0.

In one embodiment, $X^2$ is $CH_2$.

In another embodiment, $X^2$ is O.

In another embodiment, A is $CH_2$; p is 0 and q is 2.

In another embodiment, $X^1$ is O.

In certain embodiments, $R^6$ is F.

In certain embodiments, the compounds are of Formula (Ia):

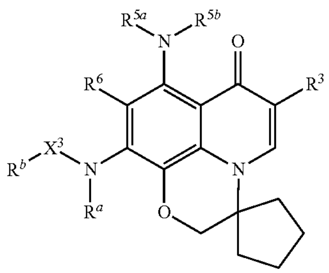

(Ia)

or a pharmaceutically acceptable derivative thereof, wherein $R^3$ is hydrogen, CN, $C(O)R^{3a}$, C(NH)NHOH or 5-tetrazolyl;

$R^a$ is OH, alkoxy or $NHR^{3b}$;

$R^{3b}$ is hydrogen, $NH_2$, OH or lower alkyl;

$R^{5a}$ and $R^{5b}$ are each independently hydrogen or lower alkyl;

$R^6$ is halo;

in each instance, independently, $R^a$ and $X^3$ are selected from (i) or (ii) as follows:

(i) $R^a$ is hydrogen or lower alkyl; and $X^3$ is substituted or unsubstituted $C_1$-$C_3$ alkylene, substituted or unsubstituted 3-6 membered cycloalkylene or substituted or unsubstituted 3-6 membered heterocyclylene, wherein the substituents when present are selected from one to four $Q^2$ groups; or (ii) $R^a$ and $X^3$ together with the nitrogen atom to which they are bonded, may form a 5 to 7 membered saturated or unsaturated ring optionally containing one or more O or S atoms, or one or more additional N atoms, in the ring;

$R^b$ is —$(CHR^{7a})_nR^7$, —$NR^{7b}R^7$, —$OR^7$, —$S(O)_nR^7$, —$NR^{7b}COY^1R^7$ or —$Y^2CONR^{7b}R^7$;

$Y^1$ is bond, O or $NR^{7b}$;

$Y^2$ is bond or O;

n is 0 or 1;

r is an integer of 0 to 2;

$R^7$ is alkyl, aryl, cycloalkyl, heterocyclyl, heteroaryl, fused heterocyclylaryl, or fused arylheterocyclyl, where $R^7$ is optionally substituted with one to five substituents, each independently selected from $Q^1$ groups;

$R^{7a}$ is hydrogen alkyl, aryl, cycloalkyl, heterocyclyl, heteroaryl, fused heterocyclylaryl, or fused arylheterocyclyl, where $R^{7a}$ is optionally substituted with one to five substituents, each independently selected from $Q^1$ groups;

$R^{7b}$ is hydrogen, alkyl, aryl, heteroaryl, aralkyl, heteroaralkyl, or fused heterocyclylaryl, where $R^{7b}$ is optionally substituted with one to five substituents, each independently selected from $Q^1$ groups;

wherein $Q^1$ is halo, hydroxy, oxo, thioxo, cyano, nitro, azido, mercapto, formyl, hydroxycarbonyl, hydroxycarbonylalkyl, alkyl, haloalkyl, alkenyl, alkynyl, cycloalkyl, heterocyclyl, aryl, heteroaryl, aralkyl, heteroaralkyl, alkoxy, haloalkoxy, cycloalkoxy, heterocyclyloxy, aryloxy, heteroaryloxy, aralkyloxy, heretoaralkyloxy, alkylcarbonyl, arylcarbonyl, heteroarylcarbonyl, alkoxycarbonyl, aryloxycarbonyl, aralkyloxycarbonyl, unsubstituted or substituted aminocarbonyl, alkylcarbonyloxy, arylcarbonyloxy, aralkylcarbonyloxy, alkoxycarbonyloxy, aryloxycarbonyloxy, aralkyloxycarbonyloxy, unsubstituted or substituted aminocarbonyloxy, unsubstituted or substituted amino, alkylthio, cycloalkylthio, arylthio, heteroarylthio, aralkylthio, heteroaralkylthio, alkylsulfinyl, cycloalkylsulfinyl, arylsulfinyl, heteroarylsulfinyl, aralkylsulfinyl, heteroaralkylsulfinyl, alkylsulfonyl, cycloalkylsulfonyl, arylsulfonyl, heteroarylsulfonyl, aralkylsulfonyl, heteroaralkylsulfonyl, alkoxysulfonyl, aryloxysulfonyl, unsubstituted or substituted aminosulfonyl or hydroxysulfonyl; and $Q^2$ is alkyl or haloalkyl.

In one embodiment, the compounds are of Formula (Ia), wherein $R^{5a}$ and $R^{5b}$ are hydrogen.

In one embodiment, the compounds are of Formula (Ia), wherein $R^3$ is CN.

In one embodiment, the compounds are of Formula (Ia), wherein $R^3$ is $C(O)R^{3a}$.

In one embodiment, the compounds are of Formula (Ia), wherein $R^3$ is C(NH)NHOH.

In one embodiment, the compounds are of Formula (Ia), wherein $R^3$ is 5-tetrazolyl.

In one embodiment, the compounds are of Formula (Ia), wherein $R^{3a}$ is OH.

In one embodiment, the compounds are of Formula (Ia), wherein $R^a$ is hydrogen.

In certain embodiments, the compounds are of Formula (Ib):

(Ib)

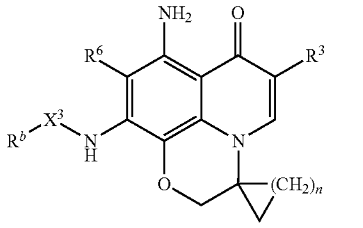

or a pharmaceutically acceptable derivative thereof, wherein $R^6$ is halo; n is 1-3; $X^3$ is substituted or unsubstituted $C_1$-$C_3$ alkylene, wherein the substituents when present are selected from one to four $Q^2$ groups; $Q^2$ is alkyl or haloalkyl; and other variables are as disclosed elsewhere herein.

In certain embodiments, the compounds are of Formula (Ic):

(Ic)

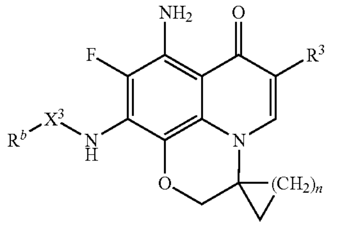

or a pharmaceutically acceptable derivative thereof, wherein n is 1-3; $X^3$ is substituted or unsubstituted $C_1$-$C_3$ alkylene, wherein the substituents when present are selected from one to four $Q^2$ groups; $Q^2$ is alkyl or haloalkyl; and other variables are as disclosed elsewhere herein.

In certain embodiments, the compounds are of Formula (Id):

(Id)

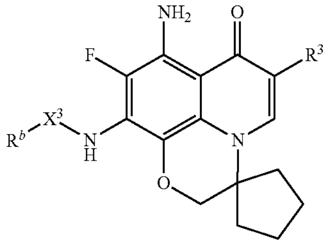

or a pharmaceutically acceptable derivative thereof, wherein $X^3$ is substituted or unsubstituted $C_1$-$C_3$ alkylene, wherein the substituents when present are selected from one to four $Q^2$ groups; $Q^2$ is alkyl or haloalkyl; $R^3$ is CN, C(O)OH, $C(O)NH_2$, C(NH)NHOH or 5-tetrazolyl; and other variables are as disclosed elsewhere herein.

In certain embodiments, compounds provided herein exhibit an $IC_{50}$ with respect to GSK3 of no more than about 20 μM, in one embodiment, no more than about 10 μM, no more than about 5 μM, or no more than 1 μM, as measured in the cell-free GSK3 kinase assay. In certain embodiments, compounds provided herein exhibit inhibitory activity that is selective with respect to GSK3, as compared to at least one other type of kinase.

In certain embodiments, GSK3 inhibitors provided herein are substantially free of antibacterial activity or having very low antibacterial activity. The antibacterial activity can be measured by methods known in the art by estimating a minimum inhibitory concentration (MIC) for test compounds (e.g. *E. Coli* and/or *S. aureus*, Clinical and Laboratory Standards Institute. Methods for Dilution Antimicrobial Susceptibility Tests for Bacteria That Grow Aerobically; Approved Standard-Sixth Edition: CLSI document M7-A4. CLSI, Wayne, Pa. (2003))

C. Preparation of the Compounds

The compounds provided herein can be prepared by methods known to one of skill in the art as showed below and following procedures similar to those described in the Examples section herein and routine modifications thereof.

Kyorin Pharmaceutical Co., Ltd., Japanese Unexamined Patent Publication S62-252772, Ube Industries, Ltd., Japanese Unexamined Patent Publication S63-264439, Bayer AG Japanese Unexamined Patent Publication H1-268679, Ihara Chemical Industry Co., Ltd., Japanese Unexamined Patent Publication H10-70584, Daiichi Seiyaku Co., Ltd., Japanese Unexamined Patent Publication S59-1489, Tokyo Tanabe Co., Ltd., Japanese Unexamined Patent Publication S62-53987, F. Hoffmann-La Roche Ltd., Japanese Unexamined Patent Publication S63-132891, H. Koga et al., *J. Med. Chem.*, 1980, 23, 1358, Y. Yoshida et al., *Synlett,* 2003, 2139,
I. Hayakawa et al., *Chem. Pharm. Bull.,* 1984, 32, 4907,
S. Atarashi et al., *Chem. Pharm. Bull.,* 1987, 35, 1986,
S. Atarashi et al., *J. Heterocyclic Chem.,* 1991, 28, 329,
H. Egawa et al., *Chem. Pharm. Bull.,* 1986, 34, 4098,
L. A. Mitscher et al., *J. Med. Chem.,* 1987, 30, 2283,
G B. Mullen et al., *J. Med. Chem.,* 1988, 31, 1694,
J. S. Kiely et al., *J. Med. Chem.,* 1988, 31, 2004,
H. Ishikawa et al., *Chem. Pharm. Bull.,* 1989, 37, 2103,
V. D. Parikh et al., *J. Heterocyclic Chem.,* 1988, 25, 1567,
H. Ishikawa et al., *Chem. Pharm. Bull.,* 1990, 38, 2459,
P. Remuzon et al., *J. Med. Chem.,* 1991, 34, 29,
D. J. Augeri et al., *J. Heterocyclic Chem.,* 1990, 27, 1509,
T. Okada et al., *J. Heterocyclic Chem.,* 1991, 28, 1067,
D. T. W. Chu et al., *J. Heterocyclic Chem.,* 1987, 24, 453, and
S. L. Dax et al., *J. Org. Chem.,* 1992, 57, 744.
J. S. Kiely et al., *J. Heterocyclic Chem.,* 1989, 26, 1675.
M. Fujita et al., *Chem. Pharm. Bull.,* 1996, 44, 987.

The compounds represented by the general formula (1) according to the present invention can be produced by Synthesis 1 or a combination of conventional methods.

Synthesis 1

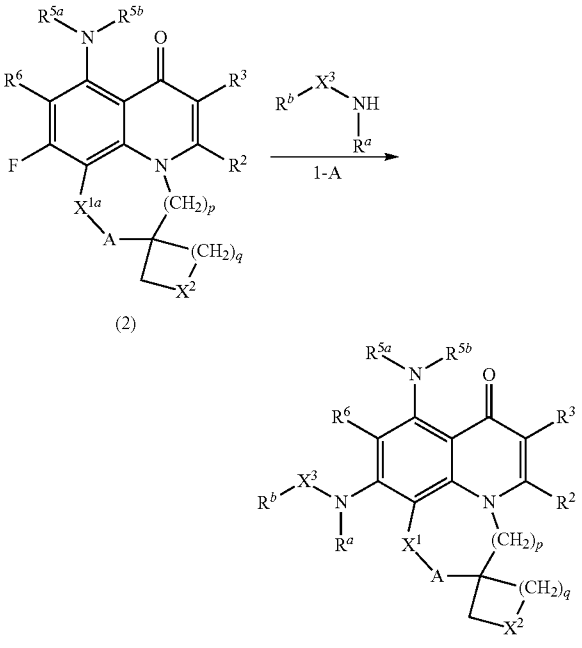

(2)

(1)

wherein $X^{1a}$ is $X^1$ or N-$PG^1$ ($PG^1$ is a protective group), and A, $R^2$, $R^3$, Rya, $R^{5b}$, $R^6$, $R^a$, $R^b$, $X^1$, $X^2$, $X^3$, p and q are as described above.

The protective group $PG^1$ represents acyl groups (such as acetyl group), lower alkoxycarbonyl groups (such as tert-butoxycarbonyl group), aryloxycarbonyl groups (such as benzyloxycarbonyl groups optionally with substitutents), aralkyl groups (such as benzyl group and p-methoxybenzyl group) or silyl groups (such as trimethylsilyl group and tert-butyldimethylsilyl group).

When $X^{1a}$ in the general formula (2) represents $X^1$, the conversion from the general formula (2) and the general formula (3) to the general formula (1) (i.e., Process 1-A) is carried out at room temperature to 180° C. for 1-48 hours by using a base (such as triethylamine, pyridine, isopropylethylamine, and 1,8-diazabicycloundecyne) in a suitable solvent (such as N,N-dimethylformamide, dimethylsulfoxide, N-methylpyrrolidone, toluene, acetonitrile, tetrahydrofran, methanol, ethanol or a mixture thereof) or solvent-free.

When $X^{1a}$ in the general formula (2) represents N-$PG^1$, the conversion from the general formula (2) and the general formula (3) to the general formula (1) (i.e., Process 1-A) can be carried out by using a general deprotection method (such as the method described in *Protecting Groups in Organic Synthesis* (John Wily and Sons (1999)) after the above-mentioned process.

Among the compounds represented by the general formula (1) according to the present invention, the compounds represented by the general formula (1b) or (1c) can be produced by Synthesis 2 as well.

Synthesis 2

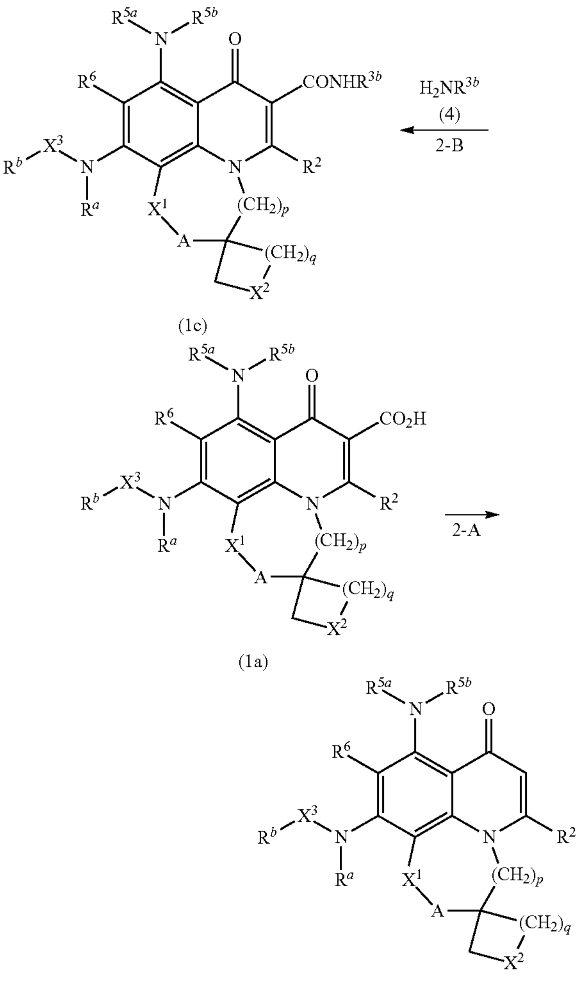

(1c)

(1a)

(1b)

wherein A, $R^a$, $R^b$, $R^2$, $R^{3b}$, $R^{5a}$, $R^{5b}$, $R^6$, $X^1$, $X^2$, $X^3$, p and q are as described above.

The conversion from the general formula (Ia) to the general formula (Ib) (i.e., Process 2-A) can be carries out at room temperature to 180° C. for 1-72 hours by using a cyanide salt (such as potassium cyanide and sodium cyanide) in a suitable solvent (such as N,N-dimethylformamide and dimethylsulfoxide).

Alternatively, the conversion can be carried out at room temperature to 250° C. for 1-72 hours in a suitable solvent (such as diphenylether, mesitylene, N,N-dimethylformamide, dimethylsulfoxide, toluene, acetonitrile, tetrahydrofuran, methanol, ethanol, acetic acid or a mixture thereof). The reaction can be carried out in the absence or in presence of acid (such as hydrochloric acid) or copper salt (such as copper chloride).

The conversion from the general formula (Ia) to the general formula (Ic) (i.e., Process 2-B) can be carried out as follows: the general formula (Ia) is first reacted with thionyl chloride, thionyl bromide, acetic anhydride, ethyl chlorocarbonate, methyl chlorocarbonate, or the like) in a suitable solvent (such as N,N-dimethylformamide, dichloromethane, chloroform, tetrahydrofuran or a mixture thereof) at −15° C. to room temperature for 5 min to 3 hours. This converts the carboxyl group to a reactive derivatizing group. The reaction can be carried out in the absence or in the presence of base (such as pyridine and triethylamine). Subsequently, the reaction product is reacted with the general formula (4) in the presence of base (such as pyridine and triethylamine) in a suitable solvent (such as N,N-dimethylformamide, dichloromethane, chloroform, tetrahydrofuran or a mixture thereof) at a temperature from 0° C. to 100° C. for 30 min to 24 hours.

Alternatively, the conversion can be performed as follows: the general formula (Ia) is reacted with the general formula (4) by using a condensation reagent (such as dicyclohexylcarbodiimide, 3-(3-dimethylaminopropyl)-1-ethylcarbodiimide chloride, diethyl cyanophosphonate, diphenylphosphoryl azide and carbonyldiimidazol) in a suitable solvent (such as N,N-dimethylformamide, dichloromethane, chloroform, tetrahydrofuran or a mixture thereof) at 0° C. to 50° C. for 1-24 hours. The reaction can be carried out in the absence or in the presence of base (such as pyridine, triethylamine, N-methylmorphorine).

Among the compounds represented by the general formula (1) according to the present invention, the compounds represented by the general formula (1d), (1e) or (1f) can be produced by Synthesis 3 as well.

Synthesis 3

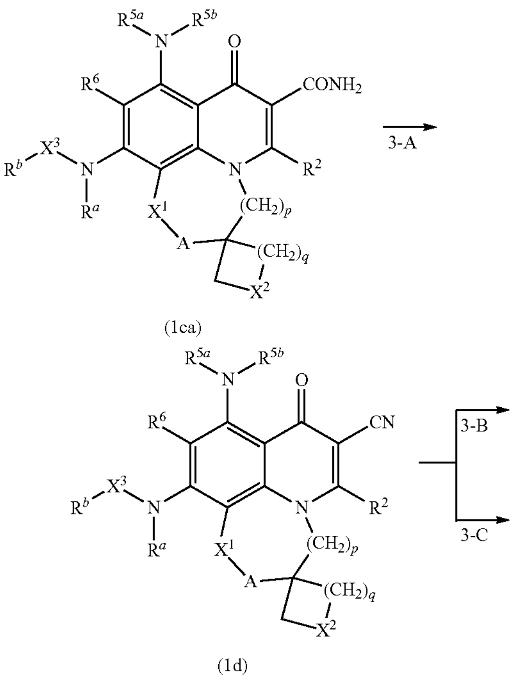

(1ca)

(1d)

-continued

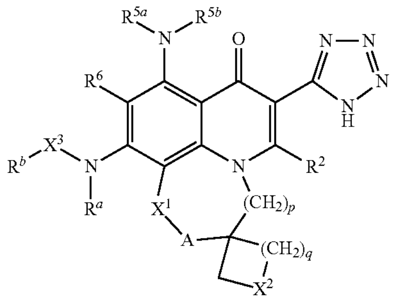

(1e)

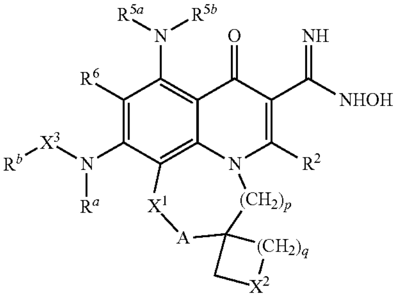

(1f)

wherein A, $R^a$, $R^b$, $R^2$, $R^{5a}$, $R^{5b}$, $R^6$, $X^1$, $X^2$, $X^3$, p and q are as described above.

The conversion from the general formula (1 ca) to the general formula (Id) (i.e., Process 3-A) can be carried out as follows: the general formula (1ca) is reacted with a dehydroxylation reagent (such as trifluoroacetic anhydride and phosphorus oxychloride) in the presence of base (pyridine and triethylamine) in a suitable solvent (such as dichloromethane, chloroform, tetrahydrofuran or a mixture thereof) at 0° C. to 50° C. for 1-24 hours. After the reaction, the reaction product can be treated with base (such as potassium carbonate, sodium hydroxide and NH silicagel) as need.

The conversion from the general formula (1d) to the general formula (1e) (i.e., Process 3-B) can be carried out at room temperature to 50° C. for 1-24 hours by using an azide compound (such as sodium azide and trimethylsilily azide) in a suitable solvent (such as 2-propanol, water or a mixture thereof) in the presence of zinc salts (such as zinc chloride and zinc bromide).

The conversion from the general formula (1d) to the general formula (1f) (i.e., Process 3-C) can be carried out at 0° C. to reflux temperature for 1-24 hours by using hydroxylamine in a suitable solvent (such as ethanol, methanol, N,N-dimethylformamide, tetrahydrofuran or a mixture thereof). The reaction can be carried out in the absence or in the presence of base (such as potassium bicarbonate, sodium carbonate, pyridine and triethylamone).

In Synthesis 1, the compounds represented by the general formula (2) can be produced by Synthesis 4.

Synthesis 4

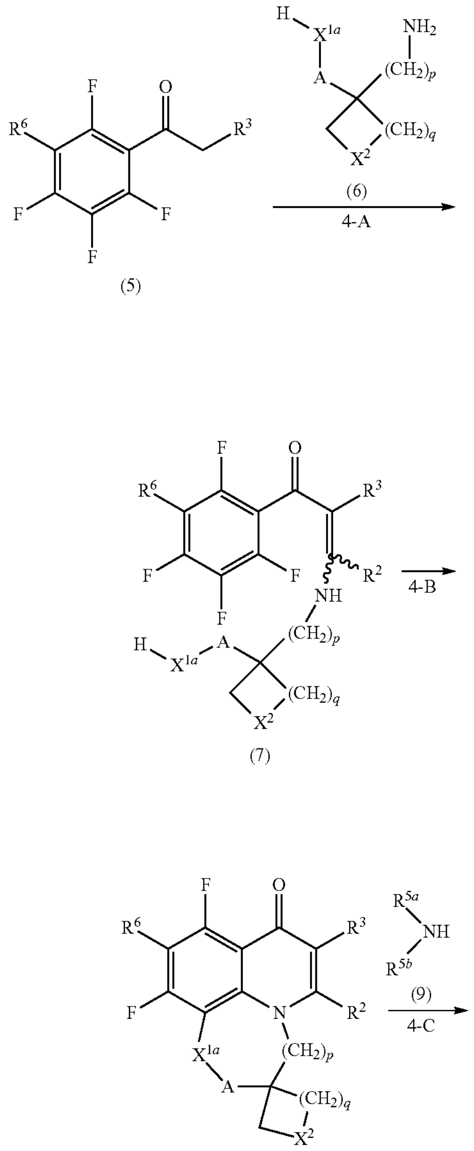

(6)

(5)

(7)

(9)

(8)

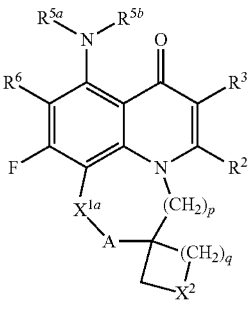

(2)

wherein A, $R^2$, $R^3$, $R^{5a}$, $R^{5b}$, $R^6$, $X^{1a}$, $X^2$, p and q are as described above.

The conversions from the general formula (5) and the general formula (6) to the general formula (7) (i.e., Process 4-A) can be performed as follows: the general formula (5) is reacted with a mixture of acetic anhydride and ortho-acid ester (such as ortho-formic acid ethyl ester and ortho-acetic ethyl ester) at 100° C. to 150° C. for 1-8 hours, and then the reaction product is reacted with the general formula (6) in a suitable solvent (such as toluene, tetrahydrofuran, methanol, ethanol, t-butanol, or a mixture thereof) at room temperature for 1-24 hours. The reaction can be carried out in the absence or in the presence of a base (potassium carbonate, sodium carbonate, t-BuOK, t-BuONa, triethylamine and pyridine).

The conversion from the general formula (7) to the general formula (8) (i.e., Process 4-B) can be carried out at 0° C. to 150° C. for 1-24 hours by using a base (such as potassium hydride, sodium hydride, potassium carbonate, sodium carbonate, t-BuOK and t-BuONa) or fluoride salt (such as potassium fluoride and sodium fluoride) in a suitable solvent (such as N,N-dimethylformamide, dimethylsulfoxide, tetrahydrofuran, or a mixture thereof).

The conversion from the general formula (8) to the general formula (2) (i.e., Process 4-C) can be carried out at room temperature to 180° C. for 1-24 hours in the presence of a base (such as triethylamine, pyridine, isopropylethylamine, and 1,8-diazabicycloundecyne) in a suitable solvent (such as N,N-dimethylformamide, dimethylsulfoxide, toluene, acetonitrile, tetrahydrofran, methanol, ethanol or a mixture thereof) in the presence of base (such as triethylamine, pyridine, isopropylethylamine, and 1,8-diazabicycloundecyne) or solvent-free.

Among the compounds represented by the general formula (2), the compounds represented by the general formula (2a) can be produced by Synthesis 5 as well.

Synthesis 5

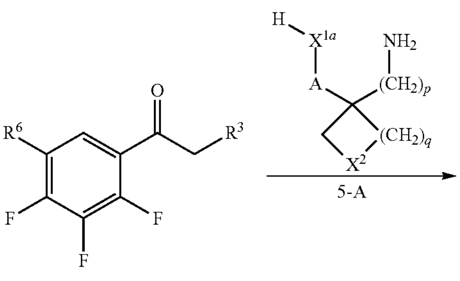

(10)

-continued

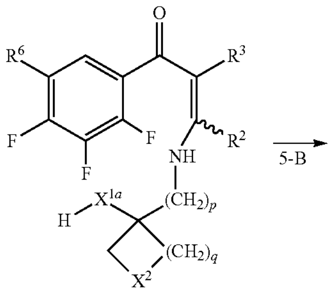

(11)

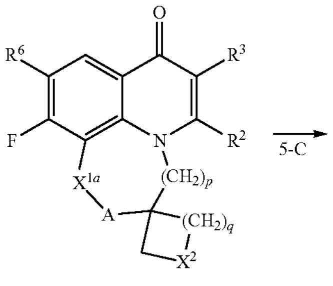

(12)

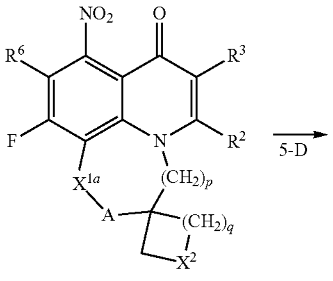

(13)

-continued

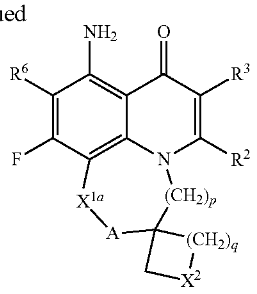

(2a)

wherein A, $R^2$, $R^3$, $R^6$, $X^{1a}$, $X^2$, p and q are as described above.

The conversion from the general formula (10) and the general formula (6) to the general formula (11) (i.e., Process 5-A) can be conducted by a method similar to Process 4-A.

The conversion from the general formula (11) to the general formula (12) (i.e., Process 5-B) can be performed by a method similar to Process 4-B.

The conversion from the general formula (12) to the general formula (13) (i.e., Process 5-C) can be conducted by general nitration, for instance, a reaction in concentrated sulfuric acid using a nitrosating reagent (such as potassium nitrate, sodium nitrate and nitric acid). The reaction can be carried out at 0° C. to 50° C. for 1-8 hours.

The conversion from the general formula (13) to the general formula (2a) (i.e., Process 5-D) can be carried out at room temperature to 120° C. for 1-48 hours by using a metal (such as reduced iron, tin and zinc) in the presence of acid (such as hydrochloric acid and acetic acid) in a suitable solvent (such as tetrahydrofuran, methanol, ethanol, water or a mixture thereof) or solvent-free.

Alternatively, the conversion can be performed by hydrogenation using metal catalyst (such as palladium on activated carbon, platinum on activated carbon, oxidized platinum and Raney nickel) in a suitable solvent (such as methanol, ethanol, ethyl acetate, tetrahydrofuran, N,N-dimethylformamide, acetic acid or a mixture thereof) at room temperature to 80° C. for 1-24 hours. The reaction can be carried out at a pressure from normal pressure to 0.5 MPa in hydrogen atmosphere.

Furthermore, the conversion can be performed by reduction using sodium hydrosulfite in a suitable solvent (such as water, methanol, ethanol, tetrahydrofuran or a mixture thereof) at room temperature to 100° C. for 1-24 hours.

In Synthesis 4 or Synthesis 5, a compound of the general formula (15), (16), (17) and (18) can be produced by Synthesis 6 as well.

Synthesis 6

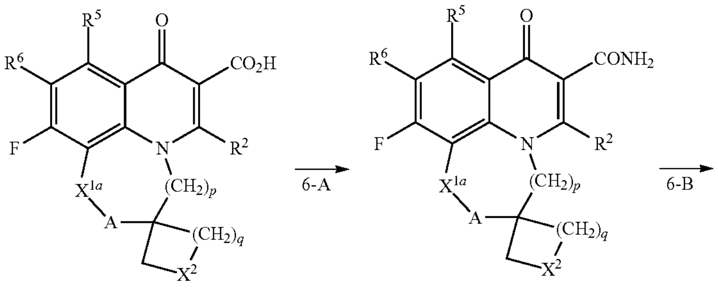

(14) (15)

-continued

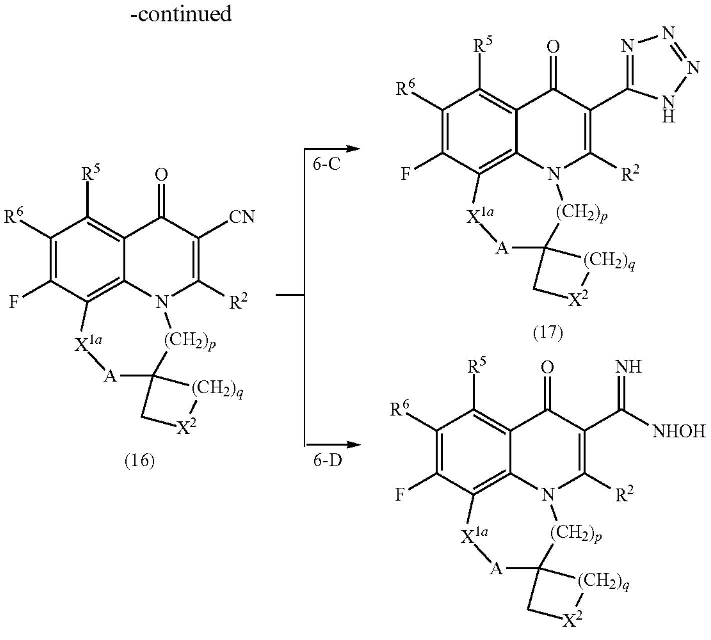

(16) (17) (18)

wherein $R^5$ is hydrogen, $NO_2$ or $R^{5a}R^{5b}N$—, and A, $R^a$, $R^b$, $R^2$, $R^6$, $X^{1a}$, $X^2$, p and q are as described above.

The conversion from the general formula (14) to the general formula (15) (i.e., Process 6-A) can be performed by a method similar to Process 2-B.

The conversion from the general formula (15) to the general formula (16) (i.e., Process 6-B) can be performed by a method similar to Process 3-A.

The conversion from the general formula (16) to the general formula (17) (i.e., Process 6-C) can be performed by a method similar to Process 3-B.

The conversion from the general formula (16) to the general formula (18) (i.e., Process 6-D) can be performed by a method similar to Process 3-C.

Among compounds represented by the general formula (13) in Synthesis 5, the compound represented by the general formula (13b) can be produced by Synthesis 7 as well.

Synthesis 7

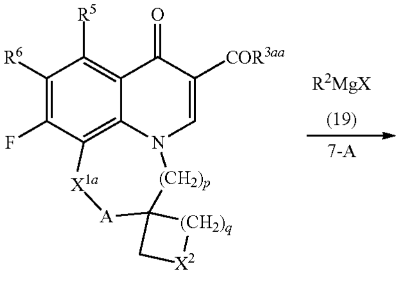

(13a)

-continued

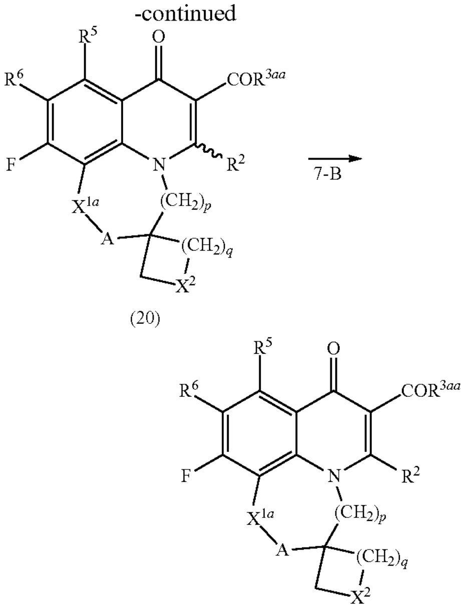

(20) (13b)

wherein $R^{3aa}$ is alkoxy, X is halogens, and A, $R^2$, $R^5$, $R^6$, $X^{1a}$, $X^2$, p and q are as described above.

The conversion from the general formula (13a) and the general formula (19) to the general formula (20) (i.e., Process 7-A) can be carried at a temperature from −78° C. to 0° C. for 1-24 hours in a suitable solvent (such as tetrahydrofuran, diethylether or a mixture thereof). The conversion can be carried out in the absence or in the presence of a copper salt (such as copper iodide and copper chloride).

The conversion from the general formula (20) to the general formula (13b) (i.e., Process 7-B) can be conducted at room temperature to 130° C. for 1-120 hours by using manganese dioxide in a suitable solvent (such as dichloromethane, chloroform, toluene, ethanol or a mixture thereof).

Alternatively, the conversion can be carried out at room temperature to 130° C. for 1-24 hour by using a quinone compound (such as dichlorodicyano-p-benzoquinone and chloranil).

Among the compounds represented by the general formula (13) in Synthesis 5, the compound represented by the general formula (13d) can be produced by Synthesis 8.

Synthesis 8

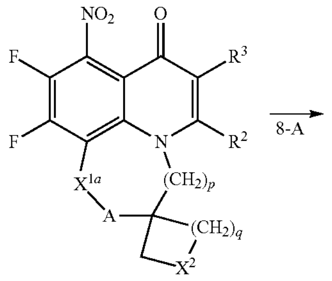

(13c)

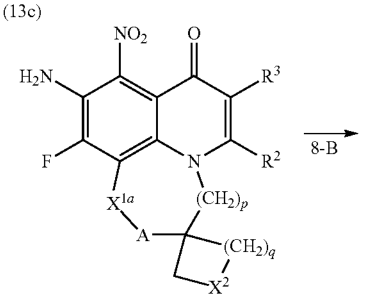

(21)

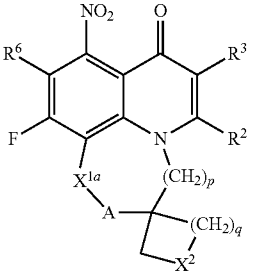

(13d)

wherein A, $R^2$, $R^3$, $X^{1a}$, $X^2$, p, and q are as described above.

The conversion from the general formula (13c) to the general formula (21) (i.e., Process 8-A) can be carried out at room temperature to −78° C. for 1 to 72 hours by using ammonium carbonate in a suitable solvent (such as N,N-dimethylformamide, dimethylsulfoxide, ethanol, methanol, water or a mixture thereof).

The conversion from the general formula (21) to the general formula (13d) (i.e., Process 8-B) can be carried out at 0° C. to 100° C. for 1-48 hours by using a nitrite ester (such as t-butyl nitrite, amyl nitrite, iso-amyl nitrite) in the presence of a copper salt (such as copper chloride and copper bromide) in a suitable solvent such as acetonitrile).

Alternatively, the conversion can be performed as follows: the general formula (21) is reacted with a nitrite salt (such as potassium nitrite and sodium nitrite) in the presence of an acid (such as hydrochloric acid, sulfuric acid, and acetic acid) in a suitable solvent (for example, tetrahydrofuran, 1,4-dioxane, $H_2O$ or a mixture thereof) at a temperature from 0° C. to room temperature for 5 min. to 1 hr, and then, the reaction product is treated with a copper salt (such as copper chloride and copper bromide) in a suitable solvent (for example, tetrahydrofuran, 1,4-dioxane, $H_2O$ or a mixture thereof) at 0° C.-100° C. for 1-48 hours.

In Synthesis 1-8, the compounds with substituent $X^{1a}$ representing N-$PG^1$ can be converted to compounds with $X^{1a}$ representing NH by a conventional method such as the method described in *Protecting Groups in Organic Synthesis* (John Wily and Sons (1999)).

In Synthesis 1-8, the compounds with substituent $R^{5a}$ and/or $R^{5b}$ representing aralkyl group which optionally with substituents can be converted to compounds with substituent $R^{5a}$ and/or $R^{5b}$ representing H by a conventional method, for example, by catalytic reduction using acid (such as hydrochloric acid and trifluoroacetic acid), inorganic base (such as potassium carbonate and sodium hydroxide), organic base (such as hydrazine), quaternary ammonium salt (such as tetrabutylammonium fluoride) and metal (such as palladium on carbon).

In Synthesis 1-8, the compounds with substituent $R^3$ representing alkoxycarbonyl group can be converted to compounds with substituent $R^3$ is COOH by a conventional method, for example, a solvent-free reaction or a reaction in a suitable solvent (such as methanol, ethanol, tetrahydrofuran, water or a mixture thereof) in the presence of either base (such as potassium hydroxide, sodium hydroxide, potassium carbonate and sodium carbonate) or acid (such as sulfuric acid, hydrochloric acid and acetic acid) at a temperature from room temperature to 120° C. for 1-48 hours.

Optical isomers of the compounds represented by the general formula (1) can be produced by using the aforementioned Syntheses 1-8 or a combination of the conventional methods, using optically active starting materials.

Alternatively, these optical isomers can be prepared from racemetes of represented by the general formula (1) by fractional crystallization using optically active acid or base, or chromatography using ciral support.

Certain exemplary reaction schemes for the preparation of compounds are shown below:

Synthesis 9

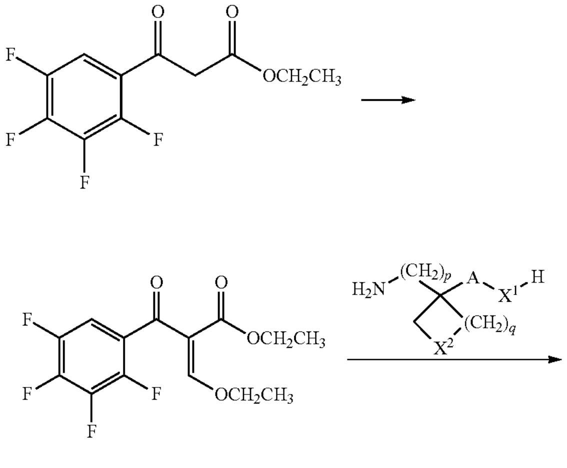

-continued
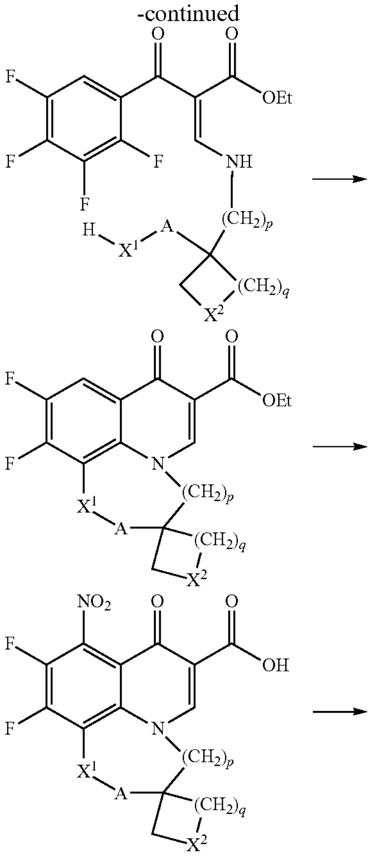
-continued
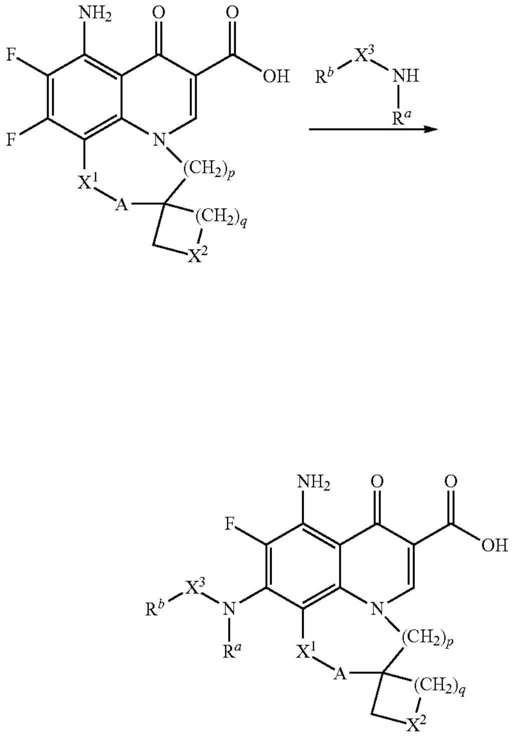
Synthesis 10
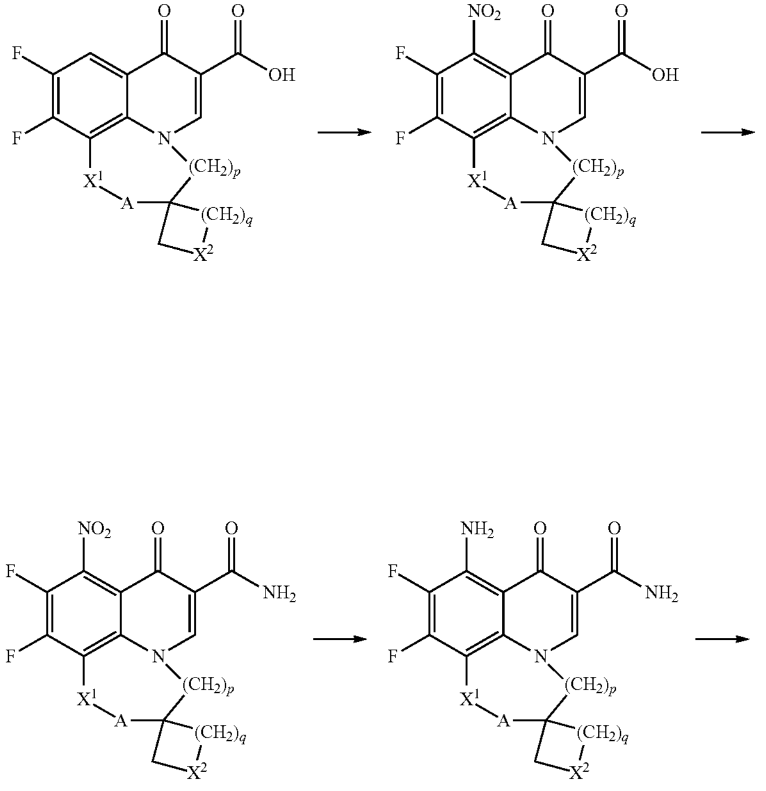

-continued
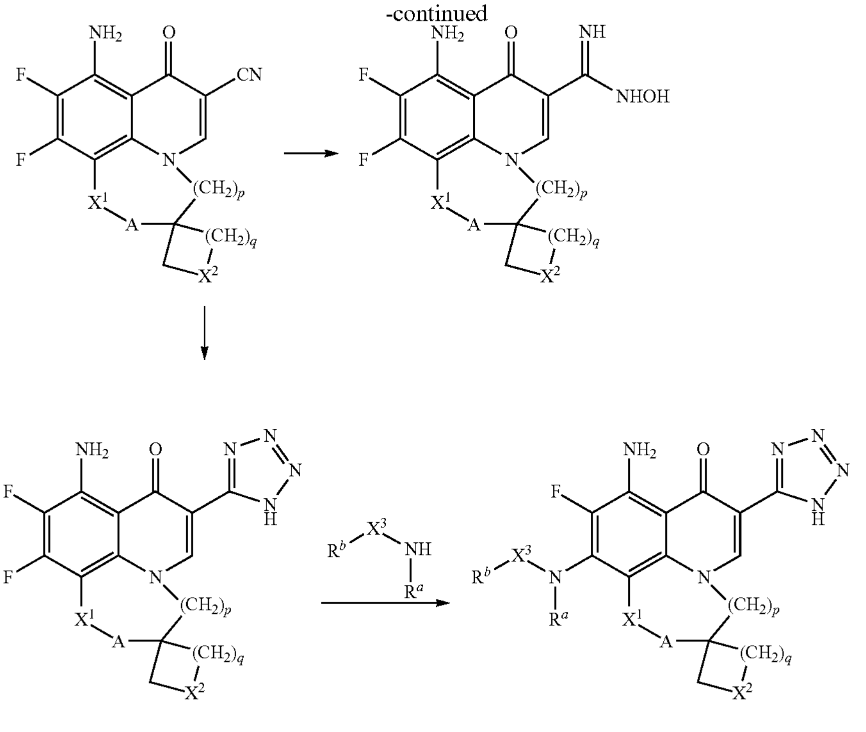
In one embodiment, the product of Synthesis 9 is 8-amino-9-fluoro-7-oxo-10-(2-(pyridin-2-ylamino)ethylamino)-2,7-dihydrospiro[[1,4]oxazino[2,3,4-]quinoline-3,1'-cyclopentane]-6-carboxylic acid (8), as illustrated in Synthesis 11.
Synthesis 11
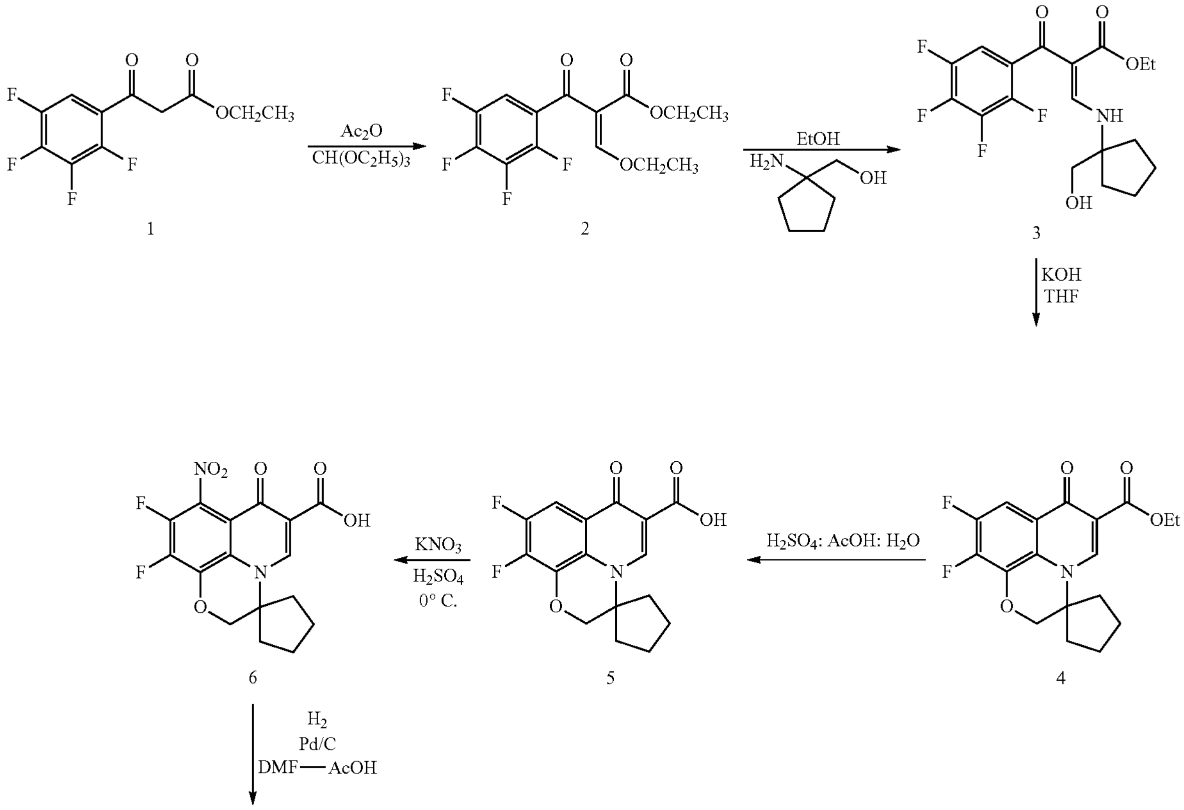

-continued

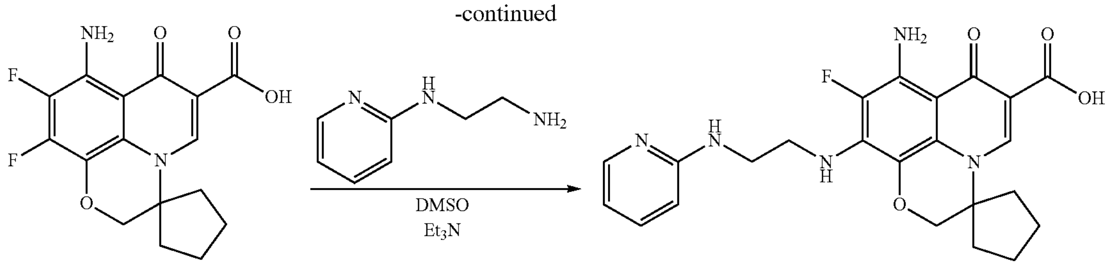

7

8

D. Pharmaceutical Compositions

The pharmaceutical compositions provided herein contain therapeutically effective amounts of one or more of compounds provided herein that are useful in the prevention, treatment, or amelioration of one or more of the symptoms of GSK-3 mediated diseases.

Pharmaceutical compositions of the compounds provided herein may be administered systemically or locally, or orally or parentelly such as rectally, subcutaneously, intramuscularly, intravenously or percutaneusly.

The compositions contain one or more compounds provided herein. The compounds can be formulated into suitable pharmaceutical preparations such as solutions, suspensions, tablets, dispersible tablets, pills, capsules, granules, powders, fine powders, injections, sustained release formulations or elixirs, for oral administration or in sterile solutions or suspensions for parenteral administration, as well as transdermal patch preparation and dry powder inhalers. In certain embodiments, the compositions provided herein can be produced by adding convenient excipients, fillers, binders, disintegrators, coating agents, sugar coating agents, pH modulators, solublizing agents, or aqueous or non-aqueous solvents according to the conventional pharmaceutical preparation techniques. Typically, the compounds described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of GSK-3 mediated diseases.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of GSK-3 mediated diseases.

In certain embodiments, a therapeutically effective dosage should produce a serum concentration of active ingredient of from about 0.1 ng/ml to about 50-100 μg/ml. In one embodiment, the pharmaceutical compositions provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing kinase-mediated, including, but not limited to, GSK-3-mediated diseases. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable derivatives thereof. The pharmaceutically therapeutically active compounds and derivatives thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum or talc, cellulose derivatives, gelatin, agar, pectin, arabic gum, olive oil, sesame oil, cacao butter, ethylene glycol, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001-100% active ingredient, in certain embodiments, about 0.1-85% or about 75-95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as GSK-3 mediated diseases. It is to be understood that such combination therapy constitutes a further aspect of the compositions and methods of treatment provided herein.

Lactose-free compositions provided herein can contain excipients that are well known in the art and are listed, for example, in the U.S. Pharmocopia (USP) SP (XXI)/NF (XVI). In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch and magnesium stearate.

Further encompassed are anhydrous pharmaceutical compositions and dosage forms containing a compound provided herein. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms as described herein can be prepared using anhydrous or low moisture containing ingredients and low moisture or low humidity conditions. Pharmaceutical compositions and dosage forms that comprise lactose and at least one active ingredient that comprises a primary or secondary amine may be, in certain embodiments, anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in certain embodiments, packaged using materials known to prevent exposure to water such that they can be included in suitable formulary kits. Examples of suitable packaging include, but are not limited to, hermetically sealed foils, plastics, unit dose containers (e.g., vials), blister packs and strip packs.

Oral Dosage Forms

Oral pharmaceutical dosage forms are either solid, gel or liquid. The solid dosage forms are tablets, capsules, granules, and bulk powders. Types of oral tablets include compressed, chewable lozenges and tablets which may be enteric coated, sugar coated or film coated. Capsules may be hard or soft gelatin capsules, while granules and powders may be provided in non effervescent or effervescent form with the combination of other ingredients known to those skilled in the art.

In certain embodiments, the formulations are solid dosage forms, such as capsules or tablets: The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, *lycopodium* and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non effervescent granules and effervescent preparations reconstituted from effervescent granules. Aqueous solutions include, for example, elixirs and syrups. Emulsions are either oil in-water or water in oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative.

An emulsion is a two phase system in which one liquid is dispersed in the form of small globules throughout another liquid. Pharmaceutically acceptable carriers used in emulsions are non aqueous liquids, emulsifying agents and preservatives. Suspensions use pharmaceutically acceptable suspending agents and preservatives. Pharmaceutically acceptable substances used in non effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such as fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (i.e., 10-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923 which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will have diameters of less than 50 microns or less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin gelatin, carbowax (polyoxyethylene glycol) and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. An exemplary weight of a rectal suppository is about 2 to 3 μm.

Tablets and capsules for rectal administration are manufactured using the same pharmaceutically acceptable substance and by the same methods as for formulations for oral administration.

Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, *CRC Crit. Ref. Biomed. Eng.* 14:201 (1987); Buchwald et al., Surgery 88:507 (1980); Saudek et al., *N. Engl. J. Med.* 321:574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984).

In some embodiments, a controlled release device is introduced into a subject in proximity of the site of inappropriate immune activation or a tumor. Other controlled release systems are discussed in the review by Langer (Science 249:1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Articles of Manufacture

The compounds or pharmaceutically acceptable derivatives can be packaged as articles of manufacture containing packaging material, a compound or pharmaceutically acceptable derivative thereof provided herein, which is used for treatment, prevention or amelioration of one or more symptoms associated with kinase activity, including, but not limited to, GSK-3 activity, and a label that indicates that the compound or pharmaceutically acceptable derivative thereof is used for treatment, prevention or amelioration of one or more symptoms of kinase-mediated, including, but not limited to, GSK-3-mediated diseases.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated.

E. Methods of Treatment

Methods of use of the compounds and compositions are also provided. The methods involve both in vitro and in vivo uses of the compounds and compositions.

In certain embodiments, provided herein are methods for inhibiting the action of GSK-3 by administering compounds and compositions provided herein. In one embodiment, the methods involve contacting GSK-3 with a compound provided herein.

F. Evaluation of Compound Activity

GSK3 inhibitory activity of the compounds provided herein can be readily detected using the assays described herein, as well as assays generally known to those of ordinary skill in the art.

Exemplary methods for identifying specific inhibitors of GSK3 include both cell-free and cell-based GSK3 kinase assays. A cell-free GSK3 kinase assay detects inhibitors that act by direct interaction with the polypeptide GSK3, while a cell-based GSK3 kinase assay may identify inhibitors that function either by direct interaction with GSK3 itself, or by interference with GSK3 expression or with post-translational processing required to produce mature active GSK3. U.S. Application No. 20050054663 describes exemplary cell-free and cell-based GSK3 kinase assays. Exemplary assays used herein are discussed briefly below:

10-25 ng of recombinant full-length human GSK3β (Upstate) is incubated in the presence or absence of compound at varying concentrations for 1 hour at 30 degrees Celsius in 20 mM MOPS, pH 7.0, 10 mM magnesium acetate, 0.2 mM EDTA, 2 mM EGTA, 30 mM magnesium chloride, 62.5 μM phospho-glycogen synthase peptide-2, 5 μM ATP, 10 mM β-glycerol phosphate, 1 mM sodium orthovanadate and 1 mM dithiothreitol. Proceed to KinaseGlo luciferase reaction.

Following the completion of the kinase reaction an equal volume of KinaseGlo luciferase reagent (Promega) is added and the luminescence read using a luminescence plate reader within 5-10 minutes. Compound activity is expressed as % inhibition relative to maximal inhibition observed at the maximal dose and 1050 values then calculated using curve fitting software (GraphPad Prizm).

EXAMPLES

Example 1

8'-amino-9'-fluoro-7'-oxo-10'-[2-(2-pyridylamino)ethylamino]spiro[cyclopentane-1,3'(2'H)-[7H]pyrido[1,2,3-de][1,4]benzoxazine-1-6'-carboxylic Acid

1A) Preparation of ethyl 3-[1-(hydroxymethyl)cyclopentylamino]-2-(2,3,4,5-tetrafluorobenzoyl)acrylate

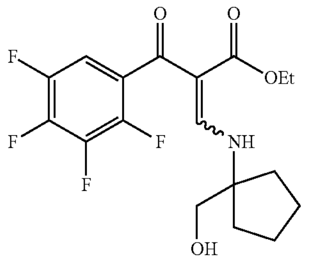 [SMILES: CCOC(=O)C(=CNC1(CO)CCCC1)C(=O)c1cc(F)c(F)c(F)c1F]

A stirred solution of ethyl 3-oxo-3-(2,3,4,5-tetrafluorophenyl)propionate (3.17 g, 12 mmol), acetic anhydride (3.34 mL, 3.6 g, 30 mmol) and triethyl orthoformate (3.00 mL, 2.6 g, 18 mmol) was heated at 130° C. for 1.5 h. The mixture was concentrated in vacuo and dried under high vacuum for 3 hours. The crude product was dissolved in EtOH (15 mL) and cooled to 0° C. and then 1-amino-1-cyclopentanemethanol (1.01 g, 8.8 mmol) was added very slowly. After 1.5 h, the solvent was removed by evaporation to yield the title compound as yellow oil (3.1 g crude) that was used in the next step without further purification.

1B) Preparation of Ethyl-9',10'-difluoro-7'-oxo spiro[cyclopentane-1,3'(2'H)-[7H]pyrido[1,2,3-de][1,4]benzoxazine]-6'-carboxylate

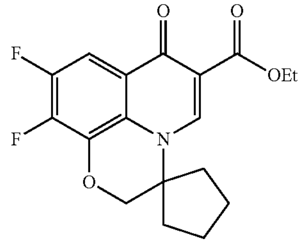 [SMILES: CCOC(=O)c1cn2c3c(c(F)c(F)cc3c1=O)OCC21CCCC1]

To a solution of 3-[1-(hydroxymethyl)cyclopentylamino]-2-(2,3,4,5-tetrafluorobenzoyl)acrylate (570 mg, 1.46 mmol) in THF (10 mL), crushed pellets of KOH (164 mg, 2.93 mmol) were added under ice-cooling. After 1.5 h more KOH was added (80 mg, 1.42 mmol) and the reaction mixture was warmed up to room temperature and stirred overnight. The reaction mixture was acidified with 0.5 N HCl to pH 2. The white precipitate was collected by filtration to give the title compound which was used crude in the next step (454 mg, 1.3 mmol, 89%).

1C) Preparation of 9', 10'-difluoro-7'-oxospiro[cyclopentane-1,3'(2'H)-[4H]pyrido[1,2,3-de][1,4]benzoxazine]-6'-carboxylic acid

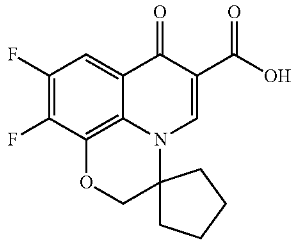 [SMILES: O=C(O)c1cn2c3c(c(F)c(F)cc3c1=O)OCC21CCCC1]

A solution of ethyl-9',10'-difluoro-7'-oxospiro[cyclopentane-1,3'(2'H)-[7H]pyrido[1,2,3-de][1,4]benzoxazine]-6'-carboxylate (13.2 g, 38 mmol) in a mixture of acetic acid/water/$H_2SO_4$ (8:6:1 v/v, 75 mL) was heated under reflux for 2 h. The reaction mixture was poured into ice water. A precipitate formed and was collected by filtration, washed with water and then dried to give the title compound (10.5 g, 32.7 mmol, 86%) as a light yellow solid.

1D) Preparation of 9',10'-difluoro-8'-nitro-7'-oxo spiro[cyclopentane-1,3'(2'H)-[7H]pyrido[1,2,3-de][1,4]benzoxazine]-6-carboxylic acid

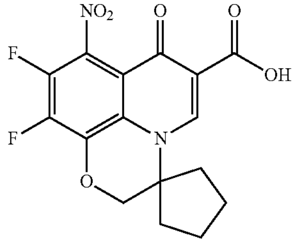

A solution of 9',10'-difluoro-7'-oxospiro[cyclopentane-1,3'(2'H)-[7H]pyrido[1,2,3-de][1,4]benzoxazine]-6'-carboxylic acid (1.8 g, 5.6 mmol) in concentrated $H_2SO_4$ (10 mL) was treated portionwise at 0° C. with solid $KNO_3$ (736 mg, 7.29 mmol). After stirring at 0° C. for 1 h, the reaction mixture was poured into 500 mL of ice-water and the resulting precipitate was removed by filtration and washed with ice-cold water. The resulting solid was dried to yield the title compound as a pale yellow solid (1.8 g, 88%).

1E) Preparation of 8'-amino-9',10'-difluoro-7'-oxospiro [cyclopentane-1,3' (2H)-[7H]pyrido[1,2,3-de][1,4]benzoxazine]-6'-carboxylic acid

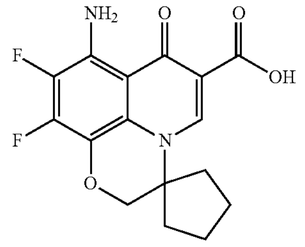 [SMILES: O=C(O)c1cn2c3c(c(F)c(F)c([N+](=O)[O-])c3c1=O)OCC21CCCC1]

A solution of 9',10'-difluoro-8'-nitro-7'-oxospiro[cyclopentane-1,3' (2'H)-[7H]pyrido[1,2,3-de][1,4]benzoxazine]-6'-carboxylic acid (3.9 g, 0.01 mmol) in ethanol/acetic acid (1:1, v/v, 100 mL) was hydrogenated under atmospheric pressure over 10% Pd/C (390 mg) at 80° C. for 18 h. Then 200 mL of DMF were added and the reaction mixture was heated until it became clear. The catalyst was removed by filtration over Celite, which was washed two times with hot DMF and the combined filtrates were concentrated in vacuo to dryness to yield the title compound (2.85 g, 73%) which was used crude in the next step.

1F) Preparation of 8'-amino-9'-fluoro-7'-oxo-10'-[2-(2-pyridylamino)ethylamino]spiro[cyclopentane-1,3'(2'H)-[7H]pyrido[1,2,3-de][1,4]benzoxazine]-6'-carboxylic Acid

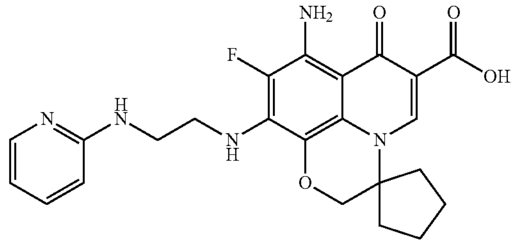 [SMILES: Nc1c(F)c(NCCNc2ccccn2)c2c3c1c(=O)c(C(=O)O)cn3C1(CCCC1)CO2]

A solution of 8'-amino-9'10'-difluoro-7'-oxospiro[cyclopentane-1,3' (2'H)-[7H]pyrido[1,2,3-de][1,4]benzoxazine]-6'-carboxylic acid (500 mg, 1.37 mmol) and N-(2-pyridyl)-1,2-ethanediamine (226 mg, 1.64 mmol) and 19 µL triethylamine in DMSO (5 mL) was stirred at 90° C. for 24 h. The reaction mixture was poured into water and the precipitate that formed was collected by filtration. The crude product was passed through a silica gel column ($CH_2Cl_2/CH_3OH$ 10:1 v/v) and then re-crystallized from diethyl ether to yield the title compound (284 mg, 42%) as a yellow solid. MS (EP) m/z: 454 ($M^+$+1). (Calcd. for $C_{23}H_{24}FN_5O_4$, 453.18).

Example 2

8-amino-9-fluoro-10-(2-(4-methylquinolin-2-ylamino)-ethylamino)-7-oxo-2,7-dihydrospiro[[1,4]oxazino[2,3,4-ij]quinoline-3,1'-cyclopenta ne]-6-carboxylic Acid

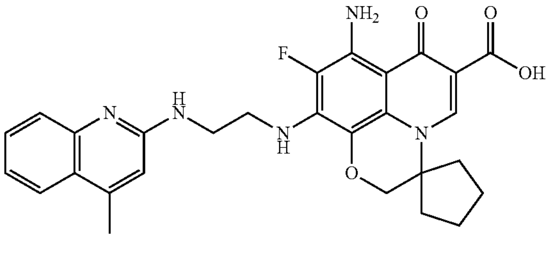 [SMILES: Cc1cc(NCCNc2c(F)c(N)c3c(=O)c(C(=O)O)cn4c3c2OCC42CCCC2)nc2ccccc12]

A solution of 8-amino-9,10-difluoro-7-oxo-2,7-dihydrospiro[[1,4]oxazino[2,3,4-ij]-quinoline-3,1'-cyclopentane]-6-carboxylic acid (13 mg, 0.04 mmol) and N1-(4-methylquinolin-2-yl)ethane-1,2-diamine (10 mg, 0.05 mmol) and 11 μL triethylamine in DMSO (0.3 mL) was stirred at 90° C. for 72 h. The reaction mixture was cooled and freeze-dried overnight. The crude product was taken up in $CH_2Cl_2$ and purified by preparative TLC to yield 8-amino-9-fluoro-10-(2-(4-methylquinolin-2-ylamino)ethylamino)-7-oxo-2,7-dihydrospiro[[1,4]oxazino[2,3,4-ij]quinoline-3,1'-cyclopentane]-6-carboxylic acid (0.8 mg, 4%) as a yellow solid. MS (EP) m/z: 518 ($M^+$+1). (Calcd. for $C_{28}H_{28}FN_5O_4$, 517.21).

Example 3

10-(3-(1H-1,2,4-triazol-1-yl)propylamino)-8-amino-9-fluoro-7-oxo-2,7-dihydrospiro[[1,4]oxazino[2,3,4-ij]quinoline-3,1'-cyclopentane]-6-carboxylic Acid

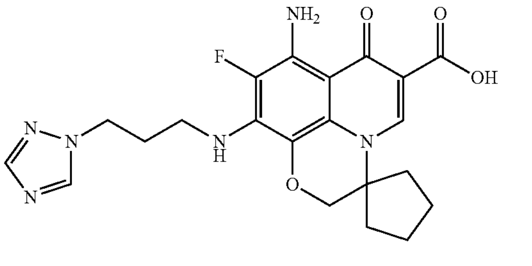 [SMILES: Nc1c(F)c(NCCCn2cncn2)c2c3c1c(=O)c(C(=O)O)cn3C1(CCCC1)CO2]

A solution of 8-amino-9,10-difluoro-7-oxo-2,7-dihydrospiro[[1,4]oxazino[2,3,4-ij]-quinoline-3,1'-cyclopentane]-6-carboxylic acid (13 mg, 0.04 mmol) and 3-(1H-1,2,4-triazol-1-yl)propan-1-amine (5 mg, 0.04 mmol) and 5.5 μL triethylamine in DMSO (0.3 mL) was stirred at 90° C. for 24 h. The reaction mixture was cooled and freeze-dried overnight. The crude product was taken up in ACN and purified by prep HPLC to yield 10-(3-(1H-1,2,4-triazol-1-yl)propylamino)-8-amino-9-fluoro-7-oxo-2,7-dihydrospiro[[1,4]oxazino[2,3,4-ij]quinoline-3,1'-cyclopentane]-6-carboxylic acid (3.2 mg, 18%) as a yellow solid. MS (EP) m/z: 443 ($M^+$+1). (Calcd. For $C_{21}H_{23}FN_6O_4$, 442.18).

Example 4

8-amino-9-fluoro-10-(3-(4-fluorophenyl)propylamino)-7-oxo-2,7-dihydrospiro[[1,4]oxazino[2,3,4-ij]quinoline-3,1'-cyclopentane]-6-carboxylic acid

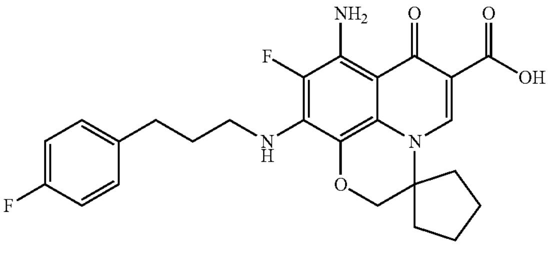 [SMILES: Nc1c(F)c(NCCCc2ccc(F)cc2)c2c3c1c(=O)c(C(=O)O)cn3C1(CCCC1)CO2]

8-amino-9-fluoro-10-(3-(4-fluorophenyl)propylamino)-7-oxo-2,7-dihydrospiro-[[1,4]oxazino[2,3,4-j]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 470 ($M^+$+1). (Calcd. For $C_{25}H_{25}F_2N_3O_4$, 469.18).

Example 5

8-amino-10-(3-(3,4-dihydroquinolin-1(2H)-yl)-propylamino)-9-fluoro-7-oxo-2,7-dihydrospiro[[1,4]oxazino[2,3,4-ij]quinoline-3,1'-cyclopentane]-6-carboxylic Acid

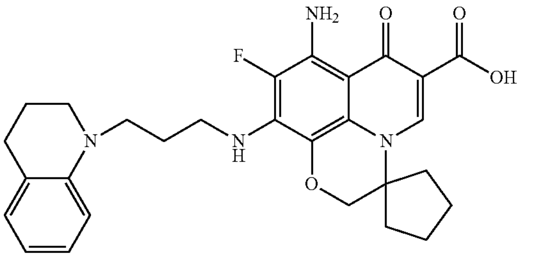 [SMILES: Nc1c(F)c(NCCCN2CCCc3ccccc32)c2c3c1c(=O)c(C(=O)O)cn3C1(CCCC1)CO2]

8-amino-10-(3-(3,4-dihydroquinolin-1(2H)-yl)propylamino)-9-fluoro-7-oxo-2,7-dihydrospiro [[1,4]oxazino[2,3,4-ij]quinoline-3,1'-cyclopentane]-6-carboxylic acid was prepared from 8-amino-9,10-difluoro-7-oxo-2,7-dihydrospiro [[1,4]oxazino[2,3,4-ij]quinoline-3,1'-cyclopentane]-6-carboxylic acid using synthetic procedures similar to those described in the examples above. MS (EP) m/z: 507 ($M^+$+1). (Calcd. For $C_{28}H_{31}FN_4O_4$, 506.23).

Example 6

8-amino-10-(4-(4-chlorophenyl)butan-2-ylamino)-9-fluoro-7-oxo-2,7-dihydrospiro[[1,4]oxazino[2,3,4-ij]quinoline-3,1'-cyclopentane]-6-carboxylic Acid

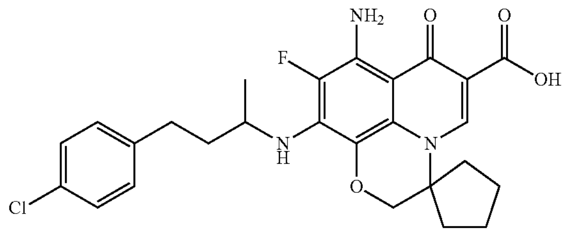 [SMILES: CC(CCc1ccc(Cl)cc1)Nc1c(F)c(N)c2c(=O)c(C(=O)O)cn3c2c1OCC31CCCC1]

8-amino-10-(4-(4-chlorophenyl)butan-2-ylamino)-9-fluoro-7-oxo-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 500 ($M^{+}$+1). (Calcd. For $C_{26}H_{27}ClFN_3O_4$, 499.17).

Example 7

8-amino-9-fluoro-10-(3-(furan-2-carboxamido)-propylamino)-7-oxo-2,7-dihydrospiro[[1,4]oxazino[2,3,4-ij]quinoline-3,1'-cyclopentane]-6-carboxylic Acid

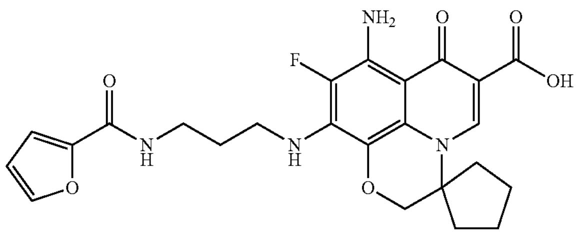 [SMILES: Nc1c(F)c(NCCCNC(=O)c2ccco2)c2c3c1c(=O)c(C(=O)O)cn3C1(CCCC1)CO2]

8-amino-9-fluoro-10-(3-(furan-2-carboxamido)propylamino)-7-oxo-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 485 ($M^{+}$+1). (Calcd. For $C_{24}H_{25}FN_4O_6$, 484.18).

Example 8

8-amino-10-(3-(adamantanecarboxamido)propylamino)-9-fluoro-7-oxo-2,7-dihydrospiro[[1,4]oxazino[2,3,4-ij]quinoline-3,1'-cyclopentane]6-carboxylic Acid

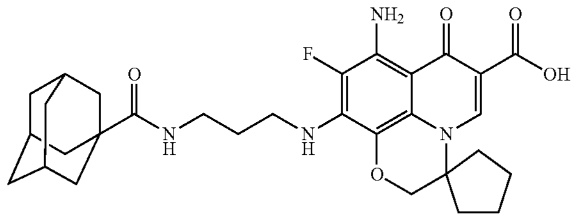 [SMILES: Nc1c(F)c(NCCCNC(=O)C23CC4CC(CC(C4)C2)C3)c2c3c1c(=O)c(C(=O)O)cn3C1(CCCC1)CO2]

8-amino-10-(3-(adamantanecarboxamido)propylamino)-9-fluoro-7-oxo-2,7-dihydrospio[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 553 ($M^{+}$+1). (Calcd. For $C_{30}H_{37}FN_4O_5$, 552.27).

Example 9

8-amino-9-fluoro-10-(2-(4-fluorophenoxy)ethylamino)-7-oxo-2,7-dihydrospiro[[1,4]oxazino[2,3,4-ij]quinoline-3,1'-cyclopentane]-6-carboxylic Acid

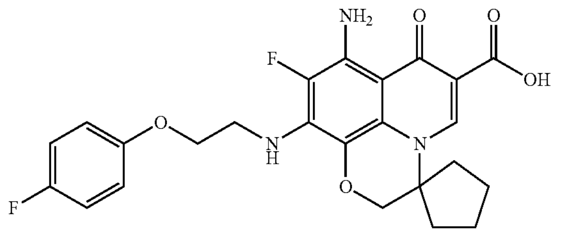 [SMILES: Nc1c(F)c(NCCOc2ccc(F)cc2)c2c3c1c(=O)c(C(=O)O)cn3C1(CCCC1)CO2]

8-amino-9-fluoro-10-(2-(4-fluorophenoxy)ethylamino)-7-oxo-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 472 ($M^{+}$+1). (Calcd. For $C_{24}H_{23}F_2N_3O_5$, 471.16).

Example 10

8-amino-10-(2-(4-chloro-3-methylphenoxy)ethylamino)-9-fluoro-7-oxo-2,7-dihydrospiro[[1,4]oxazino[2,3,4-ij]quinoline-3,1'-cyclopentane]-6-carboxylic Acid

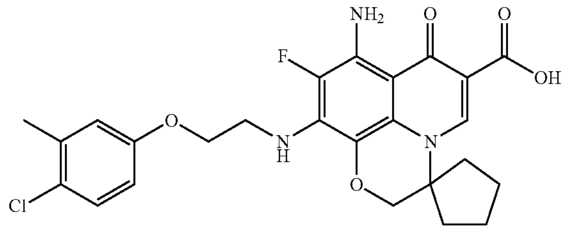 [SMILES: Cc1cc(OCCNc2c(F)c(N)c3c(=O)c(C(=O)O)cn4c3c2OCC42CCCC2)ccc1Cl]

8-amino-10-(2-(4-chloro-3-methylphenoxy)ethylamino)-9-fluoro-7-oxo-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 502 ($M^{+}$+1). (Calcd. For $C_{25}H_{25}ClFN_3O_5$, 501.15).

Example 11

10-(2-(1H-indol-3-ylthio)ethylamino)-8-amino-9-fluoro-7-oxo-2,7-dihydrospiro[[1,4]oxazino[2,3,4-ij]quinoline-3,1'-cyclopentane]-6-carboxylic Acid

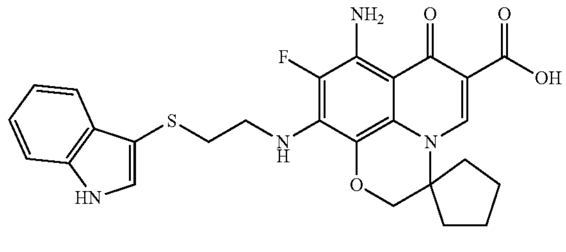 [SMILES: Nc1c(F)c(NCCSc2c[nH]c3ccccc23)c2c3c1c(=O)c(C(=O)O)cn3C1(CCCC1)CO2]

10-(2-(1H-indol-3-ylthio)ethylamino)-8-amino-9-fluoro-7-oxo-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3Y-cyclopentane]-6-carboxylic acid using synthetic procedures similar to those described in the examples above. MS (EP) m/z: 509 ($M^{+}$+1). (Calcd. For $C_{26}H_{25}FN_4O_4S$, 508.16).

Example 12

8-amino-10-(2-(4-chlorophenoxy)ethylamino)-9-fluoro-7-oxo-2,7-dihydrospiro[[1,4]oxazino[2,3,4-ij]quinoline-3,1'-cyclopentane]-6-carboxylic Acid

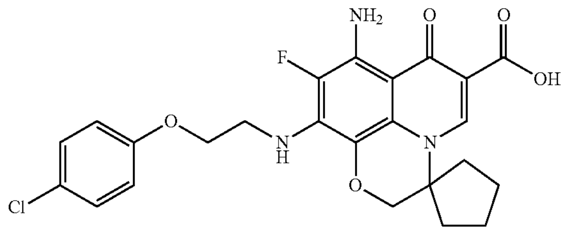 [SMILES: Nc1c(F)c(NCCOc2ccc(Cl)cc2)c2c3c1c(=O)c(C(=O)O)cn3C1(CCCC1)CO2]

8-amino-10-(2-(4-chlorophenoxy)ethylamino)-9-fluoro-7-oxo-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 487.9 ($M^{+}$+1). (Calcd. For $C_{24}H_{23}ClFN_3O_5$, 487.13).

Example 13

8-amino-10-(2-(2,4-dichlorophenoxy)ethylamino)-9-fluoro-7-oxo-2,7-dihydrospiro[[1,4]oxazino[2,3,4-ij]quinoline-3,1'-cyclopentane]-6-carboxylic Acid

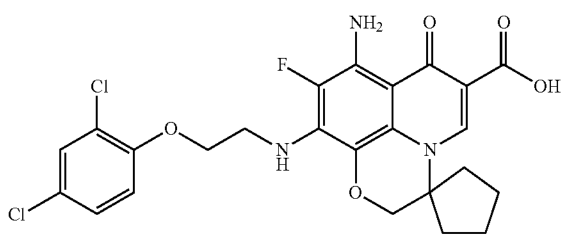 [SMILES: Nc1c(F)c(NCCOc2ccc(Cl)cc2Cl)c2c3c1c(=O)c(C(=O)O)cn3C1(CCCC1)CO2]

8-amino-10-(2-(2,4-dichlorophenoxy)ethylamino)-9-fluoro-7-oxo-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 521.9 ($M^{+}$+1). (Calcd. For $C_{24}H_{22}Cl_2FN_3O_5$, 521.09).

Example 14

8-amino-10-(3-(3,4-dimethoxyphenyl)propylamino)-9-fluoro-oxo-2,7-dihydrospiro[[1,4]oxazino[2,3,4-ij]quinoline-3,1'-cyclopentane]-6-carboxylic Acid

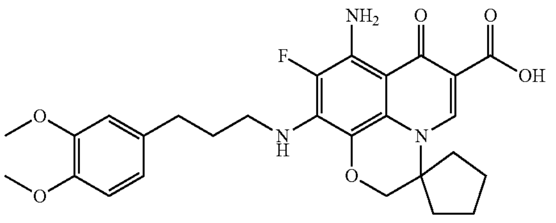 [SMILES: COc1ccc(CCCNc2c(F)c(N)c3c(=O)c(C(=O)O)cn4c3c2OCC42CCCC2)cc1OC]

8-amino-10-(3-(3,4-dimethoxyphenyl)propylamino)-9-fluoro-7-oxo-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 512 ($M^{+}$+1). (Calcd. For $C_{27}H_{30}FN_3O_6$, 511.21).

Example 15

8-amino-10-(2-(2,6-dimethylquinolin-4-ylamino)-ethylamino)-9-fluoro-7-oxo-2,7-dihydrospiro[[1,4]oxazino[2,3,4-ij]quinoline-3,1'-cyclopentane]-6-carboxylic Acid

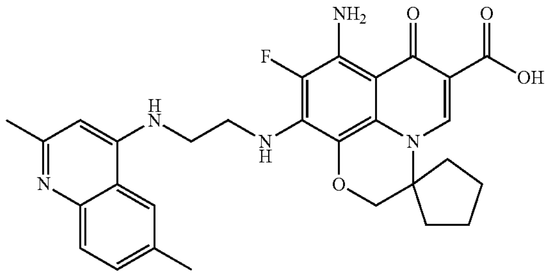 [SMILES: Cc1ccc2nc(C)cc(NCCNc3c(F)c(N)c4c(=O)c(C(=O)O)cn5c4c3OCC53CCCC3)c2c1]

8-amino-10-(2-(2,6-dimethylquinolin-4-ylamino)ethylamino)-9-fluoro-7-oxo-2,7-dihydrospiroa-1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 532 ($M^{+}$+1). (Calcd. For $C_{29}H_{30}FN_5O_4$, 531.23).

Example 16

8-amino-9-fluoro-10-(2-(3-methyl-1H-1,2,4-triazol-5-ylthio)ethylamino)-7-oxo-2,7-dihydrospiro[[1,4]oxazino[2,3,4-ij]quinoline-3,1'-cyclopentane]-6-carboxylic Acid

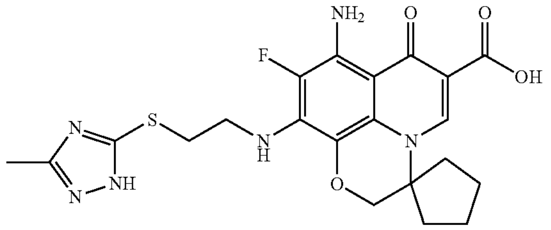 [SMILES: Cc1n[nH]c(SCCNc2c(F)c(N)c3c(=O)c(C(=O)O)cn4c3c2OCC42CCCC2)n1]

8-amino-9-fluoro-10-(2-(3-methyl-1H-1,2,4-triazol-5-ylthio)ethylamino)-7-oxo-2,7-diydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 474.9 ($M^{+}$+1). (Calcd. For $C_{21}H_{23}FN_6O_4S$, 474.15).

Example 17

8-amino-10-(2-(4-cyclohexylphenoxy)ethylamino)-9-fluoro-7-oxo-2,7-dihydrospiro[[1,4]oxazino[2,3,4-ij]quinoline-3,1'-cyclopentane]-6-carboxylic Acid

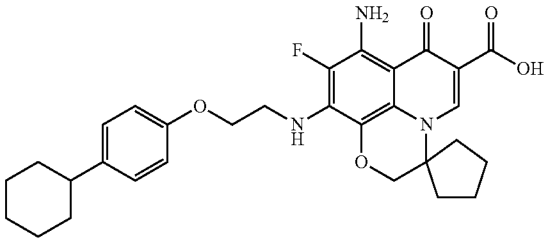 [SMILES: Nc1c(F)c(NCCOc2ccc(C3CCCCC3)cc2)c2c3c1c(=O)c(C(=O)O)cn3C1(CCCC1)CO2]

8-amino-10-(2-(4-cyclohexylphenoxy)ethylamino)-9-fluoro-7-oxo-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 536 ($M^{+}$+1). (Calcd. For $C_{30}H_{34}FN_3O_5$, 535.25).

Example 18

8-amino-9-fluoro-10-(2-(1-methyl-1H-imidazol-2-ylthio)-ethylamino)-7-oxo-2,7-dihydrospiro[[1,4]oxazino[2,3,4-ij]quinoline-3,1'-cyclopentane]-6-carboxylic Acid

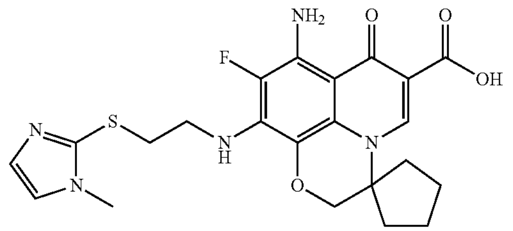 [SMILES: Cn1ccnc1SCCNc1c(F)c(N)c2c(=O)c(C(=O)O)cn3c2c1OCC31CCCC1]

8-amino-9-fluoro-10-(2-(1-methyl-1H-imidazol-2-ylthio)ethylamino)-7-oxo-2,7-dihydospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 474 ($M^+$+1). (Calcd. For $C_{22}H_{24}FN_5O_4S$, 473.15).

Example 19

8-amino-9-fluoro-7-oxo-10-(2-(piperidin-1-ylsulfonyl)-ethylamino)-2,7-dihydrospiro [[1,4]oxazino[2,3,4-ij]quinoline-3,1'-cyclopentane]-6-carboxylic Acid

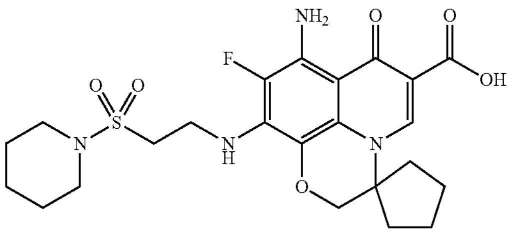 [SMILES: Nc1c(F)c(NCCS(=O)(=O)N2CCCCC2)c2c3c1c(=O)c(C(=O)O)cn3C1(CCCC1)CO2]

8-amino-9-fluoro-7-oxo-10-(2-(piperidin-1-ylsulfonyl)ethylamino)-2,7-dihydrospiro[[1, 4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 509 ($M^+$+1). (Calcd. For $C_{23}H_{29}FN_4O_6S$, 508.18).

Example 20

8-amino-10-(2-(1,1-dioxo-1H-1λ-6-benzo[d]isothiazol-3-ylamino)ethylamino)-9-fluoro-7-oxo-2,7-dihydrospiro[[1,4]oxazino[2,3,4-ij]quinoline-3,1'-cyclopentane]-6-carboxylic Acid

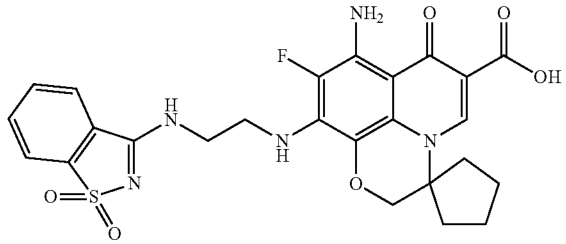 [SMILES: Nc1c(F)c(NCCNC2=NS(=O)(=O)c3ccccc32)c2c3c1c(=O)c(C(=O)O)cn3C1(CCCC1)CO2]

8-amino-10-(2-(1,1-dioxo-1H-1λ-6-benzo[d]isothiazol-3-ylamino)ethylamino)-9-fluoro-7-oxo-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]-oxazino[2,3,4-ij]-quinoline-3,1'-cyclopentane]-6-carboxylic acid using synthetic procedures similar to those described in the examples above. MS (EP) m/z: 541.9 ($M^+$+1). (Calcd. For $C_{25}H_{24}FN_5O_6S$, 541.14).

Example 21

8-amino-9-fluoro-7-oxo-10-(2-(1-phenyl-1H-tetrazol-5-ylthio)ethylamino)-2,7-dihydrospiro[[1,4]oxazino[2,3,4-ij]quinoline-3,1'-cyclopentane]-6-carboxylic Acid

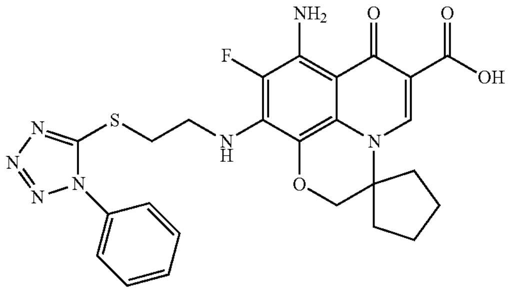 [SMILES: Nc1c(F)c(NCCSc2nnnn2-c2ccccc2)c2c3c1c(=O)c(C(=O)O)cn3C1(CCCC1)CO2]

8-amino-9-fluoro-7-oxo-10-(2-(1-phenyl-1H-tetrazol-5-ylthio)ethylamino)-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 538 ($M^+$+1). (Calcd. For $C_{25}H_{24}FN_7O_4S$, 537.16).

Example 22

10-(3-(1H-benzo[d]imidazol-1-yl)-2-hydroxypropylamino)-8-amino-9-fluoro-7-oxo-2,7-dihydrospiro[[1,4]oxazino[2,3,4-ij]quinoline-3,1'-cyclopentane]-6-carboxylic Acid

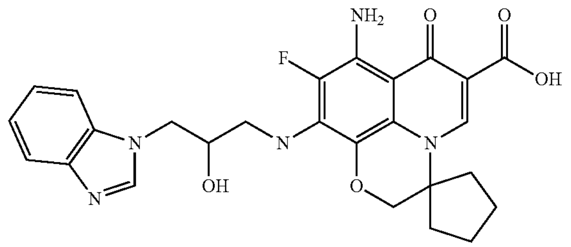 [SMILES: Nc1c(F)c(NCC(O)Cn2cnc3ccccc32)c2c3c1c(=O)c(C(=O)O)cn3C1(CCCC1)CO2]

10-(3-(1H-benzo[d]imidazol-1-yl)-2-hydroxypropylamino)-8-amino-9-fluoro-7-oxo-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro-[[1,4]oxazino-[2,3,4-ij]quinoline-3,1'-cyclopentane]-6-carboxylic acid using synthetic procedures similar to those described in the examples above. MS (EP) m/z: 508.0 ($M^{+}$+1). (Calcd. for $C_{26}H_{26}FN_5O_5$, 507.19).

Example 23

8-amino-10-(3-(ethyl(phenyl)amino)propylamino)-9-fluoro-7-oxo-2,7-dihydrospiro[[1,4]oxazino[2,3,4-ij]quinoline-3,1'-cyclopentane]-6-carboxylic Acid

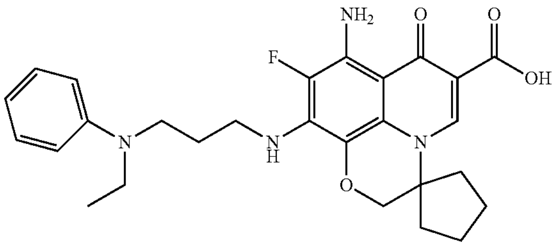 [SMILES: CCN(CCCNc1c(F)c(N)c2c(=O)c(C(=O)O)cn3c2c1OCC31CCCC1)c1ccccc1]

8-amino-10-(3-(ethyl(phenyl)amino)propylamino)-9-fluoro-7-oxo-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 495 ($M^{+}$+1). (Calcd. For $C_{27}H_{31}FN_4O_4$, 494.23).

Example 24

8-amino-9-fluoro-10-(2-(indolin-1-yl)ethylamino)-7-oxo-2,7-dihydrospiro[[1,4]oxazino[2,3,4-ij]quinoline-3,1'-cyclopentane]-6-carboxylic Acid

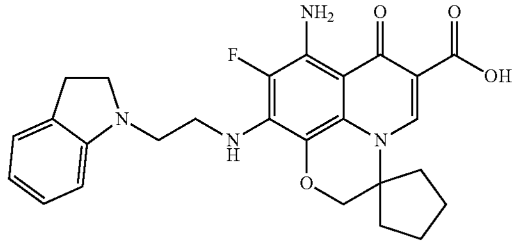 [SMILES: Nc1c(F)c(NCCN2CCc3ccccc32)c2c3c1c(=O)c(C(=O)O)cn3C1(CCCC1)CO2]

8-amino-9-fluoro-10-(2-(indolin-1-yl)ethylamino)-7-oxo-2,7-dihydrospiro[[1,4]oxazino[2,3,4-ef]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 479 ($M^{+}$+1). (Calcd. For $C_{26}H_{27}FN_4O_4$, 478.20).

Example 25

8-amino-9-fluoro-7-oxo-10-(2-(p-tolyloxy)ethylamino)-2,7-dihydrospiro[[1,4]oxazino[2,3,4-ij]-3,1'-cyclopentane]-6-carboxylic Acid

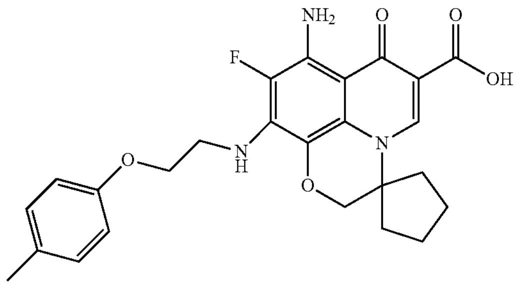 [SMILES: Cc1ccc(OCCNc2c(F)c(N)c3c(=O)c(C(=O)O)cn4c3c2OCC42CCCC2)cc1]

8-amino-9-fluoro-7-oxo-10-(2-(p-tolyloxy)ethylamino)-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 468 ($M^{+}$+1). (Calcd. For $C_{25}H_{26}FN_3O_5$, 467.19).

Example 26

8-amino-9-fluoro-7-oxo-10-(3-(pyridin-2-yl)propylamino)-2,7-dihydrospiro[[1,4]oxazino[2,3,4-ij]quinoline-3,1'-cyclopentane]-6-carboxylic Acid

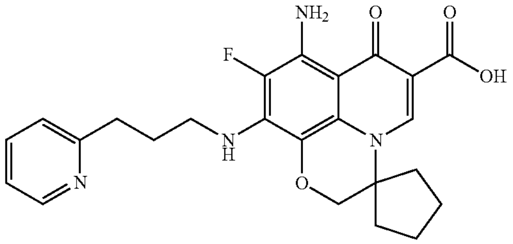 [SMILES: Nc1c(F)c(NCCCc2ccccn2)c2c3c1c(=O)c(C(=O)O)cn3C1(CCCC1)CO2]

8-amino-9-fluoro-7-oxo-10-(3-(pyridin-2-yl)propylamino)-2,7-dihydrospiro[[1,4]oxazin o[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 453 ($M^{+}$+1). (Calcd. For $C_{24}H_{25}FN_4O_4$, 452.19).

Example 27

8-amino-10-(3-(2-chlorophenyl)propylamino)-9-fluoro-7-oxo-2,7-dihydrospiro[[1,4]oxazino[2,3,4-#]quinoline-3,1'-cyclopentane]-6-carboxylic Acid

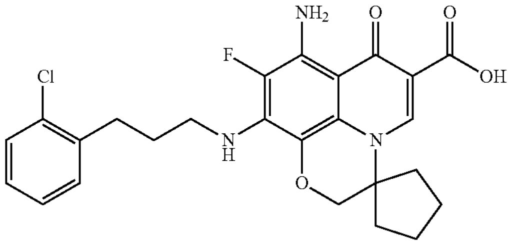 [SMILES: Nc1c(F)c(NCCCc2ccccc2Cl)c2c3c1c(=O)c(C(=O)O)cn3C1(CCCC1)CO2]

8-amino-10-(3-(2-chlorophenyl)propylamino)-9-fluoro-7-oxo-2,7-dihydrospiro [[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 486 ($M^{+}$+1). (Calcd. For $C_{25}H_{25}ClFN_3O_4$, 485.15).

Example 28

8-amino-9-fluoro-10-(3-(4-methoxyphenyl)propylamino)-7-oxo-2,7-dihydrospiro[[1,4]oxazino[2,3,4-ij]quinoline-3,1'-cyclopentane]-6-carboxylic Acid

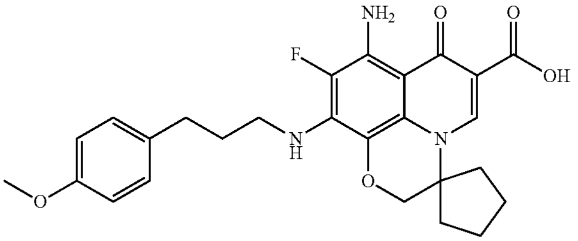 [SMILES: COc1ccc(CCCNc2c(F)c(N)c3c(=O)c(C(=O)O)cn4c3c2OCC42CCCC2)cc1]

8-amino-9-fluoro-10-(3-(4-methoxyphenyl)propylamino)-7-oxo-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 482 ($M^{+}$+1). (Calcd. For $C_{26}H_{28}FN_3O_5$, 481.20).

Example 29

8-amino-10-(3-(3,4-diethoxyphenyl)propylamino)-9-fluoro-7-oxo-2,7-dihydrospiro[[1,4]oxazino[2,3,4-ij]quinoline-3,1'-cyclopentane]-6-carboxylic Acid

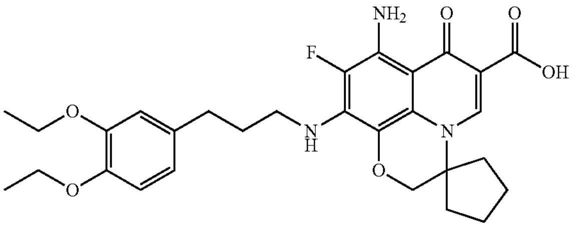 [SMILES: CCOc1ccc(CCCNc2c(F)c(N)c3c(=O)c(C(=O)O)cn4c3c2OCC42CCCC2)cc1OCC]

8-amino-10-(3-(3,4-diethoxyphenyl)propylamino)-9-fluoro-7-oxo-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 540 ($M^{+}$+1). (Calcd. For $C_{29}H_{34}FN_3O_6$, 539.24).

Example 30

8-amino-9-fluoro-10-(2-(2-methylquinolin-4-ylamino)-ethylamino)-7-oxo-2,7-dihydrospiro[[1,4]oxazino[2,3,4-ij]quinoline-3,1'-cyclopentane]-6-carboxylic Acid

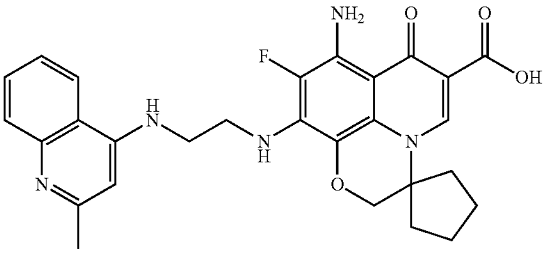 [SMILES: Cc1cc(NCCNc2c(F)c(N)c3c(=O)c(C(=O)O)cn4c3c2OCC42CCCC2)c2ccccc2n1]

8-amino-9-fluoro-10-(2-(2-methylquinolin-4-ylamino)ethylamino)-7-oxo-2,7-dihydrosiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 518 ($M^{+}$+1). (Calcd. For $C_{28}H_{28}FN_5O_4$, 517.21).

Example 31

8-amino-10-(4-(2-chlorophenyl)butan-2-ylamino)-9-fluoro-7-oxo-2,7-dihydrospiro[[1,4]oxazino[2,3,4-ij]quinoline-3,1'-cyclopentane]-6-carboxylic Acid

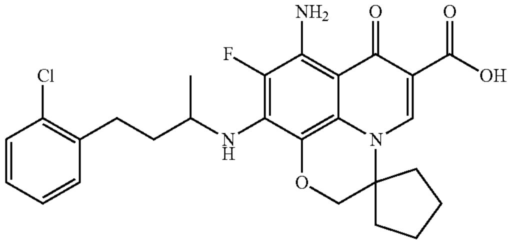 [SMILES: CC(CCc1ccccc1Cl)Nc1c(F)c(N)c2c(=O)c(C(=O)O)cn3c2c1OCC31CCCC1]

8-amino-10-(4-(2-chlorophenyl)butan-2-ylamino)-9-fluoro-7-oxo-2,7-dihydrospiro-[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 500 ($M^{+}$+1). (Calcd. For $C_{26}H_{27}ClFN_3O_4$, 499.17).

Example 32

8-amino-9-fluoro-7-oxo-10-(3-(1,3,5-trimethyl-1H-pyrazol-4-yl)propylamino)-2,7-dihydrospiro[[1,4]oxazino[2,3,4-1H]quinoline-3,1'-cyclopentane]-6-carboxylic Acid

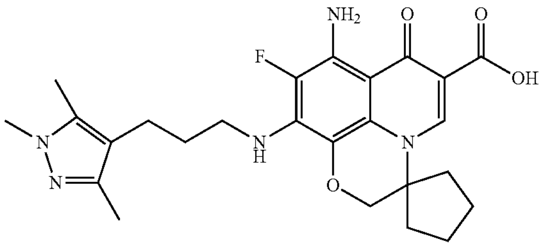 [SMILES: Cc1nn(C)c(C)c1CCCNc1c(F)c(N)c2c(=O)c(C(=O)O)cn3c2c1OCC31CCCC1]

8-amino-9-fluoro-7-oxo-10-(3-(1,3,5-trimethyl-1H-pyrazol-4-yl)propylamino)-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 484 ($M^{+}$+1). (Calcd. For $C_{25}H_{30}FN_5O_4$, 483.23).

Example 33

8-amino-9-fluoro-10-(3-(3-methoxyphenyl)propylamino)-7-oxo-2,7-dihydrospiro[[1,4]oxazino[2,3,4-ij]quinoline-3,1'-cyclopentane]-6-carboxylic Acid

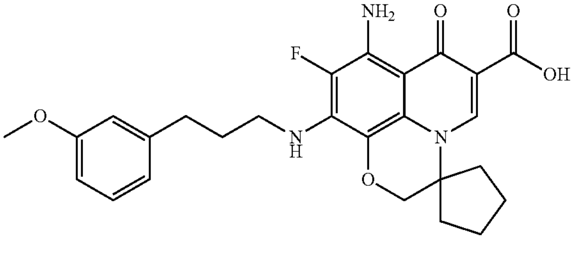 [SMILES: COc1cccc(CCCNc2c(F)c(N)c3c(=O)c(C(=O)O)cn4c3c2OCC42CCCC2)c1]

8-amino-9-fluoro-10-(3-(3-methoxyphenyl)propylamino)-7-oxo-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 482 ($M^{+}$+1). (Calcd. For $C_{26}H_{28}FN_3O_5$, 481.20).

Example 34

8-amino-9-fluoro-10-(2-(4-methoxyphenoxy)ethylamino)-7-oxo-2,7-dihydrospiro[[1,4]oxazino[2,3,4-ij]quinoline-3,1'-cyclopentane]-6-carboxylic Acid

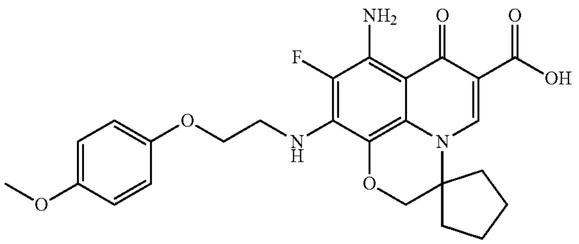

8-amino-9-fluoro-10-(2-(4-methoxyphenoxy)ethylamino)-7-oxo-2,7-dihydrospiro[[1,4]oxazino[2,3,4-ij]quinoline-3,1'-cyclopentane]-6-carboxylic acid was prepared from 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above. MS (EP) m/z: 484 ($M^+$+1). (Calcd. For $C_{25}H_{26}FN_3O_6$, 483.18).

Example 35

8-amino-9-fluoro-10-(3-(pyridin-2-yl)propylamino)-6-1H-tetrazol-5-yl)spiro-[[1,4]oxazino[2,3,4-ij]quinoline-3,1'-cyclopentan]-7(2H)-one hydrochloride 35A) Preparation of 9,10-difluoro-8-nitro-7-oxo-2,7-dihydrospiro [[1,4]oxazino[2,3,4-ij]quinoline-3,1'-cyclopentane]-6-carboxamide

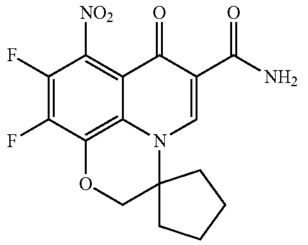 [SMILES: NC(=O)c1cn2c3c(c(F)c(F)c([N+](=O)[O-])c3c1=O)OCC21CCCC1]

9,10-difluoro-8-nitro-7-oxo-2,7-dihydrospiro[[1,4]oxazino[2,3,4-ij]quinoline-3,1'-cyclopentane]-6-carboxylic acid (3 g, 8.2 mmol) was suspended in $SOCl_2$ (25 ml) and refluxed for 3 h until a clear solution was obtained. Upon completion of the reaction, $SOCl_2$ was removed under vacuo. The remaining solid was diluted with dioxane and cooled in an ice bath. A solution of concentrated $NH_4OH$ was added carefully under vigorous stirring. A precipitate formed that was collected by filtration and washed with water. The solid was dried under vacuo to give 2.2 g (75% yield) of the title compound. This compound was used in the next step without further purification 35B) Preparation of 8-amino-9,10-difluoro-7-oxo-2,7-dihydrospiro[[1,4]oxazino[2,3,4-ij]quinoline-3,1'-cyclopentane]-6-carboxamide

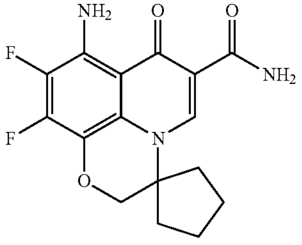

To a suspension of 9,10-difluoro-8-nitro-7-oxo-2,7-dihydrospiro[[1,4]oxazino[2,3,4-ij]quinoline-3,1'-cyclopentane]-6-carboxamide (1 g, 2.7 mmol) in a mixture of water/methanol (1:1 v/v, 30 mL) was added sodium hydrosulfite ($Na_2S_2O_4$, 3.75 g, 22 mmol). The suspension was refluxed for 5 h until all starting material had disappeared. Upon completion, the reaction mixture was cooled to room temperature and 50 ml of water were added. After 20 minutes, a light yellow solid was collected by filtration and washed with water. The solid was dried under vacuo to give 660 mg (73% yield) of the title compound that was used without further purification in the next step.

35C) Preparation of 8-amino-9,10-difluoro-7-oxo-2,7-dihydrospiro[1,4]oxazino[2,3,4-ij]quinoline-3,1'-cyclopentane]-6-carbonitrile

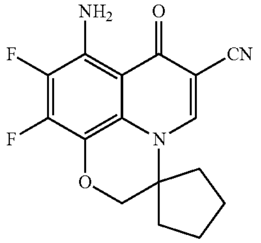 [SMILES: N#Cc1cn2c3c(c(F)c(F)c(N)c3c1=O)OCC21CCCC1]

To a cooled solution of 8-amino-9,10-difluoro-7-oxo-2,7-dihydrospiro[[1,4]oxazino 2,3,4-ij]-quinoline-3,1'-cyclopentane]-6-carboxamide (1 g, 2.9 mmol) and triethylamine (2 mL, 10 mmol.) in DCM (20 ml) was added $POCl_3$ (780 μl, 8.7 mmol.) dropwise and stirred at 0° C. for an additional 5 h. A dark colored mixture formed. Upon completion of the reaction, DCM was removed under vacuo and the residue was washed several times with water. The solid was dried under vacuum to give 540 mg (58.7% yield) of the title compound. This product is not very soluble except in DMF or DMSO and is used in the next step without further purification.

35D) Preparation of 8-amino-9,10-difluoro-6-(1H-tetrazol-5-yl)spiro[[1,4]oxazino[2,3,4-ij]quinoline-3,1'-cyclopentan]-7(2H)-one

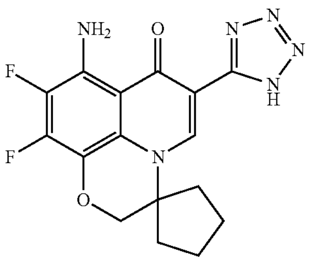 [SMILES: Nc1c(F)c(F)c2c3c1c(=O)c(-c1nnn[nH]1)cn3C1(CCCC1)CO2]

To a mixture of nitrile 8-amino-9,10-difluoro-7-oxo-2,7-dihydrospiro[[1,4]oxazino[2,3,4-ij]quinoline-3,1'-cyclopentane]-6-carbonitrile (180 mg, 0.56 mmol) in isopropanol and water (1:1 v/v, 15 ml) were added 80 mg of sodium azide (1.14 mmole) and 170 mg of zinc chloride (1.14 mmole). The mixture was heated to 110° C. for 18 h. The precipitates were collected by filtration and washed with water. The solid was dried under vacuum to give 135 mg (67% yield) of the title compound. This compound was used without further purification in the next step.

35E) Preparation of 8-amino-9-fluoro-10-(3-(pyridin-2-yl)-propylamino)-6-1H-tetrazol-5-yl)spiro[[1,4]oxazino[2,3,4-ij]quinoline-3,1'-cyclopentan]-7(2H)-one Hydrochloride

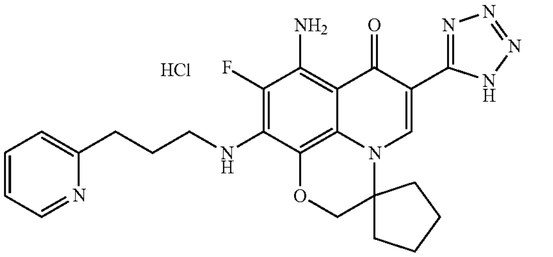 [SMILES: Nc1c(F)c(NCCCc2ccccn2)c2c3c1c(=O)c(-c1nnn[nH]1)cn3C1(CCCC1)CO2 ; Cl]

MS (EP) m/z: 477.5 (M+1). (Calcd. for $C_{24}H_{25}FN_8O_2$, 476.51).

Compounds 36-42 may be prepared from 8-amino-9,10-difluoro-7-oxo-2,7-dihydrospiro[1,4]oxazino[2,3,4-ij]quinoline-3,1'-cyclopentane]-6-carbonitrile or 8-amino-9,10-difluoro-7-oxo-2,7-dihydrospiro[[1,4]oxazino[2,3,4-ij]-quinoline-3,1'-cyclopentane]-6-carboxylic acid using synthetic procedures similar to those described in the examples above.

Example 36

8-amino-9-fluoro-7-oxo-10-(3-(pyridin-2-yl)propylamino)-2,7-dihydrospiro[[1,4]oxazino[2,3,4-#]quinoline-3,1'-cyclopentane]-6-carbonitrile Hydrochloride

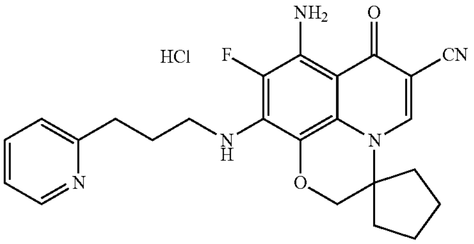 [SMILES: N#Cc1cn2c3c(c(NCCCc4ccccn4)c(F)c(N)c3c1=O)OCC21CCCC1 ; Cl]

MS (EP) m/z: 434.4 (M+1). (Calcd. for $C_{24}H_{24}FN_5O_2$, 433.48).

Example 37

Preparation of 10-(3-(1H-imidazol-1-yl)propylamino)-8-amino-9-fluoro-7-oxo-2,7-dihydrospiro[[1,4]oxazino[2,3,4-ij]quinoline-3,1'-cyclopentane]-6-carbonitrile Hydrochloride

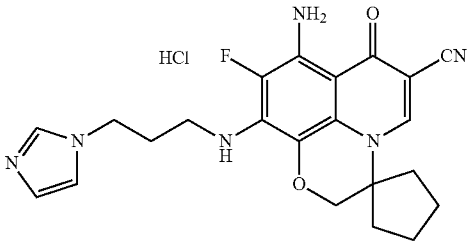 [SMILES: N#Cc1cn2c3c(c(NCCCn4ccnc4)c(F)c(N)c3c1=O)OCC21CCCC1 ; Cl]

MS (EP) m/z: 423.4 (M+1). (Calcd. for $C_{22}H_{23}FN_6O_2$, 422.46).

Example 38

8-amino-9-fluoro-7-oxo-10-(3-(1,3,5-trimethyl-1H-pyrazol-4-yl)propylamino)-2,7-dihydrospiro[[1,4]oxazino[2,3,4-ij]quinoline-3,1'-cyclopentane]-6-carbonitrile Hydrochloride

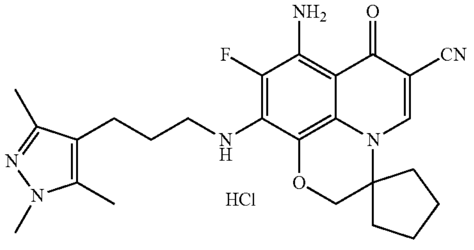 [SMILES: Cc1nn(C)c(C)c1CCCNc1c(F)c(N)c2c(=O)c(C#N)cn3c2c1OCC31CCCC1 ; Cl]

MS (EP) m/z: 465.5 (M+1). (Calcd. for $C_{25}H_{29}FN_6O_2$, 464.54).

Example 39

8-amino-9-fluoro-10-(3-(4-fluorophenyl)-3-(4-methoxyphenyl)propylamino)-7-oxo-2,7-dihydrospiro[[1,4]oxazino[2,3,4-ij]quin oline-3,1'-cyclopentane]-6-carboxylic Acid

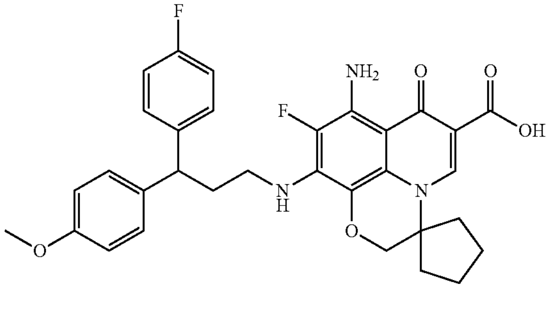 [SMILES: COc1ccc(C(CCNc2c(F)c(N)c3c(=O)c(C(=O)O)cn4c3c2OCC42CCCC2)c2ccc(F)cc2)cc1]

MS (EP) m/z: 576.6 (M+1). (Calcd. for $C_{32}H_{31}F_2N_3O_5$, 575.6).

Example 40

8-amino-10-(3-(4-chlorophenyl)propylamino)-9-fluoro-7-oxo-2,7-dihydrospiro[[1,4]oxazino[2,3,4-ij]quinoline-3,1'-cyclopentane]-6-carboxylic Acid

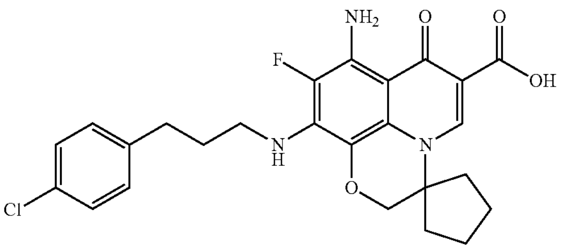

MS (EP) m/z: 486.9 (M+1). (Calcd. for $C_{25}H_{25}ClFN_3O_4$, 485.94).

Example 41

8-amino-10-(3-(3,5-dimethyl-1H-pyrazol-1-yl)propylamino)-9-fluoro-7-oxo-2,7-dihydrospiro[[1,4]oxazino[2,3,4-ij]quinoline-3,1'-cyclopentane]-6-carboxylic Acid

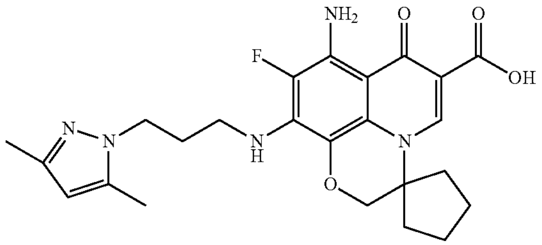 [SMILES: Cc1cc(C)n(CCCNc2c(F)c(N)c3c(=O)c(C(=O)O)cn4c3c2OCC42CCCC2)n1]

MS (EP) m/z: 470.5 (M+1). (Calcd. for $C_{24}H_{28}FN_5O_4$, 469.51).

Example 42

8-amino-9-fluoro-10-(3-(5-methyl-1H-pyrazol-4-yl)propylamino)-7-oxo-2,7-dihydrospiro[[1,4]oxazino[2,3,4-ij]quinoline-3,1'-cyclopentane]-6-carboxylic Acid

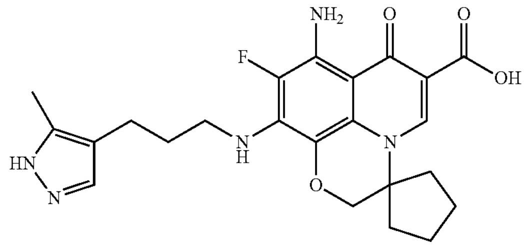 [SMILES: Cc1[nH]ncc1CCCNc1c(F)c(N)c2c(=O)c(C(=O)O)cn3c2c1OCC31CCCC1]

MS (EP) m/z: 456 (M+1). (Calcd. for $C_{23}H_{26}FN_5O_4$, 455.48).

Example 43

8'-amino-9'-fluoro-7'-oxo-10'-[3-(1-imidazolyl)propyl]spiro[cyclopentane-1,3'-(2'H)-[7H]pyrido[1,2,3-de][1,4]benzoxazine]-6'-carboximidamide 43A) Preparation of 8'-amino-9',10'-difluoro-7'-oxospiro-[cyclopentane-1,3'(2'H)-[7H]pyrido[1,2,3-de][1,4]benzoxazine]-6'-carboximidamide

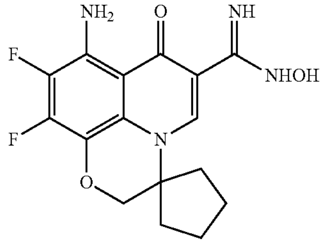

To a solution of 8-amino-9,10-difluoro-7-oxo-2,7-dihydrospiro[1,4]oxazino-[2,3,4-ij]quinoline-3,1'-cyclopentane]-6-carbonitrile (400 mg, 1.26 mmol) in 5 ml of ethonal/dimethylformamade (50:50, v:v) was added ammonium hydroxide (260 mg, 3.78 mmol) and potassium carbonate (521 mg, 3.78 mmol). The reaction mixture was heated to reflux for 3 h and then cooled down to room temperature. Undissolved inorganic material was filtered off and the filtrate was concentrated under vacuo to yield a solid material that was resuspended in methanol (50 mL), filtered, washed with methanol and dried under vacuum to give the title compound as a yellow solid (200 mg, 45% yield). MS (EP) m/z: 351 (M+1). (Calcd. for $C_{16}H_{16}F_2N_4O_3$, 350.12).

43B) Preparation of 8'-amino-9'-fluoro-7'-oxo-10'-[3-(1-imidazolyl)-propyl]spiro[cyclopentane-1,3'(2'H)-(7H]pyrido[1,2,3-de]11,41-benzoxazine]-6'-carboximidamide

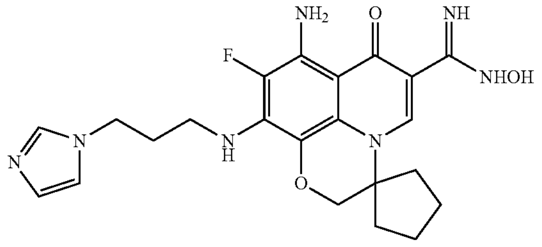

The title compound was prepared from 8'-amino-9',10'-difluoro-7'-oxospiro-[cyclopentane-1,3'(2'H)-[7H]-pyrido[1,2,3-de][1,4]benzoxazine]-6% carboximidamide according to the procedures above. MS (EP) m/z: 426.4 (M+1). (Calcd. for $C_{19}H_{20}FN_9O_2$, 425.42).

Example 44

8'-amino-9'-fluoro-7'-oxo-10'-[2-(pyridin-2-ylamino)ethylamino]spiro[cyclobutane-1,3'(2'H)-[7H]pyrido[1,2,3-de][1,4]benzoxazine]-6'-carboxylic Acid 44A) Preparation of Ethyl 3-[1-(hydroxymethyl)cyclobutylamino]-2-(2,3,4,5-tetrafluorobenzoyl)acrylate

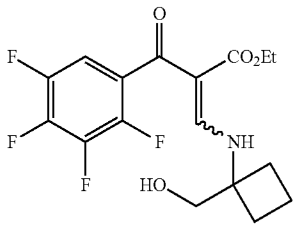 [SMILES: CCOC(=O)C(=CNC1(CO)CCC1)C(=O)c1cc(F)c(F)c(F)c1F]

A stirred solution of ethyl 3-oxo-3-(2,3,4,5-tetrafluorophenyl)propionate (2.00 g, 7.57 mmol), $Ac_2O$ (4.29 mL, 45.4 mmol) and triethyl iorthoformate (2.51 mL, 15.1 mmol) was heated at 120° C. for 3 hours. The mixture was concentrated in vacuo and dried under high vacuum. The crude product was dissolved in toluene (30 mL) and a suspension of (1-aminocyclobutyl)methanol (1.04 g, 7.57 mmol) in toluene (5 mL), triethylamine (1.06 mL, 7.57 mmol) were added under ice-cooling. The mixture was stirred for 18 h at room temperature and concentrated in vacuo to yield the crude product. The crude product was purified by column chromatography (Hexane: EtOAc 10:1→1:1) to yield the title compound (1.57 g, 55%) as a white solid. $^1$H-NMR (400 MHz, $CDCl_3$) δ 0.95-1.11 (3H, m), 1.85-1.90 (1H, m), 1.91-2.07 (2H, m), 2.17-2.26 (2H, m), 2.27-2.36 (2H, m), 3.80-3.83 (2H, m), 4.00-4.10 (2H, m), 6.95-7.13 (1H, m), 8.17-8.22 (1H, m), 9.87-11.36 (1H, m). ESIMS (+): 376 $[M+H]^+$.

44B) Preparation of Ethyl 9',10'-difluoro-7'-oxospiro[cyclobutane-1,3'(2'H)-[7H]pyrido[1,2,3-de][1,4]benzoxazine]-6'-carboxylate

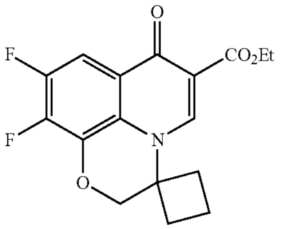 [SMILES: CCOC(=O)c1cn2c3c(c(F)c(F)cc3c1=O)OCC21CCC1]

A solution of ethyl 3-[1-(hydroxymethyl)cyclobutylamino]-2-(2,3,4,5-tetrafluorobenzoyl)acrylate (1.52 g, 4.05 mmol) in DMF (10 mL) was added to an ice-cooled suspension of 60% NaH in oil (356 mg, 8.91 mmol) in DMF (10 mL), under argon atmosphere. The reaction mixture was stirred for 4 hours and poured into ice-water. The product was extracted with AcOEt, dried over $MgSO_4$ and the crude product was purified by column chromatography (Hexane: EtOAc 2:1→AcOEt) to yield the title compound (604 mg, 44%) as a white solid. Mp 255-256° C. $^1$H-NMR (400 MHz, DMSO-$d_6$) δ 1.29 (3H, t, J=7.3 Hz), 1.91-2.07 (2H, m), 2.16-2.22 (2H, m), 2.65-2.76 (2H, m), 4.24 (2H, q, J=7.3 Hz), 4.62 (2H, s), 7.62 (1H, dd, J=10.4, 7.9 Hz), 8.80 (1H, s). ESIMS (+): 336 $[M+H]^+$.

44C) Preparation of Ethyl 9',10'-difluoro-8'-nitro-7'-oxospiro-[cyclobutane-1,3'(2'H)-[7H]pyrido[1,2,3-de][1,4]benzoxazine]-6'-carboxylate

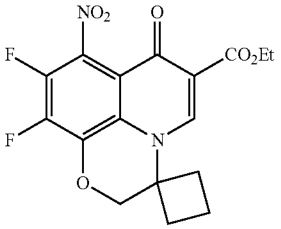 [SMILES: CCOC(=O)c1cn2c3c(c(F)c(F)c([N+](=O)[O-])c3c1=O)OCC21CCC1]

A solution of ethyl 9',10'-difluoro-7'-oxospiro[cyclobutane-1,3'(2'H)-[7H]pyrido[1,2,3-de][1,4]benzoxazine]-6'-carboxylate (580 mg, 1.73 mmol) in concentrated $H_2SO_4$ (7 mL) was treated portion wise at 0° C. with solid $KNO_3$ (245 mg, 2.42 mmol). The reaction mixture was stirred for 1 hour at 0° C. and poured into ice-water. The resulting precipitate was collected by filtration, washed with water and dried to yield the title compound (600 mg, 91%) as a pale yellow solid. $^1$H-NMR (400 MHz, DMSO-$d_6$) δ 1.30 (3H, t, J=7.3 Hz), 1.93-2.09 (2H, m), 2.16-2.25 (2H, m), 2.73-2.80 (2H, m), 4.26 (2H, q, J=7.3 Hz), 4.69 (2H, s), 8.87 (1H, s). ESIMS (+): 381 $[M+H]^+$.

44D) Preparation of Ethyl 8'-amino-9',10'-difluoro-7'-oxospiro-[cyclobutane-1,3'(2'H)-[7H]pyrido[1,2,3-de][1,4]benzoxazine]-6'-carboxylate

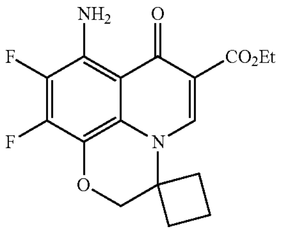

A solution of ethyl 9',10'-difluoro-8'-nitro-7'-oxospiro[cyclobutane-1,3'(2'H)-[7H]pyrido[1,2,3-de][1,4]benzoxazine]-6'-carboxylate (580 mg, 1.53 mmol) in DMF (30 mL) was treated with hydrogen under atmospheric pressure over 10% Pd/C (60 mg) at 50° C. for 3 hours. The catalyst was removed by filtration with Celite and the filtrate was poured into ice-water. The resulting precipitate was stirred for 1 hour and collected by filtration, washed with water and dried to yield the title compound (468 mg, 88%) as a pale yellow solid. $^1$H-NMR (400 MHz, DMSO-$d_6$) δ 1.29 (3H, t, J=7.3 Hz), 1.92-2.02 (2H, m), 2.10-2.19 (2H, m), 2.61-2.69 (2H, m), 4.23 (2H, q, J=7.3 Hz), 4.39 (2H, s), 7.38 (2H, brs), 8.65 (1H, brs). ESIMS (+): 351 $[M+H]^+$.

44E) Preparation of 8'-amino-9',10'-difluoro-7'-oxospiro-[cyclobutane-1,3'(2H)-[7]pyrido[1,2,3-de][1,4]benzoxazine]-6'-carboxylic Acid

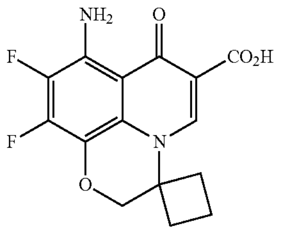 [SMILES: Nc1c(F)c(F)c2c3c1c(=O)c(C(=O)O)cn3C1(CCC1)CO2]

A solution of ethyl 8'-amino-9',10'-difluoro-7'-oxospiro[cyclobutane-1,3' (2'H)-[7H]-1]pyrido[1,2,3-de][1,4]benzoxazine]-6'-carboxylate (440 mg, 1.26 mmol) in a mixture of AcOH—$H_2O$—$H_2SO_4$ (2:1:0.3 v/v, 9.9 mL) was heated at 100° C. for 3 hours. The reaction mixture was poured into ice-water and stirred. After 30 minutes, the resulting precipitate was collected by filtration, washed with water and dried to yield the title compound (384 mg, 94%) as a yellow solid $^1$H-NMR (400 MHz, DMSO-$d_6$) δ 1.94-2.03 (2H, m), 2.14-2.20 (2H, m), 2.69-2.77 (2H, m), 4.44 (2H, s), 7.32 (2H, brs), 8.91 (1H, s), 14.67 (1H, s). ESIMS (+): 323 $[M+H]^+$.

44F) Preparation of 8'-amino-9'-fluoro-7'-oxo-10'-[2-(2-pyridylamino)ethylamino]spiro[cyclobutane-1,3'(2'H)-[7H]pyrido[1,2,3-de][1,4]benzoxazine]-6'-carboxylic Acid

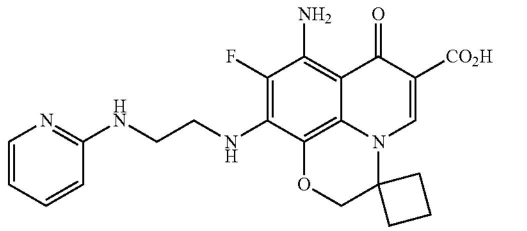 [SMILES: Nc1c(F)c(NCCNc2ccccn2)c2c3c1c(=O)c(C(=O)O)cn3C1(CCC1)CO2]

A solution of 8'-amino-9',10'-difluoro-7'-oxospiro[cyclobutane-1,3'(2H)-[7]pyrido[1,2,3-de][1,4]benzoxazine]-6'-carboxylic acid (360 mg, 1.12 mmol), N-2-pyridinyl-1,2-ethanediamine (230 mg, 1.68 mmol) and triethylamine (0.234 mL, 1.68 mmol) in DMSO (5 mL) was stirred for 3 hours at 100° C. The reaction mixture was poured into ice-water and stirred for 30 minutes. The resulting precipitate was collected by filtration, washed with water, suspended in EtOH (10 mL) and stirred at reflux for 1 hour. The suspension was cooled to room temperature, and the resulting precipitate was collected by filtration and dried to yield the title compound (459 mg, 93%) as a yellow solid. $^1$H-NMR (400 MHz, DMSO-$d_6$) δ 1.91-2.03 (2H, m), 2.08-2.17 (2H, m), 2.61-2.69 (2H, m), 3.44-3.48 (2H, m), 3.58-3.66 (2H, m), 6.35-6.40 (1H, m), 6.45-6.49 (2H, m), 6.71 (1H, t, J=5.5 Hz), 6.88 (2H, brs), 7.35 (1H, td, J=6.7, 1.8 Hz), 7.97 (1H, dd, J=4.9, 1.2 Hz), 8.71 (1H, s), 15.30 (1H, s). HRESIMS (+): 440.17267 (−0.74 mmu).

Example 45

8'-amino-9'-fluoro-7'-oxo-10'-[2-(2-pyridylamino)ethylamino)spiro[cyclobutane-1,2'(3'H)-[7H]pyrido[1,2,3-de]benzoxazepine]-6% carboxylic acid 45A) Preparation of Ethyl 3-[[1-(hydroxymethyl)cyclopentyl]-methylamino]-2-(3,4,5,6-tetrafluorobenzoyl)acrylate

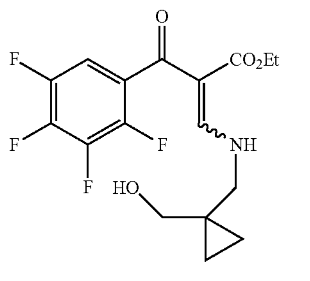 [SMILES: CCOC(=O)C(=CNCC1(CO)CC1)C(=O)c1cc(F)c(F)c(F)c1F]

A solution of ethyl 3-oxo-3-(2,3,4,5-tetrafluorophenyl)propionate (7.93 g, 30.0 mmol), $Ac_2O$ (17.0 mL, 180 mmol) and triethyl orthoformate (10.0 mL, 60.1 mmol) was heated at 120° C. for 3 hours. The mixture was concentrated in vacuo and dried under high vacuum. The crude product was dissolved in anhydrous toluene (120 mL) and [1-(aminomethyl)-cyclopropyl]]methanol (3.04 g, 30.1 mmol) was added very slowly at 0° C. The ration mixture was stirred at room temperature for 3 hours, and the solvent was removed by evaporation. The crude product was purified by column chromatography (Hexane: EtOAc 1:1) to yield the title compound (10.5 g, 94%) as a pale yellow solid. $^1$H NMR (400 MHz, $CDCl_3$) δ 0.50-0.70 (4H, m), 0.97, 1.10 (each t, J=7.3 Hz, total 3H), 1.66 (1H, t, J=4.9 Hz), 3.47 (2H, d, J=6.1 Hz), 3.56 (2H, d, J=4.9 Hz), 4.01-4.09 (2H m), 6.96-7.13 (1H, m), 8.06-8.12 (1H, m), 9.71, 11.1 (each br, total 1H). ESIMS (+): 375 [M+H].

45B) Preparation of Ethyl 10',11'-difluoro-8'-oxospiro[cyclopropane-1,3'(4'H)-[2H,8H]pyrido[1,2,3-ef][1,4]benzoxazepine]-7'-carboxylate

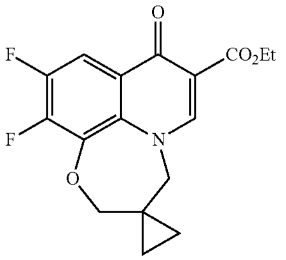 [SMILES: CCOC(=O)c1cn2c3c(c(F)c(F)cc3c1=O)OCC1(CC1)C2]

A solution of NaH (2.29 g, 57.3 mmol, 60%; in oil) in DMF (110 mL) was cooled to 0° C. and treated dropwise with Ethyl 3-[[1-(hydroxymethyl)cyclopentyl]methylamino]-2-(3,4,5,6-tetrafluorobenzoyl)aminoacrylate (9.76 g, 26.0 mmol) in DMF (15 mL). The reaction mixture was stirred at room temperature for 1 hour, and then stirred for 85° C. for 1 hour. The reaction mixture was poured into ice water and the resulting precipitate was removed by filtration and washed with water. The resulting solid was dissolved in 100 mL of EtOH—$CH_2Cl_2$ (2:1) and filtered. The filtrate was concentrated to 70 mL and the resulting precipitate was removed by filtration, washed with EtOH and dried to yield the title compound (6.73 g, 77%) as a pale yellow solid. $^1$H-NMR (400 MHz $CDCl_3$) δ 0.65 (2H, t, J=6.1 Hz), 0.82 (2H, t, J=6.1 Hz), 1.41 (3H, t, J=7.3 Hz), 4.21 (2H, s), 4.35 (2H, s), 4.39 (2H, q, J=7.3 Hz), 8.05 (1H, dd, J=10.4, 8.6 Hz), 8.25 (1H, s). ESIMS (+): 335 $[M+H]^+$.

45C) Preparation of Ethyl 9',10'-difluoro-8'-nitro-7'-oxospiro-[cyclobutane-1,2'(3'H)-[7H]pyrido[1,2,3-de][1,4]benzoxazine]-6'-carboxylate

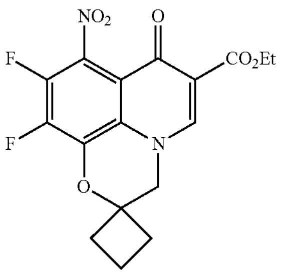 [SMILES: CCOC(=O)c1cn2c3c(c(F)c(F)c([N+](=O)[O-])c3c1=O)OC1(CCC1)C2]

Ethyl 10',11'-difluoro-8'-oxospiro[cyclobutane-1,2'(3'H)-[7H]pyrido[1,2,3-ef]-benzoxazepine]-7'-carboxylate was prepared by routine modification of the procedures shown elsewhere herein. A solution of ethyl 10',11'-difluoro-8'-oxospiro[cyclobutane-1,2'(3'H)-[7H]pyrido[1,2,3,-ef]benzoxazepine]-7'-carboxylate (1.50 g, 4.47 mmol) in concentrated $H_2SO_4$ (15 mL) was treated portionwise at 0° C. with solid $KNO_3$ (633 mg, 6.26 mmol). After stirring at 0° C. for 2 hours, the reaction mixture was poured into 100 mL of ice-water and the resulting precipitate was removed by filtration. The resulting solid was recrystallized by DMF, and washed with EtOH and dried to yield the title compound as a pale yellow solid (651 mg, 38%). $^1$H-NMR (400 MHz, DMSO-$d_6$) δ 1.27 (3H, t, J=7.3 Hz), 1.76-2.00 (2H, m), 2.15-2.25 (2H, m), 2.27-2.40 (2H, m), 4.23 (2H, q, J=7.3 Hz), 4.53 (2H, s), 8.69 (1H, s). ESIMS (+): 381 $[M+H]^+$.

45D) Preparation of Ethyl 8'-amino-9',10'-difluoro-7'-oxospiro-[cyclobutane-1,2'(3'H)-[7H]pyrido[1,2,3-de][1,4]benzoxazine]-6'-carboxylate

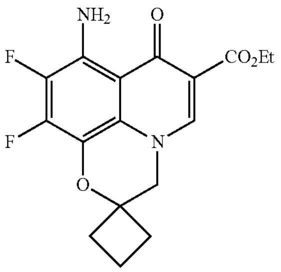 [SMILES: CCOC(=O)c1cn2c3c(c(F)c(F)c(N)c3c1=O)OC1(CCC1)C2]

A solution of ethyl 9',10'-difluoro-8'-nitro-7'-oxo-spiro[cyclobutane-1,2'(3'H)-[7H]pyrido[1,2,3-de][1,4]benzoxazine]-6'-carboxylate (450 mg, 1.15 mmol) and 10% Pd/C (40.5 mg) in DMF (20 mL) was stirred under hydrogen atmosphere(0.3 MPa) at 50° C. for 3 hours. The catalyst was removed by filtration over Celite and the filtrate was concentrated in vacuo. The resulting solid was dissolved in EtOH—$CH_2Cl_2$ (1:5) and filtered. $CH_2Cl_2$ was removed, and the resulting precipitate was removed by filtration, washed with EtOH and dried to yield the title compound (270 mg, 67%) as a pale yellow solid. $^1$H-NMR (400 MHz, DMSO-$d_6$) δ 1.27 (3H, t, J=7.3 Hz), 1.74-1.96 (2H, m), 2.02-2.13 (2H, m), 2.14-2.25 (2H, m), 4.20 (2H, q, J=7.3 Hz), 4.33 (2H, s), 7.33 (2H, brs), 8.43 (1H, s). ESIMS (+): 350$[M+H]^+$.

45E) Preparation of 8'-amino-9',10'-difluoro-7'-oxospiro-[cyclobutane-1,2'(3'H)-[7H]pyrido[1,2,3-de][1,4]benzoxazine]-6'-carboxylic Acid

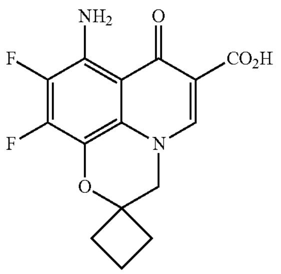 [SMILES: Nc1c(F)c(F)c2c3c1c(=O)c(C(=O)O)cn3CC1(CCC1)O2]

A solution of ethyl 8'-amino-9',10'-difluoro-7'-oxospiro[cyclobutane-1,2'(3'H)-[7H]pyrido[1,2,3-de][1,4]benzoxazine]-6'-carboxylate (247 mg, 0.705 mmol) and 1M NaOH aq. (3.5 mL) in EtOH (3.5 mL) was stirred at room 50° C. for 1.5 hours. The solvent was removed and the residue was dissolved in water. The solution was acidified to pH 7 with 2M HCl and the resulting precipitate was removed by filtration, washed with water and dried to yield the title compound (216 mg, 95%) as a yellow solid. $^1$H-NMR (400 MHz, DMSO-$d_6$) δ 1.73-1.97 (2H, m), 2.04-2.27 (4H, m), 4.50 (2H, s), 7.25 (2H, brs), 8.76 (1H, s), 14.67 (1H, s). ESIMS (+): 322[M+H]$^+$.

45F) Preparation of 8'-amino-9'-fluoro-7'-oxo-10'-[2-(2-pyridylamino)ethylamino]spiro[cyclobutane-1,2'(3'11)-[7H]pyrido[1,2,3-de][1,4]benzoxazine]-6'-carboxylic Acid

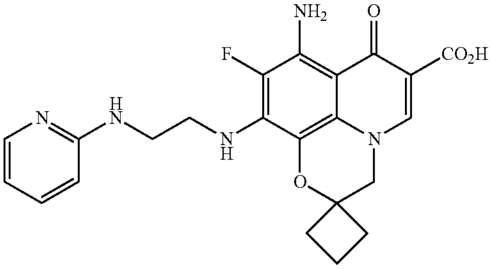 [SMILES: Nc1c(F)c(NCCNc2ccccn2)c2c3c1c(=O)c(C(=O)O)cn3CC1(CCC1)O2]

A solution of 8'-amino-9',10'-difluoro-7'-oxospiro[cyclobutane-1,2'(3'H)-[7H]pyrido[1,2,3-de][1,4]benzoxazine]-6'-carboxylic acid (200 mg, 0.621 mmol), triethylamine (0.130 mL, 0.933 mmol) and N-2-pyridyl-1,2-ethanediamine (128 mg, 0.933 mmol) in DMSO (4 mL) was stirred at 100° C. for 3 hours. The reaction mixture was poured into ice water and the resulting precipitate was removed by filtration, washed with ethanol, and then dried to yield the title compound (223 mg, 82%) as a yellow solid.

$^1$H-NMR (400 MHz, DMSO-$d_6$) δ 1.30-1.50 (2H, m), 1.53-1.73 (1H, m), 3.01-3.12 (2H, m), 3.19-3.30 (2H, m), 3.94 (2H, s), 5.65 (1H, brs), 6.01-6.12 (2H, m), 6.29 (1H, t, J=5.5 Hz), 6.43 (2H, brs), 6.90-7.01 (1H, m), 7.52-7.60 (1H, m), 8.13 (1H, s), 14.90 (1H, s). HRESIMS (+):440.17258 (Calcd for $C_{22}H_{23}FN_5O_4$, 440.17341).

Example 46

9'-amino-10'-fluoro-2',3'-dihydro-8'-oxo-11'-[2-(2-pyridylamino)ethylamino]spiro [cyclopropane-1,4'-[4H,8H]pyrido[1,2,3-ef][1,4]benzoxazepine]-7'-carboxylic Acid 46A) Preparation of Ethyl 3-[1-(2-hydroxyethyl)cyclopropylamino]-2-(2,3,4,5,-tetrafluorobenzoyl)acrylate

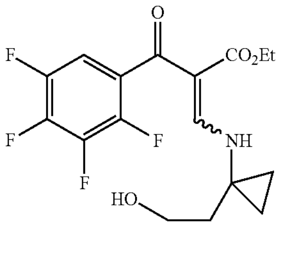 [SMILES: CCOC(=O)C(=CNC1(CCO)CC1)C(=O)c1cc(F)c(F)c(F)c1F]

A solution of ethyl 3-oxo-3-(2,3,4,5-tetrafluoropnenyl) propionate (3.09 g, 11.7 mmol), $Ac_2O$ (6.7 mL, 70.9 mmol) and triethyl orthoformate (3.90 mL, 23.5 mmol) was heated at 120° C. for 3 hours. The mixture was concentrated in vacuo and dried under high vacuum. The crude product was dissolved in anhydrous tolene (40 mL) and (1-amino-cyclopropyl)-ethanol (1.82 g, 11.7 mmol) was added very slowly at 0° C. The ration mixture was stirred at room temperature for 5 hours and diluted with toluene. The organic layer was washed with water, brine, and then dried. The solvent was removed by evaporation and the crude product was purified by column chromatography (Hexane: EtOAc 2:1→1:1) to yield the title compound (2.99 g, 68%) as a yellow oil. $^1$H-NMR (400 MHz, $CDCl_3$) δ 0.85-0.92 (2H, m), 0.94-1.11 (5H, m), 1.85-1.91 (2H, m), 3.85-3.89 (2H, m), 3.99-4.09 (2H, m), 6.95-7.13 (1H, m), 8.19 (1H, d, J=14.1 Hz), 9.84, 11.2 (each d, J=13.4 Hz, total 1H). EIMS (+) 375 [M]$^+$.

46B) Preparation of Ethyl 10',11'-difluoro-2',3'-dihydro-8'-oxospiro-[cyclopropane-1,4'-[4H,8H]pyrido[1,2,3-d][1,4]-benzoxazepine]-7'-Carboxylate

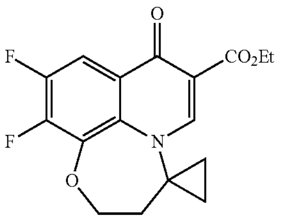 [SMILES: CCOC(=O)c1cn2c3c(c(F)c(F)cc3c1=O)OCCC21CC1]

A solution of NaH (617 mg, 15.4 mmol, 60% in oil) in DMF (30 mL) was cooled to 0° C. and treated dropwise with ethyl 3-[1-(2-hydroxyethyl)cyclopropylamino]-2-(2,3,4,5,-tetrafluorobenzoyl) propylaminoacrylate (2.63 g, 7.01 mmol) in DMF (4 mL). The reaction mixture was stirred at room temperature for 1 hour, and one additional hour at 80° C. The reaction mixture was poured into ice water and the resulting precipitate was removed by filtration and washed with water. The resulting solid was dissolved in 100 mL of EtOH and filtered. The filtrate was concentrated to 50 mL and the resulting precipitate was removed by filtration, washed with EtOH and then dried to yield the title compound (1.43 g, 61%) as a pale brown solid. $^1$H-NMR (400 MHz, DMSO-$d_6$) δ 1.03 (2H, br), 1.18 (2H, br), 1.26 (3H, t, J=7.3 Hz), 2.03-2.73 (2H, br), 4.21 (2H, q, J=7.3 Hz), 7.66 (1H, dd, J=10.4, 7.9 Hz), 8.51 (1H, s). EIMS (+) 335 [M]$^+$.

46C) Preparation of Ethyl 10',11'-difluoro-2',3'-dihydro-9'-nitro-8'-oxospiro[cyclopropane-1,4'-[4H,8H]pyrido[1,2,3-ef][1,4]benzoxazepine]-7'-carboxylate

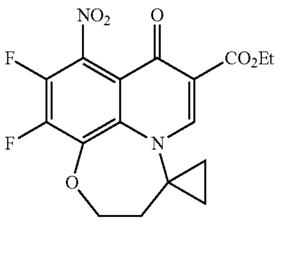 [SMILES: CCOC(=O)c1cn2c3c(c(F)c(F)c([N+](=O)[O-])c3c1=O)OCCC21CC1]

A solution of ethyl 10',11'-trifluoro-2',3'-dihydro-8'-oxospiro[cyclopropane-1,4'-[4H,8H]pyrido[1,2,3-ef][1,4]benzoxazepine]-7'-carboxylate (1.2 g, 3.58 mmol) in concentrated $H_2SO_4$ (15 mL) was treated portionwise at 0° C. with solid $KNO_3$ (510 mg, 5.04 mmol). After stirring at 0° C. for 2 hours, the reaction mixture was poured into ice-water and the resulting precipitate was removed by filtration. The resulting solid was washed with EtOH and dried to yield the title compound (554 mg, 41%) as a brown solid.

$^1$H-NMR (400 MHz, DMSO-$d_6$) δ 1.02 (2H, br), 1.10-1.27 (5H, m), 1.91-2.86 (2H, br), 4.21 (2H, q, J=7.3 Hz), 4.61 (2H, br), 4.52 (2H, br), 8.58 (1H, s). EIMS (+) 380 $[M]^+$. HREIMS (+) 380.0856 (Calcd for $C_{17}H_{14}F_2N_2O_6$, 380.0820).

46D) Preparation of Ethyl 9'-amino-10',11'-difluoro-2',3'-dihydro-8'-oxospiro[cyclopropane-1,4'-[4H,8H]pyrido[1,2,3-ej][1,4]benzoxazepine]-7'-carboxylate

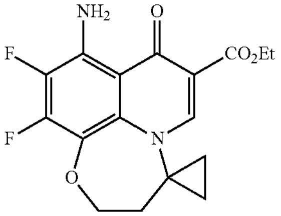

A solution of ethyl 10',11'-difluoro2',3'-dihydro-9'-nitro-8'-oxospiro-[cyclopropane-1,4'-[4H, 8H]pyrido[1,2,3-ef][1,4]benzoxazepine]-7'-carboxylate (500 mg, 1.31 mmol) and 10% Pd/C (100 mg) in DMF (30 mL) was stirred under hydrogen atmosphere at 50° C. for 1.5 hours. The catalyst was removed by filtration over Celite and the filtrate was concentrated in vacuo. The resulting solid was dissolved in $CH_2Cl_2$ and EtOH (3:1, 65 mL), and filtered. After removal of $CH_2Cl_2$ the resulting precipitate was isolated by filtration, washed with EtOH and dried to yield the title compound (355 mg, 77%) as a brown solid. $^1$H-NMR (400 MHz, DMSO-$d_6$) δ 0.99 (2H, br), 1.13 (2H, br), 1.25 (3H, t, J=7.3 Hz), 1.64-2.91 (2H, br), 4.18 (2H, q, J=7.3 Hz), 4.35 (2H, br), 7.46 (2H, br), 8.35 (1H, s). EIMS (+) 350 $[M]^+$.

46E) Preparation of 9'-amino-10',11'-difluoro-2',3'-dihydro-8'-oxospiro[cyclopropane-1,4'-[4H,8H]pyrido[1,2,3-ef][1,4]benzoxazepine]-7'-carboxylic Acid

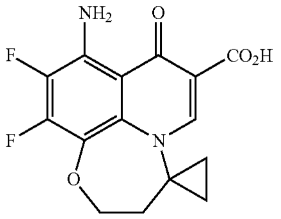 [SMILES: Nc1c(F)c(F)c2c3c1c(=O)c(C(=O)O)cn3C1(CCO2)CC1]

A solution of ethyl 9'-Amino-10',11'-difluoro-2',3'-dihydro-8'-oxospiro[cyclopropane-1,4'-[4H,8H]pyrido[1,2,3-ef][1,4]benzoxazepine]-7'-carboxylate (320 mg, 0.913 mmol) in mixture of AcOH—$H_2O$—$H_2SO_4$ (6:4:1 v/v, 5.3 mL) was heated at reflux for 1 h. The reaction mixture was poured into ice water and a precipitate was collected by filtration, washed with water and then to give the title compound $^1$H-NMR (400 MHz DMSO$_4$) δ 0.63-1.55 (4H, br), 1.90-3.11 (2H, br), 3.78-4.96 (2H, br), 7.40 (2H, s), 8.64 (1H, s), 14.5 (1H, s). EIMS (+) 322 $[M]^+$.

46F) Preparation of 9'-amino-10'-fluoro-2',3'-dihydro-8'-oxo-11'-[2-(2-pyridylamino)ethylamino]spiro[cyclopropane-1,4'-[4H,8H]pyrido[1,2,3-ef][1,4]benzoxazepine]-7'-carboxylic Acid

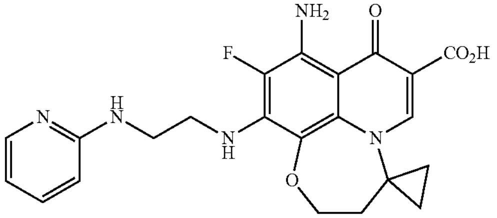 [SMILES: Nc1c(F)c(NCCNc2ccccn2)c2c3c1c(=O)c(C(=O)O)cn3C1(CCO2)CC1]

A solution of 9'-amino-10',11'-difluoro-2',3'-dihydro-8'-oxo-spiro[cyclopropane-1,4'-[4H,8]pyrido[1,2,3,-ef][1,4]benzoxazepine]-7'-carboxylic acid (150 mg, 0.465 mmol), triethylamine (0.100 mL, 0.717 mmol) and N-2-(pyridinyl)-1,2-ethanediamine (95.5 mg, 0.696 mmol) in DMSO (2 mL) was stirred at 100° C. for 3 hours. The reaction mixture was poured into ice water and the resulting precipitate was removed by filtration and washed with ethanol. The resulting solid was dissolved in DMF and filtered. The filtrate was poured into water and the resulting precipitate was removed by filtration, washed with water and dried to yield the title compound (95.6 mg, 47%) as a dark yellow solid. $^1$H-NMR (400 MHz, DMSO$_4$) δ 0.81-1.50 (4H, m), 3.40-3.51 (2H, m), 3.55-3.66 (2H, m), 3.80-4.60 (4H, m), 6.32 (1H, brs), 6.40-6.50 (2H, m), 6.70 (1H, t, J=5.5 Hz), 9.97 (2H, brs), 7.30-7.40 (1H, m), 7.90-8.00 (1H, m), 15.14 (1H, s). HRESIMS (+): 440.17315 (Calcd for $C_{22}H_{22}FN_5O_4$, 440.17340).

Example 47

9'-amino-10'-fluoro-2',3'-dihydro-8'-oxo-11'-[2-(2-pyridylamino)ethylamino]spiro [cyclobutane-1,4'-[4H,8H]pyrido[1,2,3-ef][1,4]benzoxazepine]-7'-carboxylic Acid 47A) Preparation of ethyl (1-hydroxycyclobutyl)-acetate

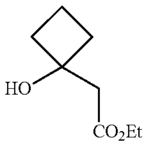

Trimethylchlorosilane (1.14 mL, 8.92 mmol) was added by syringe to a suspension of zinc powder (7.97 g, 0.122 mol) in absolute $Et_2O$ (200 mL). The mixture was stirred for 15 minutes at room temperature. The mixture was then heated to reflux, the heat source was removed, and ethyl bromoacetate (10.3 mL, 92.9 mmol) was added at such a rate that the ether solution gently boiled. The mixture was refluxed one hour then stirred for an additional hour at room temperature. A solution of cyclopentanone (6.00 g, 75.9 mmol) in ether (30 mL) was added while the temperature of the mixture was maintained at 19-20° C. by intermittent cooling. After being one hour of stirring at room temperature, the mixture was poured into iced 25% ammonia (400 mL). The aqueous phase was extracted with ether and the combined phases were dried over $K_2CO_3$. Filtration and evaporation of the solvent yielded the title compound as a colorless oil (6.50 g, 54%). $^1$H-NMR (400 MHz, $CDCl_3$) δ 1.29 (3H, t, J=7.3 Hz), 1.47-1.64 (1H, m), 1.76-1.87 (1H, m), 1.93-2.06 (2H, m), 2.12-2.22 (2H, m), 2.67 (2H, s), 3.70 (1H, s), 4.19 (2H, q, J=7.3 Hz).

47B) Preparation of Ethyl [1-(benzoylamino)cyclobutyl]acetate

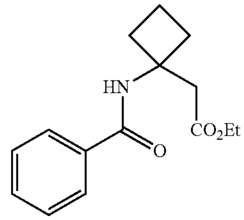 [SMILES: CCOC(=O)CC1(NC(=O)c2ccccc2)CCC1]

$H_2SO_4$ (2.20 mL, 41.3 mmol) was slowly added to a mixture of ethyl 1-hydroxycyclobutylacetate (6.45 g, 40.8 mmol) and benzonitrile (40 mL, 0.392 mol) at room temperature. The mixture was stirred for 1 hour at room temperature, then for an additional hour at 80° C. The mixture was cooled in an ice-water bath, and 2N NaOH solution was added until the mixture reached pH=7. The mixture was extracted with ethyl acetate and the combined organic extracts were dried over anhydrous $Na_2SO_4$, filtered and concentrated in vacuo. Flash chromatography (AcOEt:Hexane=5:1) of the residue gave the title compound as a colorless solid (5.40 g, 51%). $^1$H-NMR (400 MHz, $CDCl_3$) δ 1.22 (3H, t, J=7.3 Hz), 1.84-2.07 (2H, m), 2.22-2.32 (2H, m), 2.44-2.55 (2H, m), 3.05 (2H, s), 4.11 (2H, q, J=7.3 Hz), 6.73 (1H, s), 7.39-7.52 (3H, m), 7.72-7.79 (2H, m).

47C) Preparation of 2-[1-(benzylamino)cyclobutyl]ethanol

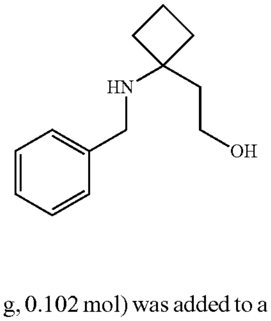

$LiAlH_4$ (3.88 g, 0.102 mol) was added to a solution of ethyl 1-(benzoylamino)-cyclobutylacetate (5.30 g, 20.3 mmol) in THF (100 mL) at room temperature. The mixture was stirred for 1 hour, then refluxed for one additional hour. The mixture was cooled in an ice-water bath, a few drops of water were added, and the mixture was allowed to stand overnight. The mixture was diluted with ethyl acetate, dried over anhydrous $Na_2SO_4$, filtered, and concentrated in vacuo. Distillation of the residue gave the title compound as a colorless oil (2.53 g, 61%). $^1$H-NMR (400 MHz, $CDCl_3$) δ 1.69-1.86 (2H, m), 1.88 (2H, t, J=5.5 Hz), 1.92-2.09 (4H, m), 3.73 (2H, s), 3.87 (2H, t, J=5.5 Hz), 7.22-7.35 (5H, m).

47D) Preparation of 2-[1-aminocyclobutyl]ethanol

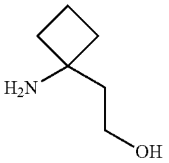

10% Pd—C (500 mg) was added to a solution of 2-[1-(benzylamino)cyclobutyl]ethanol (4.00 g, 19.5 mmol) in EtOH (100 mL) and the mixture was stirred under $H_2$ gas 0.5 MPa at room temperature for 6 hours. The mixture was filtered, and the filtrate was concentrated in vacuo. Distillation of the residue gave the title compound as a colorless oil (1.65 g, 73%). $^1$H-NMR (400 MHz, $CDCl_3$) δ 1.60-1.72 (2H, m), 1.75 (2H, t, J=5.5 Hz), 1.77-1.87 (2H, m), 2.03-2.13 (2H, m), 3.81 (2H, q, J=5.5 Hz).

47E) Preparation of Ethyl 3-[1-(2-hydroxyethyl)cyclobutylamino-]-2-(2,3,4,5-tetrafluorobenzoyl)acrylate

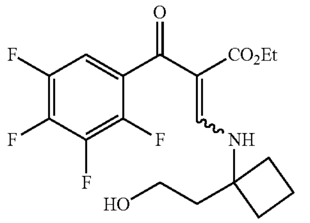 [SMILES: CCOC(=O)C(=CNC1(CCO)CCC1)C(=O)c1cc(F)c(F)c(F)c1F]

A stirred solution of 3-oxo-3-(2,3,4,5-tetrafluorophenyl)propionate (3.67 g, 13.9 mmol), $Ac_2O$ (7.89 mL, 83.5 mmol) and triethyl orthoformate (4.63 mL, 27.8 mmol) was heated at 120° C. for 3 hours. The mixture was concentrated in vacuo and dried under high vacuum. 1-amino-1-(2-hydroxyethyl)cyclobutane (1.60 g, 13.9 mmol) in anhydrous toluene (20 mL) was added slowly at 0° C. to a solution of the mixture in anhydrous toluene (50 mL). The resulting mixture was stirred at room temperature for 2 hours, and the solvent was removed by evaporation. Flash chromatography (AcOEt:Hexane=1:1) of the residue gave the title compound as a pale yellow solid (3.30 g, 61%). $^1$H-NMR (400 MHz, $CDCl_3$) δ 0.96 (0.6H, t, J=7.3 Hz), 1.09 (2.4H, t, J=7.3 Hz), 1.85-2.03 (12H, m), 2.06-2.13 (2H, m), 2.20-2.30 (2H, m), 2.32-2.43 (2H, m), 3.82-3.88 (2H, m), 4.02 (0.4H, q, J=7.3 Hz), 4.07 (1.6H, q, J=7.3 Hz), 6.94-7.03 (0.2H, m), 7.05-7.13 (0.8H, m), 8.23-8.30 (1H, m), 10.05-10.17 (0.2H, m), 11.36-11.50 (0.8H, m).

47F) Preparation of Ethyl 10',11'-difluoro-2',3'-dihydro-8'-oxospiro [cyclobutane-1,4'-[4H,8H]pyrido[1,2,3-ef][1,4]benzoxazepine]-7'-carboxylate

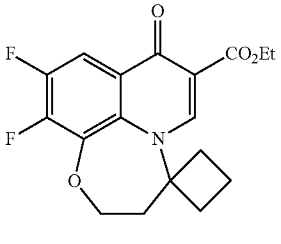 [SMILES: CCOC(=O)c1cn2c3c(c(F)c(F)cc3c1=O)OCCC21CCC1]

NaH was added (350 mg, 8.75 mmol) to a solution of ethyl 3-[1-(2-hydroxyethyl)cyclobutylamino]-2-(2,3,4,5-tetrafluorobenzoyl)acrylate (2.80 g, 7.19 mmol) in DMF (30 mL) at 0° C. The mixture was stirred at room temperature for 30 minutes, then heated at 80° C. for an additional 30 minutes. Water was added to the mixture portionwise at 0° C. and the resulting precipitate was isolated by filtration, washed successively with water and dried to give the title compound (655 mg, 26%) as a colorless solid. $^{1}$H-NMR (400 MHz, DMSO-$d_6$) δ 1.27 (3H, t, J=7.3 Hz), 1.67-1.79 (1H, m), 1.91-2.04 (1H, m), 2.42-2.53 (4H, m), 2.67 (2H, t, J=6.7 Hz), 4.24 (2H, q, J=7.3 Hz), 4.55 (2H, t, J=6.7 Hz), 7.72 (1H, dd, J=10.4 and 7.9 Hz), 8.41 (1H, s).

47G) Preparation of Ethyl 10',11'-difluoro-2',3'-dihydro-9'-nitro-8'-oxospiro[cyclobutane-1,4'-[4H,8H]pyrido[1,2,3-ej][1,4]benzoxazepine]-7'-carboxylate

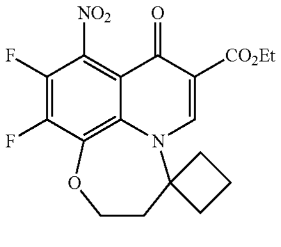 [SMILES: CCOC(=O)c1cn2c3c(c(F)c(F)c([N+](=O)[O-])c3c1=O)OCCC21CCC1]

A solution of ethyl 10',11'-difluoro-2',3'-dihydro-8'-oxospiro[cyclobutane-1,4'-[4H,8H]pyrido[1,2,3-ef][1,4]benzoxazepine]-7'-carboxylate (925 mg, 2.65 mmol) in concentrated $H_2SO_4$ (11 mL) was treated portionwise with solid $KNO_3$ (363 mg, 3.59 mmol) at 0° C. After stirring at 0° C. for 2 hours, the reaction mixture was poured into ice-water and the resulting precipitate was combined by filtration and washed with water. Flash chromatography ($CH_2Cl_2$-MeOH=10:1) of the residue give the title compound as a yellow solid (822 mg, 79%). $^{1}$H-NMR (400 MHz, DMSO-$d_6$) δ 1.27 (3H, t, J=7.3 Hz), 1.68-1.78 (1H, m), 1.90-2.03 (1H, m), 2.40-2.58 (4H, m), 2.69 (2H, t, J=6.7 Hz), 4.24 (2H, q, J=7.3 Hz), 4.63 (2H, t, J=6.7 Hz), 8.44 (1H, s).

47H) Preparation of Ethyl 9'-amino-10',11'-difluoro-2',3'-dihydro-8'-oxospiro[cyclobutane-1,4'-[4H,8H]pyrido[1,2,3-ef][1,4]benzoxazepine]-7'-carboxylate

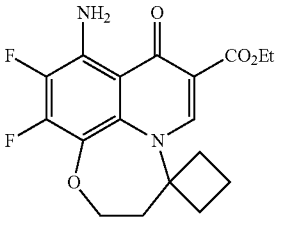 [SMILES: CCOC(=O)c1cn2c3c(c(F)c(F)c(N)c3c1=O)OCCC21CCC1]

A solution of ethyl 10',11'-difluoro-2',3'-dihydro-9'-nitro-8'-oxo-spiro-[cyclobutane-1,4'-[4H,8H]pyrido[1,2,3-ef][1,4]benzoxazepine]-7'-carboxylate (770 mg, 1.95 mmol) in DMF (70 mL) was treated with hydrogen under atmospheric pressure over 10% Pd/C (200 mg) at 50° C. for 1 hour. The catalyst was removed by filtration over Celite and the filtrate was concentrated in vacuo. Flash chromatography ($CH_2Cl_2$-MeOH=10:1) of the residue gave the title compound as a colorless solid (559 mg, 79%). $^{1}$H-NMR (400 MHz, DMSO-$d_6$) δ 1.26 (3H, t, J=7.3 Hz), 1.65-1.77 (1H, m), 1.87-2.01 (1H, m), 2.35-2.62 (6H, m), 4.21 (2H, q, J=7.3 Hz), 4.31-4.42 (2H, brt), 7.40-7.60 (2H, brs), 8.23 (1H, s).

47I) Preparation of 9'-amino-10',11'-difluoro-2',3'-dihydro-8'-oxospiro[cyclobutane-1,4'-[4H,8H]pyrido[1,2,3-d][1,4]benzoxazepine]-7'-carboxylic Acid

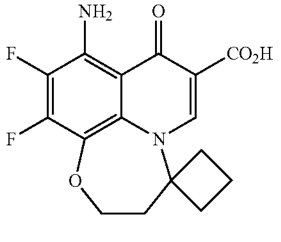 [SMILES: Nc1c(F)c(F)c2c3c1c(=O)c(C(=O)O)cn3C1(CCC1)CCO2]

2N NaOH (7.0 mL, 14.0 mmol) was added to a mixture of ethyl 9'-amino-10',11'-difluoro-2',3'-dihydro-8'-oxospiro[cyclobutane-1,4'-[4H,8H]pyrido[1,2,3-ef][1,4]benzoxazepine]-7'-carboxylate (513 mg, 1.41 mmol) in EtOH (14 mL) at room temperature and the mixture was heated at 50° C. for 3 hours. 2N HCl (7.0 mL) and water were added to the reaction mixture. The resulting precipitate was collected by filtration, washed successively with water and dried to give the title compound (427 mg, 90%) as a colorless solid. $^{1}$H-NMR (400 MHz, DMSO-$d_6$) δ 1.64-1.77 (1H, m), 1.89-2.02 (1H, m), 2.56-2.70 (2H, br), 4.30-4.50 (2H, br), 7.35-7.52 (2H, brs), 8.47 (1H, s), 14.60 (1H, s).

47J) Preparation of 9'-amino-10'-fluoro-2',3'-dihydro-8'-oxo-11'-[2-(2-pyridylamino)ethylamino]spiro[cyclobutane-1,4'-[4H,8H]pyrido[1,2,3-ef][1,4]benzoxazepine]-7'-carboxylic Acid

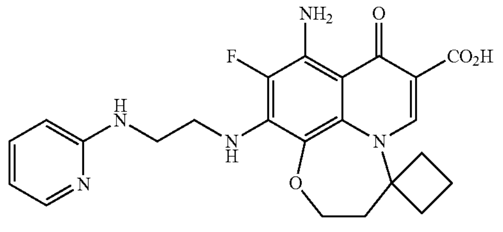 [SMILES: Nc1c(F)c(NCCNc2ccccn2)c2c3c1c(=O)c(C(=O)O)cn3C1(CCC1)CCO2]

A solution of 9'-amino-10',11'-difluoro-2',3'-dihydro-8'-oxospiro-[cyclobutane-1,4'-[4H,8H]pyrido[1,2,3-ej][1,4]benzoxazepine]-7'-carboxylic acid (186 mg, 0.553 mmol), N-(2-pyridinyl)-1,2-ethanediamine (115 mg, 0.838 mmol) and triethylamine (117 μL) in DMSO (2.5 mL) was stirred at 120° C. for 4 hours. The reaction mixture was added portionwise at 0° C. to ice-water and 2N HCl (3 drops) was added to the mixture. The resulting precipitate was isolated by filtration, washed with EtOH and dried to give the title compound (165 mg, 66%) as a yellow solid. $^1$H-NMR (400 MHz, DMSO-$d_6$) δ 1.61-1.74 (1H, m), 1.84-2.00 (1H, m), 2.30-2.65 (6H, m), 3.40-3.50 (2H, m), 3.52-3.62 (2H, m), 4.10-4.33 (2H, br), 6.20-6.30 (1H, m), 6.42-6.51 (2H, m), 6.69 (1H, t, J=5.5 Hz), 6.90-7.08 (2H, br), 7.32-7.40 (1H, m), 7.97 (1H, dd, J=4.3 and 1.2 Hz), 8.26 (1H, s), 15.23 (1H, s). HRESIMS (+) 454.18677 (Calcd for $C_{23}H_{25}FN_5O_4$, 454.18906).

Example 48

9'-amino-10'-fluoro-2',3'-dihydro-8'-oxo-11'-[2-(2-pyridylamino)ethylamino]spiro[cyclopentane-1,4'-[4H,8H]pyrido[1,2,3-ef][1,4]benzoxazepine]-7'-carboxylic Acid 48A) Preparation of ethyl 3-[1-(2-hydroxyethyl)cyclopentylamino]-2-(2,3,4,5-tetrafluorobenzoyl)acrylate

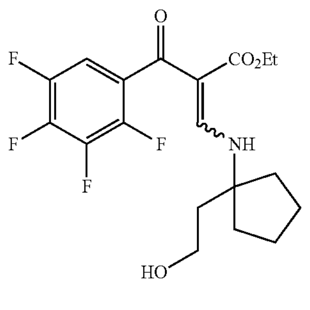 [SMILES: CCOC(=O)C(=CNC1(CCO)CCCC1)C(=O)c1cc(F)c(F)c(F)c1F]

A stirred solution of ethyl 3-oxo-3-(2,3,4,5-tetrafluorophenyl)propionate (20.3 g, 76.8 mmol), $Ac_2O$ (44.0 mL, 0.465 mol) and triethyl orthoformate (25.6 mL, 0.154 mol) was heated at 120° C. for 3 hours. The mixture was concentrated in vacuo and dried under high vacuum. 1-amino-1-(2-hydroxyethyl)cyclopentane (9.94 g, 76.9 mmol) in anhydrous toluene (50 mL) was slowly added to a solution of the mixture in anhydrous toluene (200 mL) at 0° C. The resulting mixture was stirred at room temperature for 2 hours. The solvent was removed by evaporation. Flash chromatography (AcOEt:Hexane=2:1) of the residue gave the tilte compound as a colorless solid (23.2 g, 75%). $^1$H-NMR (400 MHz, $CDCl_3$) δ 0.96 (0.6H, t, J=7.3 Hz), 1.09 (2.4H, t, J=7.3 Hz), 1.48-1.54 (1H, m), 1.74-1.90 (6H, m), 1.97-2.06 (4H, m), 3.78-3.85 (2H, m), 3.98-4.10 (2H, m), 6.95-7.12 (1H, m), 8.17-8.24 (1H, m), 9.81-9.94 (0.3H, m), 11.20-11.35 (0.7H, m).

48B) Preparation of Ethyl 6,7,8-trifluoro-1,4-dihydro-1-[1-(2-hydroxyethyl)cyclopentyl]-4-oxo-3-quinolinecarboxylate

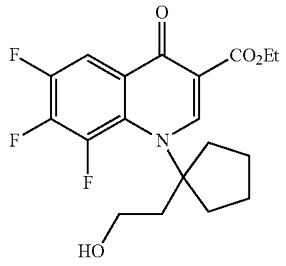 [SMILES: CCOC(=O)c1cn(C2(CCO)CCCC2)c2c(F)c(F)c(F)cc2c1=O]

To an iced solution of ethyl 3-[1-(2-hydroxyethyl)-cyclopentylamino]-2-(2,3,4,5-tetrafluorobenzoyl)acrylate (22.7 g, 56.3 mmol) in THF (200 mL) was added NaH (3.60 g, 90.0 mmol), and the mixture was stirred at room temperature for 1 hour. Water was added to the mixture portionwise at 0° C. The resulting mixture was extracted with ethyl acetate, and the combined organic extracts were concentrated in vacuo. Flash chromatography (AcOEt:Hexane=2:1) of the residue give the title compound as a colorless solid (14.1 g, 65%). $^1$H-NMR (400 MHz, DMSO-$d_6$) δ 1.27 (3H, t, J=7.3 Hz), 1.53-1.75 (4H, m), 2.10-2.26 (4H, m), 2.31-2.44 (2H, m), 4.23 (2H, q, J=7.3 Hz), 4.55-4.60 (1H, m), 7.99-8.07 (1H, m), 8.80 (1H, s).

48C) Preparation of Ethyl 10',11'-difluoro-2',3'-dihydro-8'-oxospiro[cyclopentane-1,4'-[4H,8H]pyrido[1,2,3-ef][1,4]benzoxazepine]-7'-carboxylate

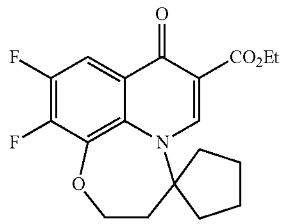 [SMILES: CCOC(=O)c1cn2c3c(c(F)c(F)cc3c1=O)OCCC21CCCC1]

To a solution of ethyl 6,7,8-trifluoro-1,4-dihydro-1-[1-(2-hydroxyethyl)cyclopentyl]-4-oxo-3-quinolinecarboxylate (3.84 g, 10.0 mmol) in DMF (40 mL) was added NaH (480 mg, 12.0 mmol), and the mixture was heated at 80° C. for 30 minutes. The mixture was treated portionwise with water at 0° C. The resulting mixture was extracted with ethyl acetate and the combined extracts were concentrated in vacuo. Flash chromatography (AcOEt:Hexane=2:1) of the residue give the title compound as a colorless solid (1.12 g, 31%). $^1$H-NMR (400 MHz, DMSO-$d_6$) δ 1.42 (3H, t, J=7.3 Hz), 1.52-1.64 (2H, m), 1.75-1.88 (2H, m), 2.11-2.21 (2H, m), 2.27-2.37

(2H, m), 2.47 (2H, t, J=6.7 Hz), 4.39 (2H, q, J=7.3 Hz), 4.47 (2H, t, J=6.7 Hz), 7.98 (1H, dd, J=9.8 and 7.9 Hz), 8.67 (1H, s).

48D) Preparation of Ethyl 10',11'-difluoro-2',3'-dihydro-9'-nitro-8'-oxospiro[cyclopentane-1,4'-[4H,8H]pyrido[1,2,3-ef][1,4]benzoxazepine]-7'-carboxylate

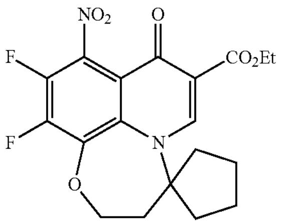

A solution of ethyl 10',11'-difluoro-2',3'-dihydro-8'-oxospiro[cyclopentane-1,4'-[4H,8H]pyrido[1,2,3-ef][1,4]benzoxazepine]-7'-carboxylate (50.0 g, 0.138 mmol) in concentrated $H_2SO_4$ (1 mL) was treated portionwise at 0° C. with solid $KNO_3$ (20.0 mg, 0.199 mmol). After stirring at 0° C. for 1 h, the reaction mixture was poured into ice-water and the resulting precipitate was combined by filtration, washed with water and dissolved in $CH_2Cl_2$-MeOH (5:1 v/v). The combined extracts were concentrated in vacuo. Flash chromatography ($CH_2Cl_2$-MeOH=10:1) of the residue gave the title compound as a yellow solid (26.0 mg, 46%). $^1$H-NMR (400 MHz, DMSO-$d_6$) δ 1.37 (3H, t, J=7.3 Hz), 1.52-1.66 (2H, m), 1.78-1.90 (2H, m), 2.15-2.30 (4H, m), 2.50 (2H, t, J=6.7 Hz), 4.36 (2H, q, J=7.3 Hz), 4.55 (2H, t, J=6.7 Hz), 8.69 (1H, s).

48E) Preparation of Ethyl 9'-amino-10',11'-difluoro-2',3'-dihydro-8'-oxospiro[cyclopentane-1,4'-[4H,8H]pyrido[1,2,3-ef][1,4]benzoxazepine]-7'-carboxylate

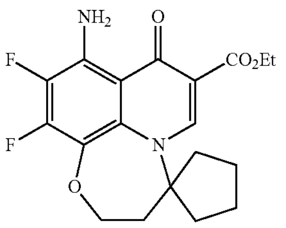 [SMILES: CCOC(=O)c1cn2c3c(c(F)c(F)c([N+](=O)[O-])c3c1=O)OCCC21CCCC1]

A solution of ethyl 10',11'-difluoro-2',3'-dihydro-9'-nitro-8'-oxospiro[cyclopentane-1,4'-[4H,8H]pyrido[1,2,3-ej][1,4]benzoxazepine]-7'-carboxylate (2.00 g, 4.90 mmol) in DMF (120 mL) was treated with hydrogen under atmospheric pressure over 10% Pd/C (400 mg) at 50° C. for 1.5 hours. The catalyst was removed by filtration over Celite and the filtrate was concentrated in vacuo. Flash chromatography ($CH_2Cl_2$-MeOH=10:1) of the residue give the title compound as a yellow solid (527 mg, 28%). $^1$H-NMR (400 MHz, DMSO-$d_6$) δ 1.26 (3H, t, J=7.3 Hz), 1.37-1.50 (2H, m), 1.65-1.77 (2H, m), 2.06-2.25 (4H, m), 2.36 (2H, t, J=6.7 Hz), 4.20 (2H, q, J=7.3 Hz), 4.30 (2H, t, J=6.7 Hz), 7.53 (2H, brs), 8.47 (1H, s).

48F) Preparation of 9'Amino-10',11'-difluoro-2',3'-dihydro-8'-oxospiro[cyclopentane-1,4'-[4H,8H]pyrido[1,2,3-4][1,4]benzoxazepine]-7'-carboxylic Acid

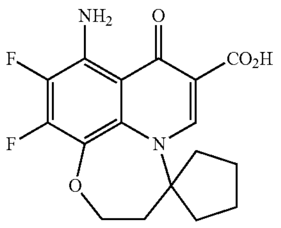

To a mixture of ethyl 9'-amino-10',11'-difluoro-2',3'-dihydro-8'-oxospiro[cyclopentane-1,4'-[4H,8H]pyrido[1,2,3-ef][1,4]benzoxazepine]-7'-carboxylate (482 mg, 1.27 mmol) in EtOH (13 mL) was added 2N NaOH (6.5 mL, 13.0 mmol) at room temperature and the mixture was heated at 50° C. for 3 hours. 2N HCl (6.5 mL) and water were added to the reaction mixture. The resulting precipitate was collected by filtration, washed successively with water and dried to give the title compound (425 mg, 96%) as a colorless solid. $^1$H-NMR (400 MHz, DMSO-$d_6$) δ 1.35-1.52 (2H, m), 1.65-1.75 (2H, m), 2.10-2.30 (4H, m), 2.43 (2H, t, J=6.7 Hz), 4.34 (2H, t, J=6.7 Hz), 7.50 (2H, brs), 8.67 (1H, s), 14.5 (1H, brs).

48G) Preparation of 9'-amino-10'-fluoro-2',3'-dihydro-8'-oxo-11'-[2-(2-pyridylamino)ethylamino]spiro[cyclopentane-1,4'-[4H,8H]pyrido[1,2,3-d][1,4]benzoxazepine]-7'-carboxylic Acid

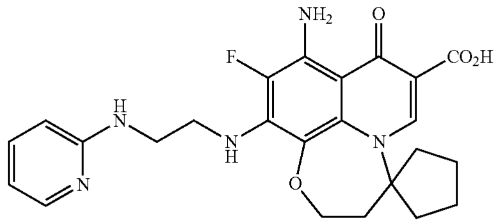 [SMILES: Nc1c(F)c(NCCNc2ccccn2)c2c3c1c(=O)c(C(=O)O)cn3C1(CCCC1)CCO2]

A solution of 9'-amino-10',11'-difluoro-2',3'-dihydro-8'-oxospiro[cyclopentane-1,4'-[4H,8H]pyrido[1,2,3-ef][1,4]benzoxazepine]-7'-carboxylic acid (200 mg, 0.571 mmol) and N-(2-pyridinyl)-1,2-ethanediamine (118 mg, 0.860 mmol) in DMSO (2.5 mL) was stirred at 100° C. for 4 hours. To the reaction mixture was added ice-water portionwise at 0° C., and the resulting precipitate was isolated by filtration and washed successively with water, $iPr_2O$ and EtOH. The resulting precipitate was dried to give the title compound (185 mg, 69%) as a pale yellow solid. $^1$H-NMR (400 MHz, DMSO-$d_6$) δ 1.34-1.49 (2H, m), 1.60-1.75 (2H, m), 2.03-2.23 (4H, m), 2.34 (2H, t, J=6.7 Hz), 3.40-3.55 (2H, m), 3.55-3.64 (2H, m), 4.17 (2H, t, J=6.7 Hz), 6.25-6.33 (1H, br), 6.43-6.51 (2H, m), 6.69 (1H, t, J=5.5 Hz), 7.06 (2H, br), 7.35 (1H, ddd, J=6.7, 6.7 and 1.8 Hz), 8.86 (1H, dd, J=4.9 and 1.2 Hz), 8.49 (1H, s), 15.1 (1H, brs). HRESIMS (+) 4678.20118 (Calcd for $C_{24}H_{27}FN_5O_4$, 468.20471).

Example 49

9'-amino-10'-fluoro-2',3'-dihydro-3'-methyl-8'-oxo11'-[2-(2-pyridylamino)ethylamino]-spiro[cyclobutane-1,4%[4H,8H]pyrido[1,2,3-ej][1,4]benzoxazepine]-7'-carboxyic Acid

49A) Preparation of Ethyl 2-(1-hydroxycyclobutyl)propionate

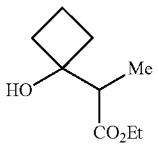 [SMILES: CCOC(=O)C(C)C1(O)CCC1]

Trimethylchlorosilane (950 μL, 7.43 mmol) was added by syringe to a suspension of zinc powder (6.65 g, 0.102 mol) in absolute $Et_2O$ (170 mL). The mixture was stirred for 15 minutes at room temperature, heated to reflux, the heat source removed, and ethyl 2-bromopropionate (10.1 mL, 77.8 mmol) was added at such a rate that the ether gently boiled. After being heated to reflux for 1 hour, the mixture was stirred for 1 hour at room temperature. A solution of cyclobutanone (5.00 g, 63.2 mmol) in $Et_2O$ (10 mL) was added while the temperature of the mixture was maintained at 19-20° C. by intermittent cooling. After stirring for 1 hour at room temperature, the mixture was poured into iced 25% ammonia (400 mL). The aqueous phase was extracted with ether, the combined organic phases were dried over $K_2CO_3$, and concentrated. the title compound was given as a colorless oil (12.9 g, 100%). $^1$H-NMR (400 MHz, $CDCl_3$) δ 1.21 (3H, d, J=6.8 Hz), 1.29 (3H, t, J=7.3 Hz), 1.51-1.64 (1H, m), 1.80-1.90 (1H, m), 1.96-2.17 (4H, m), 2.70 (1H, q, J=7.3 Hz), 3.44 (1H, s), 4.18 (2H, qd, J=7.3 and 1.2 Hz).

49B) Preparation of Ethyl 2-[1-(benzoylamino)cyclobutyl]-propionate

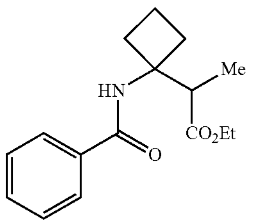 [SMILES: CCOC(=O)C(C)C1(NC(=O)c2ccccc2)CCC1]

$H_2SO_4$ (3.90 mL, 73.2 mmol) was slowly added to a mixture of ethyl 2-(1-hydroxycyclobutyl)propionate (12.5 g, 72.6 mmol) and benzonitrile (75 mL) at room temperature. The mixture was stirred for 1 hour at room temperature, then 80° C. for 1 hour. The mixture was cooled in an ice-water bath and 2N NaOH solution was added until the mixture reached pH=7. The mixture was extracted with ethyl acetate, the combined organic extracts were dried over anhydrous $Na_2SO_4$, filtered, and concentrated in vacuo. Flash chromatography (AcOEt:Hexane=5:1) of the residue gave the title compound as a pale yellow solid (9.24 g, 46%). $^1$H-NMR (400 MHz, $CDCl_3$) δ 1.25 (3H, t, J=7.3 Hz), 1.30 (3H, d, J=7.3 Hz), 1.73-1.87 (1H, m), 1.98-2.09 (2H, m), 2.21-2.32 (1H, m), 2.53-2.63 (1H, m), 2.84-2.94 (1H, m), 3.11 (1H, q, J=7.3 Hz), 4.08-4.20 (2H, m), 6.88 (1H, brs), 7.40-7.52 (3H, m), 7.75-7.80 (2H, m).

49C) Preparation of 2-[1-(benzylamino)cyclobutyl]pronanol

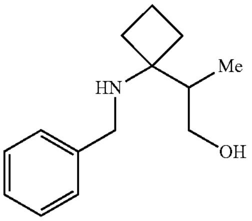 [SMILES: CC(CO)C1(NCc2ccccc2)CCC1]

$LiAlH_4$ (6.30 g, 0.166 mol) was added to a solution of ethyl 241-(benzoylamino)-cyclobutyl]propionate (9.07 g, 32.9 mmol) in THF (160 mL) and the mixture was stirred at room temperature for 1 hour, then refluxed 1 hour. The mixture was cooled in an ice-water bath, and a few drops of water were added. The mixture was diluted with ethyl acetate, dried over anhydrous $Na_2SO_4$, filtered, and concentrated in vacuo. The distillation of the residue gave the title compound as a pale yellow oil (6.92 g, 96%). $^1$H-NMR (400 MHz, $CDCl_3$) δ 1.00 (3H, d, J=6.7 Hz), 1.66-1.77 (1H, m), 1.81-1.97 (2H, m), 2.02-2.10 (1H, m), 2.10-2.24 (3J, m), 3.59 (1H, dd, J=11.0 and 7.9 Hz), 3.71 (1H, d, J=11.6 Hz), 3.74 (1H, dd, J=11.0 and 3.7 Hz), 3.89 (1H, d, J=11.6 Hz), 7.23-7.36 (5H, m).

49D) Preparation of 2-(1-aminocyclobutyl)propanol

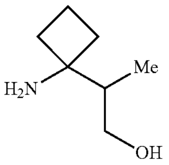

10% Pd—C (700 mg) was added to a solution of 2-[1-(benzylamino)cyclobutyl]propanol (6.81 g, 31.1 mmol) in EtOH (150 mL) and the mixture was stirred under $H_2$ gas 5 kgf/cm$^2$ at room temperature for 6 hours. The mixture was filtered, and the filtrate was concentrated in vacuo. Distillation of the residue gave the title compound as a colorless oil (2.96 g, 74%). $^1$H-NMR (400 MHz, $CDCl_3$) δ 1.03 (3H, d, J=7.3 Hz), 1.63-1.74 (3H, m), 1.78-1.94 (2H, m), 2.10-2.28 (2H, m), 3.50 (1H, dd, J=11.0 and 4.3 Hz), 3.91 (1H, dd, J=11.0 and 3.1 Hz).

49E) Preparation of ethyl 3-[1-(1-hydroxy-2-propyl)-cyclobutylamino]-2-(2,3,4,5-tetrafluorobenzoyl) acrylate

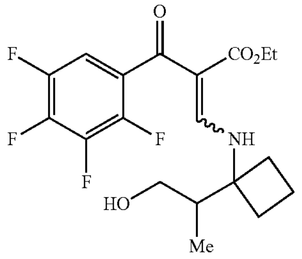 [SMILES: CCOC(=O)C(=CNC1(C(C)CO)CCC1)C(=O)c1cc(F)c(F)c(F)c1F]

A solution of 3-oxo-3-(2,3,4,5-tetrafluorophenyl)propionate (6.13 g, 23.2 mmol), $Ac_2O$ (13.2 mL, 0.140 mol) and triethyl orthoformate (7.80 mL, 46.8 mmol) was stirred at 120° C. for 3 hours. The mixture was concentrated in vacuo and dried under high vacuum. To the mixture of the residue in anhydrous toluene (100 mL) was slowly added 2-(1-aminocyclobutyl)propanol (3.00 g, 23.2 mmol) in anhydrous toluene (40 mL) at 0° C. The mixture was stirred at room temperature for 2 hours and the solvent was removed by evaporation. Flash chromatography (AcOEt:Hexane=1:1) of the residue gave the title compound as a colorless solid (6.23 g, 67%). $^1$H-NMR (400 MHz, $CDCl_3$) δ 0.95 (0.6H, t, J=7.3 Hz), 0.97 (3H, d, J=7.3 Hz), 1.09 (2.4H, t, J=7.3 Hz), 1.54 (1H, t, J=4.9 Hz), 1.85-2.15 (3H, m), 2.19-2.50 (4H, m), 3.62-3.75 (2H, m), 4.02 (0.2H, q, J=7.3 Hz), 4.07 (0.8H, q, J=7.3 Hz), 6.97-7.13 (1H, m), 8.24 (0.8H, d, J=15.3 Hz), 8.25 (0.2H, d, J=15.3 Hz), 10.03 (0.2H, d, J=14.1 Hz), 11.40 (0.8H, d, J=14.1 Hz).

49F) Preparation of ethyl 10',11'-difluoro-2',3'-dihydro-3'-methyl-8'-oxospiro[cyclobutane-1,4'-[4H,8H]pyrido[1,2,3-ef][1,4]benzoxazepine]-7'-carboxylate

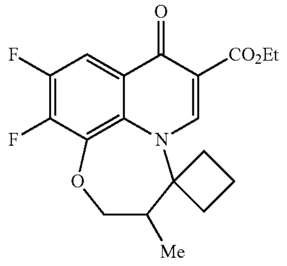 [SMILES: CCOC(=O)c1cn2c3c(c(F)c(F)cc3c1=O)OCC(C)C21CCC1]

NaH (40 mg) was added a solution of ethyl 3-[1-(1-hydroxy-2-propyl)-cyclobutylamino]-2-(2,3,4,5-tetrafluorobenzoyl)acrylate (404 mg, 1.00 mmol) in DMF (4 mL) at 0° C. Additional NaH (40 mg) was added to the mixture after one hour of stirring at 0° C. The mixture was stirred at 0° C. for an additional hour, at room temperature for 1 hour, and at 70° C. for 1 hour. Water was added portionwise to the mixture at 0° C. and the resulting precipitate was isolated by filtration, washed successively with water and ethyl acetate, and dried to give the title compound (289 mg, 80%) as a pale yellow solid. $^1$H-NMR (400 MHz, DMSO-$d_6$) δ 0.93 (3H, d, J=6.1 Hz), 1.27 (3H, t, J=7.3 Hz), 1.66-1.77 (1H, m), 1.85-2.00 (1H, m), 2.35 (1H, q, J=10.4 Hz), 2.53-2.69 (3H, m), 2.96-3.05 (1H, m), 3.82 (1H, t, J=11.6 Hz), 4.24 (2H, qd, J=7.3 and 2.4 Hz), 4.77 (1H, dd, J=12.9 and 8.9 Hz), 7.73 (1H, dd, J=10.4 and 8.6 Hz), 8.25 (1H, s).

49G) Preparation of Ethyl 10',11'-difluoro-2',3'-dihydro-3'-methyl-9'-nitro-8'-oxospiro[cyclobutane-1,4'-[4H,8H]pyrido[1,2,3-ef][1,4]benzoxazepine]-7'-carboxylate

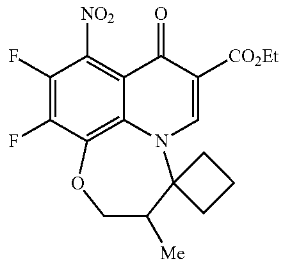 [SMILES: CCOC(=O)c1cn2c3c(c(F)c(F)c([N+](=O)[O-])c3c1=O)OCC(C)C21CCC1]

A solution of ethyl 10',11'-difluoro-2',3'-dihydro-3'-methyl-8'-oxospiro-[cyclobutane-1,4'-[4H,8H]pyrido[1,2,3-ej][1,4]benzoxazepine]-7'-carboxylate (1.00 g, 2.75 mmol) in concentrated $H_2SO_4$ (12 mL) was treated portionwise at 0° C. with solid $KNO_3$ (377 mg, 3.73 mmol). After stirring at 0° C. for 2 hours, the reaction mixture was poured into ice-water and the resulting precipitate was combined by filtration and washed with water. Recrystallization of the resulting solid from DMF (20 mL) gave the title compound as a yellow solid (923 mg, 82%). $^1$H-NMR (400 MHz, DMSO-$d_6$) δ 0.94 (3H, d, J=6.1 Hz), 1.26 (3H, t, J=7.3 Hz), 1.67-1.78 (1H, m), 1.83-1.98 (1H, m), 2.40-2.64 (4H, m), 2.92-3.05 (1H, m), 3.98 (1H, t, J=11.6 Hz), 4.24 (2H, t, J=7.3 Hz), 4.80 (1H, dd, J=11.6 and 7.9 Hz), 8.25 (1H, s).

49H) Preparation of Ethyl 9'-amino-10',11'-difluoro-2',3'-dihydro-3'-methyl-8'-oxospiro[cyclobutane-1,4'-[4H,8H]pyrido[1,2,3-ef][1,4]benzoxazepine]-7'-carboxylate

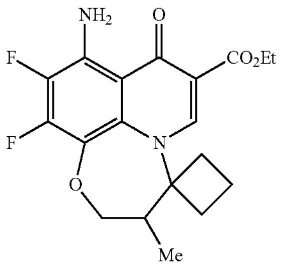 [SMILES: CCOC(=O)c1cn2c3c(c(F)c(F)c(N)c3c1=O)OCC(C)C21CCC1]

A solution of ethyl 10',11'-difluoro-2',3'-dihydro-3'-methyl-9'-nitro-8'-oxospiro[cyclobutane-1,4'-[4H,8H]pyrido[1,2,3-ef][1,4]benzoxazepine]-7'-carboxylate (900 mg, 2.20 mmol) in DMF (55 mL) was treated with hydrogen under atmospheric pressure over 10% Pd/C (180 mg) at 50° C. for 3 hours. The catalyst was removed by filtration over Celite and the filtrate was concentrated in vacuo. The residue was washed with EtOH, collected by filtration and dried to give the title compound (756 mg, 91%) as a pale yellow solid. $^1$H-NMR (400 MHz, DMSO-$d_6$) δ 0.89 (3H, brs), 1.26 (3H, t, J=7.3 Hz), 1.65-1.77 (1H, m), 1.80-1.95 (1H, m), 2.30-2.67 (4H, m), 2.82-2.94 (1H, m), 3.52-3.66 (1H, m), 4.15-4.28 (2H, m), 4.58-4.70 (1H, m), 7.40-7.65 (2H, br), 8.05 (1H, s).

49I) Preparation of 9'-amino-10',11'-difluoro-2',3'-dihydro-3'-methyl-8'-oxospiro[cyclobutane-1,4'-[4H,8H]pyrido[1,2,3-ef][1,4]benzoxazepine]-7'-carboxylic Acid

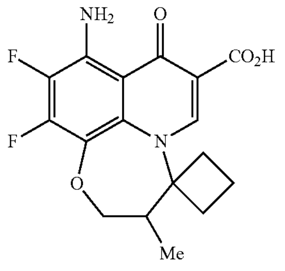 [SMILES: CC1COc2c(F)c(F)c(N)c3c(=O)c(C(=O)O)cn(c23)C12CCC2]

To a mixture of ethyl 9'-amino-10',11'-difluoro-2',3'-dihydro-3'-methyl-8'-oxospiro[cyclobutane-1,4'-[4H,8H]pyrido [1,2,3-ef][1,4]benzoxazepine]-7'-carboxylate (720 mg, 1.90 mmol) in EtOH (20 mL) was added 2N NaOH (10.0 mL) at room temperature and the mixture was heated at 50° C. for 3 hours. 2N HCl (10.0 mL) and water were added to the reaction mixture. The resulting precipitate was collected by filtration, washed with water and dried to give the title compound (654 mg, 98%) as a yellow solid. $^1$H-NMR (400 MHz, DMSO-$d_6$) δ 0.90 (3H, d, J=5.5 Hz), 1.64-1.76 (1H, m), 1.81-1.96 (1H, m), 2.35-2.72 (4H, m), 2.88-3.02 (1H, m), 3.64 (1H, t, J=11.6 Hz), 4.60-4.75 (1H, m), 7.46 (2H, brs), 8.26 (1H, s), 14.60 (1H, brs).

49J) Preparation of 9'-amino-10'-fluoro-2',3'-dihydro-3'-methyl-8'-oxo11'-[2-(2-pyridylamino)ethylamino]-spiro[cyclobutane-1,4%[4H,8H]pyrido[1,2,3-ef][1,4]benzoxazepine]-7'-carboxylic Acid

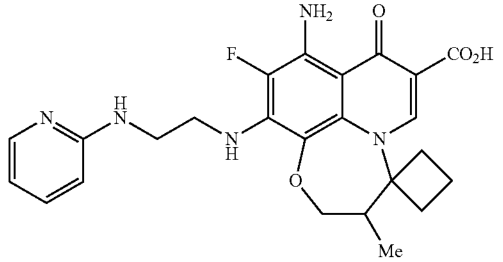 [SMILES: CC1COc2c(NCCNc3ccccn3)c(F)c(N)c3c(=O)c(C(=O)O)cn(c23)C12CCC2]

A solution of 9'-amino-10',11'-difluoro-2',3'-dihydro-3'-methyl-8'-oxospiro-[cyclobutane-1,4'-[4H,8H]pyrido[1,2,3-ef][1,4]benzoxazepine]-7'-carboxylic acid (300 mg, 0.856 mmol), N-2-(pyridinyl)-1,2-ethanediamine (177 mg, 1.29 mmol) and triethylamine (180 μL) in DMSO (4 mL) was stirred at 120° C. for 5 hours. Ice-water was added portionwise to the reaction mixture at 0° C. and the mixture was extracted with $CH_2Cl_2$. The combined organic extracts were dried over anhydrous $Na_2SO_4$, filtered, and concentrated in vacuo. Flash chromatography ($CH_2Cl_2$:MeOH=10:1) of the residue gave the title compound as a yellow amorphous solid (177 mg, 44%). $^1$H-NMR (400 MHz, DMSO-$d_6$) δ 0.86 (3H, d, J=5.5 Hz), 1.62-1.73 (1H, m), 1.79-1.93 (1H, m), 2.25-2.38 (1H, m), 2.38-2.64 (3H, m), 2.80-2.93 (1H, m), 3.27-3.50 (3H, m), 3.52-3.14 (2H, m), 4.50-4.60 (1H, m), 6.28 (1H, brs), 6.42-6.52 (2H, m), 6.69 (1H, t, J=5.5 Hz), 7.01 (2H, brs), 7.32-7.40 (1H, m), 7.96 (1H, dd, J=4.9 and 1.2 Hz), 8.07 (1H, s), 15.24 (1H, s). HRESIMS (+) 468.20923 (Calcd for $C_{24}H_{27}FN_5O_4$, 468.20471).

Example 50

9'-amino-10'-fluoro-2',3'-dihydro-2'-methyl-8'-oxo-11'-[2-(2-pyridylamino)ethylamino]spiro[cyclobutane-1,4'-[4H,8H]pyrido[1,2,3-ef][1,4]benzoxazepine]-7'-carboxylic Acid 50A) Preparation of 1-[(benzoylamino)cyclobutyl]acetaldehyde

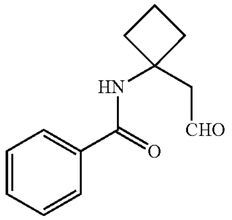 [SMILES: O=CCC1(NC(=O)c2ccccc2)CCC1]

DIBAL (40.0 mL, 1M solution in toluene) was added dropwise at −78° C. to a stirred solution of ethyl [1-(benzoylamino)cyclobutyl]acetate (6.86 g, 26.3 mmol) in THF (130 mL) over the course of 30 minutes. After stirring at −78° C. for 6 hours, MeOH (10 mL) was added dropwise to the mixture at −78° C. over the course of 30 minutes. Saturated aqueous $NH_4Cl$ (20 mL) was then added to the mixture, and the mixture was stirred at room temperature for 1 hour. The mixture was extracted with $Et_2O$, dried over anhydrous $Na_2SO_4$, filtered, and concentrated in vacuo. Flash chromatography (hexane:AcOEt=2:1) of the residue gave the title compound as a colorless solid (1.82 g, 32%). $^1$H-NMR (400 MHz, $CDCl_3$) δ 1.87-2.07 (2H, m), 2.25-2.34 (2H, m), 2.36-2.45 (2H, m), 3.28 (2H, s), 6.57 (1H, brs), 7.39-7.45 (2H, m), 7.46-7.53 (1H, m), 7.70-7.76 (2H, m), 9.79 (1H, s).

50B) Preparation of 1-[1-(benzoylamino)cyclobutyl]-2-propanol

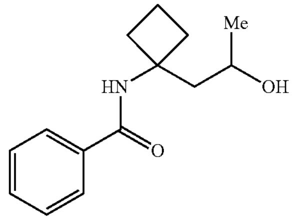 [SMILES: CC(O)CC1(NC(=O)c2ccccc2)CCC1]

Methyl magnesium chloride (14.0 mL, 3M solution in THF) was added to a stirred solution of [1-(benzoylamino) cyclobutyl]acetaldehyde (2.82 g, 13.0 mmol) in THF (30 mL) at −0° C., and the mixture was stirred at room temperature for 5 hours. Saturated aqueous $NH_4Cl$ (10 mL) was added to the mixture 0° C., and the resulting mixture was extracted with ethyl acetate. The combined organic extracts were dried over anhydrous $Na_2SO_4$, filtered, and concentrated in vacuo. Flash chromatography (hexane:AcOEt=2:1) of the residue gave the title compound as a colorless oil (2.65 g, 87%). $^1$H-NMR (400 MHz, $CDCl_3$) δ 1.25 (3H, d, J=6.1 Hz), 1.77-2.12 (5H, m), 2.28-2.40 (1H, m), 2.52 (1H, q, J=10.4 Hz), 2.75-2.85 (1H, m), 3.26 (1H, d, J=3.7 Hz), 3.97-4.07 (1H, m), 6.91 (1H, brs), 7.39-7.46 (2H, m), 7.46-7.53 (1H, m), 7.75-7.82 (2H, m).

50C) Preparation of 1-[1-(benzylamino)cyclobutyl]-2-propanol

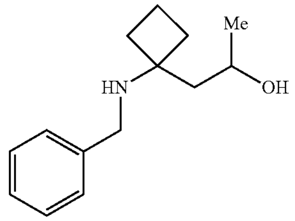 [SMILES: CC(O)CC1(NCc2ccccc2)CCC1]

$LiAlH_4$ (1.20 g, 31.6 mmol) was added to a solution of 1-[1-(benzoylamino) cyclobutyl]propanol (2.64 g, 11.3 mmol) in THF (40 mL) at room temperature. The mixture was stirred at room temperature for 1 hour and refluxed for 30 minutes. The mixture was cooled in an ice-water bath and a few drops of water were added. The mixture was then diluted with ethyl acetate, dried over anhydrous $Na_2SO_4$, filtered, and concentrated in vacuo. Flash chromatography (AcOEt) of the residue gave the title compound as a colorless oil (2.25 g, 91%). $^1$H-NMR (400 MHz, $CDCl_3$) δ 1.21 (3H, d, J=6.1 Hz), 1.63 (1H, dd, J=13.7 and 2.4 Hz), 1.73-1.90 (5H, m), 2.04-2.13 (1H, m), 2.18-2.27 (1H, m), 3.59 (1H, d, J=11.6 Hz), 3.81 (1H, d, J=11.6 Hz), 4.07-4.16 (1H, m), 7.22-7.35 (5H, m).

50D) Preparation of 1-(1-aminocyclobutyl)-2-propanol

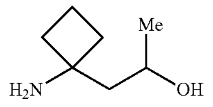

10% Pd—C (300 mg) was added to a solution of 1-[1-(benzylamino)cyclobutyl]-2-propanol (2.24 g, 10.2 mmol) in EtOH (50 mL) and the mixture was stirred under $H_2$ gas (5 kgf/cm$^2$) at room temperature for 10 hours. The mixture was filtered and the filtrate was concentrated in vacuo. Distillation of the residue gave the title compound as a pale yellow oil (1.24 g, 94%).

$^1$H-NMR (400 MHz, $CDCl_3$) δ 1.17 (3H, d, J=6.1 Hz), 1.43 (1H, ddd, J=14.7, 10.4 and 1.2 Hz), 1.61-1.69 (1H, m), 1.72 (1H, dd, J=14.7 and 1.8 Hz), 1.75-1.90 (3H, m), 1.93-2.03 (1H, m), 2.12-2.20 (1H, m), 4.00-4.08 (1H, m).

50F) Preparation of ethyl 3-[1-(2-hydroxypropyl) cyclobutylamino]-2-(2,3,4,5-tetrafluorobenzoyl) acrylate

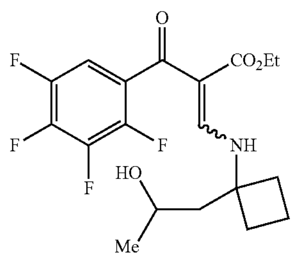 [SMILES: CCOC(=O)C(=CNC1(CC(C)O)CCC1)C(=O)c1cc(F)c(F)c(F)c1F]

A stirred solution of ethyl 3-oxo-3-(2,3,4,5-tetrafluorophenyl)propionate (2.45 g, 9.27 mmol), $Ac_2O$ (5.30 mL, 56.1 mmol) and triethyl orthoformate (3.10 mL, 18.6 mmol) was heated at 120° C. for 3 hours. The mixture was concentrated in vacuo and dried under high vacuum. To 1-[1-aminocyclobutyl]-2-propanol (1.20 g, 9.29 mmol) in anhydrous toluene (10 mL) was slowly added to a mixture of the residue in anhydrous toluene (30 mL) at 0° C. and stirred at room temperature for 2 hours. The solvent was removed by evaporation. Flash chromatography (AcOEt:Hexane=1:1) of the residue gave the title compound as a pale yellow solid (3.10 g, 83%). $^1$H-NMR (400 MHz, $CDCl_3$) δ 0.95 (0.6H, t, J=7.3 Hz), 1.09 (2.4H, t, J=7.3 Hz), 1.29 (3H, d, J=6.1 Hz), 1.51 (1H, brs), 1.83-2.05 (4H, m), 2.18-2.35 (3H, m), 2.41-2.53 (1H, m), 3.95-4.15 (3H, m), 6.96-7.13 (1H, m), 8.27 (0.8H, d, J=14.7 Hz), 8.31 (0.2H, d, J=14.7 Hz), 10.30 (0.2H, d, J=13.4 Hz), 11.56 (0.8H, d, J=13.4 Hz).

50G) Preparation of Ethyl 10',11'-difluoro-2',3'-dihydro-2'-methyl-8'-oxospiro[cyclobutane-1,4'-[4H,8H] pyrido[1,2,3-ef][1,4]benzoxazepine]-7'-carboxylate

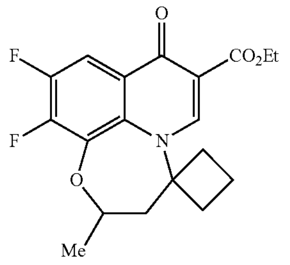 [SMILES: CCOC(=O)c1cn2c3c(c(F)c(F)cc3c1=O)OC(C)CC21CCC1]

NaH (40 mg) was added to a solution of ethyl 3-[1-(2-hydroxylpropyl)cyclobutylamino]-2-(2,3,4,5-tetrafluorobenzoyl)acrylate (404 mg, 1.00 mmol) in DMF (4 mL) at 0° C. NaH (40 mg) was added after stirring at 0° C. for 1 hour. The mixture was stirred at 0° C. for an additional hour, then at room temperature for 1 hour and at 80° C. for one additional hour. Water was added to the mixture portionwise at 0° C., and the resulting precipitate was isolated by filtration, washed successively with water and $iPr_2O$, and dried to give the title compound (244 mg, 67%) as a colorless solid. $^1$H-NMR (400 MHz, DMSO-$d_6$) δ 1.27 (3H, t, J=7.3 Hz), 1.43 (3H, d, J=6.1 Hz), 1.72 (1H, q, J=10.4 Hz), 1.90-2.04 (1H, m), 2.24 (1H, q, J=10.4 Hz), 2.34-2.43 (1H, m), 2.53-2.74 (4H, m), 4.24 (2H, q, J=7.3 Hz), 4.48-4.58 (1H, m), 7.72 (1H, qd, J=10.4 and 7.9 Hz), 8.40 (1H, s).

50H) Preparation of Ethyl 10',11'-difluoro-2',3'-dihydro-2'-methyl-9'-nitro-8'oxo-spiro[cyclobutane-1,4'-[4H,8H]pyrido[1,2,3-ef][1,4]benzoxazepine]-7'-carboxylate

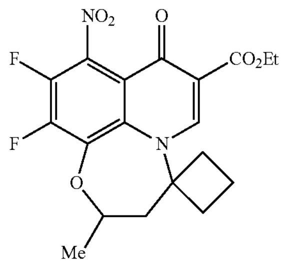 [SMILES: CCOC(=O)c1cn2c3c(c(F)c(F)c([N+](=O)[O-])c3c1=O)OC(C)CC21CCC1]

A solution of ethyl 10',11'-difluoro-2',3'-dihydro-2'-methyl-8'-oxospiro-[cyclobutane-1,4'-[4H,8H]pyrido[1,2,3-ef][1,4]benzoxazepine]-7'-carboxylate (182 mg, 0.501 mmol) in concentrated $H_2SO_4$ (2 mL) was treated portionwise at 0° C. with solid $KNO_3$ (72.0 mg, 0.712 mmol). After stirring at 0° C. for 2 hours, the reaction mixture was poured into ice-water and the resulting precipitate was isolated by filtration, washed with water and dried to give the title compound (190 mg, 93%) as a pale yellow solid. $^1$H-NMR (400 MHz, DMSO-$d_6$) δ 1.27 (3H, t, J=7.3 Hz), 1.45 (3H, d, J=6.1 Hz), 1.61-1.77 (1H, m), 1.90-2.03 (1H, m), 2.29-2.48 (3H, m), 2.57-2.72 (3H, m), 4.24 (2H, q, J=7.3 Hz), 4.62-4.73 (1H, m), 8.43 (1H, s).

50I) Preparation of Ethyl 9'-amino-10',11'-difluoro-2',3'-dihydro-2'-methyl-8'-oxospiro[cyclobutane-1,4'-[4H,8H]pyrido[1,2,3-ef][1,4]benzoxazepine]-7'-carboxylate

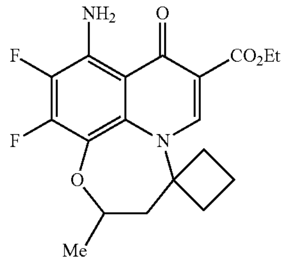 [SMILES: CCOC(=O)c1cn2c3c(c(F)c(F)c(N)c3c1=O)OC(C)CC21CCC1]

A solution of ethyl 10',11'-difluoro-2',3'-dihydro-2'-methyl-9'-nitro-8'-oxospiro-[cyclobutane-1,4'-[4H,8H]pyrido [1,2,3-ef][1,4]benzoxazepine]-7'-carboxylate (1.13 g, 2.77 mmol) in DMF (70 mL) was treated with hydrogen under atmospheric pressure over 10% Pd/C (230 mg) at 50° C. for 2 hours. The catalyst was removed by filtration through Celite and the filtrate was concentrated in vacuo. The residue was washed with EtOH, collected by filtration and dried to give the title compound (824 mg, 79%) as a pale yellow solid. $^1$H-NMR (400 MHz, DMSO-$d_6$) δ 1.26 (3H, t, J=7.3 Hz), 1.36 (3H, d, J=6.1 Hz), 1.70 (1H, q, J=10.4 Hz), 1.86-2.00 (1H, m), 2.25 (1H, q, J=10.4 Hz), 2.30-2.39 (1H, m), 2.42-2.63 (4H, m), 4.14-4.27 (2H, m), 4.27-4.37 (1H, m),7.49 (2H, brs), 8.22 (1H, s).

50.1) Preparation of 9'-amino-10',11'-difluoro-2',3'-dihydro-2'-methyl-8'-oxospiro[cyclobutane-1,4%[4H,8H]pyrido[1,2,3-ej][1,4]benzoxazepine]-7'-carboxylic Acid

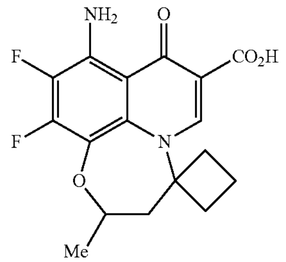 [SMILES: CC1CC2(CCC2)n2cc(C(=O)O)c(=O)c3c(N)c(F)c(F)c(c32)O1]

2N NaOH (10.0 mL) was added to a mixture of ethyl 9'-amino-10',11'-difluoro-2',3'-dihydro-2'-methyl-8'-oxospiro[cyclobutane-1,4'-[4H,8H]pyrido[1,2,3-ef][1,4]benzoxazepine]-7'-carboxylate (768 mg, 2.03 mmol) in EtOH (20 mL) at room temperature and the mixture was heated at 50° C. for 3 hours. 2N HCl (10.0 mL) and water were added to the reaction mixture. The resulting precipitate was collected by filtration, washed successively with water and dried to give the title compound (703 mg, 99%) as a yellow solid. $^1$H-NMR (400 MHz, DMSO-$d_6$) δ 1.37 (3H, d, J=6.1 Hz), 1.70 (1H, q, J=11.0 Hz), 1.88-2.02 (1H, m), 2.31 (1H, q, J=11.0 Hz), 2.37-2.69 (5H, m), 4.30-4.42 (1H, m), 7.43 (1H, brs), 8.47 (1H, s), 14.61 (1H, brs).

50K) Preparation of 9'-amino-10'-fluoro-2',3'-dihydro-2'-methyl-8'-oxo-11'-[2-(2-pyridylamino)ethylamino]spiro[cyclobutane-1,4'-[4H,8H]pyrido[1,2,3-ef][1,4]benzoxazepine]-7'-carboxylic acid

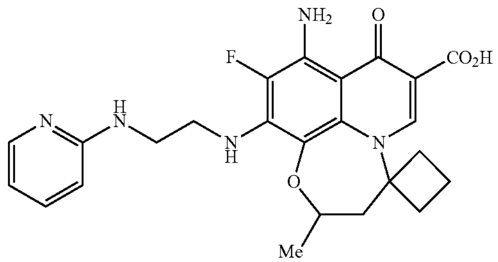 [SMILES: CC1CC2(CCC2)n2cc(C(=O)O)c(=O)c3c(N)c(F)c(NCCNc4ccccn4)c(c32)O1]

A solution of 9'-amino-10',11'-difluoro-2',3'-dihydro-2'-methyl-8'-oxospiro-[cyclobutane-1,4'-[4H,8H]pyrido[1,2,3-ef][1,4]benzoxazepine]-7'-carboxylic acid (351 mg, 1.00 mmol), N-2-pyridinyl-1,2-ethanediamine (210 mg, 1.53 mmol) and triethylamine (0.22 mL) in DMSO (5 mL) was stirred at 120° C. for 5 hours. The reaction mixture was added portionwise to ice-water at 0° C. and the mixture was extracted with $CH_2Cl_2$. The combined extracts were dried over anhydrous $Na_2SO_4$, filtered and concentrated in vacuo. Flash chromatography ($CH_2Cl_2$:MeOH=10:1) of the residue gave the title compound as a yellow amorphous solid (278 mg, 59%). $^1$H-NMR (400 MHz, DMSO-$d_6$) δ 1.29 (3H, d, J=6.1 Hz), 1.67 (1H, q, J=10.4 Hz), 1.84-1.99 (1H, m), 2.21 (1H, q, J=10.4 Hz), 2.30-2.40 (1H, m), 2.40-2.62 (4H, m), 3.40-3.50 (2H, m), 3.53-3.67 (2H, m), 4.08-4.20 (1H, m), 5.91 (1H, brs), 6.42-6.50 (2H, m), 6.65 (1H, t, J=5.5 Hz), 7.00 (2H, brs), 7.32-7.38 (1H, m), 7.94 (1H, dd, J=4.9 and 1.2 Hz), 8.25 (1H, s), 15.24 (1H, s). HRESIMS (+) 467.20453 (Calcd for $C_{24}H_{27}FN_5O_4$, 468.20471).

Example 51

9'-amino-10'-fluoro-8'-oxospiro[cyclobutane-1,3'(4'H)-[2H,8H]pyrido[1,2,3-ef][1,4]benzoxazepine]-7'-carboxylic Acid 51A) Preparation of Ethyl 5-[[1-(hydroxymethyl)cyclobutyl]-methylamino]-2-(2,3,4,5-tetrafluorobenzoyl)acrylate

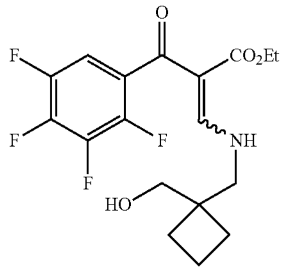 [SMILES: CCOC(=O)C(=CNCC1(CO)CCC1)C(=O)c1cc(F)c(F)c(F)c1F]

A stirred solution of ethyl 3-oxo-3-(2,3,4,5-tetrafluorophenyl)propionate (2.80 g, 10.6 mmol), $Ac_2O$ (6.01 mL, 63.6 mmol) and triethyl orthoformate (3.53 mL, 21.2 mmol) was heated at 120° C. for 3 hours. The mixture was concentrated in vacuo and dried under high vacuum. The crude product was dissolved in toluene (30 mL) and a suspension of [1-(aminomethyl)cyclobutyl]]methanol hydrochloride (1.60 g, 10.6 mmol) in toluene (20 mL) and triethylamine (1.48 mL, 10.6 mmol) were added under ice-cooling. The mixture was stirred at room temperature for 6 hours and concentrated in vacuo to yield the crude product. The crude product was purified by column chromatography (Hexane: EtOAc 10:1→2:1) to yield the title compound (1.88 g, 46%) as a white solid. $^1$H-NMR (400 MHz, $CDCl_3$) δ 0.95-1.12 (3H, m), 1.66-1.69 (1H, m), 1.81-1.91 (4H, m), 1.94-2.03 (2H, m), 3.57 (2H, d, J=6.7 Hz), 3.72 (2H, d, J=4.3 Hz), 4.00-4.10 (2H, m), 6.96-7.12 (1H, m), 8.09-8.15 (1H, m), 9.65-11.15 (1H, m).

51B) Preparation of Ethyl 10',11'-difluoro-8'-oxospiro[cyclobutane-1,3'(4'H)-[2H,8H]pyrido[1,2,3-ef][1,4]benzoxazepine]-7'-carboxylate

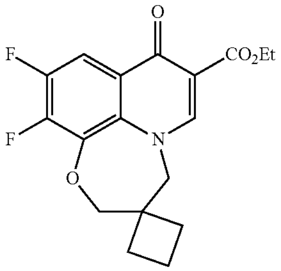 [SMILES: CCOC(=O)c1cn2c3c(c(F)c(F)cc3c1=O)OCC1(CCC1)C2]

A solution of ethyl 5-[[1-(hydroxymethyl)cyclobutyl]methylamino]-2-(2,3,4,5-tetrafluorobenzoyl)acrylate (1.88 g, 4.83 mmol) in DMF (10 mL) was added to a suspension of 60% NaH in oil (424 mg, 10.6 mmol) in DMF (15 mL) under argon atmosphere and ice-cooling. The reaction mixture was stirred at room temperature for one hour, then at 90° C. for an additional hour. The mixture was then poured into ice-water and the precipitate was collected by vacuum filtration and washed with hexane and water to yield the title compound (1.41 g, 84%) as a pale yellow solid. $^1$H-NMR (400 MHz, DMSO-$d_6$) δ 1.29 (3H, t, J=7.3 Hz), 1.80-2.09 (6H, m), 4.24 (2H, q, J=7.3 Hz), 4.43 (2H, s), 4.61 (2H, s), 7.73 (1H, dd, J=10.4, 7.9 Hz), 8.74 (1H, s). EIMS (+): 349 $[M]^+$.

51C) Preparation of Ethyl 10',11'-difluoro-9'-nitro-8'-oxospiro-[cyclobutane-1,3'(4'H)-[2H,81-f]pyrido[1,2,3-ej][1,4]benzoxazepine]-7'-carboxylate

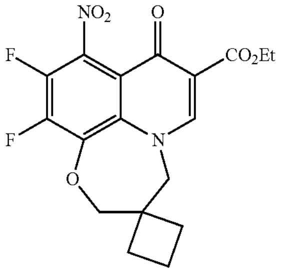 [SMILES: CCOC(=O)c1cn2c3c(c(F)c(F)c([N+](=O)[O-])c3c1=O)OCC1(CCC1)C2]

A solution of ethyl 10,11-difluoro-8-oxospiro[cyclobutane-1,3'(4'H)-[2H,8H]-pyrido[1,2,3-ef][1,4]benzoxazepine]-7-carboxylate (1.29 g, 3.69 mmol) in concentrated $H_2SO_4$ (15 mL) was treated portionwise with solid $KNO_3$ (523 mg, 5.17 mmol) at 0° C. After stirring at 0° C. for 3 hours, the reaction mixture was poured into ice-water and the resulting precipitate was removed by filtration, washed with water and suspended in hot EtOH. The reaction mixture was stirred at reflux for 1 hour, cooled to room temperature and the precipitate was collected by filtration to yield the title compound (1.20 g, 82%) as a pale yellow solid. $^1$H-NMR (400 MHz, DMSO-$d_6$) δ 1.27 (3H, t, J=7.3 Hz), 1.80-1.88 (1H, m), 1.92-2.00 (2H, m), 2.02-2.09 (3H, m), 4.23 (2H, q, J=7.3 Hz), 4.51 (2H, s), 4.61 (2H, s), 8.81 (1H, s). ESIMS (+): 395 $[M+H]^+$.

51D) Preparation of Ethyl 9'-amino-10',11'-difluoro-8'-oxospiro-[cyclobutane-1,3'(4'H)-[2H,8H]pyrido[1,2,3-ef][1,4]benzoxazepine]-7'-carboxylate

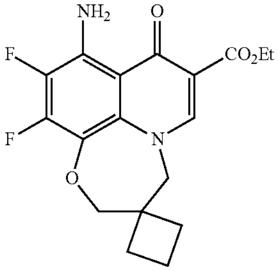 [SMILES: CCOC(=O)c1cn2c3c(c(F)c(F)c(N)c3c1=O)OCC1(CCC1)C2]

A solution of ethyl 10',11'-difluoro-9'-nitro-8'-oxo spiro[cyclobutane-1,3'(4'H)-[2H,8H]pyrido[1,2,3-ef][1,4]benzoxazepine]-7'-carboxylate (1.18 g, 2.99 mmol) in DMF (60 mL) was treated with hydrogen under pressure (0.35 MPa) over 10% Pd/C (120 mg) at 50° C. for 7 hours. The catalyst was removed by filtration through Celite and silica gel (50 g) was added to the filtrate. The mixture was stirred for 30 minutes, the silica gel was removed by filtration and the solvent was removed in vacuo. The precipitate was washed with EtOH and dried to yield the title compound (320 mg, 29%) as a pale yellow solid. $^1$H-NMR (400 MHz, DMSO-$d_6$) δ 1.26 (3H, t, J=7.3 Hz), 1.76-2.04 (6H, m), 4.17-4.26 (4H, m), 4.51 (2H, s), 7.57 (2H, brs), 8.52 (1H, s). ESIMS (+): 365 $[M+H]^+$.

51E) Preparation of 9'-amino-10',11'-difluoro-8'-oxospiro-[cyclobutane-1,3'-(4'H)-[2H,8H]pyrido[1,2,3-ej][1,4]benzoxazepine]-7'-carboxylic Acid

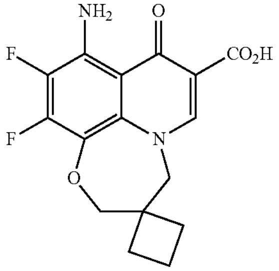 [SMILES: Nc1c(F)c(F)c2c3c1c(=O)c(C(=O)O)cn3CC1(CCC1)CO2]

A solution of ethyl 9'-amino-10',11'-difluoro-8'-oxospiro[cyclobutane-1,3'-(4'H)-[2H,8H]pyrido[1,2,3-ef][1,4]benzoxazepine]-7'-carboxylate (300 mg, 0.823 mmol) in a mixture of AcOH—$H_2O$—$H_2SO_4$ (2:1:0.3 v/v, 6.6 mL) was heated at 100° C. for 2 hours. The reaction mixture was poured into ice-water and the resulting precipitate was collected by filtration, washed with water and dried to yield the title compound (242 mg, 87%) as a brown solid $^1$H-NMR (400 MHz, DMSO-$d_6$) δ 1.76-2.07 (6H, m), 4.27 (2H, s), 4.69 (2H, s), 7.48 (2H, brs), 8.92 (1H, s), 14.63 (1H, s). ESIMS (+): 337 $[M+H]^+$.

51F) Preparation of 9'-amino-10'-fluoro-8'-oxo-11-[2-(pyridin-2-ylamino)ethylamino]spiro[cyclobutane-1,3'(4'H)-[2H,8H]pyrido[1,2,3-ef][1,4]benzoxazepine-7'-carboxylic acid

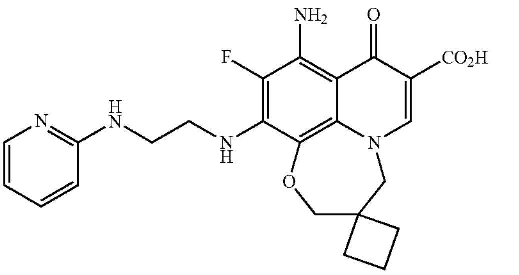 [SMILES: Nc1c(F)c(NCCNc2ccccn2)c2c3c1c(=O)c(C(=O)O)cn3CC1(CCC1)CO2]

A solution of 9'-amino-10',11'-difluoro-8'-oxospiro[cyclobutane-1,3'(4'H)-2H,8H]pyrido[1,2,3-ef][1,4]benzoxazepine]-7'-carboxylic acid (220 mg, 0.654 mmol), N-2-pyridinyl-1,2-ethanediamine (135 mg, 0.981 mmol) and triethylamine (0.137 mL, 0.981 mmol) in DMSO (5 mL) was stirred at 100° C. for 5 hours. The precipitate was removed by filtration through Celite, water was added to the filtrate and the resulting precipitate was collected by filtration, washed with EtOH and dried to yield the title compound (197 mg, 66%) as a pale brown solid. $^1$H-NMR (400 MHz, DMSO-$d_6$) δ 1.73-1.87 (3H, m), 1.91-2.06 (3H, m), 3.43-3.47 (2H, m), 3.53-3.60 (2H, m), 4.02 (2H, s), 4.55 (2H, s), 6.25-6.32 (1H, m), 6.45-6.49 (2H, m), 6.65-6.73 (1H, m), 7.02 (2H, brs), 7.35 (1H, td, J=6.7, 1.8 Hz), 7.95 (1H, dd, J=5.5, 1.2 Hz), 8.65 (1H, s), 15.25 (1H, s). HRESIMS (+): 454.18998 (+0.93 mmu).

Example 52

9'-amino-10'-fluoro-8'-oxo-11'-[2-(2-pyridylamino)ethylamino]spiro[cyclopropane-1,3'(4'H)-[2H,8H]pyrido[1,2,3-ef]benzoxazepine]-7'-carboxylic Acid 52A) Preparation of ethyl 3-[[1-(hydroxymethyl)cyclopropyl]-methylamino]-2-(pentafluorobenzoyl)acrylate

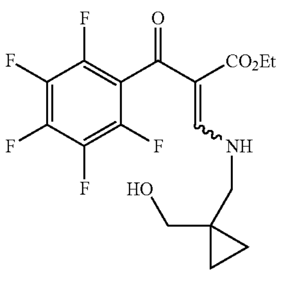 [SMILES: CCOC(=O)C(=CNCC1(CO)CC1)C(=O)c1c(F)c(F)c(F)c(F)c1F]

A solution of ethyl 3-oxo-3-(pentafluorophenyl)propionate (7.01 g, 24.8 mmol), $Ac_2O$ (14.0 mL, 148 mmol) and triethyl orthoformate (8.25 mL, 49.6 mmol) was heated at 120° C. for 2 h. The mixture was concentrated in vacuo and dried under high vacuum. The crude product was dissolved in anhydrous toluene (120 mL) and [1-(aminomethyl)-cyclopropyl]]methanol (2.51 g, 24.8 mmol) was added very slowly at 0° C. The reaction mixture was stirred at room temperature for 3 h, and the solvent was removed by evaporation. The crude product was purified by column chromatography (Hexane: EtOAc 2:1) to yield the title compound (7.30 g, 75%) as a pale yellow solid. Mp. 74.5-76.0° C. $^1$H-NMR (400 MHz, $CDCl_3$) δ 0.57-0.63 (4H, m), 1.12 (3H, t, J=7.3 Hz), 1.62 (2H, t, J=5.5 Hz), 3.50 (2H, d, J=5.5 Hz), 3.98-4.17 (2H, m), 8.17 (1H, d, J=5.5 Hz), 11.22 (1H, brs). EIMS (+) 393 $[M]^+$. Anal. Calcd for $C_{17}H_{16}F_5NO_4$: C, 51.80; H, 3.90; N, 3.56. Found: C, 51.91; H, 4.10; N, 3.56.

52B) Preparation of Ethyl 9',10',11'-trifluoro-8'-oxospiro-[cyclopropane-1,3'(4'H)-[2H,8H]pyrido[1,2,3-ef]benzoxazepine]-7'-carboxylate

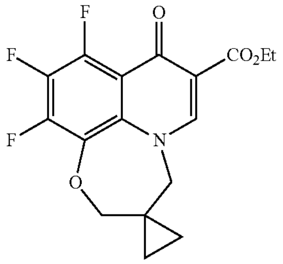 [SMILES: CCOC(=O)c1cn2c3c(c(F)c(F)c(F)c3c1=O)OCC1(CC1)C2]

A solution of NaH (920 mg, 23.0 mmol, 60% in oil) in DMF (50 mL) was cooled to 0° C. and treated dropwise with ethyl 3-[[1-(hydroxymethyl)cyclopropyl]methylamino]-2-(pentafluorobenzoyl)acrylate (4.10 g, 10.4 mmol) in DMF (10 mL). The reaction mixture was stirred 4 hours at room temperature and for an additional hour at 80° C. The reaction mixture was then poured into ice water and the resulting precipitate was removed by filtration and washed with water. The resulting solid was dissolved in 100 mL of EtOH—$CH_2Cl_2$ (2:1) and filtered. The filtrate was concentrated to 30 mL, and the resulting precipitate was removed by filtration, washed with EtOH and dried to yield the title compound (2.45 g, 67%) as a pale yellow solid. M.p. 209-211° C. $^1$H-NMR (400 MHz, DMSO) δ0.56 (2H, t, J=6.1 Hz), 0.77 (2H, t, J=6.1 Hz), 1.26 (3H, t, J=7.3 Hz), 4.20 (2H, s), 4.21 (2H, q, J=7.3 Hz), 4.49 (2H, s). EIMS (+) 353 $[M]^+$.

52C) Preparation of Ethyl 10',11'-difluoro-9'-(2,4-dimethoxybenzylamino)-8'-oxospiro[cyclopropane-1,3'(4'H)-[2H,8H]pyrido[1,2,3-ef]benzoxazepine]-7'-carboxylate

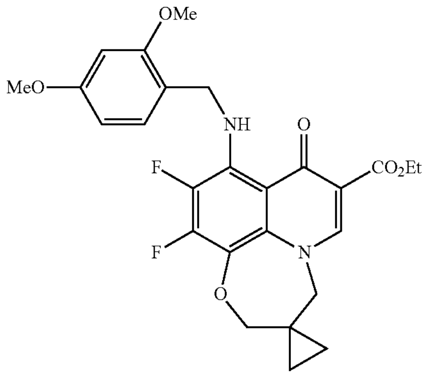 [SMILES: CCOC(=O)c1cn2c3c(c(F)c(F)c(NCc4ccc(OC)cc4OC)c3c1=O)OCC1(CC1)C2]

A solution of ethyl 9',10',11'-trifluoro-8'-oxospiro[cyclopropane-1,3'(4'H)-[2H,8H]pyrido[1,2,3-ef]benzoxazepine]-7'-carboxylate (1.51 g, 4.27 mmol) and triethylamine (0.890 mL, 6.34 mmol) and 2,4-dimethoxybenzylamine (0.635 mL, 4.29 mmol) in toluene (30 mL) was stirred at 90° C. for 6 hours. The reaction mixture was poured into water, and extracted with EtOAc. The organic layer was washed with water and brine, dried over anhydrous $Na_2SO_4$ and the solvent was removed. The crude product was purified by column chromatography (Hexane: EtOAc 2:3) to yield the title compound (1.48 g, 69%) as a yellow solid.

M.p. 131-132° C. $^1$H-NMR (400 MHz, $CDCl_3$) δ 0.58 (2H, t, J=5.5 Hz), 0.75 (2H, t, J=5.5 Hz), 1.36 (3H, t, J=7.3 Hz), 3.78 (3H, s), 3.82 (3H, s), 4.03 (2H, s), 4.26 (2H, brs), 4.35 (2H, q, J=7.3 Hz), 4.59 (2H, dd, J=6.1, 3.0 Hz), 6.37-6.46 (2H, m), 7.23 (1H, d, J=7.9 Hz), 8.01 (1H, s), 10.48 (1H, brs). EIMS (+) 500 $[M]^+$.

52D) Preparation of Ethyl 9'-amino-10',11'-difluoro-8'-oxospiro-[cyclopropane-1,3'(4'H)-[2H,8H]pyrido[1,2,3-ej]benzoxazepine]-7'-carboxylate

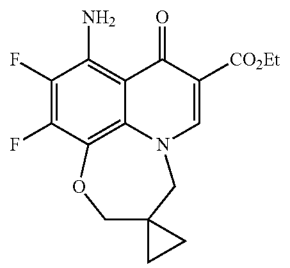 [SMILES: CCOC(=O)c1cn2c3c(c(F)c(F)c(N)c3c1=O)OCC1(CC1)C2]

A solution of ethyl 10',11'-difluoro-9'-(2,4-dimethoxybenzylamino)-8'-oxospiro-[cyclopropane-1,3'(4'H)-[2H,8H]pyrido[1,2,3-ef]benzoxazepine]-7'-carboxylate (1.42 g, 2.84 mmol) in trifluoroacetic acid (30 mL) was stirred at room temperature for 15 minutes. The reaction mixture was diluted with $CH_2Cl_2$ and washed with saturated $NaHCO_3$, brine, and dried over anhydrous $Na_2SO_4$. The solvent was removed, and the resulting solid was dissolved in DMF and filtered. The filtrate was poured into water and the resulting precipitate was removed by filtration, washed with water and dried to yield the title compound (835 mg, 84%) as a yellow solid. M.p. 278-279° C. $^1$H-NMR (400 MHz, DMSO) δ 0.50 (2H, dd, J=6.1, 4.8 Hz), 0.71 (2H, dd, J=6.1, 4.8 Hz), 1.25 (3H, t, J=7.3 Hz), 4.03 (2H, s), 4.17 (2H, q, J=7.3 Hz), 4.44 (2H, s), 7.68 (2H, brs), 8.32 (1H, s). ESIMS (+): 351 [M+H].

52E) Preparation of Ethyl 9'-amino-10',11'-difluoro-8'-oxospiro-[cyclopropane-1,3'(4'H)-(2H,8H]pyrido[1,2,3-ef]benzoxazepine]-7'-carboxylic Acid

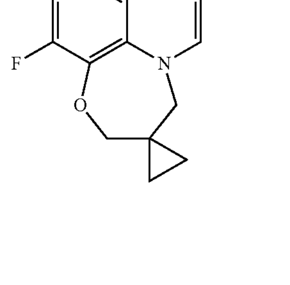

A solution of ethyl 9'-amino-10',11'-difluoro-8'-oxospiro[cyclopropane-1,3'-(4'H)-2H,8H]pyrido[1,2,3-ej]benzoxazepine]7'-carboxylate (830 mg, 2.37 mmol) and 1M NaOH aq. in EtOH (20 mL) was stirred at room 50° C. for 3 hours. The solvent was removed and the residue was dissolved in water. The solution was acidified to pH 7 with 2M HCl and the resulting precipitate was removed by filtration, washed with water, and dried to yield the title compound (757 mg, 99%) as a pale yellow solid. $^1$H-NMR 400 MHz, DMSO) δ 0.51 (2H, dd, J=6.1, 4.8 Hz), 0.73 (2H, dd, J=6.1, 4.8 Hz), 4.07 (2H, s), 4.62 (2H, s), 7.58 (2H, brs), 8.67 (1H, s), 14.66 (1H, s). ESIMS (+): 323[M+11].

52F) Preparation of 9'-amino-10'-fluoro-8'-oxo-11'-[2-(2-pyridylamino)ethylamino]spiro[cyclopropane-1,3'(4'H)-[2H,8H]pyrido[1,2,3-ef]benzoxazepine]-7'-carboxylic Acid

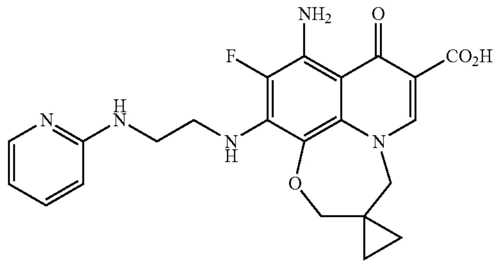 [SMILES: Nc1c(F)c(NCCNc2ccccn2)c2c3c1c(=O)c(C(=O)O)cn3CC1(CC1)CO2]

A solution of ethyl 9'-amino-10',11'-difluoro-8'-oxospiro[cyclopropane-1,3'-(4'H)-2H,8H]pyrido[1,2,3-ef]benzoxazepine]-7'-carboxylic acid (505 mg, 1.57 mmol), triethylamine (0.320 mL, 2.30 mmol) and N-2-pyridinyl-1,2-ethanediamine (322 mg, 2.35 mmol) in DMSO (8 mL) was stirred at 100° C. for 3 hours. The reaction mixture was poured into ice water and the resulting precipitate was removed by filtration, washed with ethanol, and dried to yield the title compound (595 mg, 86%) as a yellow solid.

$^1$H-NMR (400 MHz, DMSO) δ 0.39 (2H, t, J=6.1 Hz), 0.68 (2H, t, J=6.1 Hz), 3.40-3.50 (2H, m), 3.52-3.64 (2H, m), 3.86 (2H, s), 4.48 (2H, brs), 6.28 (1H, brs), 6.40-6.50 (2H, m), 6.66 (1H, t, J=5.5 Hz), 7.09 (2H, brs), 7.34 (1H, td, J=6.7, 1.8 Hz), 7.90-7.98 (1H, m), 7.90-8.00 (1H, m), 8.43 (1H, s), 15.26 (1H, s). ESIMS (+): 440$[M+H]^+$.

Example 53

9'-amino-10'-fluoro-2',3'-dihydro-8'-oxo-11'-[2-(2-pyridylamino)ethylamino]spiro [cyclobutane-1,4'-[4H,8H]pyrido[1,2,3-ef][1,4]benzodiazepine]-7'-carboxylic Acid 53A) Preparation of ethyl (1-hydroxycyclobutyl)acetate

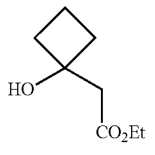 [SMILES: CCOC(=O)CC1(O)CCC1]

Trimethylchlorosilane (1.14 mL, 8.92 mmol) was added by syringe to a suspension of zinc powder (7.97 g, 0.122 mol) in absolute $Et_2O$ (200 mL). The mixture was stirred for 15 minutes at room temperature, heated to reflux, the heat source was removed, and ethyl bromoacetate (10.3 mL, 92.9 mmol) was added at such a rate that the ether solution gently boiled. After being heating for one hour at reflux, the mixture was stirred for one additional hour at room temperature. A solution of cyclopentanone (6.00 g, 75.9 mmol) in ether (30 mL) was added while the temperature of the mixture was maintained at 19-20° C. by intermittent cooling. The mixture was stirred for 1 hour at room temperature and poured into iced 25% ammonia (400 mL). The aqueous phase was extracted with ether, the combined organic phases were dried over $K_2CO_3$ and the solvent was evaporated to yield the title compound as a colorless oil (6.50 g, 54%). $^1$H-NMR (400 MHz, $CDCl_3$) δ 1.29 (3H, t, J=7.3 Hz), 1.47-1.64 (1H, m), 1.76-1.87 (1H, m), 1.93-2.06 (2H, m), 2.12-2.22 (2H, m), 2.67 (2H, s), 3.70 (1H, s), 4.19 (2H, q, J=7.3 Hz).

53B) Preparation of Ethyl [1-(benzoylamino)cyclobutyl]acetate

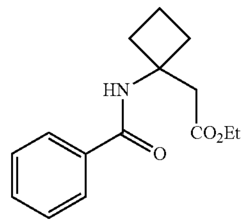 [SMILES: CCOC(=O)CC1(NC(=O)c2ccccc2)CCC1]

$H_2SO_4$ (2.20 mL, 41.3 mmol) was slowly added to a mixture of ethyl (1-hydroxycyclobutyl)acetate (6.45 g, 40.8 mmol) and benzonitrile (40 mL, 0.392 mol) at room temperature. The mixture was stirred for 1 hour at room temperature, then for an additional hour at 80° C. The mixture was cooled in an ice-water bath, and 2N NaOH solution was added until the solution reached pH=7. The mixture was extracted with ethyl acetate and the combined organic extracts were dried over anhydrous $Na_2SO_4$, filtered, and concentrated in vacuo. Flash chromatography (AcOEt:Hexane=5:1) of the residue gave the title compound as a colorless solid (5.40 g, 51%). $^1$H-NMR (400 MHz, $CDCl_3$) δ 1.22 (3H, t, J=7.3 Hz), 1.84-2.07 (2H, m), 2.22-2.32 (2H, m), 2.44-2.55 (2H, m), 3.05 (2H, s), 4.11 (2H, q, J=7.3 Hz), 6.73 (1H, s), 7.39-7.52 (3H, m), 7.72-7.79 (2H, m).

53C) Preparation of [1-(benzoylamino)cyclobutyl]acetic Acid

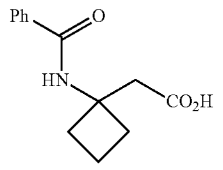 [SMILES: O=C(O)CC1(NC(=O)c2ccccc2)CCC1]

3N KOH (10 mL, 30 mmol) was added to a solution of ethyl 1-(benzoylamino)-cyclobutylacetate (3.87 g, 14.8 mmol) in EtOH (30 mL) at room temperature and the mixture was stirred for 1 hour. The reaction mixture was concentrated in vacuo and 6N HCl (5.0 mL) was added. The resulting precipitate was collected by filtration, washed successively with water and diisopropylether and dried to give the title compound (3.15 g, 91%) as a colorless solid. $^1$H-NMR (400 MHz, DMSO-$d_6$) δ 1.76-1.89 (2H, m), 2.16-2.26 (2H, m), 2.28-2.40 (2H, m), 2.90 (2H, s), 7.43 (2H, t, J=6.7 Hz), 7.50 (1H, t, J=6.7 Hz), 7.83 (2H, d, J=6.7 Hz), 8.45 (1H, s), 12.00 (1H, brs).

53D) Preparation of 11-(benzoylamino)cyclobutyl]acetamide

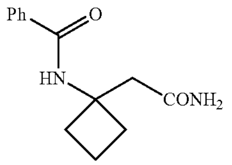 [SMILES: NC(=O)CC1(NC(=O)c2ccccc2)CCC1]

A mixture of [1-(benzoylamino)cyclobutyl]acetic acid (1.00 g, 4.29 mmol) and thionyl chloride (3.20 mL, 43.9 mmol) was stirred at room temperature for 1 hour. The mixture was concentrated in vacuo. 25% aqueous ammonia (30 mL) was added to a mixture of the residue in THF (30 mL) cooled in an ice-water bath. The mixture was stirred at room temperature for 1 hour. The mixture was then diluted with AcOEt-MeOH (3:1 v/v) and washed with water. The organic layer was dried over anhydrous $Na_2SO_4$, filtered, and concentrated in vacuo to give the title compound (925 mg, 93%) as a colorless solid. $^1$H-NMR (400 MHz, DMSO-$d_6$) δ 1.75-1.87 (2H, m), 2.14-2.23 (2H, m), 2.37-2.47 (2H, m), 2.70 (2H, s), 6.80 (1H, s), 7.29 (1H, s), 7.43 (2H, t, J=6.7 Hz), 7.50 (1H, t, J=6.7 Hz), 7.82 (2H, d, J=6.7 Hz), 8.39 (1H, s).

53E) Preparation of 2-[1-(benzylamino)cyclobutyl]ethylamine

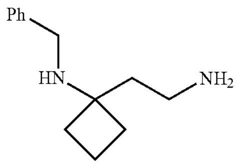 [SMILES: NCCC1(NCc2ccccc2)CCC1]

$LiAlH_4$ (570 mg, 15.0 mmol) was added portionwise to a solution of [1-(benzoylamino) cyclobutyl]acetamide (687 mg, 3.00 mmol) in THF (30 mL) at room temperature over the course of 30 minutes, and the mixture was heated to reflux for 5 hours. The mixture was cooled in an ice-water bath, aqueous THF and few drops of water were added, and the mixture was allowed to stand overnight. The mixture was filtered through celite and the solution was dried over anhydrous $Na_2SO_4$. The solution was concentrated in vacuo to give the title compound as a pale yellow oil (609 mg, 99%). $^1$H-NMR (400 MHz, $CDCl_3$) δ 1.65-1.80 (2H, m), 1.82 (2H, t, J=7.3 Hz), 1.86-2.02 (4H, m), 2.82 (2H, t, J=7.3 Hz), 3.65 (2H, s), 7.20-7.38 (5H, m).

53F) Preparation of 2-[1-(benzylamino)cyclobutyl]-N-(tert-butoxycarbonyl)ethylamine

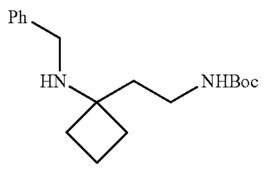 [SMILES: CC(C)(C)OC(=O)NCCC1(NCc2ccccc2)CCC1]

$Boc_2O$ (230 mg, 1.05 mmol) was added to a solution of 2-[1-(benzylamino)cyclobutyl]ethylamine (205 mg, 1.00 mmol) in THF (1 mL) in an ice-water bath. The mixture was stirred for 30 minutes in an ice-water bath. The mixture was concentrated in vacuo, and flash chromatography (AcOEt: Hexane=2:1) of the residue gave the title compound as a colorless solid (164 mg, 54%). $^1$H-NMR (400 MHz, DMSO-$d_6$) δ 1.36 (9H, s), 1.60-1.84 (6H, m), 1.84-1.94 (2H, m), 2.92-3.04 (2H, m), 3.53 (2H, s), 6.83 (1H, t, J=5.5 Hz), 7.21 (1H, t, J=7.3 Hz), 7.29 (2H, t, $J_7$ 7.3 Hz), 7.35 (2H, d J=7.3 Hz).

53G) Preparation of 2-(1-aminocyclobutyl)-N-(tert-butoxycarbonyl)ethylamine

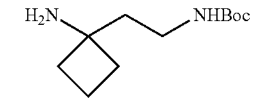

To a solution of 2-[1-(benzylamino)cyclobutyl]-N-(tert-butoxycarbonyl)ethylamine (117 mg, 0.384 mmol) in EtOH (5 mL) was added 10% Pd—C (35 mg) and the mixture was stirred under $H_2$ gas 5 kgf/cm$^2$ at room temperature for 5 h. The mixture was filtered, and the filtrate was concentrated in vacuo. The distillation of the residue gave the title compound as a colorless solid (76.0 mg, 92%). $^1$H-NMR (400 MHz, DMSO-$d_6$) δ 1.37 (9H, s), 1.49-1.58 (2H, m), 1.62-1.77 (4H, m), 1.82-1.91 (2H, m), 2.92-3.01 (2H, m), 6.78 (1H, t, J=5.5 Hz).

53H) Preparation of Ethyl 3-[1-[2-(tert-butoxycarbonylamino)ethyl]cyclobutylamino]-2-(2,3,4,5-tetrafluorobenzoyl)acrylate A stirred solution of ethyl 3-oxo-3-(2,3,4,5-tetrafluorophenyl)propionate (5.28 g, 20.0

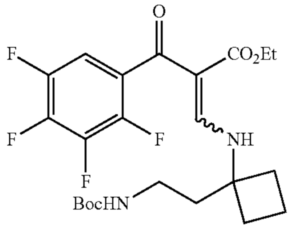 [SMILES: CCOC(=O)C(=CNC1(CCNC(=O)OC(C)(C)C)CCC1)C(=O)c1cc(F)c(F)c(F)c1F]

mmol), $Ac_2O$ (11.4 mL, 0.121 mol) and triethyl orthoformate (6.66 mL, 40.0 mmol) was heated at 120° C. for 3 hours. The mixture was concentrated in vacuo and dried under high vacuum. 2-[1-(benzylamino)cyclobutyl]-N-(tert-butoxycarbonyl)ethylamine (4.29 g, 20.0 mmol) in anhydrous toluene (30 mL) was slowly added to a mixture of the residue in anhydrous toluene (70 mL) at 0° C. and stirred at room temperature for 1 hour. The solvent was removed by evaporation, and flash chromatography (AcOEt:Hexane=2:1) of the residue gave the title compound as a pale yellow oil (9.10 g, 93%). $^1$H-NMR (400 MHz, $CDCl_3$) δ 0.98 (0.7H, t, J=7.3 Hz), 1.10 (2.3H, t, J=7.3 Hz), 1.43 (9H, s), 1.90-2.07 (4H, m), 2.17-2.38 (4H, m), 3.12-3.23 (2H, m), 4.00-4.15 (2H, m), 4.53-4.65 (1H, br), 6.95-7.03 (0.7H, m), 7.05-7.13 (0.3H, m), 8.13 (1H, d, J=14.1 Hz), 9.88 (0.3H, d, J=13.5 Hz), 11.29 (0.7H, d, J=13.5 Hz). HRMS (ESI$^+$) for $C_{18}H_{19}F_4NO_4$ $[M+H]^+$: calcd, 489.20126; found, 489.20200.

53I) Preparation of Ethyl 1'-(tert-butoxycarbonyl)-10',11'-difluoro-2',3'-dihydro-8'-oxospiro[cyclobutane-1,4'-[4H,8H]pyrido[1,2,3-d][1,4]benzodiazepine]-7'-carboxylate

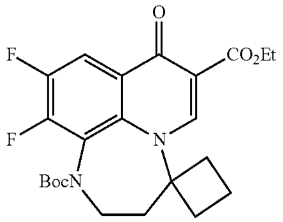 [SMILES: CCOC(=O)c1cn2c3c(c(F)c(F)cc3c1=O)N(C(=O)OC(C)(C)C)CCC21CCC1]

A solution of ethyl 3-[1-[2-(tert-butoxycarbonylamino)ethyl]cyclobutylamino]-2-(2,3,4,5-tetrafluorobenzoyl)acrylate (500 mg, 1.02 mmol) in DMF (5 mL) was cooled in an ice-water bath. NaH (82.0 mg, 2.05 mmol) was added and the mixture was stirred for 30 minutes, then at room temperature for 2 hours. The mixture was cooled 0° C. and water was added portionwise to the mixture. The resulting precipitate was combined by filtration, washed successively with water and diisopropylether and dried to give the title compound (312 mg, 68%) as a pale yellow solid. $^1$H-NMR (400 MHz, DMSO-$d_6$) δ 1.28 (3H, t, J=7.3 Hz), 1.42 (5H, s), 1.54 (4H, s), 1.67-1.80 (1H, m), 1.80-1.95 (1H, m), 2.10-2.22 (1H, m), 2.22-2.37 (2H, m), 2.40-2.56 (1H, m), 2.65-2.80 (2H, m), 4.17-4.37 (3H, m), 7.93-8.01 (1H, m), 8.47 (0.44H, s), 8.51 (0.56H, s).

53J) Preparation of Ethyl 10',11'-difluoro-2',3'-dihydro-9'-nitro-8'-oxospiro[cyclobutane-1,4'-[4H,8H]pyrido[1,2,3-ef][1,4]benzodiazepine]-7'-carboxylate

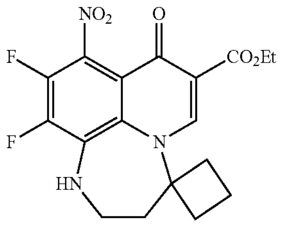 [SMILES: CCOC(=O)c1cn2c3c(c(F)c(F)c([N+](=O)[O-])c3c1=O)NCCC21CCC1]

A solution of ethyl 1'-(tert-butoxycarbonyl)-10',11'-difluoro-2',3'-dihydro-8'-oxospiro[cyclobutane-1,4'-[4H,8H]-pyrido[1,2,3-ef][1,4]benzodiazepine]-7'-carboxylate (5.50 g, 12.3 mmol) in concentrated $H_2SO_4$ (60 mL) was treated portionwise at 0° C. with solid $KNO_3$ (1.37 g, 13.6 mmol). After stirring at 0° C. for 1 hour, the reaction mixture was poured into ice-water and the resulting precipitate was combined by filtration and washed with water. Flash chromatography ($CH_2Cl_2$—AcOEt=1:1) of the residue gave the title compound as a yellow solid (3.28 g, 68%). $^1$H-NMR (400 MHz, DMSO-$d_6$) δ 1.26 (3H, t, J=7.3 Hz), 1.63-1.75 (1H, m), 1.85-1.98 (1H, m), 2.35-2.57 (6H, m), 3.47-3.55 (2H, m), 4.22 (2H, q, J=7.3 Hz), 6.96-7.02 (1H, m), 8.32 (1H, s).

53K) Preparation of Ethyl 9'-amino-10',11'-difluoro-2',3'-dihydro-8'-oxospiro[cyclobutane-1,4'-14H,81-f] pyrido[1,2,3-ef][1,4]benzodiazepine]-7'-carboxylate

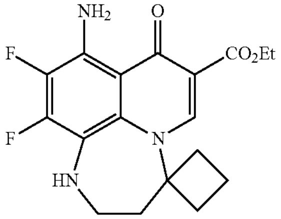 [SMILES: CCOC(=O)c1cn2c3c(c(F)c(F)c(N)c3c1=O)NCCC21CCC1]

A solution of ethyl 10',11'-difluoro-2',3'-dihydro-9'-nitro-8'-oxospiro[cyclobutane-1,4'-[4H,8H]pyrido[1,2,3-ej][1,4] benzodiazepine]-7'-carboxylate (1.23 g, 3.13 mmol) in DMF (77 mL) was treated with hydrogen under atmospheric pressure over 10% Pd/C (250 mg) at 50° C. for 1 hour. The catalyst was removed by filtration over Celite and the filtrate was concentrated in vacuo. Flash chromatography ($CH_2Cl_2$-MeOH=2:1) of the residue give the title compound as a yellow solid (1.00 g, 88%). $^1$H-NMR (400 MHz, DMSO-$d_6$) δ 1.25 (3H, t, J=7.3 Hz), 1.62-1.73 (1H, m), 1.82-1.96 (1H, m), 2.24-2.41 (4H, m), 2.45-2.60 (2H, m), 3.27-3.38 (2H, m), 4.19 (2H, q, J=7.3 Hz), 5.28-5.34 (1H, m), 7.10 (2H, brs), 8.12 (1H, s).

53L) Preparation of 9'-amino-10',11'-difluoro-2',3'-dihydro-8'-oxospiro[cyclobutane-1,4'-[4H,8H]pyrido [1,2,3-ef][1,4]benzodiazepine]-7'-carboxylic Acid

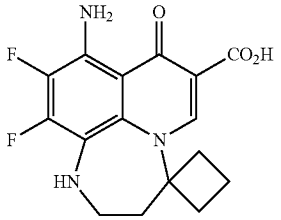 [SMILES: Nc1c(F)c(F)c2c3c1c(=O)c(C(=O)O)cn3C1(CCC1)CCN2]

2N NaOH (7.0 mL, 14.0 mmol) was added to a mixture of ethyl 9'-amino-10',11'-difluoro-2',3'-dihydro-8'-oxospiro[cyclobutane-1,4'-[4H,8H]pyrido[1,2,3-ef][1,4]-benzodiazepine]-7'-carboxylate (515 mg, 1.41 mmol) in EtOH (15 mL) at room temperature and the mixture was heated for 3 hours at 50° C. 2N HCl (7.0 mL) and water were added to the reaction mixture. The resulting precipitate was collected by filtration, washed successively with water and dried to give the title compound (397 mg, 83%) as a yellow solid. $^1$H-NMR (400 MHz, DMSO-$d_6$) δ 1.61-1.73 (1H, m), 1.82-1.97 (1H, m), 2.30-2.44 (4H, m), 2.55-2.69 (2H, m), 3.25-3.50 (2H, m), 5.53-5.59 (1H, br), 7.03 (2H, brs), 8.35 (1H, s), 14.75 (1H, s).

53M) Preparation of 9'-amino-10'-fluoro-2',3'-dihydro-8'-oxo-11'-[2-(2-pyridylamino)ethylamino]spiro [cyclobutane-1,4'-[4H,8H]pyrido[1,2,3-ef][1,4]benzodiazepine]-7'-carboxylic Acid

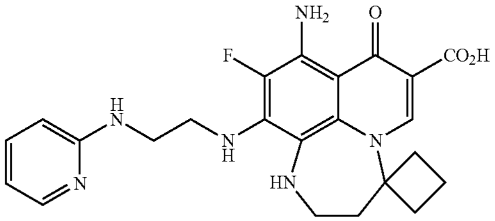 [SMILES: Nc1c(F)c(NCCNc2ccccn2)c2c3c1c(=O)c(C(=O)O)cn3C1(CCC1)CCN2]

A solution of 9'-amino-10',11'-difluoro-2',3'-dihydro-8'oxo-spiro[cyclobutane-1,4'-[4H,8H]pyrido[1,2,3-ef][1,4] benzodiazepine]-7'-carboxylic acid (300 mg, 0.895 mmol), N-(2-pyridinyl)-1,2-ethanediamine (185 mg, 1.35 mmol) and triethylamine (0.23 mL) in DMSO (4 mL) was stirred at 120° C. for 5 hours. The reaction mixture was added portionwise to ice-water and the mixture was extracted with $CH_2CH_2$. The organic layer was dried over anhydrous $Na_2SO_4$, and concentrated in vacuo. Flash chromatography ($CH_2Cl_2$-MeOH=10:1) of the residue gave the title compound as a yellow solid (259 mg, 64%). $^1$H-NMR (400 MHz, DMSO-$d_6$) δ 1.58-1.70 (1H, m), 1.78-1.92 (1H, m), 2.21-2.38 (4H, m), 2.43-2.60 (2H, m), 3.19-3.37 (2H, m), 3.37-3.51 (4H, m), 4.50 (1H, t, J=5.5 Hz), 5.50-5.58 (1H, br), 6.42-6.51 (2H, m), 6.65 (1H, t, J=5.5 Hz), 6.82 (2H, brs), 7.36 (1H, td, J=6.7 and 1.8 Hz), 7.95 (1H, dd, J=4.9 and 1.2 Hz), 8.18 (1H, s), 15.28 (1H, s). HRESIMS (+) 453.20466 (Calcd for $C_{23}H_{26}FN_6O$, 453.20504).

Example 54

8'-amino-9'-fluoro-7'-oxo-10'-[2-(2-pyridylamino) ethylamino]spiro[oxolane-3,3'(2'H)-[7H]pyrido[1,2,3-de][1,4]benzoxazine]-6'-carboxylic Acid 54A) Preparation of [3-(tert-butoxycarbonylamino)oxolan-3-yl]methanol

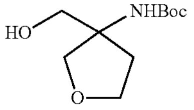

To a solution of 1-(tert-butoxycarbonylamino)cyclopentanecarboxylic acid (6.57 g, 28.4 mmol) in THF (60 mL) was added LiAlH4 (2.89 g, 61.0 mol) at room temperature. After stirred for 5 h, the reaction mixture was poured into ice-water and stirred for 30 min. To the mixture was added AcOEt and stirred for 30 min. The mixture was filtered and the filtrate was extracted with AcOEt. The extraction mixture was washed with water and brine, dried over MgSO4, and concentrated in vacuo. The residue was purified by column chromatography (Hexane:AcOEt 1:1) to give [3-(tert-butoxycarbonylamino)oxolan-3-yl]methanol (2.82 g, 46%) as a colorless solid. $^1$H-NMR (400 MHz, DMSO-$d_6$) δ1.36 (9H, s), 1.84-1.91 (1H, m), 1.93-2.02 (1H, m), 3.46 (2H, d, J=5.5 Hz), 3.59-3.62 (1H, d, J=8.6 Hz), 3.66-3.70 (3H, m), 4.83 (1H, t, J=5.5 Hz), 6.78 (1H, brs).

54B) Preparation of (3-aminooxolan-3-yl)methanol hydrochloride

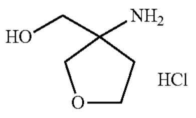

A solution of [3-(tert-butoxycarbonylamino)oxolan-3-yl] methanol (2.50 g, 11.5 mmol) in 4M HCl-dioxane (30 mL) was stirred at room temperature for 2 h. The mixture was concentrated in vacuo and dried to give (3-aminooxolan-3-yl)methanol hydrochloride as a pale brown oil (2.17 g, quant.). $^1$H-NMR (400 MHz, DMSO-$d_6$) δ 1.89-2.01 (2H, m), 3.51-3.58 (2H, m), 3.66 (2H, s), 3.71-3.76 (1H, m), 3.86-3.92 (1H, m), 8.33 (3H, brs).

54C) Preparation of Ethyl 3-[3-[1-(hydroxymethyl)] oxolanylamino]-(2,3,4,5-tetrafluorobenzoyl)acrylate

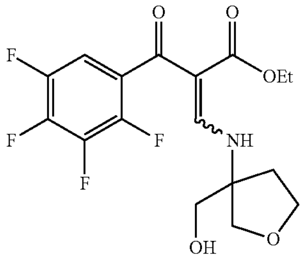 [SMILES: CCOC(=O)C(=CNC1(CO)CCOC1)C(=O)c1cc(F)c(F)c(F)c1F]

A stirred solution of ethyl 2,3,4,5-tetrafluorobenzoyl acetate (3.04 g, 11.5 mmol), $Ac_2O$ (6.52 mL, 69.0 mmol) and triethyl orthoformate (3.83 mL, 23.0 mmol) was heated at 130° C. for 3 h. The mixture was concentrated in vacuo and dried under high vacuum. The crude product was dissolved in EtOH (50 mL) and (3-aminooxolan-3-yl)methanol hydrochloride (2.17 g, 11.5 mmol), triethylamine (1.92 mL, 13.8 mmol) were added. After stirred at room temperature for 17 h, the mixture was concentrated in vacuo to yield crude product. The crude product was purified by column chromatography (Hexane: EtOAc 4:1→1:2) to yield 3-∂3-[1-(hydroxymethyl) oxolanylamino]-(2,3,4,5-tetrafluorobenzoyl)acrylate (4.18 g, 93%) as a yellow oil. $^1$H-NMR (400 MHz, DMSO) δ 0.87 (3H×¼, t, J=7.3 Hz), 0.99 (3H×¾, t, J=7.3 Hz), 2.09-2.14 (2H, m), 3.56-3.74 (3H, m), 3.78-3.97 (5H, m), 5.50 (1H×¼, t, J=5.5 Hz), 5.54 (1H×¾, t, J=5.5 Hz), 7.33-7.46 (1H, m), 8.20-8.27 (1H, m), 9.88 (1H×¼, d, J=14.7 Hz), 11.27 (1H×¾, d, J=14.7 Hz).

54D) Preparation of Ethyl-9',10'-difluoro-7'-oxospiro [oxolane-3,3% 2'H)-[7H]pyrido[1,2,3-de][1,4]benzoxazine]-6'-carboxylate

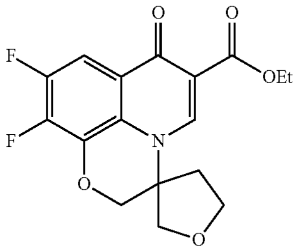 [SMILES: CCOC(=O)c1cn2c3c(c(F)c(F)cc3c1=O)OCC21CCOC1]

To a solution of 3-[3-[1-(hydroxymethyl)oxolanylamino]-2-(2,3,4,5-tetrafluorobenzoyl)-acrylate (3.94 g, 10.6 mmol) in DMF (50 mL), 60% NaH in oil (892 mg, 22.3 mmol) was added under argon atmosphere and ice-cooling. After stirred at 60° C. for 5 h, the reaction mixture was poured into ice-water and the resulting precipitate was collected by filtration, washed with water and EtOH, and dried to yield ethyl 9',10'-difluoro-7'-oxospiro-[oxolane-3,3'(2'H)-[7H]pyrido[1,2,3-de][1,4]benzoxazine]-6'-carboxylate (2.93 g, 79%) as a colorless solid. $^1$H-NMR (400 MHz, DMSO-$d_6$) δ 1.27 (3H, t, J=7.3 Hz), 2.38-2.42 (2H, m), 3.78 (1H, d, J=10.4 Hz), 3.92-3.98 (1H, m), 4.09-4.14 (1H, m), 4.20-4.25 (3H, m), 4.57 (1H, d, J=11.6 Hz), 4.65 (1H, d, J=11.6 Hz), 7.67 (1H, dd, J=10.4, 8.6 Hz), 8.50 (1H, s).

54E) Preparation of Ethyl-9',10'-difluoro-8'-nitro-7'-oxospiro-[oxolane-3,3'(2'H)-[7H]pyrido[1,2,3-de][1,4]benzoxazine]-6'-carboxylate

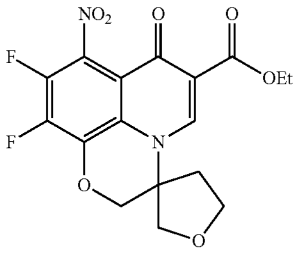

A solution of ethyl 9',10'-difluoro-7'-oxospiro[oxolane-3,3'(2'H)-[7H]pyrido[1,2,3-de][1,4]benzoxazine]-6'-carboxylate (2.90 g, 8.26 mmol) in concentrated $H_2SO_4$ (40 mL) was treated portion wise at 0° C. with solid $KNO_3$ (1.17 g, 11.6 mmol). After stirring at 0° C. for 2 h, the reaction mixture was poured into ice-water and the resulting precipitate was collected by filtration, washed with water and dried to yield ethyl 9',10'-difluoro-8'-nitro-7'-oxospiro[oxolane-3,3'(2'H)-[7H] pyrido-[1,2,3-de][1,4]benzoxazine]-6'-carboxylate (3.20 g, 98%) as a colorless solid. $^1$H-NMR (400 MHz, DMSO-$d_6$) δ1.26 (3H, t, J=7.3 Hz), 2.41-2.46 (2H, m), 3.78 (1H, d, J=10.4 Hz), 3.92-3.98 (1H, m), 4.09-4.14 (1H, m), 4.21-4.29 (3H, m), 4.62 (1H, d, J=11.6 Hz), 4.72 (1H, d, J=11.6 Hz), 8.53 (1H, s).

54F) Preparation of Ethyl-8'-amino-9',10'-difluoro-7'-oxospiro-[oxolane-3,3'(2')-[7H]pyrido[1,2,3-de][1,4]benzoxazine]-6'-carboxylate

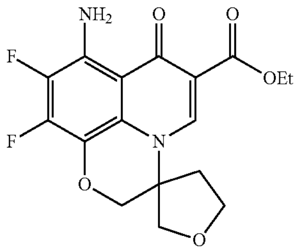 [SMILES: CCOC(=O)c1cn2c3c(c(F)c(F)c([N+](=O)[O-])c3c1=O)OCC21CCOC1]

A mixture of ethyl 9',10'-difluoro-8'-nitro-7'-oxospiro[oxolane-3,3'(2'H)-[7H]pyrido[1,2,3-de][1,4]benzoxazine]-6'-carboxylate (3.15 g, 7.95 mmol) and iron (2.66 mg, 47.7 mmol) in AcOH (40 mL) was stirred at 90° C. for 5 h. After the reaction mixture was concentrated in vacuo, DMF was added and the mixture was filtrated through Celite. The filtrate was poured into water and the resulting precipitate was collected by filtration and dried to yield ethyl 8'-amino-9',10'-difluoro-7'-oxospiro[oxolane-3,3'(2'H)-[7H]pyrido[1,2,3-de][1,4]benzoxazine]-6'-carboxylate (1.54 g, 53%) as a colorless solid. $^1$H-NMR (400 MHz, DMSO-$d_6$) δ 1.25 (3H, t, J=7.3 Hz), 2.29-2.38 (2H, m), 3.72 (1H, d, J=11.0 Hz), 3.90-3.96 (1H, m), 4.06-4.11 (1H, m), 4.15 (1H, d, J=11.0 Hz), 4.19 (2H, q, J=7.3 Hz), 4.32 (1H, d, J=11.0 Hz), 4.41 (1H, d, J=11.0 Hz), 7.42 (2H, brs), 8.34 (1H, s).

54G) Preparation of 8'-amino-9',10'-difluoro-7'-oxospiro[oxolane-3,3'(2'H)[7H]pyrido[1,2,3-de][1,4]benzoxazine]-6'-carboxylic Acid

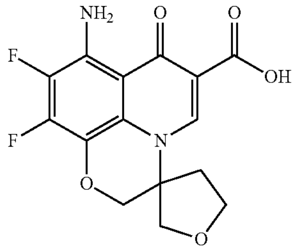 [SMILES: Nc1c(F)c(F)c2c3c1c(=O)c(C(=O)O)cn3C1(CCOC1)CO2]

A solution of ethyl 8'-amino-9',10'-difluoro-7'-oxospiro[oxolane-3,3'(2'H)-[7H]pyrido[1,2,3-de][1,4]benzoxazine]-6'-carboxylate (1.51 g, 4.12 mmol) in a mixture of AcOH—$H_2O$—$H_2SO_4$ (2:1:0.3 v/v, 26.4 mL) was heated at 100° C. for 2 h. The reaction mixture was poured into ice-water and stirred. After 30 min, the resulting precipitate was collected by filtration, washed with water and dried to yield 8'-amino-9',10'-difluoro-7'-oxospiro[oxolane-3,3' (2'H)-[7H]pyrido[1,2,3-de][1,4]benzoxazine]-6'-carboxylic acid (1.32 g, 95%) as a pale yellow solid $^1$H-NMR (400 MHz, DMSO-$d_6$) δ 2.38-2.44 (2H, m), 3.76 (1H, d, J=11.0 Hz), 3.91-3.97 (1H, m), 4.09-4.14 (1H, m), 4.25 (1H, d, J=11.0 Hz), 4.38 (1H, d, J=11.0 Hz), 4.50 (1H, d, J=11.0 Hz), 7.36 (2H, brs), 8.59 (1H, s), 14.62 (1H, s).

54H) Preparation of 8'-amino-9'-fluoro-7'-oxo-10'-[3-(2-pyridyl) propylamino]spiro[oxolane-1,3'(2'H)-[7H]pyrido[1,2,3-de][1,4]benzoxazine]-6'-carboxylic Acid

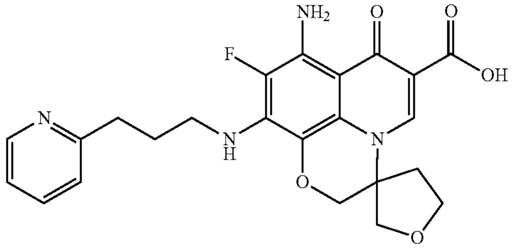 [SMILES: Nc1c(F)c(NCCCc2ccccn2)c2c3c1c(=O)c(C(=O)O)cn3C1(CCOC1)CO2]

A solution of 8'-amino-9',10'-difluoro-7'-oxospiro[oxolane-3,3'(2'H)-[7H]pyrido[1,2,3-de][1,4]benzoxazine]-6'-carboxylic acid (300 mg, 0.887 mmol), 3-(2-pyridyl)propylamine (181 mg, 1.33 mmol) and triethylamine (0.185 mL, 1.33 mmol) in DMSO (4 mL) was stirred at 100° C. for 6 h. To the reaction mixture, water and saturated $NH_4Cl$ solution were added to pH<4 and stirred for 30 min. The resulting precipitate was collected by filtration, washed with water and EtOH, and dried to yield 8'-amino-9'-fluoro-7'-oxo-10'-[3-(2-pyridyl)propylamino]spiro[oxolane-3,3'(2'H)-[7H ]pyrido[1,2,3-de][1,4]benzoxazine]-6'-carboxylic acid (373 mg, 93%) as a pale yellow solid. $^1$H-NMR (400 MHz, DMSO-$d_6$) δ 1.90-1.98 (2H, m), 2.26-2.39 (2H, m), 2.77 (2H, t, J=7.3 Hz), 3.42-3.51 (2H, m), 3.73 (1H, d, J=10.4 Hz), 3.91-3.97 (1H, m), 4.07-4.13 (1H, m), 4.16 (1H, d, J=10.4 Hz), 4.24 (1H, d, J=11.0 Hz), 4.35 (1H, d, J=11.0 Hz), 6.01-6.10 (1H, m), 6.92 (2H, brs), 7.18 (1H, dd, J=6.7, 5.5 Hz), 7.24 (1H, d, J=7.9 Hz), 7.67 (1H, td, J=7.3, 1.8 Hz), 8.42 (1H, s), 8.45 (1H, d, J=4.3 Hz), 15.27 (1H, s). HRESIMS (+) 455.17350 (Calcd for $C_{23}H_{23}FN_4O_5$, 455.17307).

Examples 55-81

By using the procedures set out above, the compounds of example 55 to 81 were prepared:

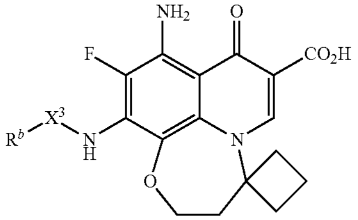

| Example No. | $R^b$—$X^3$— | Data |
|---|---|---|
| 55 | 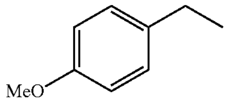 | $^1$H-NMR (400 MHz, DMSO-$d_6$) δ 1.62-1.73 (1H, m), 1.85-1.99 (1H, m), 2.35-2.47 (4H, m), 2.52-2.62 (2H, m), 3.68 (3H, s), 4.22-4.32 (2H, m), 4.49 (2H, d, J = 5.5 Hz), 6.39-6.42 (2H, m), 6.83 (1H, d, J = 8.6 Hz), 6.95 (2H, brs), 7.16 (1H, d, J = 8.6 Hz), 8.26 (1H, s), 15.17 (1H, s). HRESIMS (+): 454.18220 (calcd for $C_{24}H_{25}FN_3O_5$, 454.17782). |
| 56 | 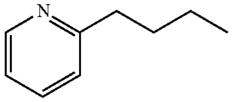 | $^1$H-NMR (400 MHz, DMSO-$d_6$) δ 1.61-1.74 (1H, m), 1.85-1.97 (3H, m), 2.38-2.56 (6H, m), 2.74 (2H, t, J = 7.3 Hz), 3.37-3.45 (2H, m), 4.18-4.36 (2H, m), 5.92 (1H, t, J = 5.5 Hz), 6.99 (2H, brs), 7.18 (1H, dd, J = 6.7, 4.9 Hz), 7.23 (1H, d, J = 7.9 Hz), 7.67 (1H, td, J = 7.9, 1.8 Hz), 8.26 (1H, s), 8.45 (1H, dd, J = 4.9, 1.8 Hz), 15.21 (1H, brs). HRESIMS (+): 453.19699 (Calcd for $C_{24}H_{26}FN_4O_4$, 453.19381) |
| 57 | 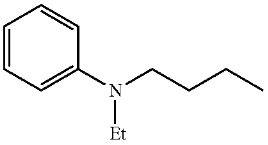 | $^1$H-NMR (400 MHz, DMSO-$d_6$) δ 1.02 (3H, t, J = 7.3 Hz), 1.60-1.81 (3H, m), 1.83-1.98 (1H, m), 2.35-2.64 (6H, m), 3.23-3.37 (4H, m), 3.80-3.50 (2H, m), 4.20-4.32 (2H, m), 5.90-6.00 (1H, m), 6.50 (1H, t, J = 7.3 Hz), 6.56 (2H, d, J = 8.6 Hz), 7.00 (2H, brs), 7.05 (2H, t, J = 8.6 Hz), 8.27(1H, s), 15.22 (1H, s). HRESIMS (+): 495.24079 (Calcd for $C_{27}H_{32}FN_4O_5$, 495.24076). |
| 58 | 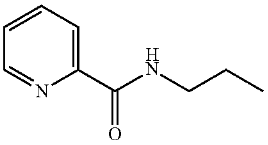 | $^1$H-NMR (400 MHz, DMSO-$d_6$) δ 1.57-1.71 (1H, m), 1.80-1.94 (1H, m), 2.28-2.61 (6H, m), 3.47-3.55 (2H, m), 3.55-3.62 (2H, m), 4.12-4.30 (2H, m), 5.94 (1H, t, J = 6.1 Hz), 6.97 (2H, brs), 7.55-7.60 (1H, m), 7.92-8.02 (2H, m), 8.25 (1H, s), 8.59-8.64 (1H, m), 8.90 (1H, t, J = 6.1 Hz), 15.20 (1H, s). HRESIMS (+): 482.18452 (Calcd for $C_{24}H_{25}FN_5O_5$, 482.18397). |
| 59 | 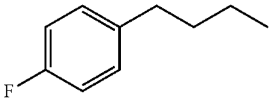 | $^1$H-NMR (400 MHz, DMSO-$d_6$) δ 1.60-1.72 (1H, m), 1.73-1.87 (2H, m), 1.90-2.00 (1H, m), 2.33-2.69 (8H, m), 3.35-3.41 (2H, m), 4.15-4.35 (2H, m), 5.84 (1H, brs), 6.98 (2H, brs), 7.07 (2H, t, J = 8.6 Hz), 7.20 (2H, dd, J = 8.6, 6.1 Hz), 8.26 (1H, s), 15.22 (1H, s). HRESIMS (+): 470.18822 (Calcd for $C_{25}H_{26}F_2N_3O_4$, 470.18822). |
| 60 | 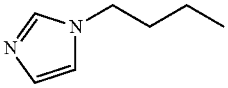 | $^1$H-NMR (400 MHz, DMSO-$d_6$) δ 1.61-1.74 (1H, m), 1.86-2.01 (3H, m), 2.38-2.46 (4H, m), 2.51-2.58 (2H, m), 3.27-3.37 (2H, m), 4.00 (2H, t, J = 7.3 Hz), 4.17-4.35 (2H, m), 5.86-5.94 (1H, m), 6.87 (1H, s), 6.99 (2H, brs). 7.16 (1H, s), 7.61 (1H, s), 8.27 (1H, s), 15.20 (1H, s). HRESIMS (+): 442.19136 (Calcd for $C_{22}H_{25}FN_5O_4$, 442.18906). |
| 61 | 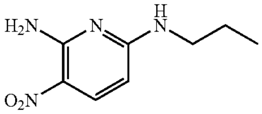 | $^1$H-NMR (400 MHz, DMSO-$d_6$) δ 1.58-1.71 (1H, m), 1.78-1.93 (3H, m), 2.31-2.42 (4H, m), 3.31-3.63 (4H, m), 4.13-4.30 (2H, m), 5.88-6.02 (2H, m), 7.00 (2H, brs). 7.59-7.74 (1H, m), 7.93 (1H, d, J = 9.2 Hz), 8.01-8.09 (1H, m), 8.25 (1H, s), 15.19 (1H, s). HRESIMS (+): 514.18612 (Calcd for $C_{23}H_{25}FN_7O_6$, 514.18503). |
| 62 | 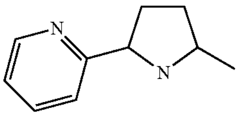 | $^1$H-NMR (400 MHz, DMSO-$d_6$) δ 1.59-1.73 (1H, m), 1.82-1.98 (1H, m), 2.01-2.14 (1H, m), 2.16-2.28 (1H, m), 2.42-2.56 (6H, m), 3.37-3.54 (3H, m), 3.65 (1H, dd J = 10.4, 6.1 Hz), 4.17-4.35 (2H, m), 4.51-4.63 (1H, m), 5.50 (1H, d, J = 7.3 Hz), 6.43 (1H, d, J = 8.6 Hz), 6.53 (1H, dd, J = 7.3, 4.9 Hz), 7.06 (2H, brs), 7.43-7.49 (1H, m), 8.03 (1H, dd, J = 4.9, 1.2 Hz), 8.28 (1H,s), 15.15 (1H,s). HRESIMS (+): 480.20444 (Calcd for $C_{25}H_{27}FN_5O_4$, 480.20471). |

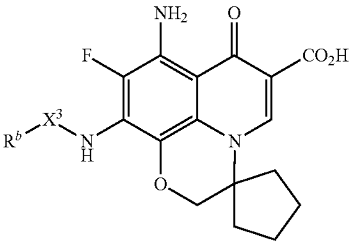

| Example No. | $R^b$—$X^3$— | Data |
|---|---|---|
| 63 | 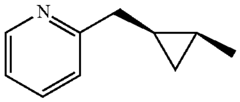 racemate | $^1$H-NMR (400 MHz, $CDCl_3$) δ 0.58-0.62 (1H, m), 1.08-1.14 (1H, m), 1.35-1.44 (1H, m), 1.81-1.92 (2H, m), 1.95-2.10 (6H, m), 2.89 (1H, dd, J = 14.7, 9.2 Hz), 3.00-3.10 (2H, m), 4.03 (2H, s), 6.26 (2H, brs), 6.44 (1H, brs), 7.15 (1H, dd, J = 7.3, 4.9 Hz), 7.21 (1H, d, J = 7.3 Hz), 7.62 (1H, td, J = 7.3, 1.8 Hz), 8.51 (1H, s), 8.54 (1H, d, J = 4.3 Hz), 15.36 (1H, s). HRESIMS (+): 465.19382 (calcd for $C_{25}H_{25}FN_4O_4$, 465.19381). |
| 64 | 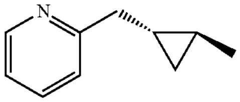 racemate | $^1$H-NMR (400 MHz, $CDCl_3$) δ 0.81-0.90 (2H, m), 1.41-1.50 (1H, m), 1.80-1.92 (2H, m), 1.95-2.09 (6H, m), 2.62 (1H, dd, J = 14.7, 8.6 Hz), 2.87-2.95 (1H, m), 3.10 (1H, dd, J = 14.7, 5.5 Hz), 3.99 (2H, s), 4.65-4.71 (1H, m), 6.27 (2H, brs), 7.15 (1H, dd, J = 6.7, 5.5 Hz), 7.22 (1H, d, J = 7.9 Hz), 8.51 (1H, s), 8.55 (1H, d, J = 4.3 Hz), 15.24 (1H, s). HRESIMS (+): 465.19312 (calcd for $C_{25}H_{25}FN_4O_4$, 465.19381). |
| 65 | 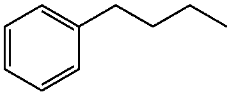 | MS (EP) m/z: 452.0 ($M^+$ + 1). (Calcd. For $C_{25}H_{26}FN_3O_4$, 451.19). |
| 66 | 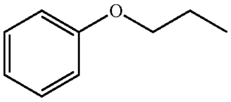 | MS (EP) m/z: 454.0 ($M^+$ + 1). (Calcd. For $C_{24}H_{24}FN_3O_5$, 453.17). |
| 67 | 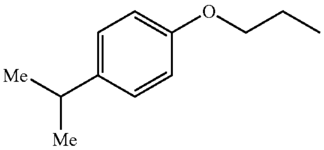 | MS (EP) m/z: 496.0 ($M^+$ + 1). (Calcd. For $C_{27}H_{30}FN_3O_5$, 495.22). |
| 68 | 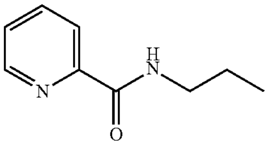 | $^1$H-NMR (400 MHz, DMSO-$d_6$) δ 1.76-1.84 (4H, m), 1.89-1.99 (4H, m), 3.48-3.56 (2H, m), 3.60-3.68 (2H, m), 4.10 (2H, s), 5.92-5.99 (1H, m), 6.88 (2H, brs), 7.54-7.59 (1H, m), 7.92-8.01 (2H, m), 8.34 (1H, s), 8.61 (1H, dd, J = 4.9, 1.2 Hz), 8.90 (1H, t, J = 5.5 Hz), 1.525 (1H, s). HRESIMS (+): 482.18487 (Calcd for $C_{24}H_{25}FN_5O_5$, 482.18397). |
| 69 | 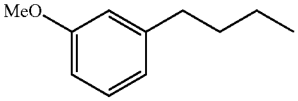 | MS (EP) m/z: 482 ($M^+$ + 1). (Calcd. For $C_{26}H_{28}FN_3O_5$, 481.20) |
| 70 | 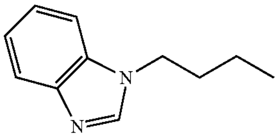 | MS (EP) m/z: 492.0 ($M^+$ + 1). (Calcd. For $C_{26}H_{26}FN_5O_4$, 491.20). |

-continued

| Example No. | $R^b$—$X^3$— | Data |
|---|---|---|
| 71 | 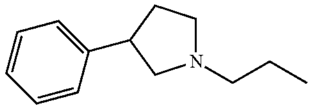 | MS (EP) m/z: 507.1 ($M^+$ + 1). (Calcd. For $C_{28}H_{31}FN_4O_4$, 506.23). |
| 72 | 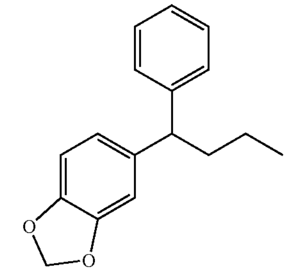 | MS (EP) m/z: 572.0 ($M^+$ + 1). (Calcd. For $C_{32}H_{30}ClFN_3O_6$, 571.21). |
| 73 | 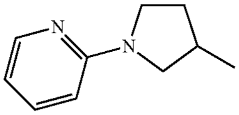 | $^1$H-NMR (400 MHz, DMSO-$d_6$) δ 1.75-1.86 (4H, m), 1.90-2.03 (4H, m), 2.07-2.19 (1H, m), 2.20-2.31 (1H, m), 3.38-3.48 (2H, m), 3.49-3.58 (1H, m), 3.64-3.72 (1H, m), 4.14 (2H, s), 4.59-4.65 (1H, m), 5.61 (1H, d, J = 7.9 Hz), 6.44 (1H, d, J = 8.6 Hz), 6.53 (1H, dd, J = 6.1, 4.9 Hz), 6.92 (2H, brs), 7.43-7.49 (1H, m), 8.04 (1H, dd, J = 4.9, 1.2 Hz), 8.37 (1H, s).<br>HRESIMS (+): 480.30794 (Calcd for $C_{25}H_{27}FN_5O_4$, 480.20471). |
| 74 | 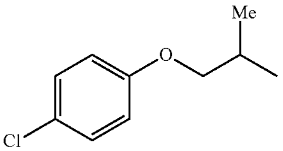 | MS (ESP) m/z: 502.0 ($M^+$ + 1). (Calcd. For $C_{25}H_{25}ClFN_3O_5$, 501.15). |
| 75 | 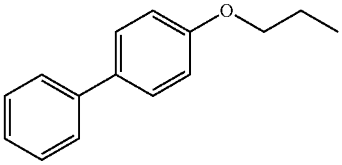 | MS (EP) m/z: 530.0 ($M^+$ + 1). (Calcd. For $C_{30}H_{28}FN_3O_5$, 529.20). |
| 76 | 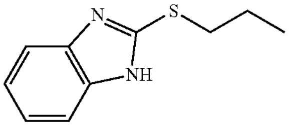 | MS (EP) m/z: 510.0 ($M^+$ + 1). (Calcd. For $C_{25}H_{24}FN_5O_4S$, 509.15). |
| 77 | 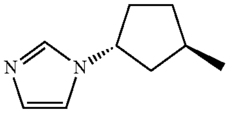<br>racemate | $^1$H-NMR (400 MHz, DMSO-$d_6$) δ 1.60-1.90 (6H, m), 1.93-2.05 (4H, m), 2.10-2.35 (4H, m), 4.19 (2H, s), 4.50-4.60 (1H, m), 4.76 (1H, qui, J = 7.3 Hz), 5.61 (1H, d, J = 6.1 Hz), 6.89 (1H, s), 6.94 (2H, brs), 7.24 (1H, s), 7.69 (1H, s), 15.23 (1H, s).<br>HRESIMS (+): 468.20413 (Calcd for $C_{24}H_{27}FN_5O_4$, 468.20471). |
| 78 | 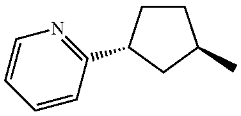<br>racemate | $^1$H-NMR (400 MHz, DMSO-$d_6$) δ 1.60-1.90 (6H, m), 1.96-2.23 (8H, m), 3.44 (1H, qui, J = 7.9 Hz), 4.16 (2H, s), 4.52-4.60 (1H, m), 5.43 (1H, d, J = 6.7 Hz), 6.94 (2H, brs), 7.17 (1H, dd, J = 6.7, 4.9 Hz), 7.26 (1H, d, J = 7.3 Hz), 7.67 (1H, td, J = 7.3, 1.2 Hz), 8.36 (1H, s), 8.49 (1H, d, J = 3.7 Hz), 15.26 (1H, s).<br>HRESIMS (+): 479.21004 (Calcd for $C_{26}H_{28}FN_4O_4$, 479.20940). |

-continued

| Example No. | $R^b$—$X^3$— | Data |
|---|---|---|
| 79 | 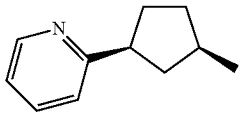 racemate | $^1$H-NMR (400 MHz, DMSO-$d_6$) δ 1.65-1.70 (1H, m), 1.73-2.05 (11H, m), 2.06-2.18 (1H, m), 2.30-2.40 (1H, m), 3.36-3.50 (1H, m), 4.17 (1H, d, J = 11.6 Hz), 4.22 (1H, d, J = 11.6 Hz), 4.52-4.55 (1H, m), 6.84-7.05 (3H, m), 7.23 (1H, dd, J = 7.3, 5.5 Hz), 7.31 (1H, d, J = 7.3 Hz), 7.71 (1H, t, J = 7.3 Hz), 8.35 (1H, s), 8.59 (1H, d, J = 4.3 Hz), 15.30 (1H, s). HRESIMS (+): 479.20996 (Calcd for $C_{26}H_{28}FN_4O_4$, 479.20940). |
| 80 | 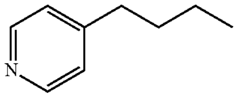 | $^1$H-NMR (400 MHz, DMSO-$d_6$) δ 1.75-2.05 (10H, m), 2.64 (2H, t, J = 7.6 Hz), 3.39-3.49 (2H, m), 4.11 (2H, s), 5.91-6.01 (1H, m), 6.90 (1H, brs), 7.22 (2H, d, J = 5.5 Hz), 8.35 (1H, s), 8.43 (1H, d, J = 5.5 Hz), 15.3 (1H, s). HRESIMS (+): 453.19373 (calcd for $C_{24}H_{26}FN_4O_4$, 453.19381). |
| 81 | 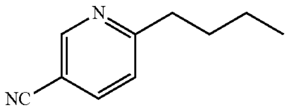 | $^1$H-NMR (400 MHz, DMSO-$d_6$) δ 1.74-2.06 (10H, m), 2.87 (2H, t, J = 7.6 Hz), 3.48-3.51 (2H, m), 4.12 (2H, s), 5.97 (1H, brs), 6.90 (1H, brs), 8.19 (1H, dd, J = 7.9, 1.8 Hz), 8.35 (1H, s), 8.90 (1H, d, J = 1.2 Hz), 15.3 (1H, s). HRESIMS (+): 478.18896 (calcd for $C_{25}H_{25}FN_5O_4$, 478.18906). |

Example 82

9'-amino-10'-fluoro-2',3'-dihydro-8'-oxo-11'-[2-(2-pyridylamino)ethylamino]spiro[cyclobutane-1,4'-[4H,8H]pyrido[1,2,3-ej][1,5]benzoxazepine]

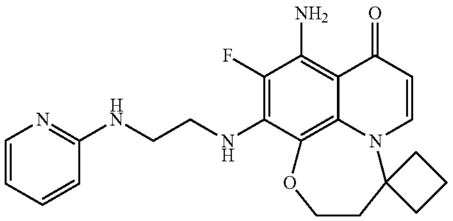 [SMILES: Nc1c(F)c(NCCNc2ccccn2)c2c3c1c(=O)ccn3C1(CCC1)CCO2]

A mixture of 9'-amino-10'-fluoro-2',3'-dihydro-8'-oxo-11'-[2-(2-pyridylamino)-ethylamino]spiro[cyclobutane-1,4'-[4H,8H]pyrido[1,2,3-ef][1,5]benzoxazepine]-7'-carboxylic acid (300 mg, 0.662 mmol) and sodium cyanide (325 mg, 6.63 mmol) in anhydrous DMSO (6 mL) was stirred at 120° C. for 3 hours. After cooling, the reaction mixture was poured into water (100 mL) and extracted with EtOAc. The extraction mixture was washed with water and brine, dried over $Na_2SO_4$, and concentrated in vacuo. The residue was purified by column chromatography (Chromatorex NH-DM2035 (Fuji Sylysia Chemical Co., Ltd.) EtOAc) to give the title compound (197 mg, 72%) as a yellow solid. $^1$H-NMR (400 MHz, DMSO-$d_6$) δ 1.60-1.72 (1H, m), 1.80-1.93 (1H, m), 2.28-2.44 (6H, m), 3.39 (2H, q, J=5.5 Hz), 3.45-3.53 (2H, m), 4.10-4.19 (2H, m), 5.55 (1H, td, J=6.1, 2.4 Hz), 5.64 (1H, d, J=7.9 Hz), 6.42-6.47 (2H, m), 6.61 (1H, t, J=5.5 Hz), 7.01 (2H, brs), 7.31-7.36 (1H, m), 7.44 (1H, d, J=7.9 Hz), 7.94 (1H, dd, J=4.9, 1.2 Hz). HRESIMS (+): 410.19901 (calcd for $C_{22}H_{25}FN_5O_2$, 410.19923).

Examples 83-85

The following compounds were prepared in the same manner that 9'-amino-10'-fluoro-2',3'-dihydro-8'-oxo-11'-[2-(2-pyridylamino)ethylamino]spiro[cyclobutane-1,4'-[4H,8H] pyrido[1,2,3-ef][1,5]benzoxazepine] was prepared above. The compounds were prepared according to the procedure of example 82:

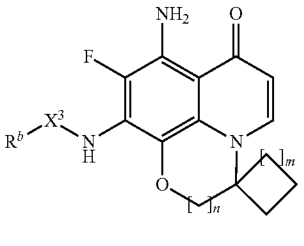

| Example No. | $R^b$—$X^3$— | m | n | Data |
|---|---|---|---|---|
| 83 | 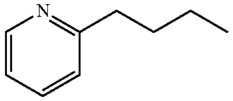 | 1 | 2 | $^1$H-NMR (400 MHz, DMSO-$d_6$) δ 1.59-1.73 (1H, m), 1.81-1.93 (3H, m), 2.28-2.45 (6H, m), 2.73 (2H, t, J = 7.3 Hz), 4.16-4.25 (2H, m), 5.27 (1H, td, J = 6.7, 2.4 Hz), 5.64 (1H, d, J = 7.3 Hz), 7.00 (2H, brs), 7.17 (1H, dd, J = 4.9, 4.9 Hz), 7.21 (1H, d, J = 7.3 Hz), 7.44 (1H, d, J = 7.3 Hz), 7.66 (1H, td, J = 7.3, 1.8 Hz), 8.45 (1H, dd, J = 4.9, 1.8 Hz). HRESIMS (+): 409.20524 (Cacld for $C_{23}H_{26}FN_4O_2$, 409.203988). |

-continued

| Example No. | $R^b$—$X^3$— | m | n | Data |
|---|---|---|---|---|
| 84 | 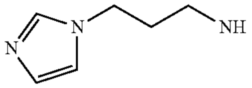 | 1 | 2 | $^1$H-NMR (400 MHz, DMSO-$d_6$) δ 1.63-1.74 (1H, m), 1.83-1.97 (3H, m), 2.29-2.45 (6H, m), 3.24-3.35 (2H, m), 3.99 (2H, t, J = 6.7 Hz), 4.16-4.26 (2H, m), 5.23-5.30 (1H, m), 5.65 (1H, d, J = 7.9 Hz), 6.86 (1H, d, J = 1.2 Hz), 7.01 (2H, brs), 7.14 (1H, t, J = 1.2 Hz), 7.45 (1H, d, J = 7.9 Hz), 7.50 (1H, s). HRESIMS (+): 398.20165 (Calcd for $C_{21}H_{25}FN_5O_2$, 398.19923). |
| 85 | 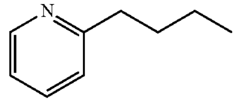 | 2 | 1 | $^1$H-NMR (400 MHz, $CDCl_3$) δ 1.78-2.00 (8H, m), 2.02-2.09 (2H, m), 2.89 (2H, t, J = 7.3 Hz), 3.42-3.60 (2H, m), 3.94 (2H, s), 4.38 (1H, brs), 5.93 (1H, d, J = 7.3 Hz), 6.39 (2H, brs), 7.12 (1H, dd, J = 7.3, 4.9 Hz), 7.15-7.19 (1H, m), 7.31(1H, d, J = 7.3 Hz), 7.59 (1H, td, J = 7.9, 1.2 Hz), 8.53 (1H, d, J = 4.3 Hz). HRESIMS (+): 409.20371 (calcd for $C_{23}H25FN_4O_2$, 409.20398). |

Example 86

9'-amino-10'-fluoro-2',3'-dihydro-8'-oxo-11'-[2-(2-pyridyl-amino)-ethylamino]spiro[cyclobutane-1,4'-[4H,8H]pyrido[1, 2,3-ef][1,5]benzoxazepine]-7'-carboxamide

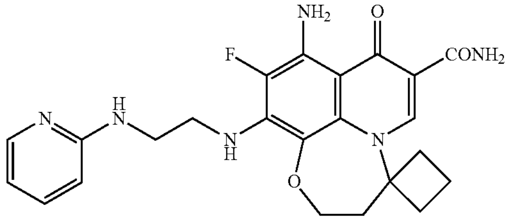 [SMILES: NC(=O)c1cn2c3c(c(NCCNc4ccccn4)c(F)c(N)c3c1=O)OCCC21CCC1]

Triethylamine (0.14 mL, 1.00 mmol) and ethyl chloroformate (0.076 mL, 0.795 mmol) were added to a solution of 9'-amino-10'-fluoro-2',3'-dihydro-8'-oxo-11'-[2-(2-pyridylamino)-ethylamino]spiro[cyclobutane-1,4'-[4H,8H]pyrido [1,2,3-ef][1,5]benzoxazepine]-7'-carboxylic acid (300 mg, 0.662 mmol) in DMF (5 mL) at 0° C. After stirring at 0° C. for 1.5 hours, 25% aqueous $NH_3$ (5 mL) was added. The mixture was stirred at room temperature for 6 hours. The reaction mixture was poured into water (200 mL) and extracted with EtOAc. The mixture was washed with water and brine, dried over $Na_2SO_4$, and concentrated in vacuo. The residue was purified by column chromatography ($CH_2Cl_2$:MeOH 50:1) to give the title compound (270 mg, 90%) as a yellow solid. $^1$H-NMR (400 MHz, DMSO-$d_6$) δ 1.62-1.73 (1H, m), 1.90 (1H, q, J=9.2 Hz), 2.28-2.47 (6H, m), 3.42 (2H, q, J=5.5 Hz), 3.49-3.57 (2H, m), 4.11-4.25 (2H, m), 5.85-5.89 (1H, m), 6.42-6.49 (2H, m), 6.64 (1H, t, J=5.5 Hz), 7.08 (2H, brs), 7.26 (1H, d, J=4.9 Hz), 7.31-7.37 (1H, m), 7.95 (1H, dd, J=4.9, 1.2 Hz), 8.26 (1H, s), 9.13 (1H, d, J=4.9 Hz). HRESIMS (+): 453.20594 (calcd for $C_{23}H_{26}FN_6O_3$, 453.20504).

Example 87

8'-amino-9'-fluoro-7'-oxo-10'-[3-(2-pyridyl) propylamino]spiro[oxolane-1,3'(2'H)-[7H]pyrido[1,2,3-de][1,4]benzoxazine]-6'-carboxamide

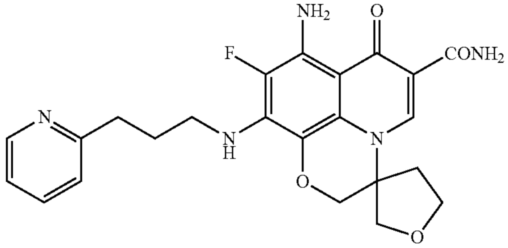 [SMILES: NC(=O)c1cn2c3c(c(NCCCc4ccccn4)c(F)c(N)c3c1=O)OCC21CCOC1]

The title compound was prepared from the compound of example 54 according to the procedure of example 86. $^1$H-NMR (400 MHz, DMSO-$d_6$) δ1.88-1.96 (2H, m), 2.18-2.25 (1H, m), 2.30-2.37 (1H, m), 2.76 (2H, t, J=7.3 Hz), 3.37-3.47 (2H, m), 3.72 (1H, d, J=10.4 Hz), 3.91-3.96 (1H, m), 4.05-4.12 (2H, m), 4.21 (1H, d, J=11.6 Hz), 4.29 (1H, d, J=11.6 Hz), 5.62-5.69 (1H, m), 7.01 (2H, brs), 7.17 (1H, dd, J=6.7, 5.5 Hz), 7.23 (1H, d, J=7.9 Hz), 7.33 (1H, d, J=4.3 Hz), 7.67 (1H, td, J=7.3, 1.8 Hz), 8.45 (1H, d, J=4.3 Hz), 8.48 (1H, s), 9.18 (1H, d, J=4.9 Hz).

Example 88

9'-amino-10'-fluoro-2',3'-dihydro-8'-oxo-11'-[2-(2-pyridylamino)ethylamino]spiro[cyclobutane-1,4'-[4H,8H]pyrido[1,2,3-ef][1,5]benzoxazepine]-7'-carbohydrazide

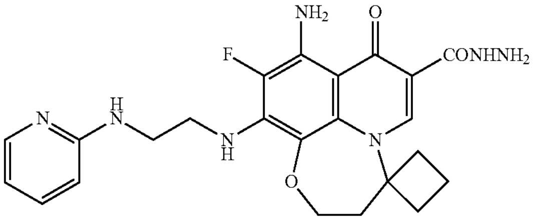

Triethylamine (0.185 mL, 1.33 mmol) and ethyl chloroformate (0.100 mL, 1.04 mmol) were added to a solution of 9'-amino-10'-fluoro-2',3'-dihydro-8'-oxo-11'-[2-(2-pyridylamino)ethylamino]spiro[cyclobutane-1,4'-[4H,8H]pyrido[1,2,3-ef][1,5]benzoxazepine]-7'-carboxylic acid (400 mg, 0.882 mmol) in DMF (6 mL) at 0° C. After stirring at 0° C. for 1.5 hours, hydrazine monohydrate (4 mL) was added. The mixture was stirred at room temperature for 6 hours. The reaction mixture was poured into water (100 mL) and the solid was collected by filtration and dried to give the title compound (369 mg, 89%) as a yellow solid. $^{1}$H-NMR (400 MHz, DMSO-$d_6$) δ 1.63-1.73 (1H, m), 1.83-1.97 (1H, m), 2.26-2.55 (6H, m), 3.42 (2H, q, J=6.1 Hz), 3.49-3.57 (2H, m), 4.12-4.25 (2H, m), 4.47 (2H, d, J=4.3 Hz), 5.87 (1H, td, J=6.1, 1.8 Hz), 6.42-6.48 (2H, m), 6.64 (1H, t, J=5.5 Hz), 7.07 (2H, brs), 7.31-7.37 (1H, m), 7.95 (1H, dd, J=5.5, 1.2 Hz), 8.23 (1H, s), 10.47 (1H, s). HRESIMS (+): 468.2143 (calcd for $C_{23}H_{27}FN_7O_3$, 468.2159).

Example 89

9'-amino-10'-fluoro-2',3'-dihydro-8'oxo-11'-[2-(2-pyridylamino)ethylamino]spiro[cyclobutane-1,4%[4H,8H]pyrido[1,2,3-ef][1,5]benzoxazepine]-7'-carbohydroxamic Acid

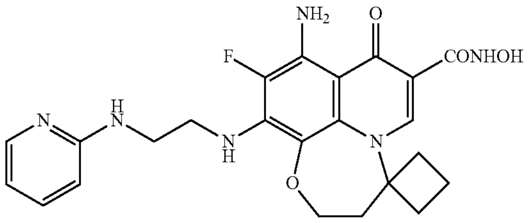

Triethylamine (0.185 mL, 1.33 mmol) and ethyl chloroformate (0.100 mL, 1.04 mmol) were added to a solution of 9'-amino-10'-fluoro-2',3'-dihydro-8'-oxo-11'-[2-(2-pyridylamino)ethylamino]spiro[cyclobutane-1,4'-[4H,8H]pyrido[1,2,3-ef][1,5]benzoxazepine]-7'-carboxylic acid (400 mg, 0.882 mmol) in DMF (6 mL) at 0° C. After stirring at 0° C. for 1.5 hours, 50% aqueous $NH_2OH$ (3 mL) was added. The mixture was stirred at room temperature for 6 hours and poured into water (60 mL). The resulting solid was collected by filtration and dried. Recrystallization of the residue from MeOH gave the title compound (135 mg, 33%) as a yellow solid. $^{1}$H-NMR (400 MHz, DMSO-$d_6$) δ 1.62-1.73 (1H, m), 1.84-1.97 (1H, m), 2.28-2.56 (6H, m), 3.42 (2H, q, J=6.1 Hz), 3.50-3.57 (2H, m), 4.12-4.26 (2H, m), 5.87-5.93 (1H, m), 6.42-6.48 (2H, m), 6.64 (1H, t, J=5.5 Hz), 7.05 (2H, brs), 7.32-7.36 (1H, m), 7.95 (1H, dd, J=4.9, 1.2 Hz), 8.22 (1H, s), 9.02 (1H, d, J=1.8 Hz), 11.54 (1H, d, J=1.8 Hz). HRESIMS (+): 469.2036 (calcd for $C_{23}H_{26}FN_6O_4$, 469.2000).

Example 90

9'-amino-10'-fluoro-2',3'-dihydro-N-methyl-8'-oxo-11'-[2-(2-pyridylamino)ethylamino]spiro[cyclobutane-1,4%[4H,8H]pyrido[1,2,3-ef][1,5]benzoxazepine]-7'-carboxamide

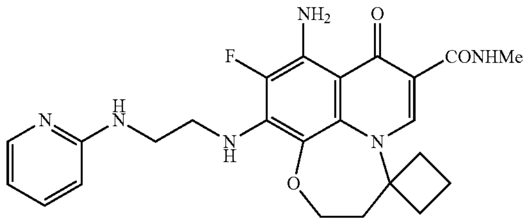

Triethylamine (0.185 mL, 1.33 mmol) and ethyl chloroformate (0.100 mL, 1.04 mmol) were added to a solution of 9'-amino-10'-fluoro-2',3'-dihydro-8'-oxo-11'-[2-(2-pyridylamino)ethylamino]spiro[cyclobutane-1,4'-[4H,8H]pyrido[1,2,3-d][1,5]benzoxazepine]-7'-carboxylic acid (400 mg, 0.882 mmol) in DMF (6 mL) at 0° C. After stirring at 0° C. for 1.5 hours, 2 M methylamine in THF (4 mL) was added. The mixture was stirred at room temperature for 6 hours. The reaction mixture was poured into water (60 mL) and extracted with EtOAc. The extraction mixture was washed with water and brine, dried over $Na_2SO_4$, and concentrated in vacuo. The residue was purified by column chromatography ($CH_2Cl_2$: MeOH 20:1) to give the title compound (370 mg, 90%) as a yellow solid. $^{1}$H-NMR (400 MHz, DMSO-$d_6$) δ 1.62-1.73 (1H, m), 1.84-1.97 (1H, m), 2.28-2.48 (6H, m), 3.41 (3H, d, J=4.9 Hz), 2.79 (2H, q, J=5.5 Hz), 3.49-3.56 (2H, m), 4.12-4.24 (2H, m), 5.85 (1H, td, J=5.5, 2.4 Hz), 6.42-6.48 (2H, m), 6.61-6.66 (1H, m), 7.07 (2H, brs), 7.31-7.36 (1H, m), 7.94 (1H, dd, J=4.9, 1.8 Hz), 8.25 (1H, s), 9.64 (1H, q, J=4.9 Hz). HRESIMS (+): 467.2182 (calcd for $C_{23}H_{28}FN_6O_3$, 467.2207).

Example 91

9'-amino-10'-fluoro-2',3'-dihydro-8'-oxo-11'-[2-(2-pyridylamino)ethylamino]spiro [cyclobutane-1,4'-[4H,8H]pyrido[1,2,3-d][1,5]benzoxazepine]-7'-carbonitrile 91A) Preparation of 9'-amino-10',11'-difluoro-2',3'-dihydro-8'-oxospiro-[cyclobutane-1,4'-[4H,8H]pyrido[1,2,3-ef][1,5]benzoxazepine]-7'-carboxamide

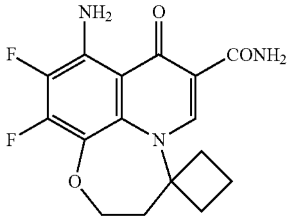 [SMILES: NC(=O)c1cn2c3c(c(F)c(F)c(N)c3c1=O)OCCC21CCC1]

Triethylamine (2.50 mL, 17.9 mmol) and ethyl chloroformate (1.36 mL, 14.2 mmol) were added to a suspension of 9'-amino-10',11'-difluoro-2',3'-dihydro-8'-oxospiro-[cyclobutane-1,4'-[4H,8H]pyrido[1,2,3-ef][1,5]benzoxazepine]-7'-carboxylic acid (4.00 g, 11.9 mmol) in DMF (200 mL). After stirring at 0° C. for 2 hours, 25% aqueous $NH_3$ (7 mL) was added and the mixture was stirred at room temperature for 3 hours. The reaction mixture was poured into water (1.5 L) and the resulting precipitate was collected by filtration, washed with water and dried to give the title compound (3.23 g, 81%) as a brown solid. $^1$H-NMR (400 MHz, DMSO-$d_6$) δ 1.64-1.76 (1H, m), 1.87-2.00 (1H, m), 2.35-2.48 (4H, m), 2.53-2.64 (2H, m), 4.30-4.42 (2H, m), 7.33-7.68 (3H, m), 8.44 (1H, s), 8.94 (1H, d, J=4.3 Hz). ESIMS (+): 336 $[M+H]^+$.

91B) Preparation of 9'-amino-10',11'-difluoro-2',3'-dihydro-8'-oxospiro-[cyclobutane-1,4'-[4H,8H]pyrido[1,2,3-ef][1,5]benzoxazepine]-7'-carbonitrile

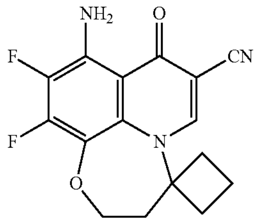 [SMILES: N#Cc1cn2c3c(c(F)c(F)c(N)c3c1=O)OCCC21CCC1]

Triethylamine (4.38 mL, 31.4 mmol) and a solution of trifluoroacetic anhydride (2.68 mL, 19.3 mmol) in $CH_2Cl_2$ (30 mL) were added to a suspension of 9'-amino-10',11'-difluoro-2',3'-dihydro-8'-oxospiro[cyclobutane-1,4'-[4H, 8H]pyrido[1,2,3-d][1, 5]benzoxazepine]-7'-carboxamide (1.70 g, 5.06 mmol) in $CH_2Cl_2$ (120 mL) at 0° C. After stirring at 0° C. for 1 hour, the reaction mixture was washed with water, saturated aqueous $NaHCO_3$ and brine, dried over $Na_2SO_4$, and concentrated in vacuo. The residue was purified by column chromatography (Chromatorex NH-DM2035 (Fuji Sylysia Chemical Co., Ltd.) Hexane:$CH_2Cl_2$ 1:1) to give the title compound (1.12 g, 70%) as a colorless solid. $^1$H-NMR (400 MHz, DMSO-$d_6$) δ 1.62-1.73 (1H, m), 1.83-1.96 (1H, m), 2.35-2.57 (6H, m), 4.32-4.42 (2H, m), 7.48 (2H, brs), 8.41 (1H, s). ESIMS (+): 318 $[M+H]^+$.

91C) Preparation of 9'-amino-10'-fluoro-2',3'-dihydro-8'-oxo-11'-[2-(2-pyridylamino)ethylamino]spiro[cyclobutane-1,4'-[4H,8H]pyrido[1,2,3-ef][1,5]benzoxazepine]-7'-carbonitrile

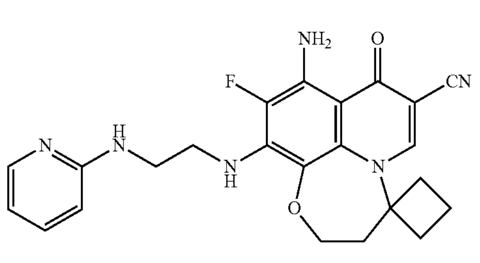 [SMILES: N#Cc1cn2c3c(c(NCCNc4ccccn4)c(F)c(N)c3c1=O)OCCC21CCC1]

A mixture of 9'-amino-10',11'-difluoro-2',3'-dihydro-8'-oxospiro[cyclobutane-1,4'-[4H,8H]pyrido[1,2,3-ef][1,5]benzoxazepine]-7'-carbonitrile (830 mg, 2.62 mmol), N-(2-pyridyl)-1,2-ethanediamine (718 mg, 5.23 mmol) and triethylamine (0.730 mL, 0.330 mmol) in anhydrous DMSO (16 mL) was stirred at 60° C. for 10 hours. After cooling, the reaction mixture was poured into ice-water (150 mL). The resulting precipitate was collected by filtration, washed with water and dried. The obtained solid was purified by column chromatography (Chromatorex NH-DM2035 (Fuji Sylysia Chemical Co., Ltd.) Hexane:$CH_2Cl_2$ 1:2→$CH_2Cl_2$→$CH_2Cl_2$:MeOH 100:1) to give the title compound (860 mg) as a brown solid. The solid was purified again by column chromatography ($CH_2Cl_2$:MeOH 30:1) to give the title compound (500 mg, 44%) as a yellow solid. $^1$H-NMR (400 MHz, DMSO-$d_6$) δ 1.58-1.72 (1H, m), 1.80-1.92 (1H, m), 2.30-2.47 (6H, m), 3.41 (2H, q, J=6.1 Hz), 3.48-3.56 (2H, m), 4.13-4.24 (2H, m), 5.93-6.01 (1H, m), 6.42-6.48 (2H, m), 6.65 (1H, t, J=6.1 Hz), 7.05 (2H, brs), 7.31-7.37 (1H, m), 7.94 (1H, dd, J=4.9, 1.2 Hz), 8.16 (1H, s). HRESIMS (+): 435.19403 (calcd for $C_{23}H_{24}FN_6O_2$, 435.19443).

Example 92

8'-amino-9'-fluoro-7'-oxo-10'-[3-(2-pyridyl) propylamino]spiro[oxolane-1,3'(2'H)-[7H]pyrido[1,2,3-de][1,4]benzoxazine]-6'-carbonitrile

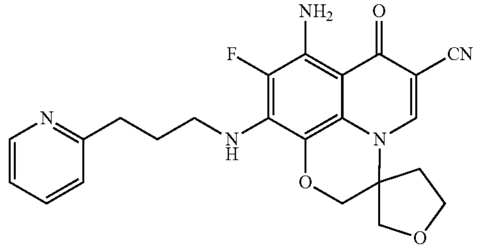 [SMILES: N#Cc1cn2c3c(c(NCCCc4ccccn4)c(F)c(N)c3c1=O)OCC21CCOC1]

A mixture of 8'-amino-9'-difluoro-7'-oxo-10'-[3-(2-pyridyl)propylamino]-spiro [oxolane-1,3'(2'H)-[4H]pyrido[1,2,3-de][1,4]benzoxazine]-6'-carboxamide (165 mg, 0.364 mmol), $POCl_3$ (167 mg, 1.09 mmol) and triethylamine (0.254 mL, 1.82 mmol) in $CH_2Cl_2$ (2 mL) was stirred at room temperature for 10 h. To the reaction mixture, saturated aqueous $NaHCO_3$ was added to pH>7 and extracted with AcOEt. The organic layer was wash with brine and dried over MgSO4, and the solvent was removed in vacuo. The crude product was purified by column chromatography (Hexane:EtOAc 1:1→EtOAc→EtOAc:MeOH 10:1) to yield 8'-amino-9'-fluoro-7'-oxo-10'-[3-(2-pyridyl)-propylamino]spiro[oxolane-1,3'(2'G)-[7H]pyrido[1,2,3-de][1,4]benzoxazine]-6'-carbonitrile (42.4 mg, 27%) as a pale yellow solid. $^1$H-NMR (400 MHz, DMSO-$d_6$) δ1.88-1.95 (2H, m), 2.17-2.25 (1H, m), 2.35-2.42 (1H, m), 2.75 (2H, t, J=7.3 Hz), 3.38-3.46 (2H, m), 3.70 (1H, d, J=10.4 Hz), 3.89 (1H, td, J=8.6, 5.5 Hz), 3.97 (1H, d, J=10.4 Hz), 4.13-4.19 (1H, m), 4.22 (1H, d, J=11.6 Hz), 4.24 (1H, d, J=11.6 Hz), 5.73-5.80 (1H, m), 6.99 (2H, brs), 7.18 (1H, dd, J=6.7, 5.5 Hz), 7.23 (1H, d, J=7.9 Hz), 7.67 (1H, td, J=7.3, 1.8 Hz), 8.23 (1H, s), 8.45 (1H, d, J=4.3 Hz). HRESIMS (+) 436.17877 (Calcd for $C_{23}H_{22}FN_5O_3$, 436.17849).

Example 93

9'-amino-10'-fluoro-2',3'-dihydro-8'-oxo-11'-[3-(1-imidazolyl)propylamino]spiro-[cyclobutane-1,4% [4H,8H]pyrido-[1,2,3-ef][1,5]benzoxazepine]-7'-carbonitrile

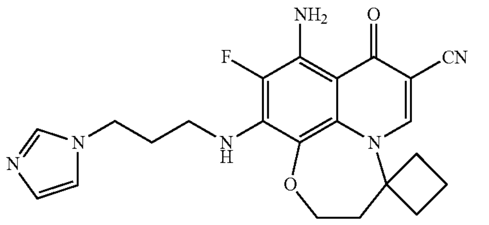 [SMILES: N#Cc1cn2c3c(c(NCCCn4ccnc4)c(F)c(N)c3c1=O)OCCC21CCC1]

The title compound was prepared from 9'-amino-10',11'-difluoro-2',3'-dihydro-8'-oxospiro[cyclobutane-1,4'-[4H, 8H]pyrido[1,2,3-ef][1,5]benzoxazepine]-7'-carbonitrile using synthetic procedures similar to those described in the examples above. $^1$H-NMR (400 MHz, $CDCl_3$) δ 1.80-2.04 (2H, m), 2.06-2.13 (1H, m), 2.38-2.55 (6H, m), 3.44 (2H, dq, J=2.4, 6.7 Hz), 4.06 (2H, t, J=6.7 Hz), 4.31-4.40 (2H, m), 4.46 (1H, td, J=6.7, 1.8 Hz), 6.50 (2H, brs), 6.93 (1H, t, J=1.2 Hz), 7.09 (1H, t, J=1.2 Hz), 7.49 (1H, s), 7.65 (1H, s). HRESIMS (+): 423.19445 (calcd for $C_{23}H_{23}FN_6O_2$, 423.19448).

Example 94

9'-amino-10'-fluoro-2',3'-dihydro-6'-methyl-8'-oxo-11'-[2-(2-pyridylamino)ethylamino]spiro[cyclobutane-1,4%[4H,8H]pyrido[1,2,3-ef][1,5]benzoxazepine]-7'-carboxylic Acid 94A) Preparation of Ethyl 10',11'-difluoro-2',3',6',7-tetrahydro-6'-methyl-9'-nitro-8'-oxospiro[cyclobutane-1,4'-[4H,8H]pyrido[1,2,3-ef][1,5]benzoxaepine]-7'-carboxylate

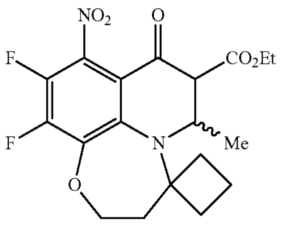 [SMILES: CCOC(=O)C1C(=O)c2c3c(c(F)c(F)c2[N+](=O)[O-])OCCC2(CCC2)N3C1C]

3 M Methylmagnesium chloride in THF (10.8 mL, 32.4 mmol) was added under argon atmosphere to a stirred mixture of ethyl 10',11'-difluoro-2',3'-dihydro-9'-nitro-8'-oxo spiro [cyclobutane-1,4'-[4H,8H]pyrido[1,2,3-ef][1,5]benzoxazepine]-7'-carboxylate (3.88 g, 9.84 mmol) and cuprous iodide (562 mg, 2.95 mmol) in THF (200 mL) at −78° C. The reaction mixture was stirred at room temperature for 24 hours, poured into water (1 L). Concentrated HCl (50 mL) was added to pH<1 and the mixture stirred for 30 minutes. The crude product was extracted with AcOEt, washed with saturated aqueous $NaHCO_3$ and brine, dried over $MgSO_4$ and the solvent was removed in vacuo. The crude product was purified by column chromatography (Hexane:EtOAc 20:1→5:1) to yield the title compound (1.71 g, 42%) as a yellow solid. $^1$H-NMR (400 MHz, DMSO-$d_6$) δ 1.09 (3H, d, J=6.1 Hz), 1.27 (3H, t, J=7.3 Hz), 1.60-1.69 (1H, m), 1.72-1.83 (1H, m), 1.94-2.15 (4H, m), 2.24-2.35 (1H, m), 2.51-2.57 (1H, m), 4.28 (2H, q, J=7.3 Hz), 4.39-4.50 (2H, m), 4.58-4.63 (1H, m), 11.64 (1H, s).

94B) Preparation of Ethyl 10',11'-difluoro-2',3'-dihydro-6'-methyl-9'-nitro-8'-oxospiro[cyclobutane-1,4'-[4H,8H]pyrido[1,2,3-d][1,5]benzoxazepine]-7'-carboxylate

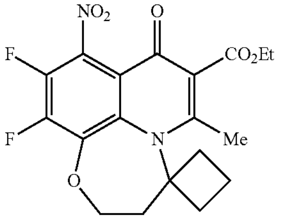 [SMILES: CCOC(=O)c1c(C)n2c3c(c(F)c(F)c([N+](=O)[O-])c3c1=O)OCCC21CCC1]

A mixture of ethyl 10',11'-difluoro-2',3',6',7'-tetrahydro-6'-methyl-9'-nitro-8'-oxospiro[cyclobutane-1,4'-[4H,8H]pyrido[1,2,3-ef][1,5]benzoxazepine]-7'-carboxylate (1.50 g, 3.66 mmol) and manganese dioxide (32.0 g, 366 mmol) in $CH_2Cl_2$ (40 mL) was stirred at room temperature for 40 hours. The mixture was filtered through Celite and the filtrate concentrated in vacuo. The crude product was purified by column chromatography (Hexane:EtOAc 2:1→1:2) to yield the title compound (168 mg, 11%) as a pale yellow solid. $^1$H-NMR (400 MHz, DMSO-$d_6$) δ 1.25 (3H, t, J=7.3 Hz), 1.59-1.67 (1H, m), 1.81-1.88 (1H, m), 2.08-2.18 (1H, m), 2.27 (3H, s), 2.34-2.54 (4H, m), 2.80-2.92 (1H, m), 4.20-4.27 (2H, m), 4.63-4.83 (2H, m).

94C) Preparation of Ethyl 9'-amino-10',11'-difluoro-2',3'-dihydro-6'-methyl-8'-oxospiro[cyclobutane-1,4'-[4H,8H]pyrido[1,2,3-ef][1,5]benzoxazepine]-7'-carboxylate

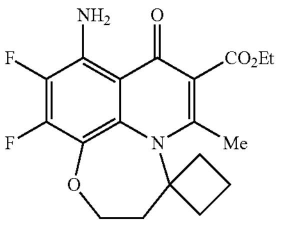 [SMILES: CCOC(=O)c1c(C)n2c3c(c(F)c(F)c(N)c3c1=O)OCCC21CCC1]

A mixture of ethyl 10',11'-difluoro-2',3'-dihydro-6'-methyl-9'-nitro-8'-oxospiro-[cyclobutane-1,4'-[4H,8H]pyrido [1,2,3-ef][1,5]benzoxazepine]-7'-carboxylate (160 mg, 0.392 mmol) and iron (146 mg, 2.35 mmol) in AcOH (4 mL) was stirred at 90° C. for 3 hours. The reaction mixture was concentrated in vacuo and 1 M aqueous HCl was added. The crude product was extracted with AcOEt, washed successively with saturated aqueous $NaHCO_3$ and brine, dried over $MgSO_4$ and the solvent was removed in vacuo. The residue was dried to yield the title compound (146 mg, 98%) as a yellow amorphous solid. $^1$H-NMR (400 MHz, DMSO-$d_6$) δ 1.24 (3H, t, J=7.3 Hz), 1.58-1.65 (1H, m), 1.75-1.87 (1H, m), 1.93-2.05 (1H, m), 2.16 (3H, s), 2.22-2.34 (2H, m), 2.37-2.46

(1H, m), 2.51-2.60 (1H, m), 2.68-2.80 (1H, m), 4.18-4.24 (2H, m), 4.26-4.36 (1H, m), 4.53-4.64 (1H, m), 7.23 (2H, brs).

94D) Preparation of 9'-amino-10',11'-difluoro-2',3'-dihydro-6'-methyl-8'-oxospiro[cyclobutane-1,4'-[4H, 8H]pyrido[1,2,3-ef][1,5]benzoxazepine]-7'-carboxylic Acid

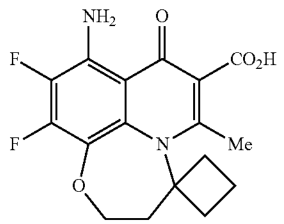 [SMILES: Cc1c(C(=O)O)c(=O)c2c(N)c(F)c(F)c3c2n1C1(CCC1)CCO3]

A mixture of ethyl 9'-amino-10',11'-difluoro-2',3'-dihydro-6'-methyl-8'-oxospiro-[cyclobutane-1,4'-[4H,8H]pyrido[1,2,3-ef][1,5]benzoxazepine]-7'-carboxylate (136 mg, 0.359 mmol) and 1M aq. NaOH (1.4 mL) in EtOH (1.4 mL) was stirred at reflux for 5 hours. The reaction mixture was concentrated in vacuo, the residue dissolved in water, and 2M aq. HCl was added to pH<3. The resulting precipitate was collected by filtration in vacuo, washed with water and dried to yield the title compound (110 mg, 87%) as a yellow solid. $^1$H-NMR (400 MHz, DMSO-$d_6$) δ 1.53-1.61 (1H, m), 1.77-1.85 (1H, m), 1.97-2.05 (1H, m), 2.28-2.40 (3H, m), 2.52-2.58 (1H, m), 2.60 (3H, s), 2.76-2.84 (1H, m), 4.38 (1H, td, J=12.2, 4.3 Hz), 4.62 (1H, dd, J=12.2, 6.7 Hz), 7.27 (2H, brs), 15.18 (1H, brs).

94E) Preparation of 9'-amino-10'-fluoro-2',3'-dihydro-6'-methyl-8% oxo-11'-[2-(2-pyridylamino)ethylamino]spiro[cyclobutane-1,4% [4H,8H]pyrido[1,2,3-ej][1,5]benzoxazepine]-7'-carboxylic Acid

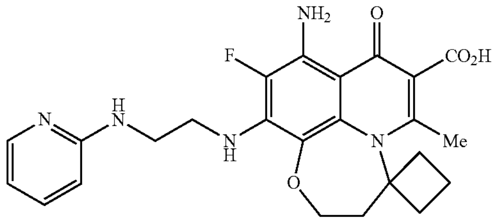 [SMILES: Cc1c(C(=O)O)c(=O)c2c(N)c(F)c(NCCNc3ccccn3)c3c2n1C1(CCC1)CCO3]

A solution of 9'-amino-10',11'-difluoro-2',3'-dihydro-6'-methyl-8'-oxospiro-[cyclobutane-1,4'-[4H,8H]pyrido[1,2,3-ef][1,5]benzoxazepine]-7'-carboxylic acid (100 mg, 0.285 mmol), N-(2-pyridyl)-1,2-ethanediamine (58.7 mg, 0.428 mmol) and triethylamine (0.0597 mL, 0.428 mmol) in DMSO (3 mL) was stirred at 100° C. for 5 h. After the reaction mixture was poured into saturated aq. $NH_4Cl$, the crude product was extracted with $CH_2Cl_2$, washed with brine, dried over $MgSO_4$ and the solvent was removed in vacuo. The crude product was purified by preparative thin layer chromatography (EtOAc: MeOH 20:1) to yield the title compound (70.3 mg, 53%) as a yellow solid. $^1$H-NMR (400 MHz, DMSO-$d_6$) δ 1.49-1.59 (1H, m), 1.72-1.79 (1H, m), 1.85-1.92 (1H, m), 2.23-2.32 (2H, m), 2.37-2.45 (2H, m), 2.57 (3H, s), 2.66-2.75 (1H, m), 3.40-3.47 (2H, m), 3.51-3.62 (2H, m), 4.19 (1H, td, J=12.2, 3.7 Hz), 4.49 (1H, dd, J=12.2, 6.7 Hz), 6.10-6.16 (1H, m), 6.43-6.49 (2H, m), 6.64-6.70 (1H, m), 6.88 (2H, brs), 7.34 (1H, t, J=6.7 Hz), 7.95-7.96 (1H, m), 16.08 (1H, brs). HRESIMS (+): 468.20454 (Calcd for $C_{24}H_{26}FN_5O_4$, 468.2047).

Example 95

9'-amino-10'-chloro-2',3'-dihydro-8'-oxo-11'-[2-(2-pyridylamino)ethylamino]spiro [cyclobutane-1,4'-[4H,8H]pyrido[1,2,3-ef][1,5]benzoxazepine]-7'-carboxylic acid 95A) Preparation of Ethyl 10'-amino-11'-fluoro-2',3'-dihydro-9'-nitro-8'-oxospiro[cyclobutane-1,4'-[4H, 8H]pyrido[1,2,3-ef][1,5]benzoxazepine]-7% carboxylate

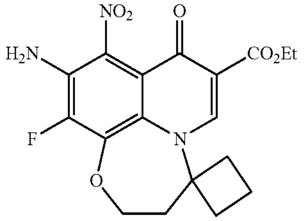 [SMILES: CCOC(=O)c1cn2c3c(c(F)c(N)c([N+](=O)[O-])c3c1=O)OCCC21CCC1]

A mixture of ethyl 10',11'-difluoro-2',3'-dihydro-9'-nitro-8'-oxospiro[cyclobutane-1,4'-[4H,8H]pyrido[1,2,3-ef][1,5] benzoxazepine]-7'-carboxylate (5.00 g, 12.7 mmol) and $(NH_4)_2CO_3$ (11.0 g, 114 mmol) in DMF (50 mL) was stirred at 90° C. for 21 hours. The reaction mixture was poured into water, the resulting precipitate was collected by filtration in vacuo, washed successively with hot AcOEt and hot EtOH and dried to yield the title compound (2.51 g, 50%) as a yellow solid. $^1$H-NMR (400 MHz, DMSO-$d_6$) δ 1.24 (3H, t, J=7.3 Hz), 1.65-1.76 (1H, m), 1.88-2.00 (1H, m), 2.41-2.46 (4H, m), 2.60-2.63 (2H, m), 4.19 (2H, q, J=7.3 Hz), 4.47-4.50 (2H, m), 6.07 (2H, brs), 8.26 (1H, s).

95B) Preparation of Ethyl 10'-chloro-11'-fluoro-2'3,-dihydro-9'-nitro-8'-oxospiro[cyclobutane-1,4'-[4H, 8H]pyrido[1,2,3-ef][1,5]benzoxazepine]-7'-carboxylate

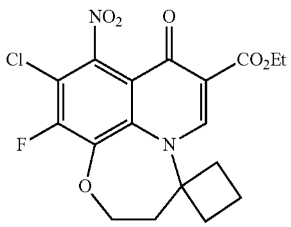 [SMILES: CCOC(=O)c1cn2c3c(c(F)c(Cl)c([N+](=O)[O-])c3c1=O)OCCC21CCC1]

Ethyl 10'-amino-11'-fluoro-2',3'-dihydro-9'-nitro-8'-oxospiro[cyclobutane-1,4'-[4H,81-1]pyrido[1,2,3-ef][1,5]benzoxazepine]-7'-carboxylate (2.51 g, 6.41 mmol) was added to a mixture of tert-butyl nitrite (1.14 mL, 9.62 mmol) and copper (II) chloride (1.81 g, 12.8 mmol) in $CH_3CN$ (64 mL), and the mixture was stirred at room temperature for 20 hours. The reaction mixture was poured into water (300 mL), concentrated HCl (50 mL) was added to pH<1, and resulting precipitate was collected by filtration, washed with hot EtOH and dried to yield the title compound (2.17 g, 82%) as a pale yellow solid. $^1$H-NMR (400 MHz, DMSO-$d_6$) δ 1.25 (3H, t, J=7.3 Hz), 1.67-1.75 (1H, m), 1.92-1.99 (1H, m), 2.41-2.53 (4H, m), 2.66-2.69 (2H, m), 4.22 (2H, q, J=7.3 Hz), 4.60-4.63 (2H, m), 8.42 (1H, s).

95C) Preparation of Ethyl 9'-amino-10'-chloro-11'-fluoro-2',3'-dihydro-8'-oxospiro[cyclobutane-1,4'-[4H,8H]pyrido[1,2,3-ef][1,5]benzoxazepine]7'-carboxylate

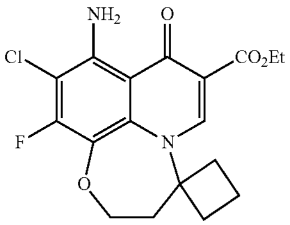 [SMILES: CCOC(=O)c1cn2c3c(c(F)c(Cl)c(N)c3c1=O)OCCC21CCC1]

A mixture of ethyl 10'-chloro-11'-fluoro-2',3'-dihydro-9'-nitro-8'-oxospiro-[cyclobutane-1,4'-[4H,8]pyrido[1,2,3-ef][1,5]benzoxazepine]-7'-carboxylate (2.17 g, 5.28 mmol) and iron (1.97 g, 31.7 mmol) in AcOH (50 mL) was stirred at 90° C. for 5 hours. The reaction mixture was concentrated in vacuo, the residue was dissolved in AcOEt and stirred for 30 minutes. The resulting precipitate was removed by filtration through Celite. The filtrate was washed successively with water, saturated aqueous $NaHCO_3$ and brine, dried over $MgSO_4$, and the solvent was removed in vacuo. The crude product was washed with hot EtOH to yield the title compound (1.03 g, 51%) as a pale yellow solid. $^1$H-NMR (400 MHz, DMSO-$d_6$) δ 1.25 (3H, t, J=7.3 Hz), 1.65-1.75 (1H, m), 1.89-1.96 (1H, m), 2.38-2.47 (4H, m), 2.52-2.59 (2H, m), 4.20 (2H, q, J=7.3 Hz), 4.30-4.41 (2H, m), 7.33-7.55 (2H, m), 8.23 (1H, s).

95D) Preparation of 9'-amino-10'-chloro-11'-fluoro-2',3'-dihydro-8'-oxospiro[cyclobutane-1,4'-[4H,8H]pyrido[1,2,3-ef][1,5]benzoxazepine]-7'-carboxylic acid

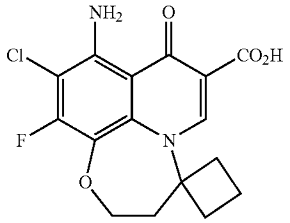 [SMILES: Nc1c(Cl)c(F)c2c3c1c(=O)c(C(=O)O)cn3C1(CCC1)CCO2]

A solution of ethyl 9'-amino-10'-chloro-11'-fluoro-2',3'-dihydro-8'-oxospiro-[cyclobutane-1,4'-[4H,8H]pyrido[1,2,3-d][1,5]benzoxazepine]-7'-carboxylate (1.03 g, 2.70 mmol) in a mixture of AcOH—$H_2O$—$H_2SO_4$ (2:1:0.3 v/v, 6.6 mL) was heated at 100° C. for 2 hours. Ice-water was added and the mixture stirred for 30 minutes. The resulting precipitate was collected by filtration in vacuo, washed with water and dried to yield the title compound (908 mg, 95%) as a colorless solid. $^1$H-NMR (400 MHz, DMSO-$d_6$) δ1.65-1.74 (2H, m), 1.88-1.99 (2H, m), 2.40-2.69 (4H, m), 4.25-4.51 (2H, m), 7.73 (2H, brs), 8.49 (1H, s), 14.56 (1H, s).

95E) Preparation of 9'-amino-10'-chloro-2',3'-dihydro-8'-oxo-11'-[2-(2-pyridylamino)ethylamino]spiro[cyclobutane-1,4'-[4H,8H]pyrido[1,2,3-ef][1,5]benzoxazepine]-7'-carboxylic Acid

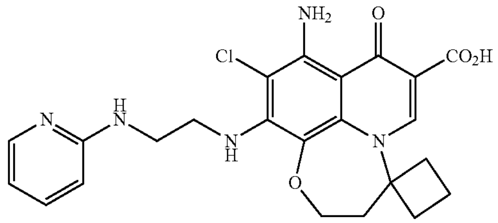 [SMILES: Nc1c(Cl)c(NCCNc2ccccn2)c2c3c1c(=O)c(C(=O)O)cn3C1(CCC1)CCO2]

A solution of 9'-amino-10'-chloro-11'-fluoro-2',3'-dihydro-8'-oxospiro [cyclobutane-1,4'-[4H,8H]pyrido[1,2,3-ef][1,5]benzoxazepine]-7'-carboxylic acid (900 mg, 2.55 mmol), N-2-pyridinyl-1,2-ethanediamine (525 mg, 3.83 mmol) and triethylamine (0.534 mL, 3.83 mmol) in DMSO (10 mL) was stirred at 100° C. for 7 hours. Saturated aqueous $NH_4Cl$ was added to the reaction mixture until pH<3, and the resulting precipitate was collected by vacuum filtration and washed with water. The crude product was purified by preparative thin layer chromatography ($CH_2Cl_2$: MeOH 50:1) to yield the title compound (565 mg, 47%) as a yellow solid. $^1$H-NMR (400 MHz, DMSO-$d_6$) δ 1.64-1.72 (1H, m), 1.86-1.98 (1H, m), 2.32-2.66 (6H, m), 3.40-3.44 (2H, m), 3.62-3.66 (2H, m), 3.94-4.53 (2H, m), 6.00 (1H, t, J=5.5 Hz), 6.44-6.47 (2H, m), 6.66 (1H, t, J=5.5 Hz), 7.07-7.63 (3H, m), 7.94 (1H, dd, J=5.5, 1.2 Hz), 8.29 (1H, s), 15.15 (1H, s). HRESIMS (+): 470.15831 (Calcd for $C_{23}H_{24}ClN_5O_4$, 470.1595).

Examples 96-98

Compounds 96-98 may be prepared from 8-amino-9,10-difluoro-7-oxo-2,7-dihydrospiro[[1,4]oxazino[2,3,4-ij]-quinoline-3,1'-cyclopentane]-6-carboxylic acid or 9'-amino-10',11'-difluoro-2',3'-dihydro-8'-oxospiro-[cyclobutane-1,4'-[4H,8H]pyrido[1,2,3-ef][1,4]benzoxazepine]-7'-carboxylic acid using synthetic procedures similar to those described in the examples above.

Example 96

10-(3-(1H-imidazol-1-yl)propylamino)-8-amino-9-fluoro-7-oxo-2,7-dihydrospiro[[1,4]oxazino[2,3,4-ij]quinoline-3,1'-cyclopentane]-6-carboxylic Acid

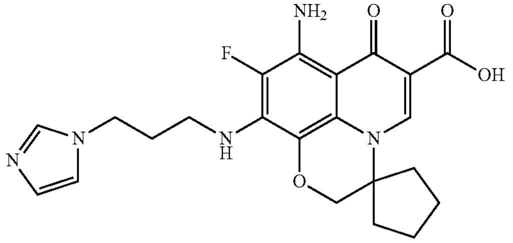 [SMILES: Nc1c(F)c(NCCCn2ccnc2)c2c3c1c(=O)c(C(=O)O)cn3C1(CCCC1)CO2]

MS (EP) m/z: 442.0 (M+1). (Calcd. For $C_{22}H_{24}FN_5O_4$, 441.18).

Example 97

9-amino-10-fluoro-8-oxo-11-(3-(pyridin-2-ylamino)-pyrrolidin-1-yl)-3,8-dihydro-2H-spiro[[1,4]oxazepino[2,3,4-ij]quinoline-4,1'-cyclobutane]-7-carboxylic Acid

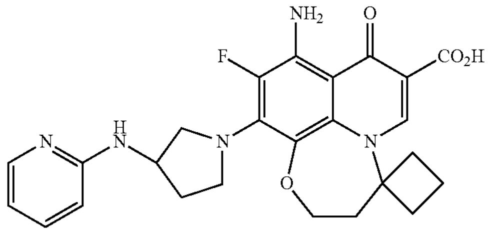 [SMILES: Nc1c(F)c(N2CCC(Nc3ccccn3)C2)c2c3c1c(=O)c(C(=O)O)cn3C1(CCC1)CCO2]

$^1$H-NMR (400 MHz, DMSO-$d_6$) δ 1.59-1.73 (1H, m), 1.81-1.97 (2H, m), 2.05-2.19 (1H, m), 2.47-2.51 (6H, m), 3.42-3.53 (1H, m), 3.85-3.97 (3H, m), 4.11-4.29 (3H, m), 6.44-6.51 (2H, m), 6.75 (1H, d, J=6.1 Hz), 6.94 (2H, brs), 7.32-7.39 (1H, m), 7.96 (1H, dd, J=6.1, 1.2 Hz), 8.26 (1H, s), 15.13 (1H, brs). HRESIMS (+): 480.20547 (Calcd for $C_{25}H_{27}FN_5O_4$, 480.20471).

Example 98

8'-amino-9'-fluoro-7'-oxo-10'-(3-(pyridin-2-ylamino) pyrrolidin-1-yl)-2',7'-dihydro-1'H-spiro[cyclopentane-1,3'-pyrido[3,2,1-ij]quinoline]-6'-carboxylic Acid

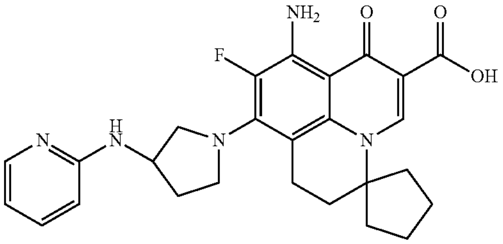 [SMILES: Nc1c(F)c(N2CCC(Nc3ccccn3)C2)c2c3c1c(=O)c(C(=O)O)cn3C1(CCCC1)CC2]

$^1$H-NMR (400 MHz, DMSO-$d_6$) δ 1.72-2.04 (9H, m), 2.08-2.19 (1H, m), 3.50-3.58 (1H, m), 3.71-3.80 (1H, m), 3.81-3.90 (1H, m), 3.95-4.02 (1H, m), 4.08 (2H, s), 4.33-4.42 (1H, m), 6.44-6.51 (2H, m), 6.76 (1H, d, J=6.1 Hz), 6.88 (2H, brs), 7.32-7.38 (1H, m), 7.97 (2H, dd, J=4.9, 1.2 Hz), 8.38 (1H, s), 15.19 (1H, s). HRESIMS (+):480.20378 (Calcd for $C_{25}H_{27}FN_5O_4$, 480.20471).

Example 99

9-amino-10-fluoro-6-methyl-11-(2-(pyridin-2-ylamino)-ethylamino)-2H-spiro[[1,4]oxazepino[2,3,4-ij]quinoline-4,1'-cyclobutan]-8(3H)-one

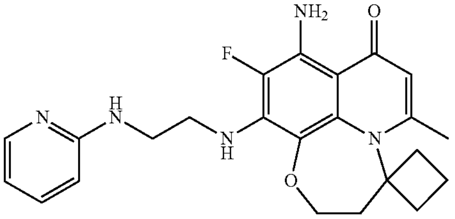 [SMILES: Cc1cc(=O)c2c(N)c(F)c(NCCNc3ccccn3)c3c2n1C1(CCC1)CCO3]

A mixture of 9'-amino-10'-fluoro-2',3'-dihydro-6'-methyl-8'-oxo-11'-[2-(2-pyridylamino)ethylamino]spiro[cyclobutane-1,4'-[4H,8H]pyrido[1,2,3-d][1,5]benzoxazepine]-7'-carboxylic acid (42.7 mg, 0.0913 mmol) and sodium cyanide (46.1 mg, 0.913 mmol) in anhydrous DMSO (2 mL) was stirred at 150° C. for 8 hours. After cooling, the reaction mixture was poured into saturated aqueous $NaHCO_3$ and extracted with EtOAc. The extraction mixture was washed with brine, dried over $MgSO_4$, and concentrated in vacuo. The residue was purified by preparative TLC (Silica gel 60 (Merck Co., Ltd.) EtOAc: MeOH 10:1) to give the title compound (20.8 mg, 54%) as a yellow solid. $^1$H-NMR (400 MHz, DMSO-$d_6$) δ 1.52-1.60 (1H, m), 1.73-1.79 (1H, m), 2.10 (3H, s), 3.27-3.33 (6H, m), 3.37-3.41 (2H, m), 3.43-3.51 (2H, m), 3.96-4.53 (2H, m), 5.41-5.47 (1H, m), 5.57 (1H, s), 6.42-6.47 (2H, m), 6.60 (1H, t, J=5.5 Hz), 6.84 (2H, brs), 7.33 (1H, dd, J=6.7, 1.8 Hz), 7.93-7.95 (1H, m). HRESIMS (+): 424.21446 (calcd for $C_{23}H_{26}FN_5O_2$, 424.21488).

Example: 100

8'-amino-9'-fluoro-7'-oxo-10'-[3-(4,6-bistrifluoropyridin-2-yl)propylamino]spiro[oxolane-1,3'(2'H)-[7H] pyrido[1,2,3-de][1,4]benzoxazine]-6'-carbonitrile 100A) Preparation of tert-butyl 3-(4,6-bistrifluoromethylpyridin-2-yl) propylcarbamate

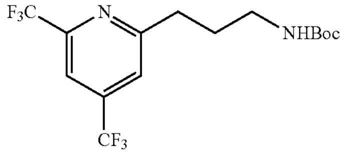 [SMILES: CC(C)(C)OC(=O)NCCCc1cc(C(F)(F)F)cc(C(F)(F)F)n1]

To a stirred solution of tert-butyl allylcarbamate (1.95 g, 12.4 mmol) in THF (12 mL), 0.5 mol/L 9-borabicyclo[3.3.1] nonane (29.8 mL, 14.9 mmol) was added under argon atmosphere at room temperature. After stirred at room temperature for 4 h, a solution of 2-bromo-4,6-bistrifluoromethylpyridine (3.65 g, 12.4 mmol) in DMF (12 mL), $Pd(OAc)_2$ (278 mg, 1.24 mmol), DPPF (859 mg, 1.55 mmol) and $K_2CO_3$ (2.92 g, 21.1 mmol) were added to the reaction mixture and stirred at room temperature for 7 h. To the reaction mixture, water was added and the crude product was extracted with EtOAc, washed with brine, dried over $NaSO_4$ and the solvent was removed in vacuo. The crude product was purified by column chromatography (Hexane:EtOAc 10:1→2:1) to yield tert-butyl 3-(4,6-bistrifluoromethylpyridin-2-yl)propylcarbamate (3.41 g, 74%) as a colorless solid. $^1$H NMR ($CDCl_3$, 400 MHz) δ 1.44 (9H, s), 1.96-2.03 (2H, m), 2.98-3.02 (2H, m), 3.20-3.25 (2H, m), 4.71 (1H, brs), 7.59 (1H, s), 7.72 (1H, s). CIMS (+) 373 $[M+H]^+$.

100B) Preparation of 3-(4,6-bistrifluoropyridin-2-yl)propylamine

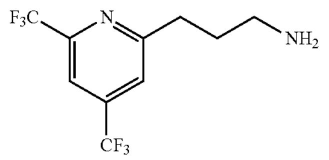 [SMILES: NCCCc1cc(C(F)(F)F)cc(C(F)(F)F)n1]

A solution of tert-butyl 3-(4,6-bistrifluoromethylpyridin-2-yl)propylcarbamate (3.10 g, 8.33 mmol) in 4 mol/L hydrogen chloride in EtOAc (20 mL) was stirred at room temperature for 30 min. The solvent was removed in vacuo and to the precipitate, 1 mol/L aq. NaOH was added to alkalify and the crude product was extracted with EtOAc, washed with brine, dried over $NaSO_4$ and the solvent was removed in vacuo. The precipitate was dried to yield 3-(4,6-bistrifluoropyridin-2-yl) propylamine (2.26 g, quant.) as a yellow oil. $^1$H NMR (DMSO-$d_6$, 400 MHz) δ 1.54 (2H, brs), 1.73-1.80 (2H, m), 2.56 (2H, t, J=6.7 Hz), 2.96 (2H, t, J=7.9 Hz), 8.06 (1H, s), 8.09 (1H, s). CIMS (+) 273 $[M+H]^+$.

100C) Preparation of 8'-amino-9',10-difluoro-7'-oxospiro[oxolane-3,3'(2'H)-[7H]pyrido[1,2,3-de][1,4]benzoxazine]-6'-carboxamide

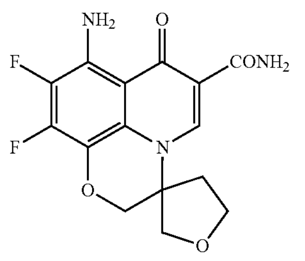 [SMILES: NC(=O)c1cn2c3c(c(F)c(F)c(N)c3c1=O)OCC21CCOC1]

A solution of 8'-amino-9'-fluoro-7'-oxo-10'-[3-(pyridin-2-yl)propylamino]spiro[oxolane-1,3'(2'H)-[7H]pyrido[1,2,3-de][1,4]benzoxazine]-6'-carboxylic acid (1.00 g, 2.96 mmol), ethyl chloroformate (0.312 mL, 3.26 mmol) and triethylamine (0.495 mL, 3.55 mmol) in DMF (15 mL) was stirred under argon atmosphere and ice-cooling for 2 h. To the reaction mixture, 25% aqueous $NH_3$ (1 mL) was added and stirred at room temperature for 2 h. To the reaction mixture, water was added and the crude product was extracted with EtOAc, washed with brine, dried over $NaSO_4$ and the solvent was removed in vacuo. The precipitate was dried to yield 8'-amino-9',10-difluoro-7'-oxospiro[oxolane-3,3'(2'H)-[7H]pyrido[1,2,3-de][1,4]benzoxazine]-6'-carboxamide (186 mg, 81%) as a pale yellow solid.

$^1$H NMR (DMSO-$d_6$, 400 MHz) δ 2.25-2.32 (1H, m), 2.35-2.42 (1H, m), 3.74 (1H, d, J=11.0 Hz), 3.91-3.97 (1H, m), 4.06-4.12 (1H, m), 4.16 (1H, d, J=11.0 Hz), 4.34 (1H, d, J=11.6 Hz), 4.45 (1H, d, J=11.6 Hz), 7.41 (2H, brs), 7.54 (1H, d, J=4.3 Hz), 8.63 (1H, s), 8.98 (1H, d, J=4.3 Hz).

100D) Preparation of 8'-amino-9',10-difluoro-7'-oxospiro [oxolane-3,3'(2'11)-[7H]pyrido[1,2,3-de][1,4]benzoxazine]-6'-carbonitrile

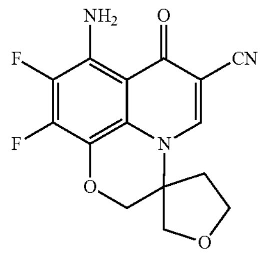 [SMILES: N#Cc1cn2c3c(c(F)c(F)c(N)c3c1=O)OCC21CCOC1]

To a stirred solution of 8'-amino-9',10-difluoro-7'-oxospiro [oxolane-3,3'(2'H)-[7H]pyrido[1,2,3-de][1,4]benzoxazine]-6'-carboxamide (860 mg, 2.55 mmol) and triethylamine (1.78 mL, 12.8 mmol) in $CH_2Cl_2$ (26 mL), phosphoryl chloride (1.17 g, 7.65 mmol) was added under ice-cooling and stirred at room temperature for 5 h. The solvent was removed in vacuo and to the crude product, MeOH—$H_2O$ (1:2, 50 mL) was added. After stirred for 30 min, the resulting precipitate was collected by filtration, washed with water and dried to yield 8'-amino-9',10-difluoro-7'-oxospiro[oxolane-3,3'(2'H)-[7H]pyrido[1,2,3-de][1,4]benzoxazine]-6'-carbonitrile (683 mg, 84%) as a pale yellow solid.

$^1$H NMR (DMSO-$d_6$, 400 MHz) δ 2.22-2.29 (1H, m), 2.42-2.46 (1H, m), 3.72 (1H, d, J=10.4 Hz), 3.88 (1H, td, J=8.6, 6.1 Hz), 4.05 (1H, d, J=10.4 Hz), 4.16-4.22 (1H, m), 4.37 (1H, d, J=11.6 Hz), 4.38 (1H, d, J=11.6 Hz), 7.40 (2H, brs), 8.46 (1H, s).

100E) Preparation of 8'-amino-9'-fluoro-7'-oxo-10'-[3-(4,6-bistrifluoropyridin-2-yl)propylamino]spiro [oxolane-1,3'(2'H)-[7H]pyrido[1, 2,3-de][1,4]benzoxazine]-6'-carbonitrile

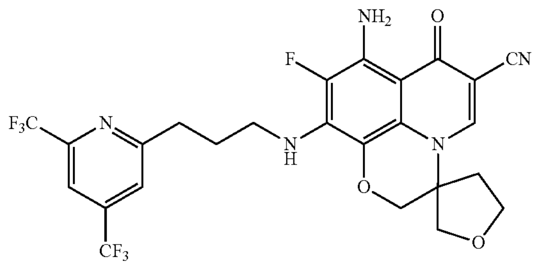 [SMILES: N#Cc1cn2c3c(c(NCCCc4cc(C(F)(F)F)cc(C(F)(F)F)n4)c(F)c(N)c3c1=O)OCC21CCOC1]

A solution of 8'-amino-9',10-difluoro-7'-oxospiro [oxolane-3,3'(2'H)-[7H]pyrido[1,2,3-de][1,4]benzoxazine]-6'-carbonitrile (320 mg, 1.00 mmol), 3-(4,6-bistrifluoromethylpyridine-2-yl)propylamine (408 mg, 1.50 mmol) and triethylamine (0.210 mL, 1.50 mmol) in DMSO (5 mL) was stirred at 100° C. for 6 h then at 120° C. for 2 h. To the reaction mixture, saturated aqueous $NH_4Cl$ was added to neutralize and the crude product was extracted with EtOAc, washed with brine, dried over $NaSO_4$ and the solvent was removed in vacuo. The crude product was purified by column chromatography (Hexane: EtOAc 5:1→1:1) to yield 8'-amino-9'- fluoro-7'-oxo-10'-[3-(4,6-bistrifluoropyridin-2-yl)propylamino]spiro[oxolane-1,3'(2'H)-[7H]pyrido[1,2,3-de][1,4]benzoxazine]-6'-carbonitrile (387 mg, 68%) as a pale yellow solid.

$^1$H NMR (DMSO-$d_6$, 400 MHz) δ 1.95-2.02 (2H, m), 2.17-2.24 (1H, m), 2.35-2.42 (1H, m), 2.99 (2H, t, J=7.6 Hz), 3.40-3.49 (2H, m), 3.69 (1H, d, J=10.4 Hz), 3.88 (1H, td, J=9.2, 5.5 Hz), 3.96 (1H, d, J=10.4 Hz), 4.14-4.20 (1H, m), 4.21 (1H, d, J=11.0 Hz), 4.24 (1H, d, J=11.0 Hz), 5.71-5.81 (1H, m), 6.97 (2H, brs), 8.07 (1H, s), 8.10 (1H, s), 8.24 (1H, s).

HRESIMS (+) 572.15292 (calcd for $C_{25}H_{21}F_7N_5O_3$).

Examples 101-108

By using the procedures set out above, the compounds of example 101 to 108 were prepared:

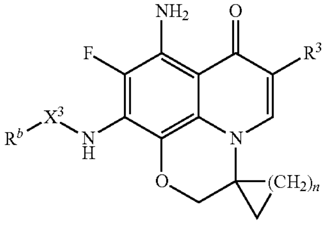

| Example No. | $R^b$—$X^3$— | n | $R^3$ | Data |
|---|---|---|---|---|
| 101 | 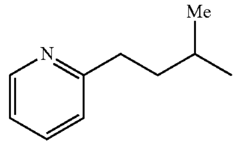 | 3 | COOH | $^1$H-NMR (DMSO-$d_6$, 400 MHz) δ 1.21 (3H, d, J = 6.1 Hz), 1.77-1.89 (5H, m), 1.90-2.04 (5H, m), 2.80 (2H, t, J = 7.3 Hz), 3.95-4.06 (1H, m), 4.12 (2H, s), 5.31 (1H, d, J = 9.2 Hz), 6.91 (2H, brs), 7.14-7.22 (2H, m), 7.65 (1H, td, J = 7.9, 1.8 Hz), 8.36 (1H, s) ,8.45 (1H, d, J = 4.3 Hz), 15.26 (1H, s). HREIMS (+): 467.20949 (Calcd. for $C_{25}H_{27}FN_4O_4$, 467.20946). |
| 102 | 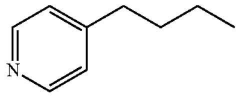 | 3 | COOH | $^1$H-NMR (DMSO-$d_6$, 400 MHz) δ 1.75-2.05 (10H, m), 2.63 (2H, t, J = 7.3 Hz), 3.39-3.49 (2H, m), 4.11 (2H, s), 5.91-6.01 (1H, m), 6.90 (2H, brs), 7.22 (2H, d, J = 5.5 Hz), 8.35 (1H, s), 8.43 (1H, d, J = 5.5 Hz), 15.27 (1H, s). HRESIMS(+): 453.19373. (Calcd. for $C_{24}H_{25}FN_4O_4$, 453.10381). |
| 103 | 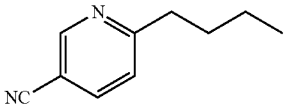 | 3 | COOH | $^1$H-NMR (DMSO-$d_6$, 400 MHz) δ 1.74-2.06 (10H, m), 2.87 (2H, t, J = 7.3 Hz), 3.48-3.51 (2H, m), 4.12(2H, s), 5.97 (1H, s), 6.90 (2H, s), 7.50 (2H, d, J = 7.9 Hz), 8.35 (1H, dd, J = 7.9, 1.8 Hz), 8.35 (1H, s), 8.90 (1H, d, J = 1.2 Hz), 15.28 (1H, s). HREIMS (+): 478.18896. (Calcd. for $C_{25}H_{25}FN_5O_4$, 478.18905). |
| 104 | 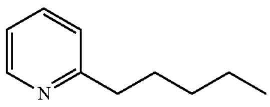 | 3 | COOH | $^1$H-NMR (400 MHz, DMSO-$d_6$) δ 1.55 (2H, quint, J = 7.3 Hz), 1.68 (2H, quint, J = 7.3 Hz), 1.76-1.88 (4H, m), 1.90-2.06 (4H, m), 2.7 (2H, t, J = 7.3 Hz), 3.37-3.48 (2H, m), 4.12 (2H, s), 5.87-5.98 (1H, m), 6.90 (2H, s), 7.15 (1H, dd, J = 7.0, 5.2 Hz), 7.21 (1H, d, J = 7.9 Hz), 7.65 (1H, td, J = 7.5, 1.4 Hz), 8.34 (1H, s), 8.43 (1H, d, J = 4.3 Hz), 15.3 (1H, s). HREIMS (+): 467.20952 (Calcd. for $C_{25}H_{27}FN_4O_4$, 467.20946). |
| 105 | 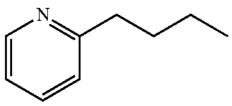 | 1 | COOH | $^1$H NMR (DMSO-$d_6$, 400 MHz) δ 1.14 (2H, t, J = 6.7 Hz), 1.61 (2H, t, J = 6.7 Hz), 1.91-1.98 (2H, m), 2.77 (2H, t, J = 7.9 Hz), 3.43-3.51(2H, m), 4.19 (2H, s), 5.96-6.03 (1H, m), 6.89 (2H, brs), 7.17 (1H, dd, J = 7.3, 4.9 Hz), 7.24 (1H, d, J = 7.3 Hz), 7.67 (1H, td, J = 7.3, 1.8 Hz), 8.12 (1H, s), 8.45 (1H, d, J = 4.3 Hz), 15.27 (1H, s). |
| 106 | 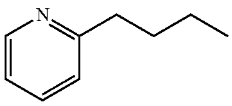 | 1 | $CONH_2$ | $^1$H NMR (DMSO-$d_6$, 400 MHz) δ 1.12 (2H, t, J = 6.7 Hz), 1.47 (2H, t, J = 6.7 Hz), 1.89-1.96 (2H, m), 2.76 (2H, t, J = 7.9 Hz), 3.38-3.47 (2H, m), 4.15 (2H, s), 5.59-5.62 (1H, m), 6.98 (2H, brs), 7.17 (1H, dd, J = 7.3, 4.9 Hz), 7.24 (1H, d, J = 7.3 Hz), 7.28 (1H, d, J = 4.3 Hz), 7.67 (1H, td, J = 7.9, 1.8 Hz), 8.10 (1H, s), 8.45 (1H, d, J = 3.7 Hz), 9.15 (1H, d, J = 4.3 Hz). |

-continued

| | | | | |
|---|---|---|---|---|
| 107 | 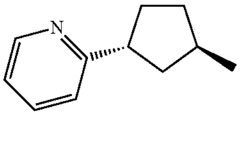 trans | 1 | COOH | $^1$H NMR (DMSO-$d_6$, 400 MHz) δ 1.14 (2H, t, J = 6.7 Hz), 1.62 (2H, t, J = 6.7 Hz), 1.70-1.82 (2H, m), 2.00-2.26 (4H, m), 3.40-3.49 (1H, m), 4.22 (2H, s), 4.53 (1H, brs), 5.41 (1H, d, J = 6.7 Hz), 6.93 (2H, brs), 7.17 (1H, dd, J = 7.3, 4.9 Hz), 7.26 (1H, d, J = 7.9 Hz), 7.67 (1H, td, J = 7.3, 1.8 Hz), 8.13 (1H, s), 8.49 (1H, d, J = 4.3 Hz), 1.524 (1H, s). |
| 108 | 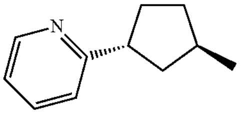 trans | 1 | CN | $^1$H NMR (DMSO-$d_6$, 400 MHz) δ 1.05 (2H, t, J = 6.1 Hz), 1.64 (2H, t, J = 6.1 Hz), 1.68-1.81 (2H, m), 1.98-2.04 (1H, m), 2.07-2.21 (3H, m), 3.39-3.47 (1H, m), 4.16 (2H, s), 4.42-4.52 (1H, m), 5.15 (1H, dd, J = 7.9, 1.8 Hz), 6.99 (2H, brs), 7.17 (1H, dd, J = 7.3, 4.9 Hz), 7.26 (1H, d, J = 7.3 Hz), 7.67 (1H, td, J = 7.3, 1.8 Hz), 8.21 (1H, s), 8.48 (1H, d, J = 37 Hz). |

Example 109 and 110

(+)-8'-amino-9'-fluoro-7'-oxo-10'-[3-(pyridin-2-yl)propylamino]spiro[oxolane-1,3'(2'H)-[7H]pyrido[1,2,3-de][1,4]benzoxazine]-6'-carbonitrile and (−)-8'-amino-9'-fluoro-7'-oxo-10'-[3-(pyridin-2-yl)propylamino]spiro[oxolane-1,3'(2'H)-[7H]pyrido[1,2,3-de][1,4]benzoxazine]-6'-carbonitrile

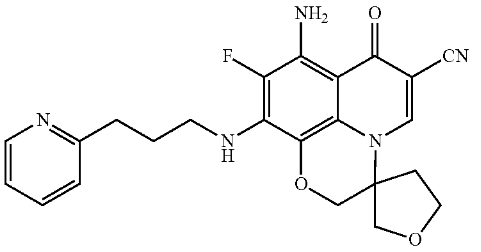 [SMILES: N#Cc1cn2c3c(c(NCCCc4ccccn4)c(F)c(N)c3c1=O)OCC21CCOC1]

Racemic 8'-amino-9'-fluoro-7'-oxo-10'-[3-(pyridin-2-yl)propylamino]spiro[oxolane-1,3'(2'H)-[7H]pyrido[1,2,3-de][1,4]benzoxazine]-6'-carbonitrile (250 mg) was separated by preparative HPLC using a Chiralpak IA column (ϕ20×250 mm) and MeCN as the eluent at a flow rate 9 mL/min for 1 h. The UV detector was set at 254 nm, the injection loop volume was 5 mL, and the injection load was 34-36 mg in a MeCN solution.

Example 109; 102 mg, >99% purify with >99% e.e. (Chiralpak IA column (ϕ4.6×250 mm), MeCN, 1 mL/min, Rt=13.6 min), $[\alpha]_D^{25}$+10.2 (c 1.00, $CHCl_3$) Example 110; 107 mg, >99% purify with >99% e.e. (Chiralpak IA column (ϕ4.6×250 mm), MeCN, 1 mL/min, Rt=34.35 min), $[\alpha]_D^{25}$−7.9 (c 1.00, $CHCl_3$)

Examples 111-114 a) Ethyl 3-(1-(hydroxymethyl)cyclopropylamino)-2-(2,3,4,5-tetrafluorobenzoyl)-acrylate

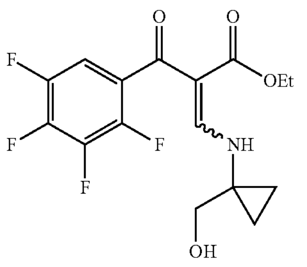 [SMILES: CCOC(=O)C(=CNC1(CO)CC1)C(=O)c1cc(F)c(F)c(F)c1F]

A stirred solution of ethyl 3-oxo-3-(2,3,4,5-tetrafluorophenyl)propionate (10.0 g, 37.8 mmol), acetic anhydride (50 mL) and triethyl orthoformate (10.0 mL, 56.7 mmol) was heated at 130° C. for 3 h. The mixture was concentrated and dried under high vacuum for 5 hours. The crude product was dissolved in DCM (50 mL) and then 1-amino-1-cyclopropylmethanol (3.9 g, 45.3 mmol) was added dropwise at room temperature. After 1.5 h, the solvent was removed by evaporation to yield the title compound as a yellow solid (9 g) that was used in the next step without further purification. MS (EP) m/z: 362 ($M^+$+1). (Calcd. For $C_{16}H_{15}F_4NO_4$, 361.29)

b) Ethyl 9,10-difluoro-7-oxo-2,7-dihydrospiro[[1,4]oxazino[2,3,4-ij]quinoline-3,1'-cyclopropane]-6-carboxylate

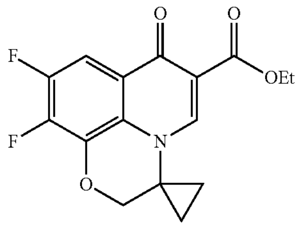 [SMILES: CCOC(=O)c1cn2c3c(c(F)c(F)cc3c1=O)OCC21CC1]

A mixture of ethyl 3-(1-(hydroxymethyl)cyclopropylamino)-2-(2,3,4,5-tetrafluoro-benzoyl)acrylate (300 mg, 0.83 mmol), $K_2CO_3$ powder (344 mg, 2.49 mmol), and 3 ml of anhydrous DMF were heated in a CEM Discover microwave for 10 min at 200° C. After that the sample was rapidly cooled to room temperature yielding a dark brown liquid. The DMF was removed by evaporation to give a dark solid. The solid was dissolved in 50 ml of ethylacetate and washed two times with 10 ml of water. The organic layer was dried over $Na_2SO_4$ to afford a light yellow solid as the title compound which was used without further purification in the next step (133 mg, 0.415 mmol). MS (EP) m/z: 322 ($M^+$+1). (Calcd. for $C_{16}H_{13}F_2NO_4$, 321.28)

c) 9,10-difluoro-7-oxo-2,7-dihydrospiro[[1,4]oxazino[2,3,4-ij]quinoline-3,1'-cyclopropane]-6-carboxylic Acid

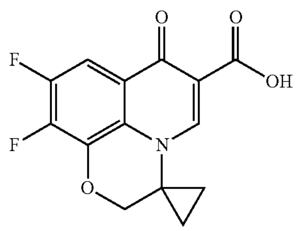

To a solution of ethyl 9,10-difluoro-7-oxo-2,7-dihydrospiro[[1,4]oxazino[2,3,4-ij]quinoline-3,1'-cyclopropane]-6-carboxylate (1.3 g, 4 mmol) in EtOH/water (50:50 v/v, 55 mL) was added $K_2CO_3$ powder (1.65 g, 12 mmol) and the mixture was heated under reflux for 2 h. The solvent was removed to dryness. The remaining solid was acidified to pH6 by using 2N acetic acid. A precipitate formed and was collected by filtration, washed with water and then dried to give the title compound (0.656 g, 2.24 mmol as a light yellow solid. $^1$H-NMR (400 MHz, DMSO-$d_6$) δ 1.29 (2H, t), 1.8 (2H, t), 4.56 (2H, s), 7.84 (1H, m), 8.51 (1H, s), 14.3 (1H, b). MS (EP) m/z: 294 ($M^+$+1). (Calcd for $C_{14}H_9F_2NO_4$, 293.22)

d) 9,10-difluoro-8-nitro-7-oxo-2,7-dihydrospiro[[1,4]oxazino[2,3,4-ij]quinoline-3,1'-cyclopropane]-6-carboxylic Acid

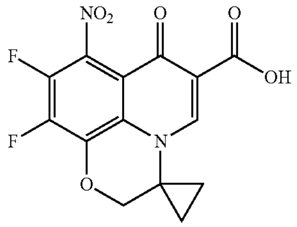 [SMILES: O=C(O)c1cn2c3c(c(F)c(F)c([N+](=O)[O-])c3c1=O)OCC21CC1]

The title compound was prepared from 9,10-difluoro-7-oxo-2,7-dihydrospiro[[1,4]oxazino[2,3,4-ij]quinoline-3,1'-cyclopropane]-6-carboxylic acid using synthetic procedures similar to those as described in the examples above. MS (EP) m/z: 339 ($M^+$+1). (Calcd for $C_{14}H_8F_2N_2O_6$, 338.22)

e) 9,10-difluoro-8-nitro-7-oxo-2,7-dihydrospiro[[1,4]oxazino[2,3,4-ij]quinoline-3,1'-cyclopropane]-6-carboxamide

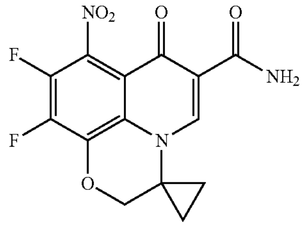 [SMILES: NC(=O)c1cn2c3c(c(F)c(F)c([N+](=O)[O-])c3c1=O)OCC21CC1]

The title compound was prepared from 9,10-difluoro-8-nitro-7-oxo-2,7-dihydrospiro[[1,4]oxazino[2,3,4-ij]quinoline-3,1'-cyclo propane]-6-carboxylic acid using synthetic procedures similar to those described in the examples above. $^1$H-NMR (400 MHz, DMSO-$d_6$) δ 1.32 (2H, t), 1.7 (2H, t), 4.58 (2H, s), 7.66 (1H, b), 8.46 (1H, s), 8.59 (1H, b). MS (EP) m/z: 338 ($M^+$+1). (Calcd for $C_{14}H_9F_2N_3O_5$, 337.24).

f) 8-amino-9,10-difluoro-7-oxo-2,7-dihydrospiro[[1,4]oxazino[2,3,4-ij]quinoline-3,1'-cyclopropane]-6-carboxamide

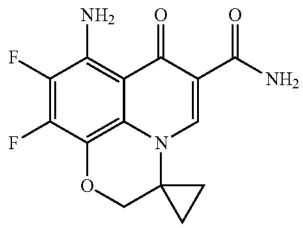 [SMILES: NC(=O)c1cn2c3c(c(F)c(F)c(N)c3c1=O)OCC21CC1]

The title compound was prepared from 9,10-difluoro-8-nitro-7-oxo-2,7-dihydrospiro[[1,4]oxazino[2,3,4-ij]quinoline-3,1'-cyclo propane]-6-carboxamide using synthetic procedures similar to those described in the examples above. $^1$H-NMR (400 MHz, DMSO-$d_6$) δ 1.17 (2H, t), 1.55 (2H, t), 4.26 (2H, s), 7.30 (2H, b), 8.26 (1H, s). MS (EP) m/z: 308 ($M^+$+1). (Calcd for $C_{14}H_{11}F_2N_3O_3$, 307.25).

g) 8-amino-9,10-difluoro-7-oxo-2,7-dihydrospiro[[1,4]oxazino[2,3,4-ij]quinoline-3,1'-cyclopropane]-6-carbonitrile

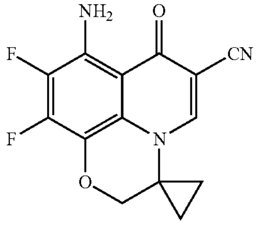 [SMILES: N#Cc1cn2c3c(c(F)c(F)c(N)c3c1=O)OCC21CC1]

The title compound was prepared from 8-amino-9,10-difluoro-7-oxo-2,7-dihydrospiro[[1,4]oxazino[2,3,4-ij]quinoline-3,1'-cyclopropane]-6-carboxamide using synthetic procedures similar to those described in the examples above. $^1$H-NMR (400 MHz, DMSO-$d_6$) δ 1.18 (2H, t), 1.77 (2H, t), 4.31 (2H, s), 7.41 (2H, b), 8.51 (1H, s). MS (EP) m/z: 290 ($M^+$+1). (Calcd for $C_{14}H_9F_2N_3O_2$, 289.24).

Example 111

10-(3-(1H-pyrazol-1-yl)propylamino)-8-amino-9-fluoro-7-oxo-2,7-dihydrospiro[[1,4]oxazino[2,3,4-ij]quinoline-3,1'-cyclopropane]-6-carbonitrile

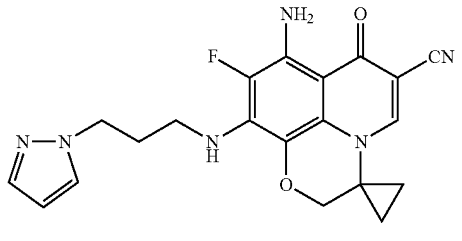 [SMILES: N#Cc1cn2c3c(c(NCCCn4cccn4)c(F)c(N)c3c1=O)OCC21CC1]

The title compound was prepared from 8-amino-9,10-difluoro-7-oxo-2,7-dihydrospiro[[1,4]oxazino[2,3,4-ij]quinoline-3,1'-cyclopropane]-6-carbonitrile and pyrazolepropylamine using synthetic procedures similar to those described in the examples above. $^1$H-NMR (400 MHz, DMSO-$d_6$) δ 1.16 (2H, t), 1.58 (2H, t), 1.99 (2H, m), 3.65 (2H, m), 4.16 (2H, s), 4.26 (2H, m), 6.29 (1H, s), 7.49 (1H, s), 7.63 (1H, s), 8.04 (1H, s). MS (EP) m/z: 395 ($M^+$+1). (Calcd for $C_{20}H_{19}FN_6O_2$, 394.40).

Example 112

8-amino-9-fluoro-7-oxo-10-(3-(pyridin-3-yl)propylamino)-2,7-dihydrospiro[[1,4]oxazino[2,3,4-ij]quinoline-3,1'-cyclopropane]-6-carbonitrile

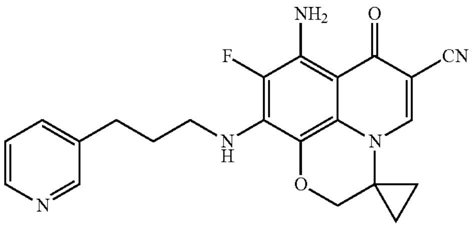 [SMILES: N#Cc1cn2c3c(c(NCCCc4cccnc4)c(F)c(N)c3c1=O)OCC21CC1]

A solution of 8-amino-9,10-difluoro-7-oxo-2,7-dihydrospiro[[1,4]oxazino-[2,3,4-ij]quinoline-3,1'-cyclopropane]-6-carbonitrile (150 mg, 0.52 mmol), 3-(pyridine-3-yl)propan-1-amine (176 mg, 1.3 mmol), and triethylamine (108 μL, 1.3 mmol) in DMSO (3 mL) was stirred at 120° C. for 15 hr. The reaction mixture was cooled and concentrated. The crude product was taken up in acetonitrile and purified by preparative HPLC to yield the title compound as a yellow solid (52.9 mg). MS (EP) m/z: 406.2 ($M^+$+1). (Calcd for $C_{22}H_{20}FN_5O_2$, 405.42). $^1$H NMR (400 MHz, $D_2O$) δ 1.20 (2H, t), 1.50 (2H, t), 2.00 (2H, m,), 2.94 (2H, m,), 3.51 (2H, m), 4.14 (2H, s), 7.86 (1H, m), 8.03 (1H, m), 8.41 (1H, m), 8.52 (1H, m), 8.58 (1H, s)

Example 113

8-amino-9-fluoro-7-oxo-10-(3-(pyridin-2-yl)propylamino)-2,7-dihydrospiro[[1,4]oxazino[2,3,4-ij]quinoline-3,1'-cyclopropane]-6-carbonitrile

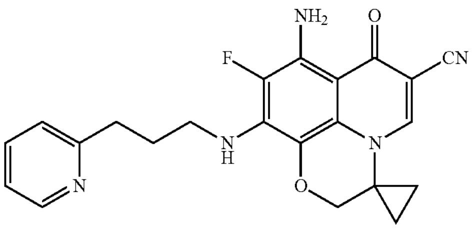 [SMILES: N#Cc1cn2c3c(c(NCCCc4ccccn4)c(F)c(N)c3c1=O)OCC21CC1]

A solution of 8-amino-9,10-difluoro-7-oxo-2,7-dihydrospiro[[1,4]oxazino[2,3,4-ij]quinoline-3,1'-cyclopropane]-6-carbonitrile (320 mg, 1.1 mmol) and 3-(pyridine-2-yl)propan-1-amine (270 mg, 2 mmol) and triethylamine (221 μL, 2.7 mmol) in DMSO (8 mL) was stirred at 120° C. for 15 hr. The reaction mixture was added portion wise to water and was extracted with ethyl acetate. The organic layer was dried over sodium sulfate and concentrated under vacuum. The dry residue was purified by column chromatograph (ethylacetate, to ethylacetate-MeOH 10:1) to yield the title compound (76.9 mg) as a yellow solid. MS (EP) m/z: 406.2 ($M^+$+1). (Calcd for $C_{22}H_{20}FN_5O_2$, 405.42). $^1$H NMR (400 MHz, $CD_3OD$) δ 1.15 (2H, t), 1.59 (2H, t), 2.03 (2H, t), 2.88 (2H, t), 3.54 (2H, m), 4.15 (2H, s), 7.23 (1H, m), 7.33 (1H, m), 7.74 (1H, m), 8.04 (1H, s), 8.42 (1H, m)

Example 114

8-amino-9-fluoro-7-oxo-10-(3-(pyridin-4-yl)propylamino)-2,7-dihydrospiro[[1,4'-oxazino [2,3,4-ij] quinoline-3,1'-cyclopentane]-6-carbonitrile The title compound may be prepared from 8-amino-9,10-difluoro-7-oxo-2,7-dihydrospiro[1,4]oxazino[2,3,4-ij] quinoline-3,1'-cyclopentane]-6-carbonitrile using synthetic procedures similar to those described in the examples above.

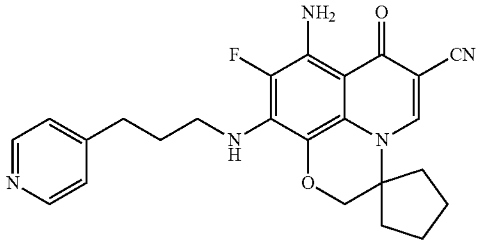 [SMILES: N#Cc1cn2c3c(c(NCCCc4ccncc4)c(F)c(N)c3c1=O)OCC21CCCC1]

MS (EP) m/z: 434.2 (M+1). (Calcd. for $C_{24}H_{24}FN_5O_2$, 433.49). $^1$H NMR (400 MHz, DMSO) δ 8.69 (d, J=6.5 Hz, 2H), 8.35 (s, 1H), 7.74 (d, J=6.2 Hz, 2H), 5.74 (s, 1H), 4.03 (s, 2H), 3.42-3.37 (m, 2H), 2.86-2.82 (m, 2H), 1.92-1.90 (m, 2H), 1.88-1.82 (m, 4H), 1.71-1.65 (m, 4H)

Glycogen Synthesis Activity in Hep G2 Cells

Hep G2 cells were obtained from the Japanese Collection of Research Bioresources and were grown in standard culture medium; a low-glucose Dulbecco's modified Eagle's medium (DMEM) containing 10% fetal calf serum supplemented with 100 U/mL penicillin and 100 μg/mL streptomycin, in a humidified and 5% $CO_2$ atmosphere kept at 37° C. The Hep G2 cells were harvested with 0.25% trypsin solution containing 1 mM EDTA and were seeded on 12 well plates at $1\times10^5$ cells per well. Following a culture for 3 days, the cells were washed once with phosphate buffered saline (PBS), and were incubated with serum-free low-glucose DMEM supplemented with 100 U/mL penicillin and 100 μg/mL streptomycin. Following a culture for 3 hours, compounds provided herein at various concentrations and 2.5 μCi/mL D-[2-$^3$H] glucose (PerkinElmer, Boston, Mass., USA) were added to the serum-free low-glucose DMEM. A vehicle control of DMSO (0.3%, final concentration) was also used. The total volume per well of the reaction medium was 1.0 mL of serum-free low-glucose DMEM. After incubation at 37° C. for 3 hours, the medium was aspirated and cells were washed twice with PBS, and 0.25 mL of 1 N KOH containing 0.4 mg/mL carrier glycogen was added. After incubation at 37° C. for 30 minutes, 0.25 mL of 48.8% (w/v) KOH was added to each well for cell lysis. After incubation at 95° C. for 30 min, 1.5 mL of 95% (v/v) ethanol was added to the cell lysate. Total glycogen was precipitated overnight at −20° C. Glycogen precipitates were recovered by centrifugation at 19,000×g for 30 minutes at 4° C. Precipitates were washed once with 1 mL of 70% (v/v) ethanol, and were re-suspended in 0.5 mL water. [$^3$H]Glucose incorporation into glycogen was assessed using a liquid scintillation counter (Packard Instrument Co., Meriden, Conn., USA).

Animal Study: Oral Glucose Tolerance Test

Male Crlj: CD1 (ICR) mice were obtained from Charles River Laboratories Japan (Yokohama, Japan). All mice were given a standard diet (Clea Japan, Tokyo, Japan) and tap water ad libitum. All institutional guidelines for animal care and use were applied in this study. Test compounds were suspended in 0.3% carboxymethyl-cellulose sodium salt (CMC-Na; Sigma, St. Louis, Mo.). After fasting for 15-17 hours, the test compound (3, 10, 30, 100 or 300 mg/kg) or vehicle (0.3% CMC-Na) was orally administered to 7-week-old ICR mice. Glucose solution (5 g/kg) was orally administered at 30 minutes after test compound treatment. Blood samples were collected from tail vein using capillary tubes containing EDTA.2K before test compound treatment, and at 0, 0.5, 1, and 2 hours after glucose load. The blood samples were centrifuged at 2,500×g for 5 minutes and separated plasma was kept on ice and analyzed in the same day. Plasma glucose levels were determined using the glucose C II-test (Wako Pure Chemical Industries, Osaka, Japan). The sum of plasma glucose levels at 0.5 and 1 hr after glucose load was compared to that of vehicle treatment, and results were presented as percent decrease.

In Tables 1 and 2, the $IC_{50}$ (nM) for GSK313 are represented as follows: A≦15; B=16-60; C=61-150; D≧150 and ND=no data.

TABLE 1

| Exemplary Compounds and Their Activity. | | |
|---|---|---|
| Compound | Structure | GSK3β $IC_{50}$ |
| 1 | 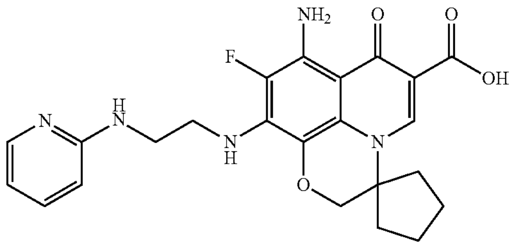 [SMILES: Nc1c(F)c(NCCNc2ccccn2)c2c3c1c(=O)c(C(=O)O)cn3C1(CCCC1)CO2] | A |
| 2 | 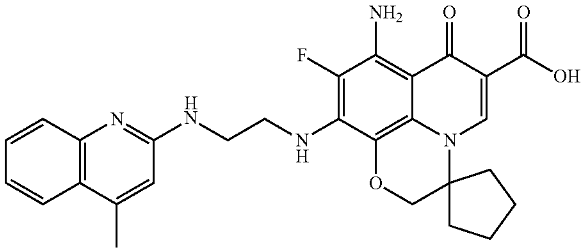 [SMILES: Cc1cc(NCCNc2c(F)c(N)c3c(=O)c(C(=O)O)cn4c3c2OCC42CCCC2)nc2ccccc12] | C |
| 3 | 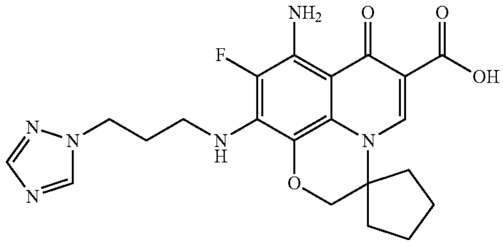 [SMILES: Nc1c(F)c(NCCCn2cncn2)c2c3c1c(=O)c(C(=O)O)cn3C1(CCCC1)CO2] | C |
| 4 | 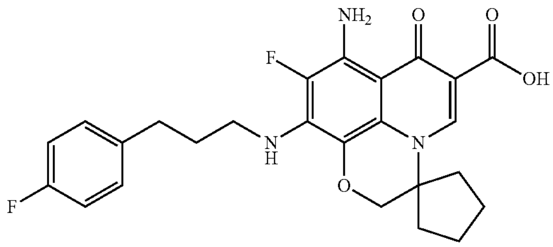 [SMILES: Nc1c(F)c(NCCCc2ccc(F)cc2)c2c3c1c(=O)c(C(=O)O)cn3C1(CCCC1)CO2] | A |

TABLE 1-continued
Exemplary Compounds and Their Activity.
| Compound | Structure | GSK3β $IC_{50}$ |
| --- | --- | --- |
| 5 | 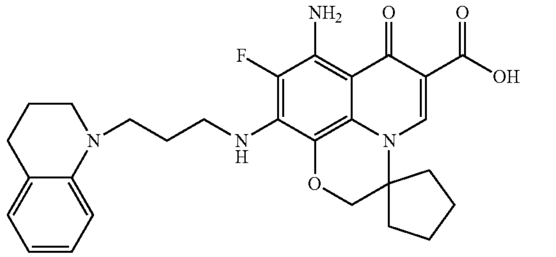 [SMILES: Nc1c(F)c(NCCCN2CCCc3ccccc32)c2c3c1c(=O)c(C(=O)O)cn3C1(CCCC1)CO2] | B |
| 6 | 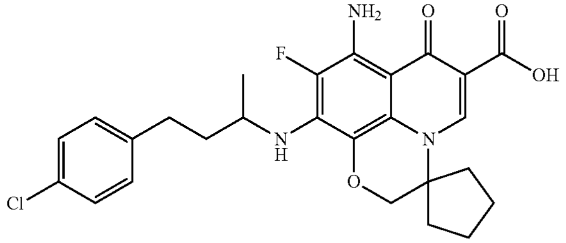 [SMILES: CC(CCc1ccc(Cl)cc1)Nc1c(F)c(N)c2c(=O)c(C(=O)O)cn3c2c1OCC31CCCC1] | B |
| 7 | 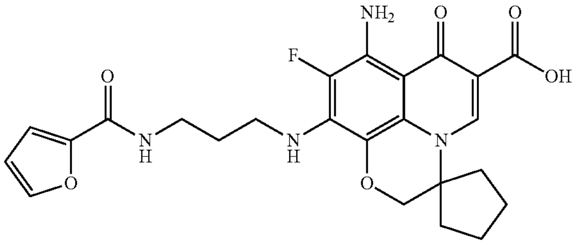 [SMILES: Nc1c(F)c(NCCCNC(=O)c2ccco2)c2c3c1c(=O)c(C(=O)O)cn3C1(CCCC1)CO2] | B |
| 8 | 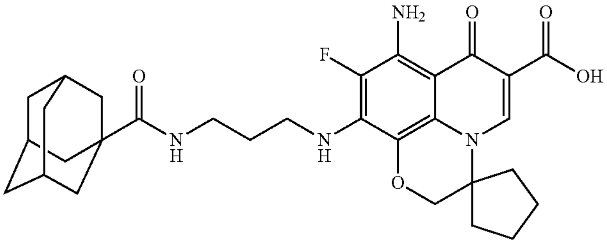 [SMILES: Nc1c(F)c(NCCCNC(=O)C23CC4CC(CC(C4)C2)C3)c2c3c1c(=O)c(C(=O)O)cn3C1(CCCC1)CO2] | B |
| 9 | 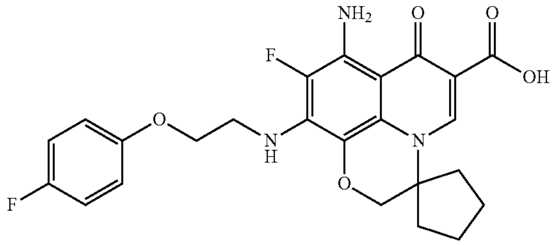 | B |
| 10 | 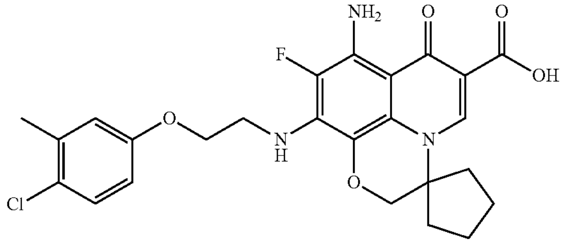 [SMILES: Cc1cc(OCCNc2c(F)c(N)c3c(=O)c(C(=O)O)cn4c3c2OCC42CCCC2)ccc1Cl] | B |

TABLE 1-continued
Exemplary Compounds and Their Activity.
| Compound | Structure | GSK3β $IC_{50}$ |
|---|---|---|
| 11 | 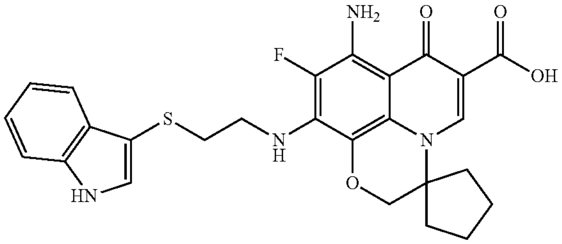 [SMILES: Nc1c(F)c(NCCSc2c[nH]c3ccccc23)c2c3c1c(=O)c(C(=O)O)cn3C1(CCCC1)CO2] | A |
| 12 | 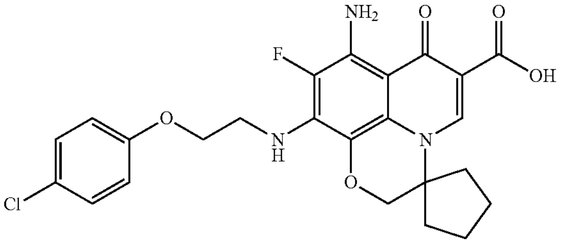 [SMILES: Nc1c(F)c(NCCOc2ccc(Cl)cc2)c2c3c1c(=O)c(C(=O)O)cn3C1(CCCC1)CO2] | C |
| 13 | 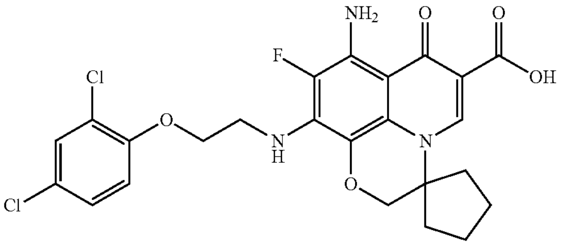 [SMILES: Nc1c(F)c(NCCOc2ccc(Cl)cc2Cl)c2c3c1c(=O)c(C(=O)O)cn3C1(CCCC1)CO2] | C |
| 14 | 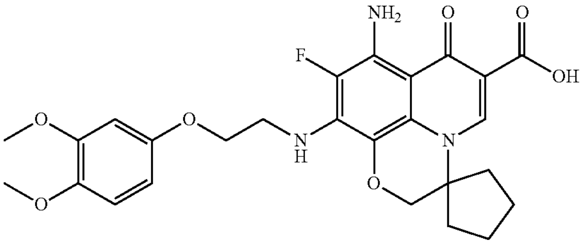 [SMILES: COc1ccc(OCCNc2c(F)c(N)c3c(=O)c(C(=O)O)cn4c3c2OCC42CCCC2)cc1OC] | A |
| 15 | 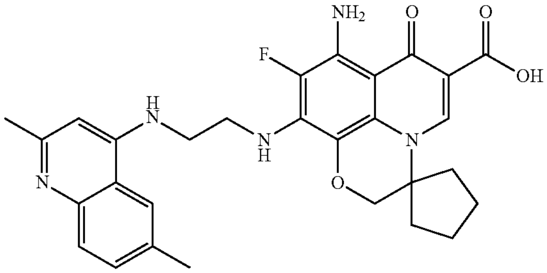 [SMILES: Cc1ccc2nc(C)cc(NCCNc3c(F)c(N)c4c(=O)c(C(=O)O)cn5c4c3OCC53CCCC3)c2c1] | A |
| 16 | 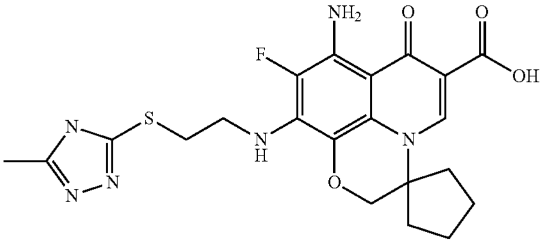 [SMILES: Cc1nnc(SCCNc2c(F)c(N)c3c(=O)c(C(=O)O)cn4c3c2OCC42CCCC2)[nH]1] | A |

TABLE 1-continued
| Exemplary Compounds and Their Activity. | | |
|---|---|---|
| Compound | Structure | GSK3β $IC_{50}$ |
| 17 | 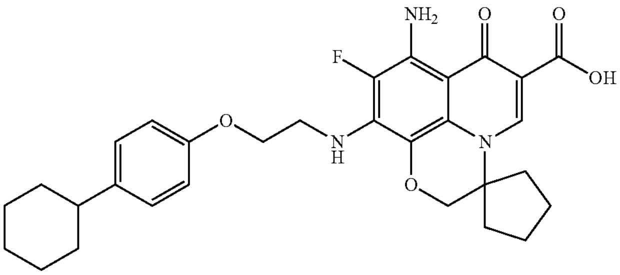 [SMILES: Nc1c(F)c(NCCOc2ccc(C3CCCCC3)cc2)c2c3c1c(=O)c(C(=O)O)cn3C1(CCCC1)CO2] | D |
| 18 | 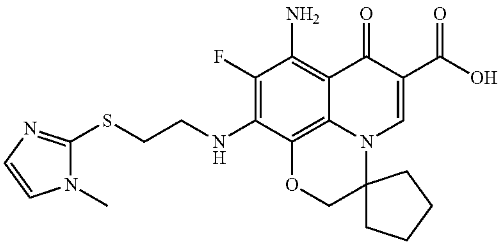 [SMILES: Cn1ccnc1SCCNc1c(F)c(N)c2c(=O)c(C(=O)O)cn3c2c1OCC31CCCC1] | A |
| 19 | 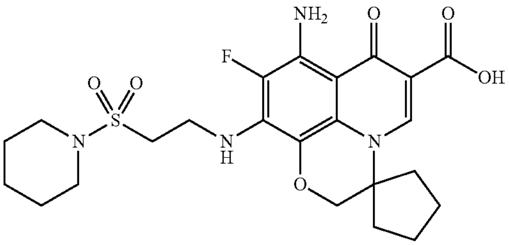 [SMILES: Nc1c(F)c(NCCS(=O)(=O)N2CCCCC2)c2c3c1c(=O)c(C(=O)O)cn3C1(CCCC1)CO2] | C |
| 20 | 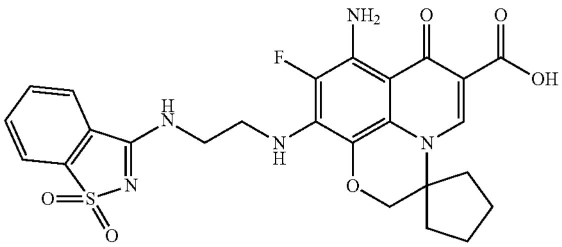 [SMILES: Nc1c(F)c(NCCNC2=NS(=O)(=O)c3ccccc32)c2c3c1c(=O)c(C(=O)O)cn3C1(CCCC1)CO2] | A |
| 21 | 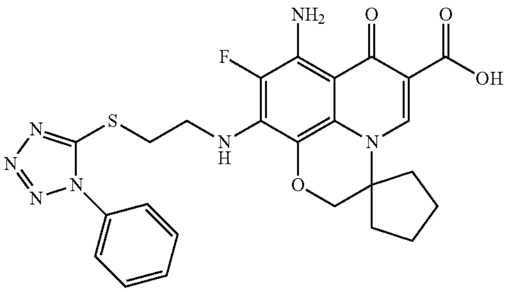 [SMILES: Nc1c(F)c(NCCSc2nnnn2-c2ccccc2)c2c3c1c(=O)c(C(=O)O)cn3C1(CCCC1)CO2] | A |

TABLE 1-continued
| Exemplary Compounds and Their Activity. | | |
|---|---|---|
| Compound | Structure | GSK3β $IC_{50}$ |
| 22 | 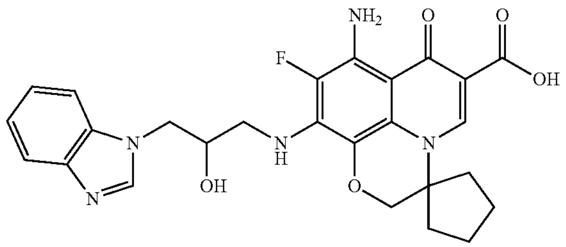 [SMILES: Nc1c(F)c(NCC(O)Cn2cnc3ccccc32)c2c3c1c(=O)c(C(=O)O)cn3C1(CCCC1)CO2] | C |
| 23 | 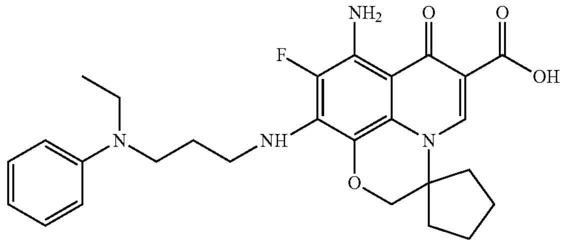 [SMILES: CCN(CCCNc1c(F)c(N)c2c(=O)c(C(=O)O)cn3c2c1OCC31CCCC1)c1ccccc1] | A |
| 24 | 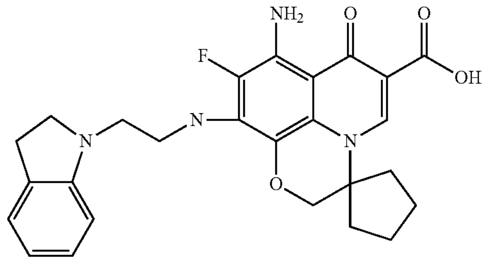 [SMILES: Nc1c(F)c(NCCN2CCc3ccccc32)c2c3c1c(=O)c(C(=O)O)cn3C1(CCCC1)CO2] | C |
| 25 | 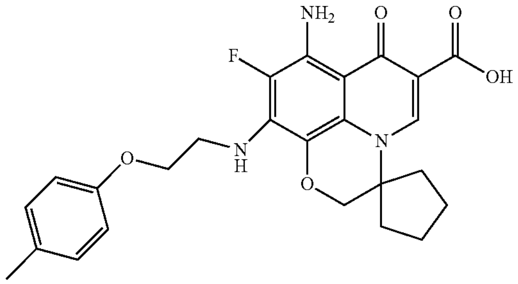 [SMILES: Cc1ccc(OCCNc2c(F)c(N)c3c(=O)c(C(=O)O)cn4c3c2OCC42CCCC2)cc1] | B |
| 26 | 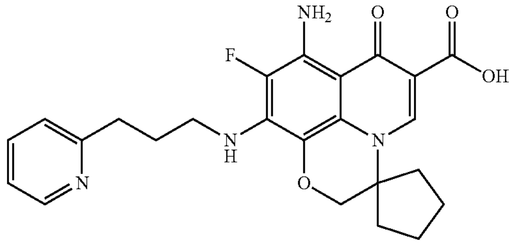 [SMILES: Nc1c(F)c(NCCCc2ccccn2)c2c3c1c(=O)c(C(=O)O)cn3C1(CCCC1)CO2] | A |

TABLE 1-continued
| Exemplary Compounds and Their Activity. | | |
|---|---|---|
| Compound | Structure | GSK3β $IC_{50}$ |
| 27 | 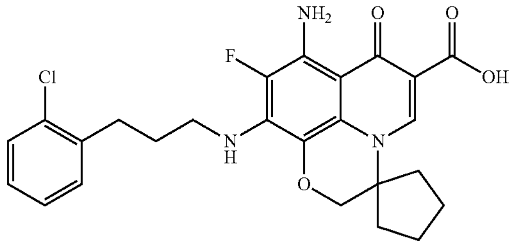 [SMILES: Nc1c(F)c(NCCCc2ccccc2Cl)c2c3c1c(=O)c(C(=O)O)cn3C1(CCCC1)CO2] | A |
| 28 | 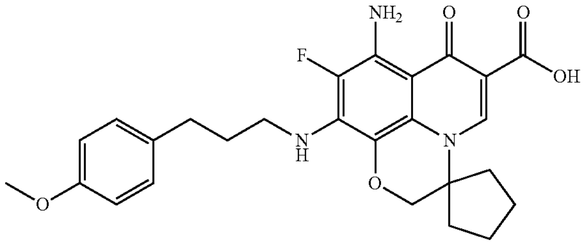 [SMILES: COc1ccc(CCCNc2c(F)c(N)c3c(=O)c(C(=O)O)cn4c3c2OCC42CCCC2)cc1] | A |
| 29 | 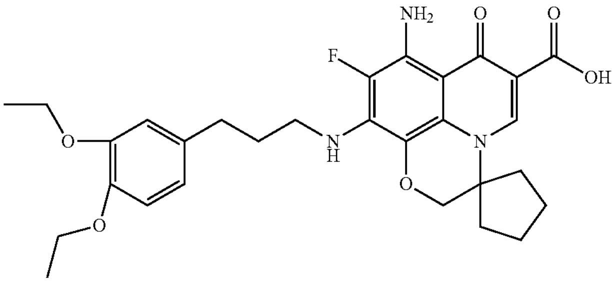 [SMILES: CCOc1ccc(CCCNc2c(F)c(N)c3c(=O)c(C(=O)O)cn4c3c2OCC42CCCC2)cc1OCC] | B |
| 30 | 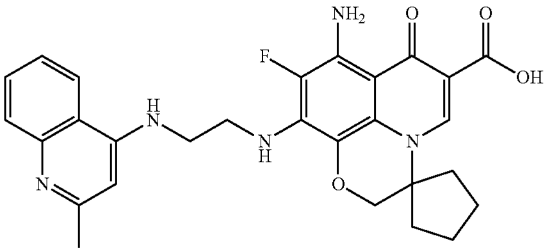 [SMILES: Cc1cc(NCCNc2c(F)c(N)c3c(=O)c(C(=O)O)cn4c3c2OCC42CCCC2)c2ccccc2n1] | A |
| 31 | 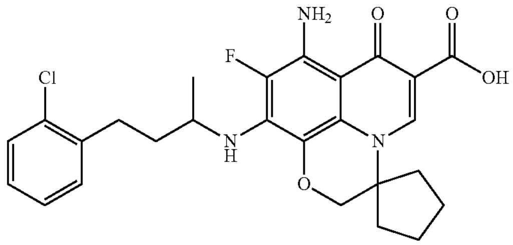 [SMILES: CC(CCc1ccccc1Cl)Nc1c(F)c(N)c2c(=O)c(C(=O)O)cn3c2c1OCC31CCCC1] | B |
| 32 | 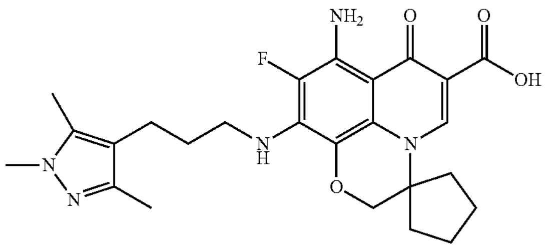 [SMILES: Cc1nn(C)c(C)c1CCCNc1c(F)c(N)c2c(=O)c(C(=O)O)cn3c2c1OCC31CCCC1] | A |

TABLE 1-continued
| Exemplary Compounds and Their Activity. | | |
|---|---|---|
| Compound | Structure | GSK3β $IC_{50}$ |
| 33 | 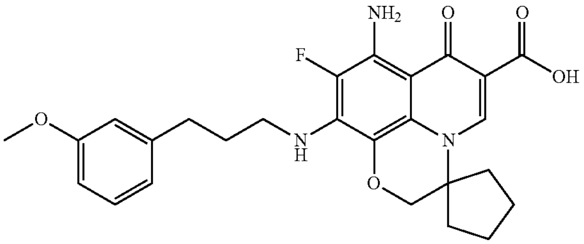 [SMILES: COc1cccc(CCCNc2c(F)c(N)c3c(=O)c(C(=O)O)cn4c3c2OCC42CCCC2)c1] | A |
| 34 | 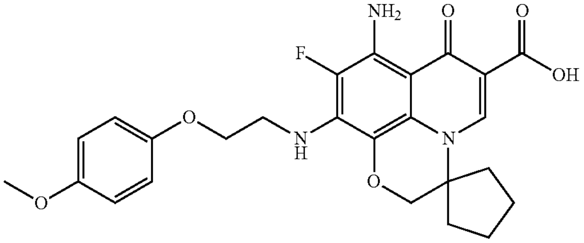 [SMILES: COc1ccc(OCCNc2c(F)c(N)c3c(=O)c(C(=O)O)cn4c3c2OCC42CCCC2)cc1] | C |
| 35 | 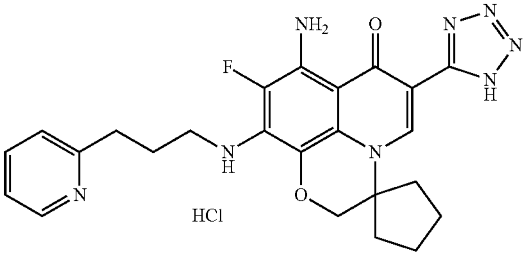 [SMILES: Nc1c(F)c(NCCCc2ccccn2)c2c3c1c(=O)c(-c1nnn[nH]1)cn3C1(CCCC1)CO2 ; Cl] HCl | B |
| 36 | 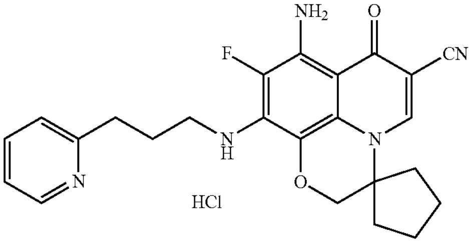 [SMILES: N#Cc1cn2c3c(c(NCCCc4ccccn4)c(F)c(N)c3c1=O)OCC21CCCC1 ; Cl] HCl | A |
| 37 | 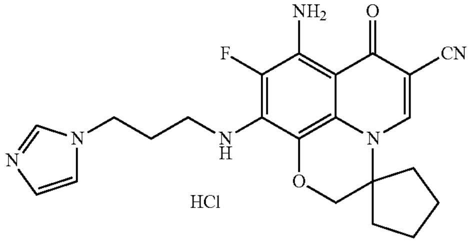 [SMILES: N#Cc1cn2c3c(c(NCCCn4ccnc4)c(F)c(N)c3c1=O)OCC21CCCC1 ; Cl] HCl | A |
| 38 | 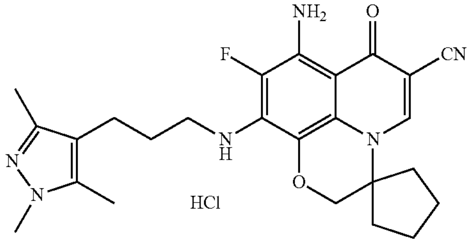 [SMILES: Cc1nn(C)c(C)c1CCCNc1c(F)c(N)c2c(=O)c(C#N)cn3c2c1OCC31CCCC1 ; Cl] HCl | A |

TABLE 1-continued
| Exemplary Compounds and Their Activity. | | |
|---|---|---|
| Compound | Structure | GSK3β $IC_{50}$ |
| 39 | 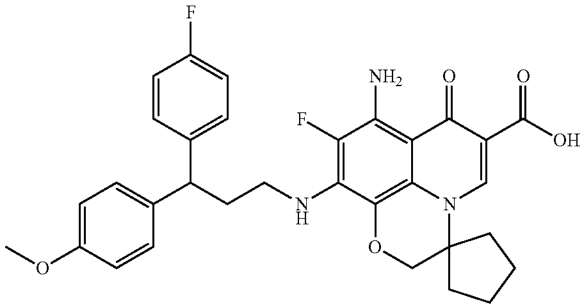 [SMILES: COc1ccc(C(CCNc2c(F)c(N)c3c(=O)c(C(=O)O)cn4c3c2OCC42CCCC2)c2ccc(F)cc2)cc1] | A |
| 40 | 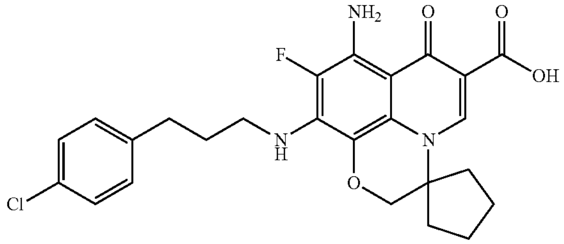 [SMILES: Nc1c(F)c(NCCCc2ccc(Cl)cc2)c2c3c1c(=O)c(C(=O)O)cn3C1(CCCC1)CO2] | D |
| 41 | 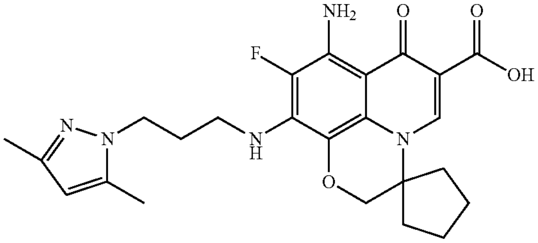 [SMILES: Cc1cc(C)n(CCCNc2c(F)c(N)c3c(=O)c(C(=O)O)cn4c3c2OCC42CCCC2)n1] | B |
| 42 | 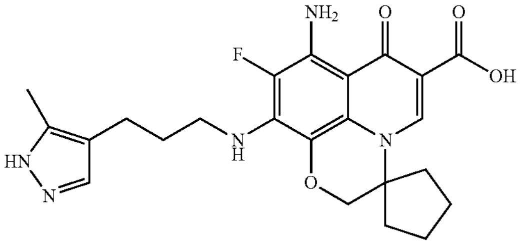 [SMILES: Cc1[nH]ncc1CCCNc1c(F)c(N)c2c(=O)c(C(=O)O)cn3c2c1OCC31CCCC1] | A |
| 43 | 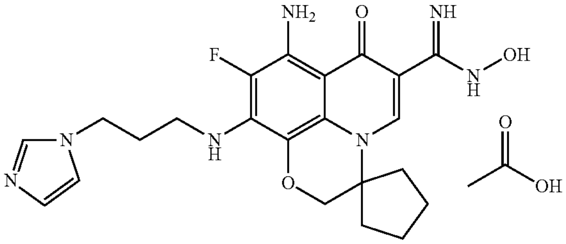 | C |

TABLE 1-continued
| Exemplary Compounds and Their Activity. | | |
|---|---|---|
| Compound | Structure | GSK3β $IC_{50}$ |
| 44 | 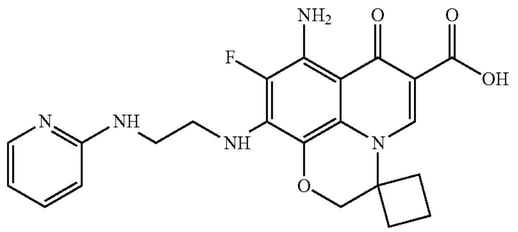 [SMILES: Nc1c(F)c(NCCNc2ccccn2)c2c3c1c(=O)c(C(=O)O)cn3C1(CCC1)CO2] | B |
| 45 | 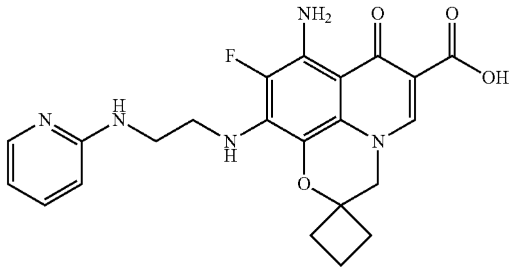 [SMILES: Nc1c(F)c(NCCNc2ccccn2)c2c3c1c(=O)c(C(=O)O)cn3CC1(CCC1)O2] | C |
| 46 | 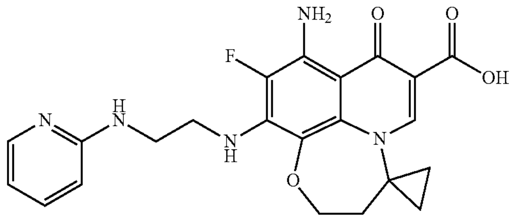 [SMILES: Nc1c(F)c(NCCNc2ccccn2)c2c3c1c(=O)c(C(=O)O)cn3C1(CCO2)CC1] | B |
| 47 | 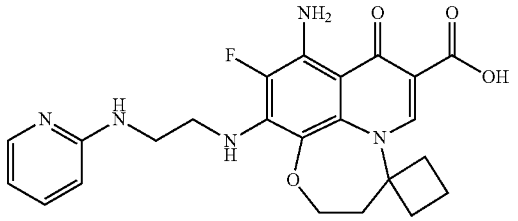 [SMILES: Nc1c(F)c(NCCNc2ccccn2)c2c3c1c(=O)c(C(=O)O)cn3C1(CCC1)CCO2] | B |
| 48 | 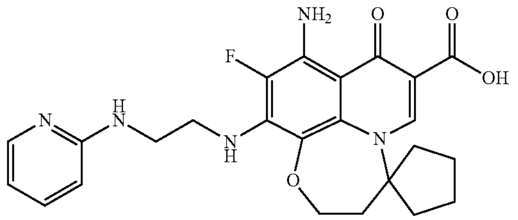 [SMILES: Nc1c(F)c(NCCNc2ccccn2)c2c3c1c(=O)c(C(=O)O)cn3C1(CCCC1)CCO2] | D |
| 49 | 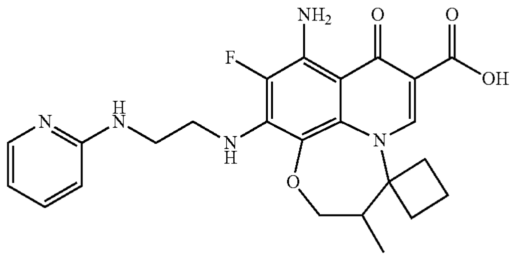 [SMILES: CC1COc2c(NCCNc3ccccn3)c(F)c(N)c3c(=O)c(C(=O)O)cn(c23)C12CCC2] | A |

TABLE 1-continued
Exemplary Compounds and Their Activity.
| Compound | Structure | GSK3β $IC_{50}$ |
|---|---|---|
| 50 | 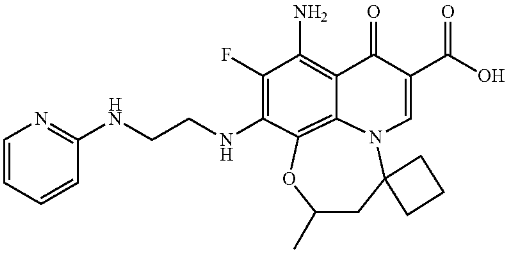 [SMILES: CC1CC2(CCC2)n2cc(C(=O)O)c(=O)c3c(N)c(F)c(NCCNc4ccccn4)c(c32)O1] | D |
| 51 | 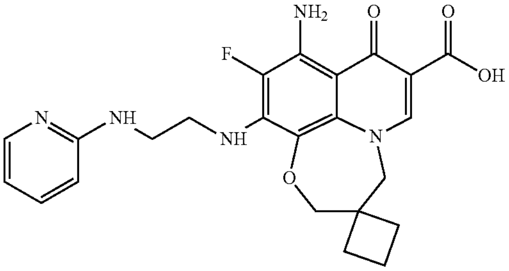 [SMILES: Nc1c(F)c(NCCNc2ccccn2)c2c3c1c(=O)c(C(=O)O)cn3CC1(CCC1)CO2] | C |
| 52 | 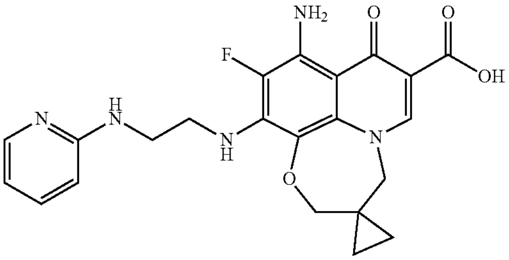 [SMILES: Nc1c(F)c(NCCNc2ccccn2)c2c3c1c(=O)c(C(=O)O)cn3CC1(CC1)CO2] | D |
| 53 | 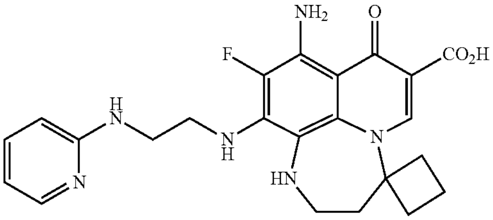 [SMILES: Nc1c(F)c(NCCNc2ccccn2)c2c3c1c(=O)c(C(=O)O)cn3C1(CCC1)CCN2] | B |
| 54 | 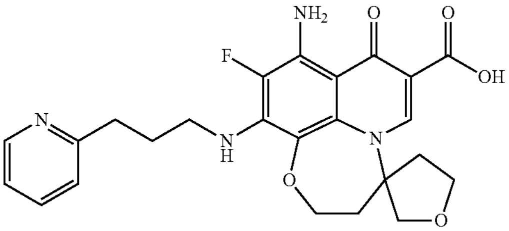 [SMILES: Nc1c(F)c(NCCCc2ccccn2)c2c3c1c(=O)c(C(=O)O)cn3C1(CCOC1)CCO2] | B |
| 55 | 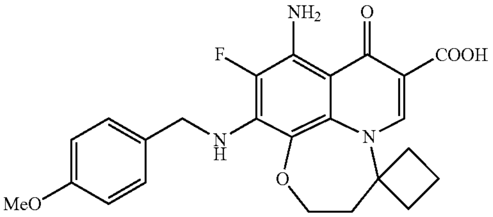 [SMILES: COc1ccc(CNc2c(F)c(N)c3c(=O)c(C(=O)O)cn4c3c2OCCC42CCC2)cc1] | C |

TABLE 1-continued
| Exemplary Compounds and Their Activity. | | |
|---|---|---|
| Compound | Structure | GSK3β $IC_{50}$ |
| 56 | 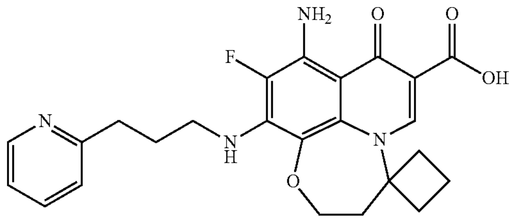 [SMILES: Nc1c(F)c(NCCCc2ccccn2)c2c3c1c(=O)c(C(=O)O)cn3C1(CCC1)CCO2] | A |
| 57 | 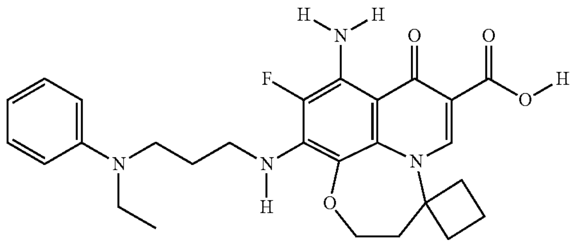 [SMILES: CCN(CCCNc1c(F)c(N)c2c(=O)c(C(=O)O)cn3c2c1OCCC31CCC1)c1ccccc1] | B |
| 58 | 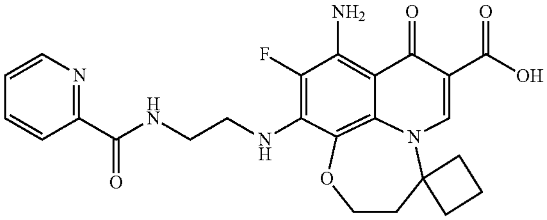 [SMILES: Nc1c(F)c(NCCNC(=O)c2ccccn2)c2c3c1c(=O)c(C(=O)O)cn3C1(CCC1)CCO2] | B |
| 59 | 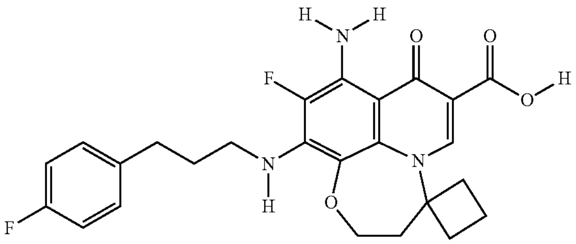 [SMILES: Nc1c(F)c(NCCCc2ccc(F)cc2)c2c3c1c(=O)c(C(=O)O)cn3C1(CCC1)CCO2] | A |
| 60 | 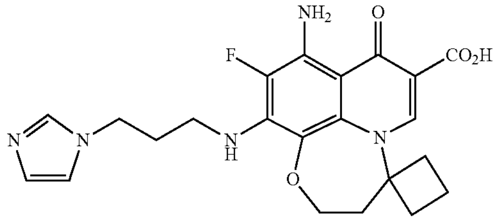 [SMILES: Nc1c(F)c(NCCCn2ccnc2)c2c3c1c(=O)c(C(=O)O)cn3C1(CCC1)CCO2] | A |
| 61 | 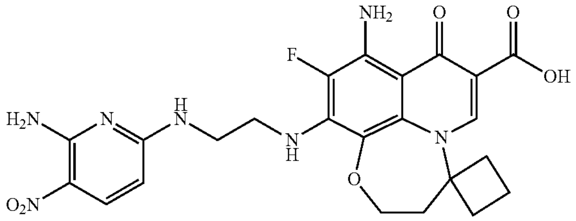 [SMILES: Nc1nc(NCCNc2c(F)c(N)c3c(=O)c(C(=O)O)cn4c3c2OCCC42CCC2)ccc1[N+](=O)[O-]] | C |

TABLE 1-continued
| Exemplary Compounds and Their Activity. | | |
|---|---|---|
| Compound | Structure | GSK3β $IC_{50}$ |
| 62 | 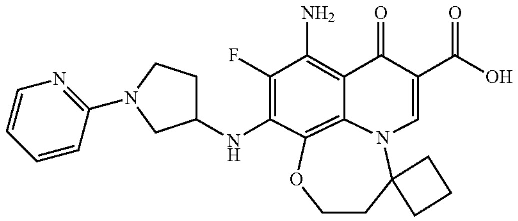 [SMILES: Nc1c(F)c(NC2CCN(c3ccccn3)C2)c2c3c1c(=O)c(C(=O)O)cn3C1(CCC1)CCO2] | D |
| 63 | 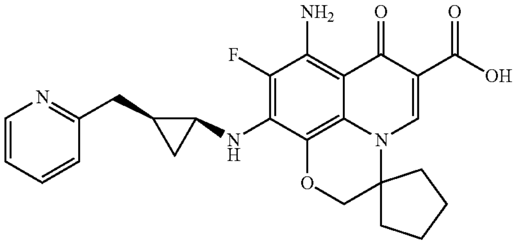 [SMILES: Nc1c(F)c(N[C@H]2C[C@H]2Cc2ccccn2)c2c3c1c(=O)c(C(=O)O)cn3C1(CCCC1)CO2] | D |
| 64 | 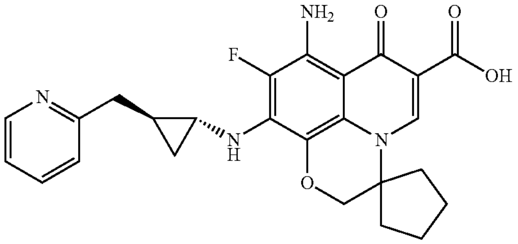 [SMILES: Nc1c(F)c(N[C@@H]2C[C@H]2Cc2ccccn2)c2c3c1c(=O)c(C(=O)O)cn3C1(CCCC1)CO2] | B |
| 65 | 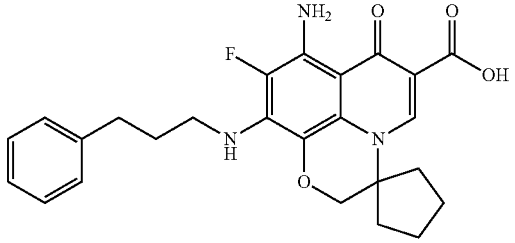 [SMILES: Nc1c(F)c(NCCCc2ccccc2)c2c3c1c(=O)c(C(=O)O)cn3C1(CCCC1)CO2] | A |
| 66 | 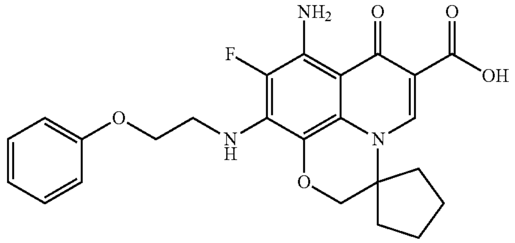 [SMILES: Nc1c(F)c(NCCOc2ccccc2)c2c3c1c(=O)c(C(=O)O)cn3C1(CCCC1)CO2] | D |
| 67 | 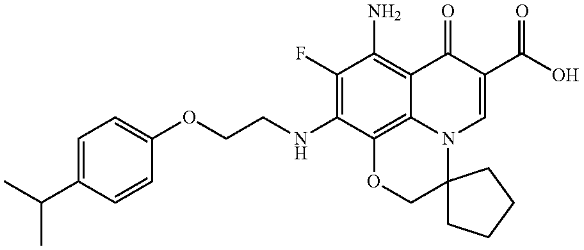 [SMILES: CC(C)c1ccc(OCCNc2c(F)c(N)c3c(=O)c(C(=O)O)cn4c3c2OCC42CCCC2)cc1] | D |

TABLE 1-continued
| Exemplary Compounds and Their Activity. | | |
|---|---|---|
| Compound | Structure | GSK3β IC$_{50}$ |
| 68 | 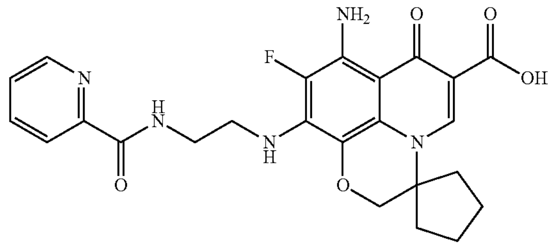 [SMILES: Nc1c(F)c(NCCNC(=O)c2ccccn2)c2c3c1c(=O)c(C(=O)O)cn3C1(CCCC1)CO2] | B |
| 69 | 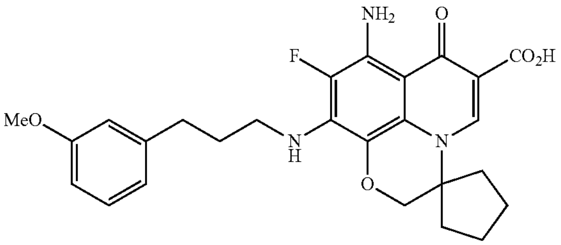 [SMILES: COc1cccc(CCCNc2c(F)c(N)c3c(=O)c(C(=O)O)cn4c3c2OCC42CCCC2)c1] | A |
| 70 | 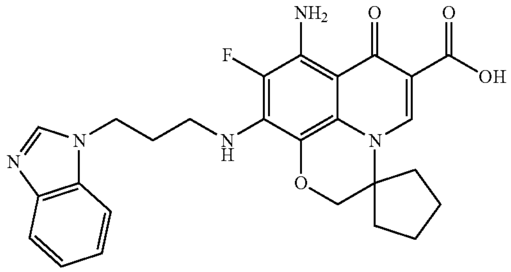 [SMILES: Nc1c(F)c(NCCCn2cnc3ccccc32)c2c3c1c(=O)c(C(=O)O)cn3C1(CCCC1)CO2] | A |
| 71 | 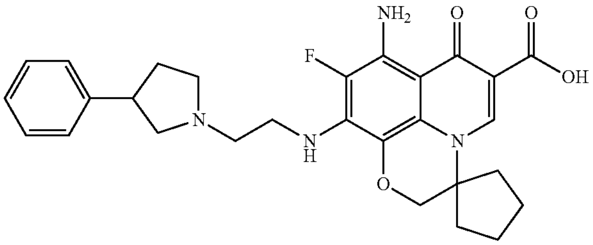 [SMILES: Nc1c(F)c(NCCN2CCC(c3ccccc3)C2)c2c3c1c(=O)c(C(=O)O)cn3C1(CCCC1)CO2] | D |
| 72 | 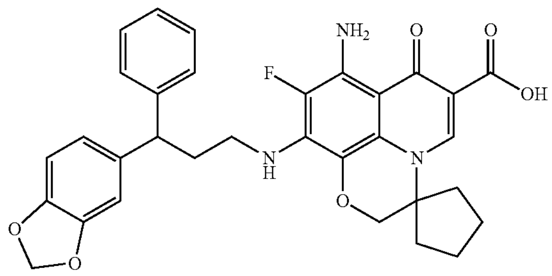 [SMILES: Nc1c(F)c(NCCC(c2ccccc2)c2ccc3c(c2)OCO3)c2c3c1c(=O)c(C(=O)O)cn3C1(CCCC1)CO2] | D |

TABLE 1-continued
| Exemplary Compounds and Their Activity. | | |
|---|---|---|
| Compound | Structure | GSK3β $IC_{50}$ |
| 73 | 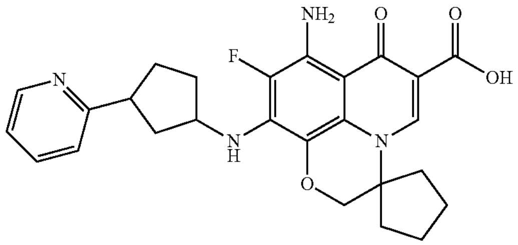 [SMILES: Nc1c(F)c(NC2CCC(c3ccccn3)C2)c2c3c1c(=O)c(C(=O)O)cn3C1(CCCC1)CO2] | D |
| 74 | 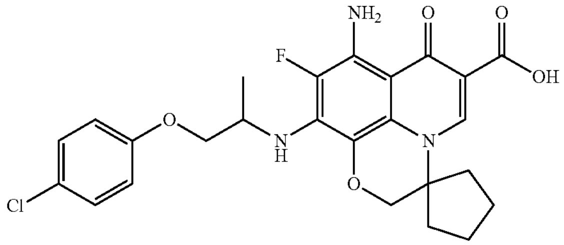 | D |
| 75 | 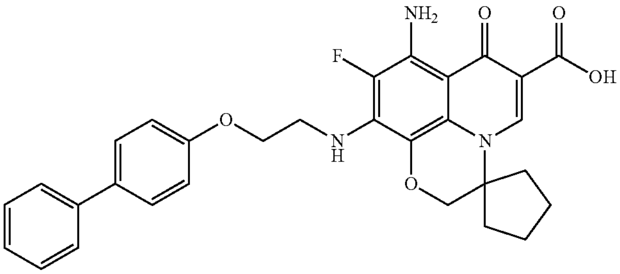 [SMILES: Nc1c(F)c(NCCOc2ccc(-c3ccccc3)cc2)c2c3c1c(=O)c(C(=O)O)cn3C1(CCCC1)CO2] | D |
| 76 | 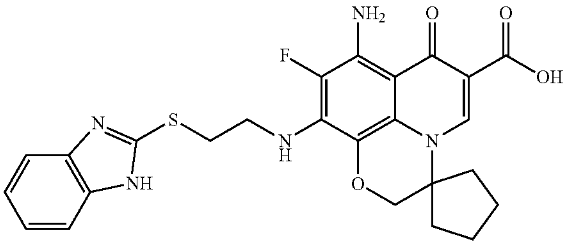 [SMILES: Nc1c(F)c(NCCSc2nc3ccccc3[nH]2)c2c3c1c(=O)c(C(=O)O)cn3C1(CCCC1)CO2] | D |
| 77 | 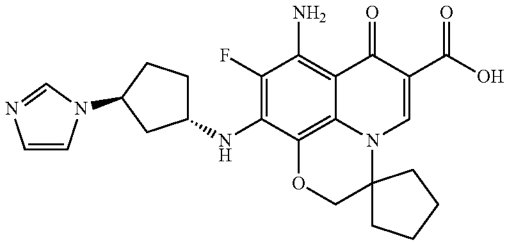 [SMILES: Nc1c(F)c(N[C@H]2CC[C@H](n3ccnc3)C2)c2c3c1c(=O)c(C(=O)O)cn3C1(CCCC1)CO2] | A |
| 78 | 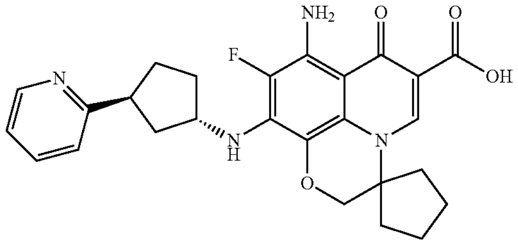 [SMILES: Nc1c(F)c(N[C@H]2CC[C@H](c3ccccn3)C2)c2c3c1c(=O)c(C(=O)O)cn3C1(CCCC1)CO2] | A |

TABLE 1-continued
Exemplary Compounds and Their Activity.
| Compound | Structure | GSK3β $IC_{50}$ |
| --- | --- | --- |
| 79 | 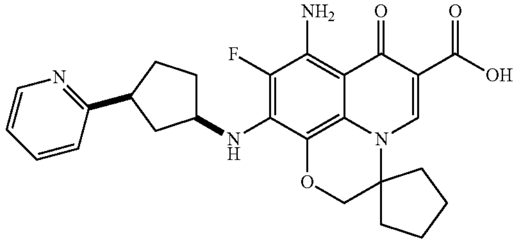 [SMILES: Nc1c(F)c(N[C@@H]2CC[C@H](c3ccccn3)C2)c2c3c1c(=O)c(C(=O)O)cn3C1(CCCC1)CO2] | D |
| 80 | 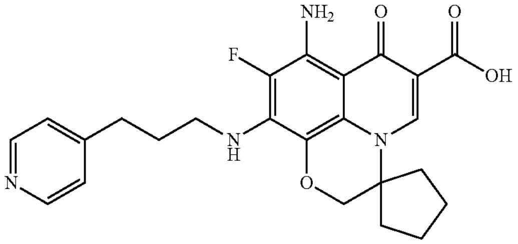 [SMILES: Nc1c(F)c(NCCCc2ccncc2)c2c3c1c(=O)c(C(=O)O)cn3C1(CCCC1)CO2] | A |
| 81 | 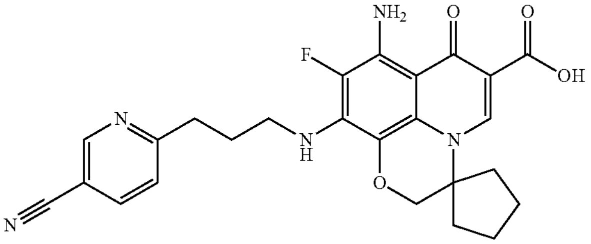 [SMILES: N#Cc1ccc(CCCNc2c(F)c(N)c3c(=O)c(C(=O)O)cn4c3c2OCC42CCCC2)nc1] | A |
| 82 | 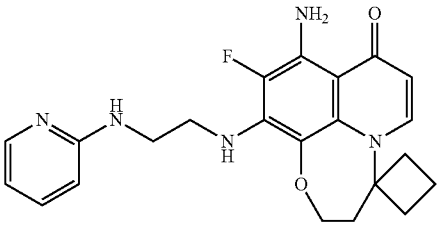 [SMILES: Nc1c(F)c(NCCNc2ccccn2)c2c3c1c(=O)ccn3C1(CCC1)CCO2] | B |
| 83 | 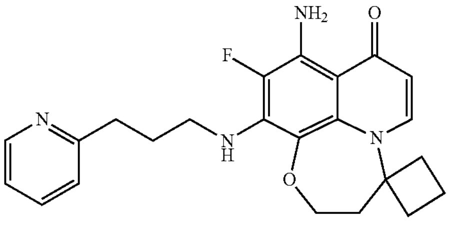 [SMILES: Nc1c(F)c(NCCCc2ccccn2)c2c3c1c(=O)ccn3C1(CCC1)CCO2] | C |
| 84 | 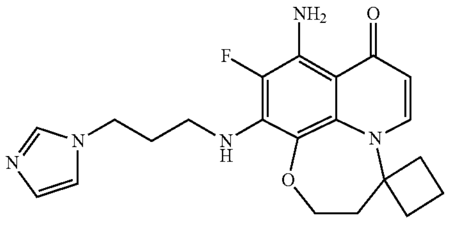 [SMILES: Nc1c(F)c(NCCCn2ccnc2)c2c3c1c(=O)ccn3C1(CCC1)CCO2] | A |

TABLE 1-continued
| Exemplary Compounds and Their Activity. | | |
|---|---|---|
| Compound | Structure | GSK3β $IC_{50}$ |
| 85 | 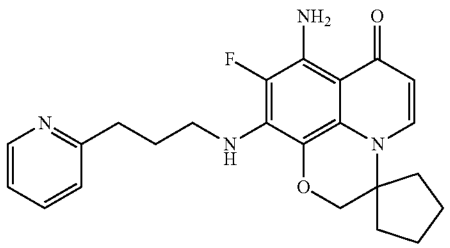 [SMILES: Nc1c(F)c(NCCCc2ccccn2)c2c3c1c(=O)ccn3C1(CCCC1)CO2] | B |
| 86 | 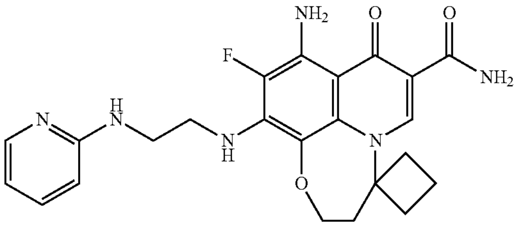 [SMILES: NC(=O)c1cn2c3c(c(NCCNc4ccccn4)c(F)c(N)c3c1=O)OCCC21CCC1] | A |
| 87 | 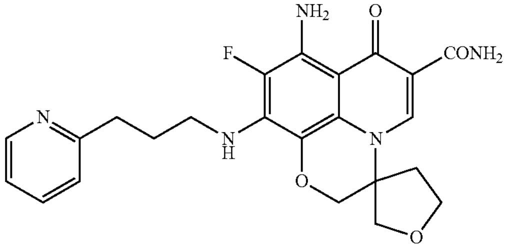 [SMILES: NC(=O)c1cn2c3c(c(NCCCc4ccccn4)c(F)c(N)c3c1=O)OCC21CCOC1] | ND |
| 88 | 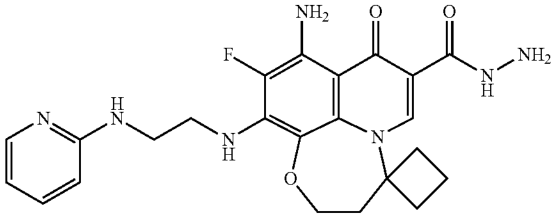 [SMILES: NNC(=O)c1cn2c3c(c(NCCNc4ccccn4)c(F)c(N)c3c1=O)OCCC21CCC1] | A |
| 89 | 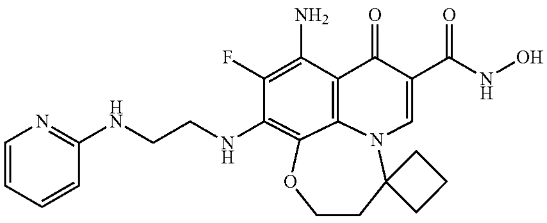 [SMILES: Nc1c(F)c(NCCNc2ccccn2)c2c3c1c(=O)c(C(=O)NO)cn3C1(CCC1)CCO2] | A |
| 90 | 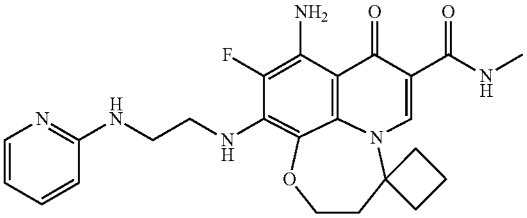 [SMILES: CNC(=O)c1cn2c3c(c(NCCNc4ccccn4)c(F)c(N)c3c1=O)OCCC21CCC1] | D |

TABLE 1-continued
Exemplary Compounds and Their Activity.
| Compound | Structure | GSK3β $IC_{50}$ |
| --- | --- | --- |
| 91 | 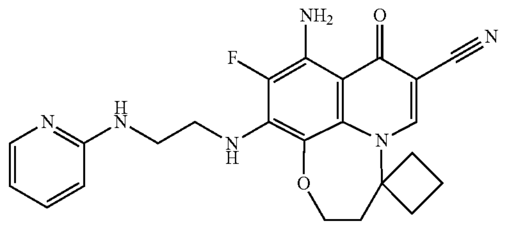 [SMILES: N#Cc1cn2c3c(c(NCCNc4ccccn4)c(F)c(N)c3c1=O)OCCC21CCC1] | B |
| 93 | 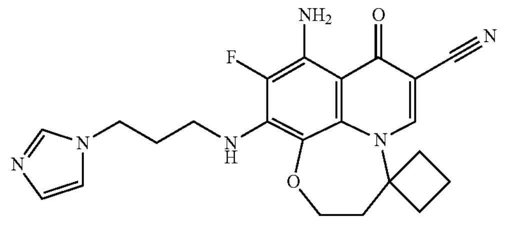 [SMILES: N#Cc1cn2c3c(c(NCCCn4ccnc4)c(F)c(N)c3c1=O)OCCC21CCC1] | B |
| 94 | 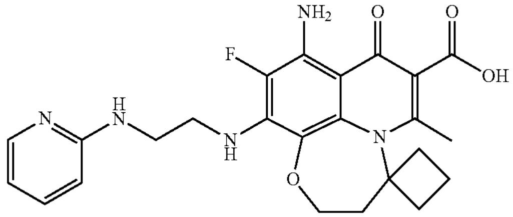 [SMILES: Cc1c(C(=O)O)c(=O)c2c(N)c(F)c(NCCNc3ccccn3)c3c2n1C1(CCC1)CCO3] | B |
| 95 | 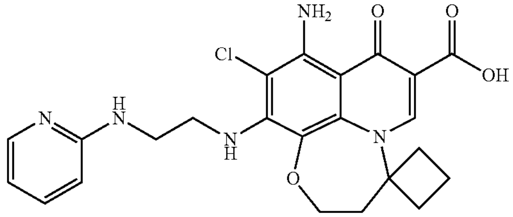 [SMILES: Nc1c(Cl)c(NCCNc2ccccn2)c2c3c1c(=O)c(C(=O)O)cn3C1(CCC1)CCO2] | C |
| 96 | 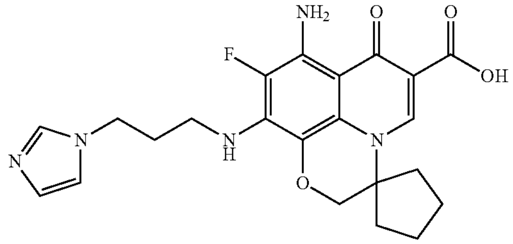 [SMILES: Nc1c(F)c(NCCCn2ccnc2)c2c3c1c(=O)c(C(=O)O)cn3C1(CCCC1)CO2] | A |
| 97 | 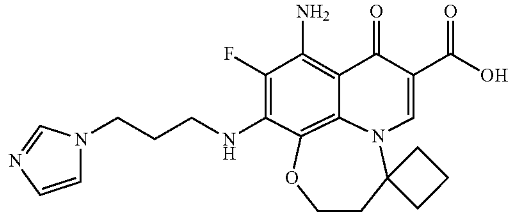 [SMILES: Nc1c(F)c(NCCCn2ccnc2)c2c3c1c(=O)c(C(=O)O)cn3C1(CCC1)CCO2] | B |

TABLE 1-continued

| Exemplary Compounds and Their Activity. | | |
|---|---|---|
| Compound | Structure | GSK3β $IC_{50}$ |
| 98 | 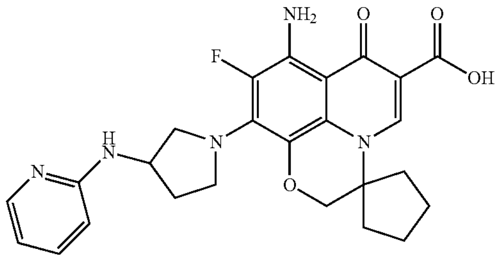 [SMILES: Nc1c(F)c(N2CCC(Nc3ccccn3)C2)c2c3c1c(=O)c(C(=O)O)cn3C1(CCCC1)CO2] | D |
| 99 | 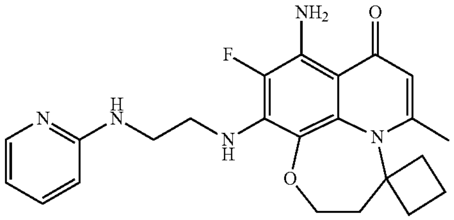 [SMILES: Cc1cc(=O)c2c(N)c(F)c(NCCNc3ccccn3)c3c2n1C1(CCC1)CCO3] | D |

TABLE 2

| Exemplary Compounds and Their Activity. | |
|---|---|
| Structure | GSK3β $IC_{50}$ |
| 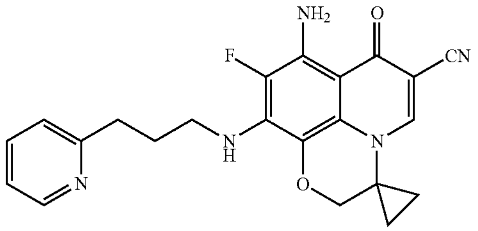 [SMILES: N#Cc1cn2c3c(c(NCCCc4ccccn4)c(F)c(N)c3c1=O)OCC21CC1] | A |
| 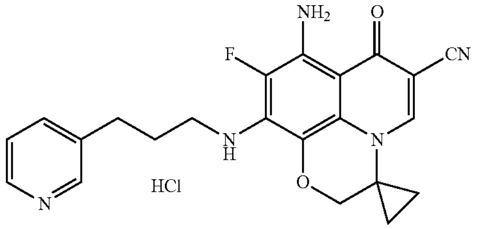 [SMILES: N#Cc1cn2c3c(c(NCCCc4cccnc4)c(F)c(N)c3c1=O)OCC21CC1 ; Cl] | A |
| 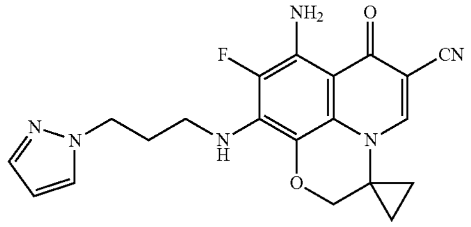 | A |

TABLE 2-continued

| Exemplary Compounds and Their Activity. | |
|---|---|
| Structure | GSK3β $IC_{50}$ |
| 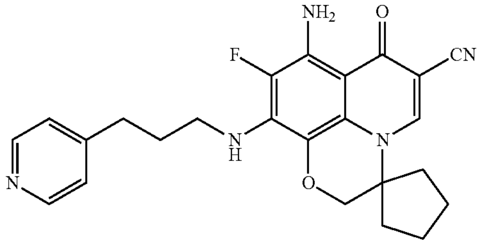 | A |

Dog Emesis Study

Male beagle dogs were obtained from Japan Laboratory Animals Inc. (Tokyo, Japan). The dogs were fed on a standard diet (Oriental Yeast, Tokyo, Japan). Water was available ad libitum. Test compounds were dissolved in dimethyl sulfoxide (100 mg/mL) followed by a dilution with 50% polyethylene glycol 400 to give a concentration of 1, 3 and 10 mg/mL. The dogs were dosed intravenously via cephalic vein with the compounds (0.1, 0.3 and 1 mg/kg, 0.1 mL/kg). Blood samples were collected from opposite cephalic vein into evacuated tube containing EDTA-2K (VENOJECT II, Terumo, Tokyo, Japan) at 0.17, 0.5, 1, 2, and 4 h postdose and kept on ice. Plasma samples were separated by centrifugation (2200×g, 10 min, 4° C.) and stored at −20° C. The plasma samples were mixed with 2 volume of the mixture of methanol and acetonitrile (1:1, v/v) containing internal standard and centrifuged at 13400×g for 3 min. The supernatant was diluted 20 times with 15% acetonitrile and a 10-1 μL aliquot was subjected into LC/MS/MS system. Separation by HPLC was conducted with a Waters Alliance 2795 Separations Module (Waters Corp., MA). Mass spectra were determined using a Micromass Quattro Ultima Pt (Waters Corp.) with an electrospray ionization interface in the MRM mode using positive ion pairs.

The following compounds were tested in this study:

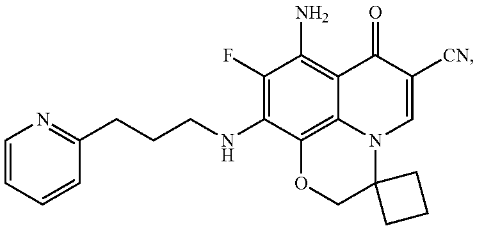

,

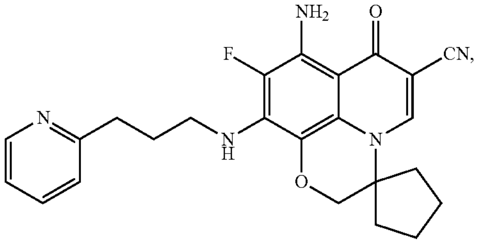

,

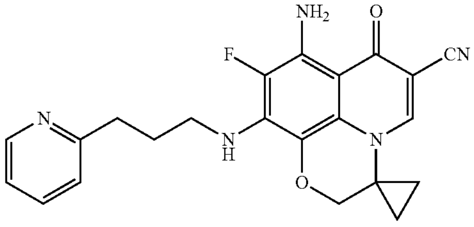

and

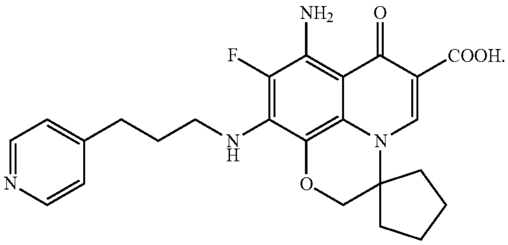

.

In certain embodiments, the test compounds showed $T_{1/2}$ in the range of 0.5 to 1 h. In certain embodiments, the test compounds showed $C_{10min}$ in the range 3-7 μm. In certain embodiments, emesis was examined in dogs treated with test compounds.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

What is claimed is:

1. A compound of Formula (I):

(I)

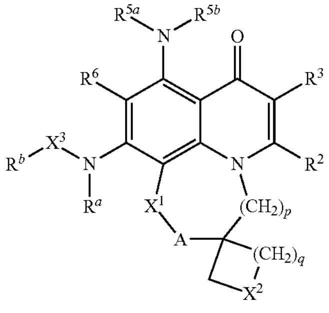

or a pharmaceutically acceptable salt thereof, wherein $R^2$ is hydrogen or lower alkyl;

$R^3$ is hydrogen, CN, $C(O)R^{3a}$, C(NH)NHOH or 5-tetrazolyl;

$R^{3a}$ is OH, alkoxy or $NHR^{3b}$;

$R^{3b}$ is hydrogen, $NH_2$, OH or lower alkyl;

$R^{5a}$ and $R^{5b}$ are each independently hydrogen, lower alkyl or aralkyl which is optionally substituted with one to three substituents, each independently selected from $Q^0$ groups;

where $Q^0$ is halo, cyano, nitro, $NH_2$, alkyl or alkoxy;

$R^6$ is halo;

in each instance, independently, $R^a$ and $X^3$ are selected from (i) or (ii) as follows:

(i) $R^a$ is hydrogen or lower alkyl; and $X^3$ is substituted or unsubstituted $C_1$-$C_3$ alkylene, substituted or unsubstituted 3-6 membered cycloalkylene or substituted or unsubstituted 3-6 membered heterocyclylene, wherein the substituents when present are selected from one to four $Q^2$ groups; or (ii) $R^a$ and $X^3$ together with the nitrogen atom to which they are bonded, may form a 5 to 7 membered saturated or unsaturated ring optionally containing one or more O or S atoms, or one or more additional N atoms, in the ring;

$R^b$ is $-(CHR^{7a})_nR^7$, $-NR^{7b}R^7$, $-OR^7$, $-S(O)_rR^7$, $-NR^{7b}COY^1R^7$ or $-Y^2CONR^{7b}R^7$; $Y^1$ is bond, O or $NR^{7b}$;

$Y^2$ is bond or O;

n is 0 or 1;

r is an integer of 0 to 2;

$R^7$ is alkyl, aryl, cycloalkyl, heterocyclyl, heteroaryl, fused heterocyclylaryl, or fused arylheterocyclyl, where $R^7$ is optionally substituted with one to five substituents, each independently selected from $Q^1$ groups;

$R^{7a}$ is hydrogen, alkyl, aryl, cycloalkyl, heterocyclyl, heteroaryl, fused heterocyclylaryl, or fused arylheterocyclyl, where $R^{7a}$ is optionally substituted with one to five substituents, each independently selected from $Q^1$ groups;

$R^{7b}$ is hydrogen, alkyl, aryl, heteroaryl, aralkyl, heteroaralkyl, or fused heterocyclylaryl, where $R^{7b}$ is optionally substituted with one to five substituents, each independently selected from $Q^1$ groups;

wherein $Q^1$ is halo, hydroxy, oxo, thioxo, cyano, nitro, azido, mercapto, formyl, hydroxycarbonyl, hydroxycarbonylalkyl, alkyl, haloalkyl, alkenyl, alkynyl, cycloalkyl, heterocyclyl, aryl, heteroaryl, aralkyl, heteroaralkyl, alkoxy, haloalkoxy, cycloalkoxy, heterocyclyloxy, aryloxy, heteroaryloxy, aralkyloxy, heretoaralkyloxy, alkylcarbonyl, arylcarbonyl, heteroarylcarbonyl, alkoxycarbonyl, aryloxycarbonyl, aralkyloxycarbonyl, unsubstituted or substituted aminocarbonyl, alkylcarbonyloxy, arylcarbonyloxy, aralkylcarbonyloxy, alkoxycarbonyloxy, aryloxycarbonyloxy, aralkyloxycarbonyloxy, unsubstituted or substituted aminocarbonyloxy, unsubstituted or substituted amino, alkylthio, cycloalkylthio, arylthio, heteroarylthio, aralkylthio, heteroaralkylthio, alkylsulfinyl, cycloalkylsulfinyl, arylsulfinyl, heteroarylsulfinyl, aralkylsulfinyl, heteroaralkylsulfinyl, alkylsulfonyl, cycloalkylsulfonyl, arylsulfonyl, heteroarylsulfonyl, aralkylsulfonyl, heteroaralkylsulfonyl, alkoxysulfonyl, aryloxysulfonyl, unsubstituted or substituted aminosulfonyl or hydroxysulfonyl;

$X^1$ is O;

$X^2$ is $CH_2$, O, $NR^1$ or S;

$R^1$ is hydrogen or lower alkyl;

A is substituted or unsubstituted $C_1$ alkylene, wherein the substituents when present are selected from one to four $Q^2$ groups;

where $Q^2$ is alkyl or haloalkyl;

p is 0; and q is an integer of 0 to 2.

2. The compound of claim 1, wherein $R^{5a}$ and $R^{5b}$ are hydrogen.

3. The compound of claim 1, wherein $R^2$ is hydrogen.

4. The compound of claim 1, wherein $Y^1$ is bond.

5. The compound of claim 1, wherein $R^3$ is CN.

6. The compound of claim 1, wherein $R^3$ is $C(O)R^{3a}$.

7. The compound of claim 1, wherein $R^3$ is C(NH)NHOH.

8. The compound of claim 1, wherein $R^3$ is 5-tetrazolyl.

9. The compound of claim 6, wherein $R^{3a}$ is OH.

10. The compound of claim 1, wherein $R^a$ is hydrogen.

11. The compound of claim 1, wherein $X^3$ is substituted or unsubstituted $C_1$-$C_3$ alkylene, wherein the substituents when present are selected from one to four $Q^2$ groups, where $Q^2$ is alkyl or haloalkyl.

12. The compound of claim 1, wherein A is substituted with from one to four $Q^2$ groups, wherein $Q^2$ is alkyl or haloalkyl.

13. The compound of claim 1, wherein $X^2$ is $CH_2$.

14. The compound of claim 1, wherein $X^2$ is O.

15. The compound of claim 13, wherein A is $CH_2$; and q is 2.

16. The compound of claim 1, wherein $R^6$ is F.

17. A compound of claim 1, having Formula (Ia):

(Ia)

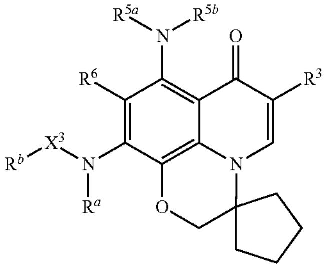

or a pharmaceutically acceptable salt thereof, wherein $R^3$ is hydrogen, CN, $C(O)R^{3a}$, C(NH)NHOH or 5-tetrazolyl;

$R^{3a}$ is OH, alkoxy or $NHR^{3b}$;

$R^{3b}$ is hydrogen, $NH_2$, OH or lower alkyl;

$R^{5a}$ and $R^{5b}$ are each independently hydrogen or lower alkyl;

$R^6$ is halo;

in each instance, independently, $R^a$ and $X^3$ are selected from (i) or (ii) as follows:

(i) $R^a$ is hydrogen or lower alkyl; and $X^3$ is substituted or unsubstituted $C_1$-$C_3$ alkylene, substituted or unsubstituted 3-6 membered cycloalkylene or substituted or unsubstituted 3-6 membered heterocyclylene, wherein the substituents when present are selected from one to four $Q^2$ groups; or (ii) $R^a$ and $X^3$ together with the nitrogen atom to which they are bonded, may form a 5 to 7 membered saturated or unsaturated ring optionally containing one or more O or S atoms, or one or more additional N atoms, in the ring;

$R^b$ is $—(CHR^{7a})_nR^7$, $—NR^{7b}R^7$, $—OR^7$, $—S(O)_lR^7$, $—NR^{7b}COY^1R^7$ or $—Y^2CONR^{7b}R^7$;

$Y^1$ is bond, O or $NR^{7b}$;

$Y^2$ is bond or O;

n is 0 or 1;

l is an integer of 0 to 2;

$R^7$ is alkyl, aryl, cycloalkyl, heterocyclyl, heteroaryl, fused heterocyclylaryl, or fused arylheterocyclyl, where $R^7$ is optionally substituted with one to five substituents, each independently selected from $Q^1$ groups;

$R^{7a}$ is hydrogen, alkyl, aryl, cycloalkyl, heterocyclyl, heteroaryl, fused heterocyclylaryl, or fused arylheterocyclyl, where $R^{7a}$ is optionally substituted with one to five substituents, each independently selected from $Q^1$ groups;

$R^{7b}$ is hydrogen, alkyl, aryl, heteroaryl, aralkyl, heteroaralkyl, or fused heterocyclylaryl, where $R^{7b}$ is optionally substituted with one to five substituents, each independently selected from $Q^1$ groups;

wherein $Q^1$ is halo, hydroxy, oxo, thioxo, cyano, nitro, azido, mercapto, formyl, hydroxycarbonyl, hydroxycarbonylalkyl, alkyl, haloalkyl, alkenyl, alkynyl, cycloalkyl, heterocyclyl, aryl, heteroaryl, aralkyl, heteroaralkyl, alkoxy, haloalkoxy, cycloalkoxy, heterocyclyloxy, aryloxy, heteroaryloxy, aralkyloxy, heretoaralkyloxy, alkylcarbonyl, arylcarbonyl, heteroarylcarbonyl, alkoxycarbonyl, aryloxycarbonyl, aralkyloxycarbonyl, unsubstituted or substituted aminocarbonyl, alkylcarbonyloxy, arylcarbonyloxy, aralkylcarbonyloxy, alkoxycarbonyloxy, aryloxycarbonyloxy, aralkyloxycarbonyloxy, unsubstituted or substituted aminocarbonyloxy, unsubstituted or substituted amino, alkylthio, cycloalkylthio, arylthio, heteroarylthio, aralkylthio, heteroaralkylthio, alkylsulfinyl, cycloalkylsulfinyl, arylsulfinyl, heteroarylsulfinyl, aralkylsulfinyl, heteroaralkylsulfinyl, alkylsulfonyl, cycloalkylsulfonyl, arylsulfonyl, heteroarylsulfonyl, aralkylsulfonyl, heteroaralkylsulfonyl, alkoxysulfonyl, aryloxysulfonyl, unsubstituted or substituted aminosulfonyl or hydroxysulfonyl; and $Q^2$ is alkyl or haloalkyl.

18. The compound of claim 17, wherein $R^{5a}$ and $R^{5b}$ are hydrogen.

19. The compound of claim 17, wherein $R^3$ is CN.

20. The compound of claim 17, wherein $R^3$ is $C(O)R^{3a}$.

21. The compound of claim 17, wherein $R^3$ is C(NH) NHOH.

22. The compound of claim 17, wherein $R^3$ is 5-tetrazolyl.

23. The compound of claim 20, wherein $R^{3a}$ is OH.

24. The compound of claim 17, wherein $R^a$ is hydrogen.

25. A compound selected from
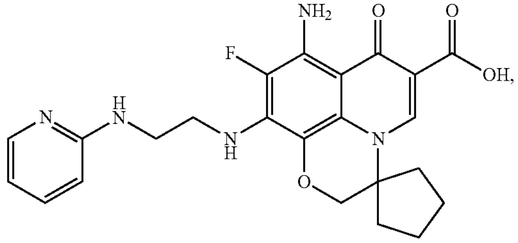
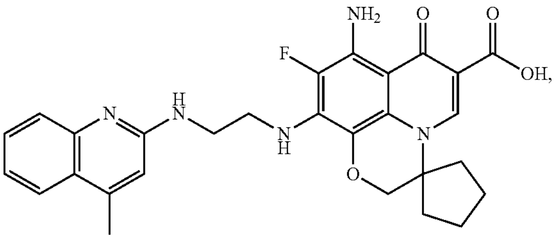
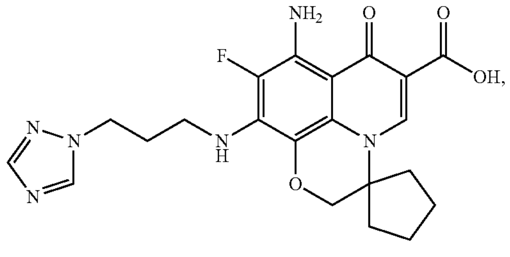
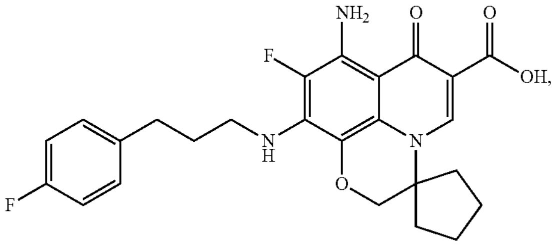
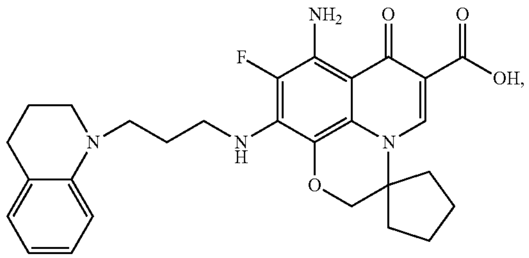
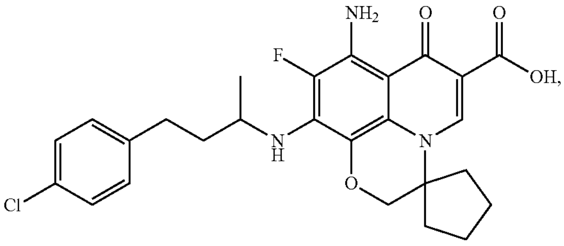
-continued
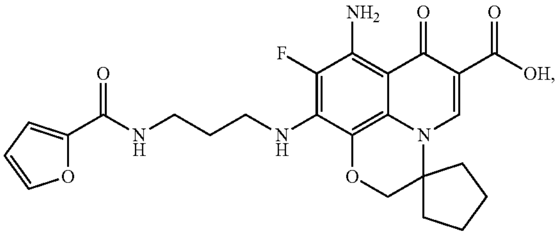
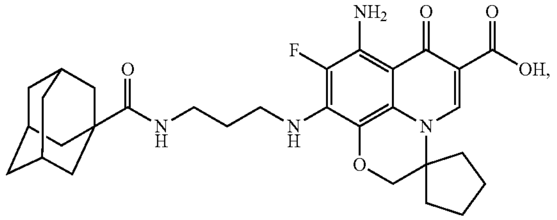
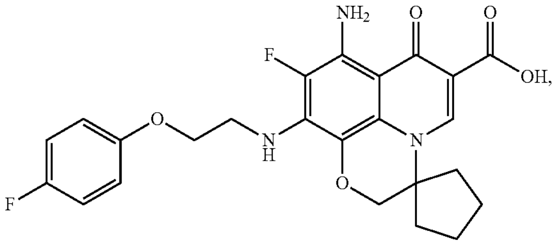
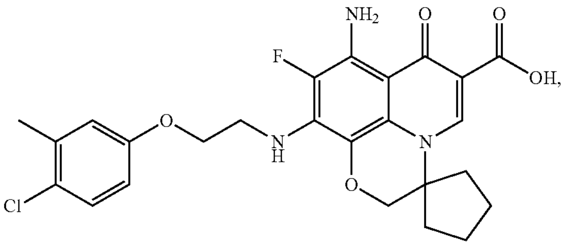
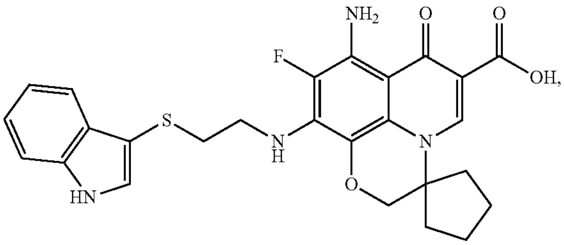
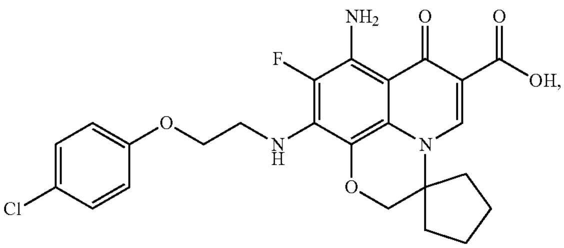
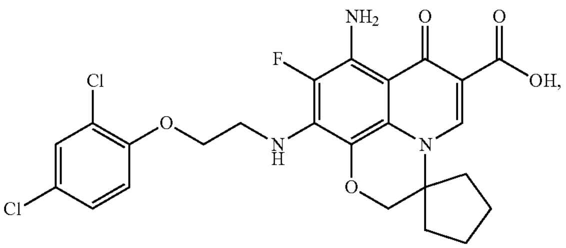

-continued
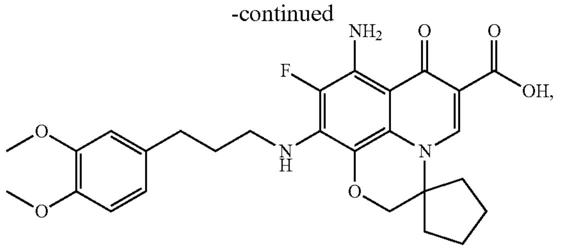
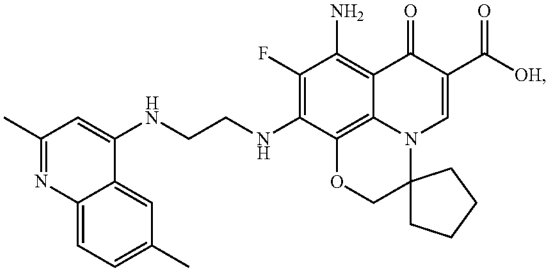
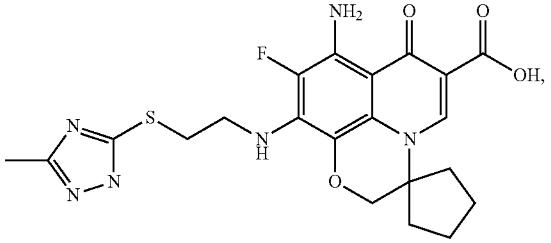
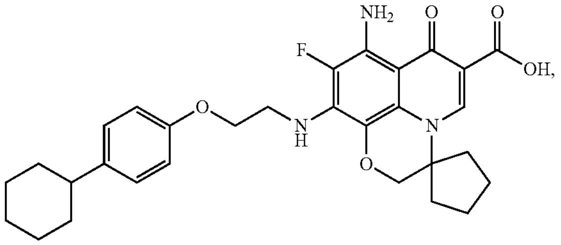
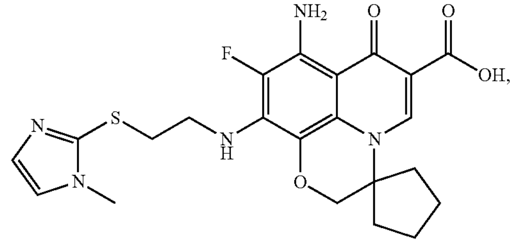
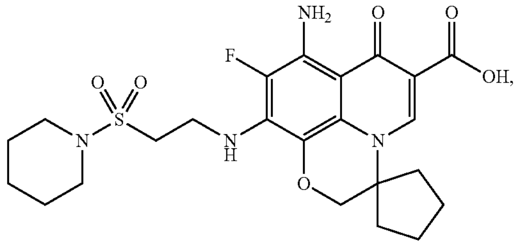
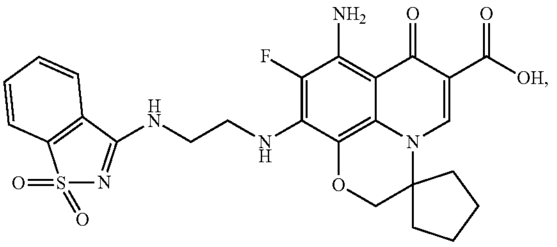
-continued
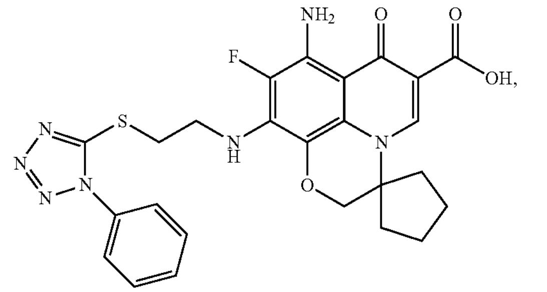
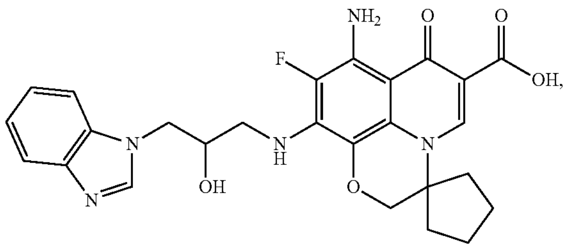
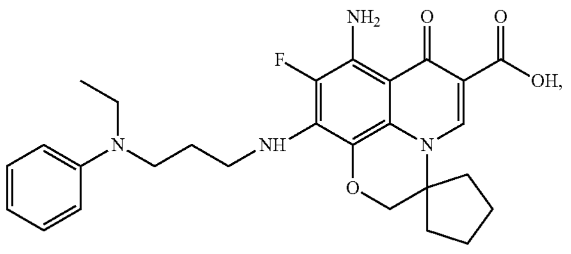
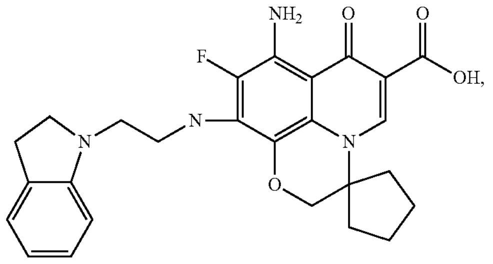
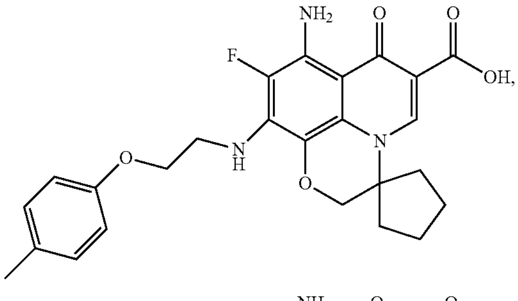
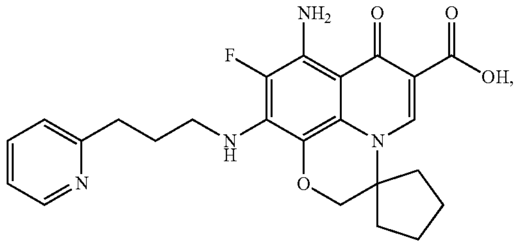

-continued
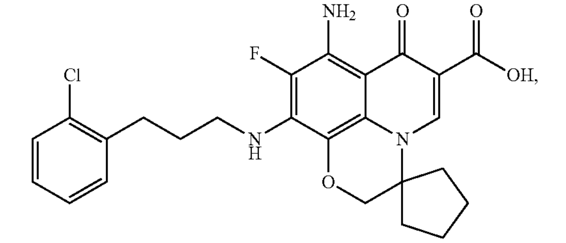
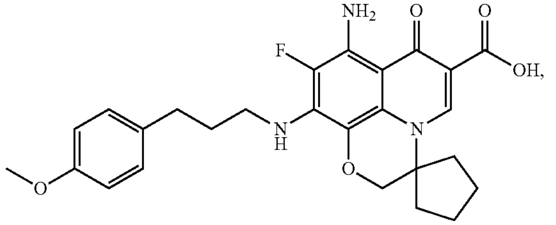
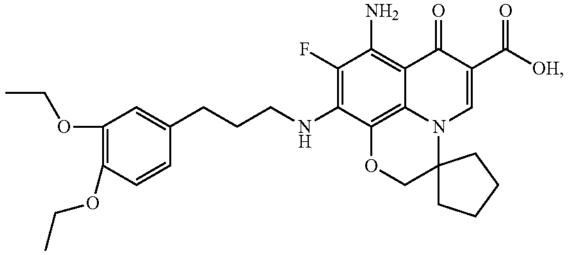
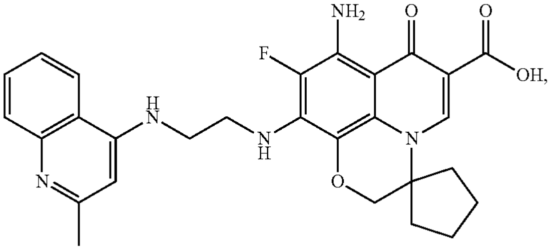
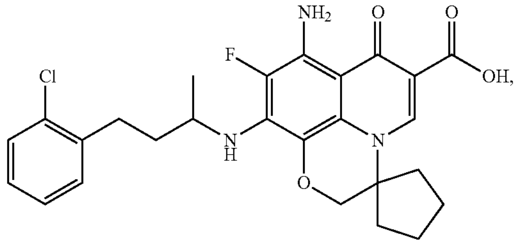
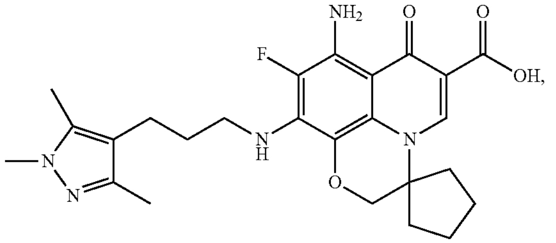
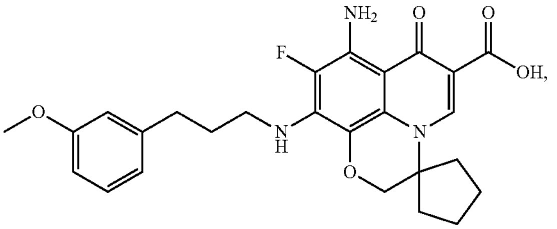
-continued
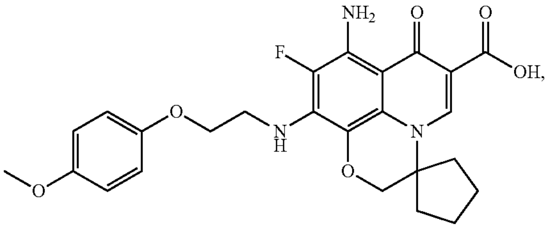
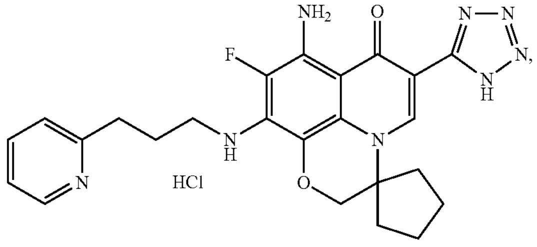
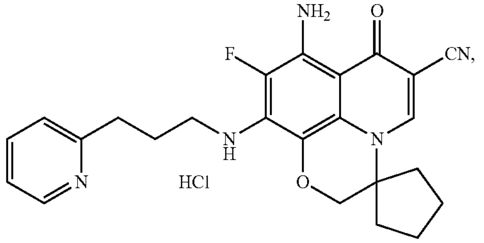
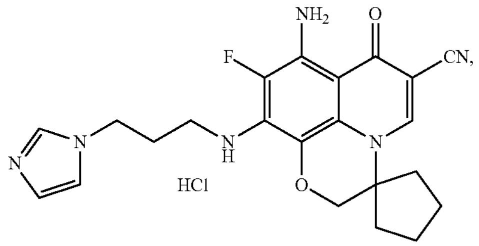
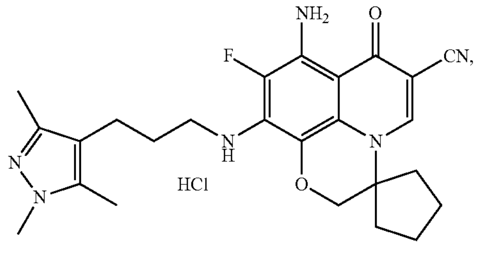
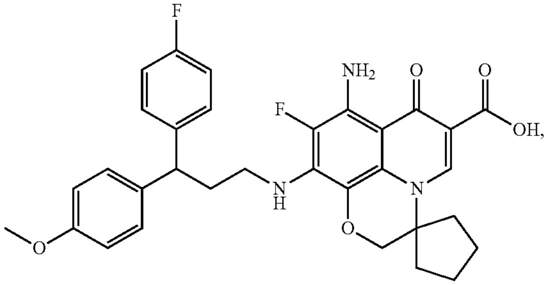

-continued
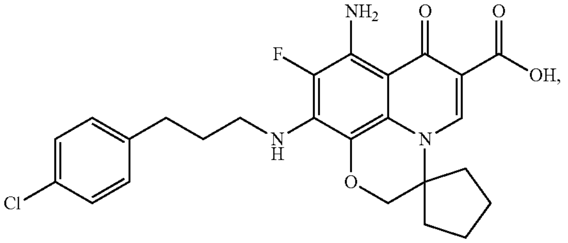
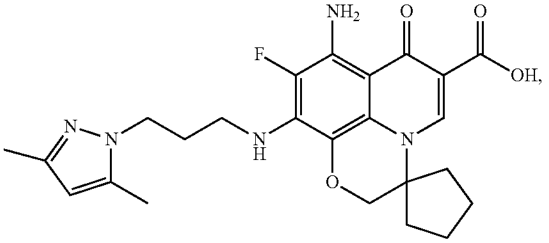
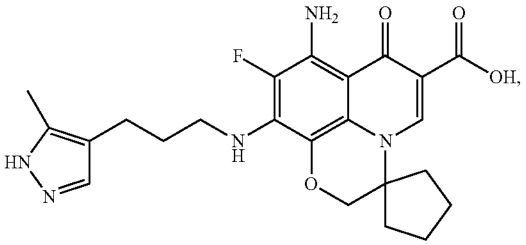
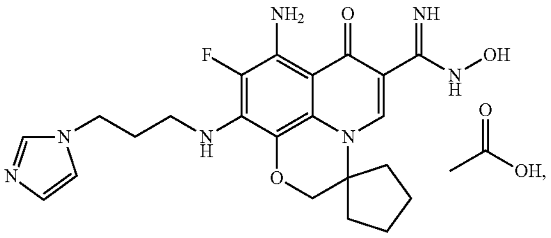
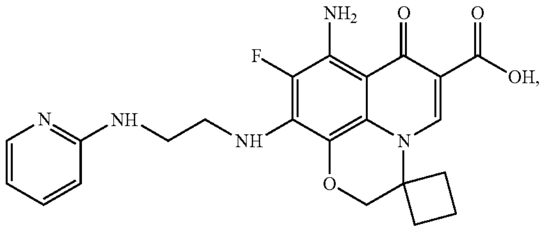
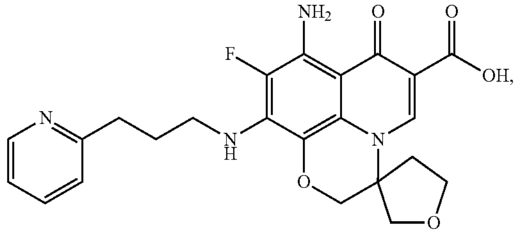
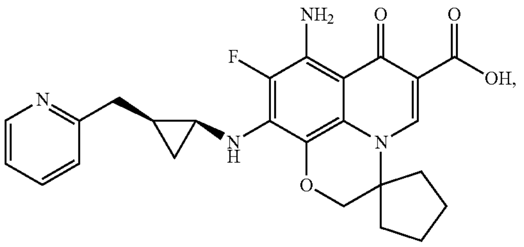
-continued
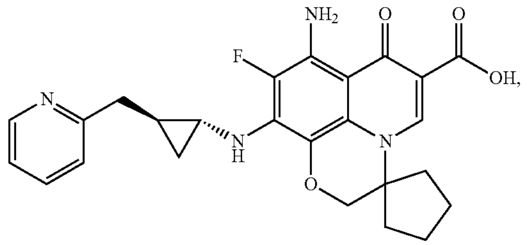
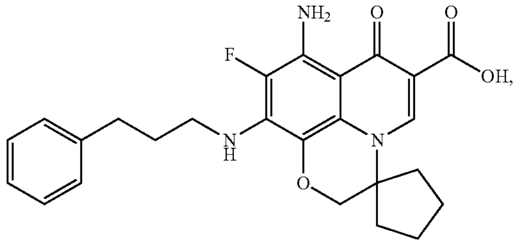
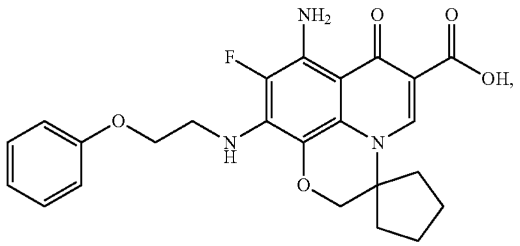
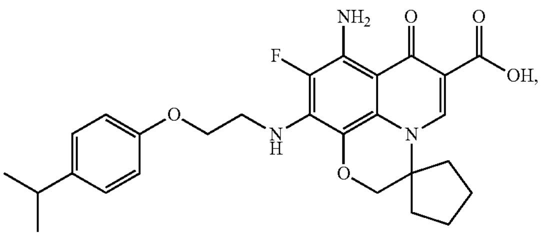
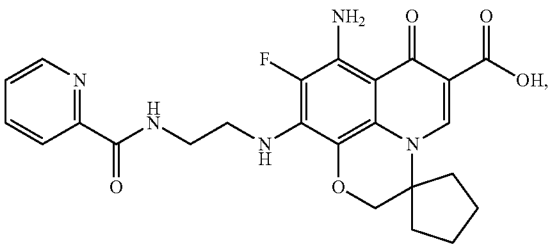
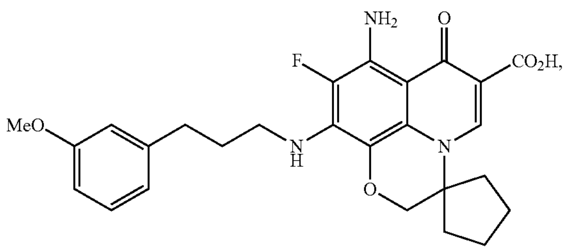

-continued
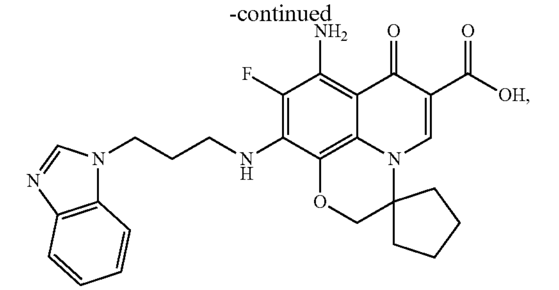
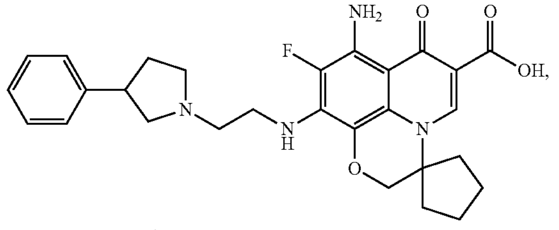
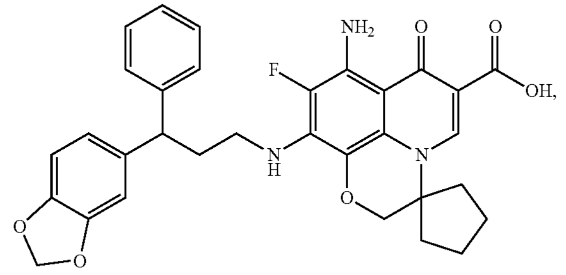
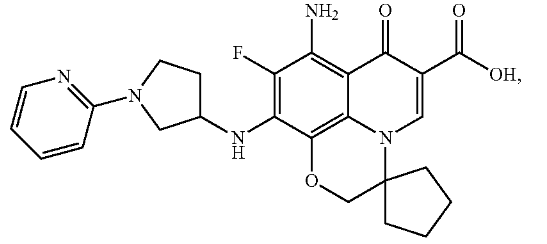
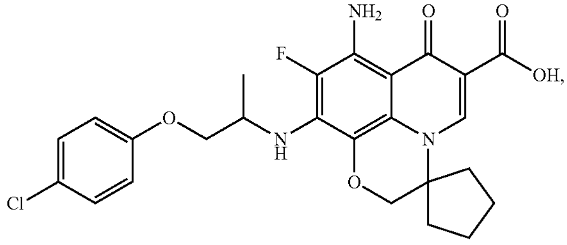
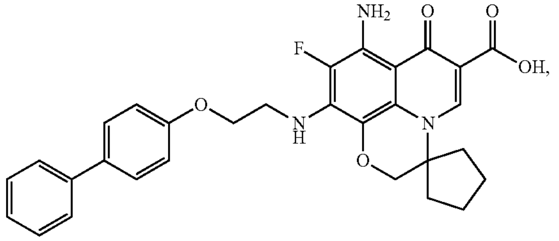
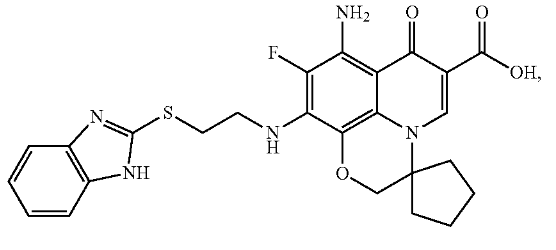
-continued
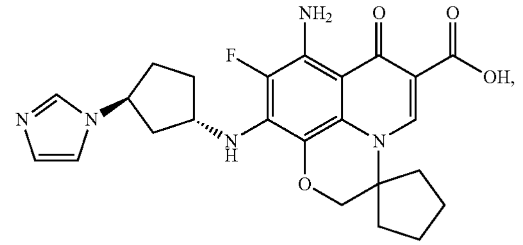
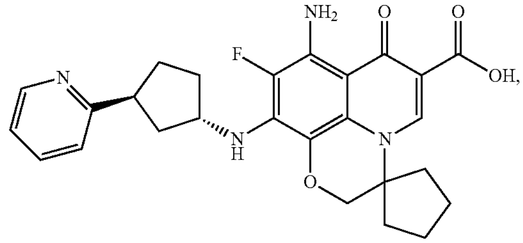
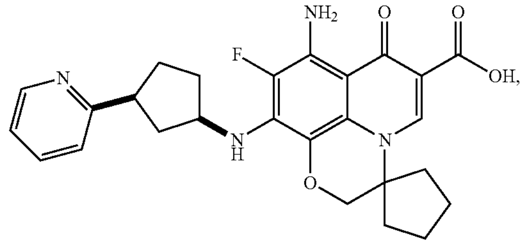
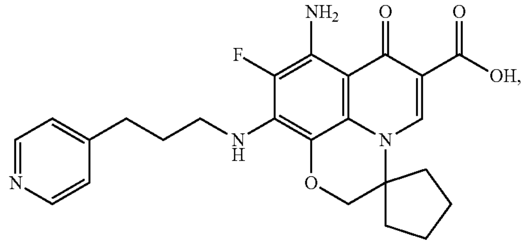
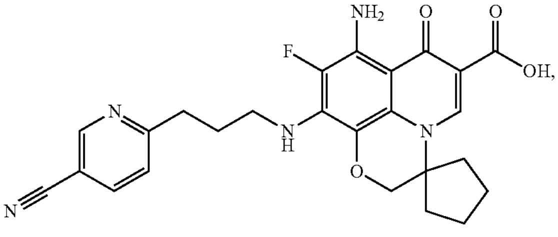
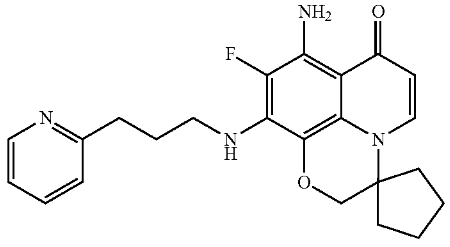
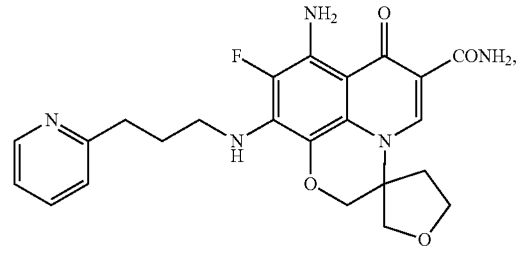

-continued
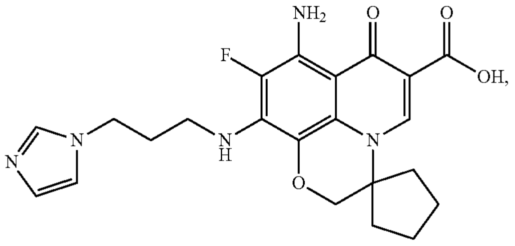
and
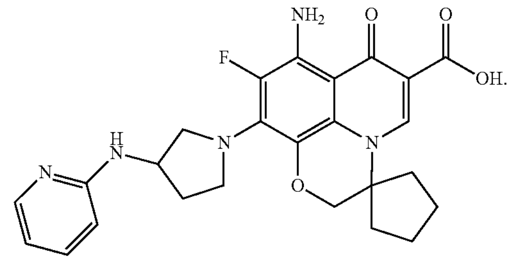
26. A compound selected from
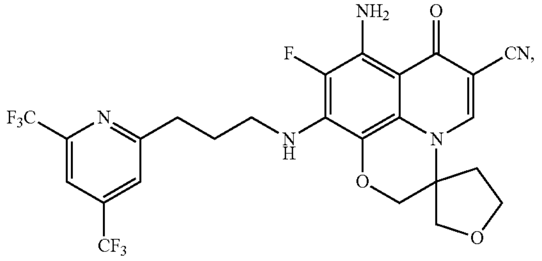
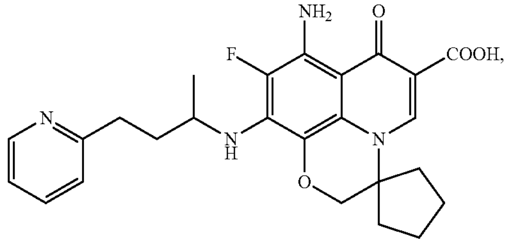
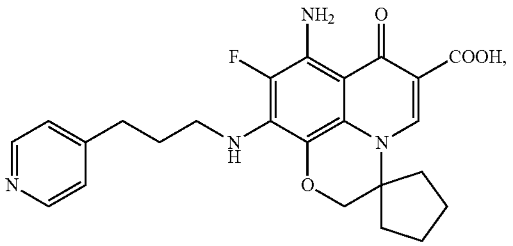
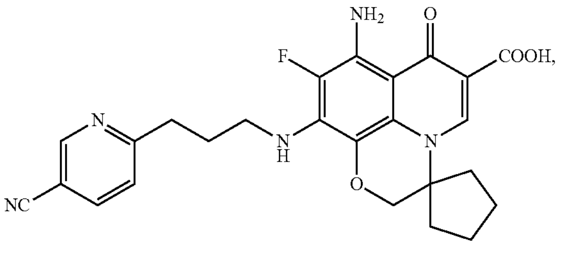
-continued
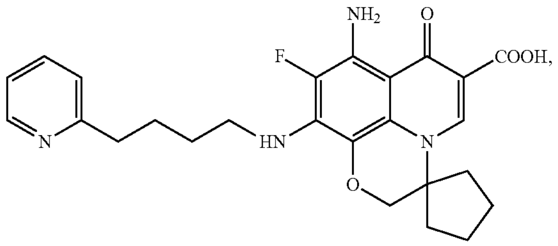
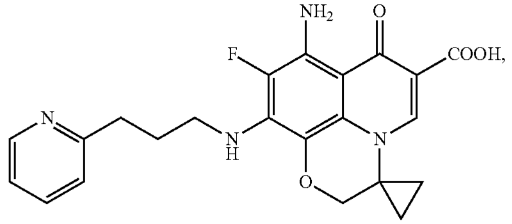
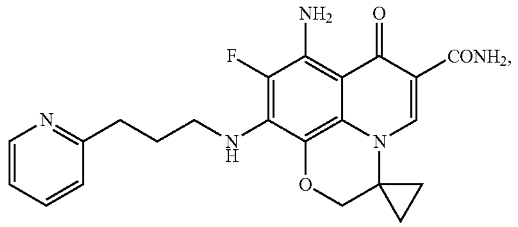
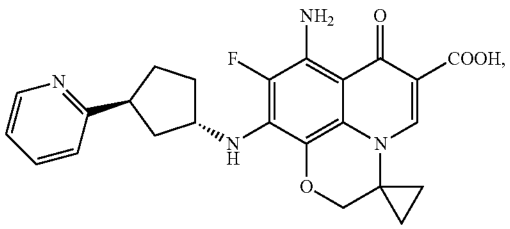
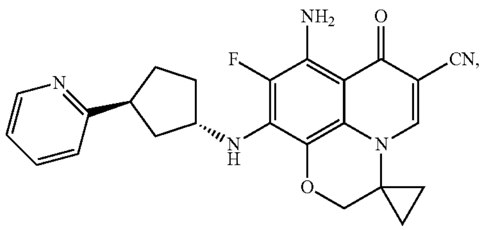
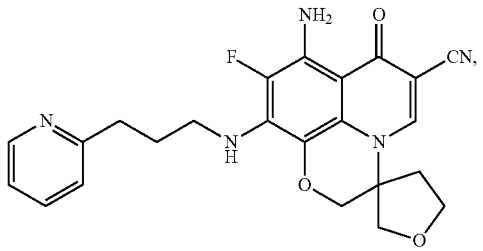
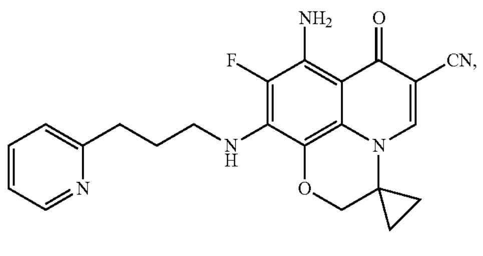

-continued
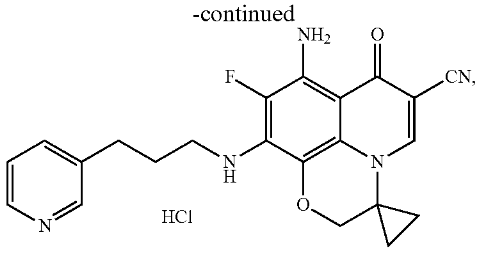
,
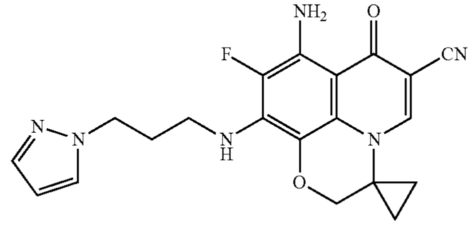 [SMILES: N#Cc1cn2c3c(c(NCCCn4cccn4)c(F)c(N)c3c1=O)OCC21CC1]
and
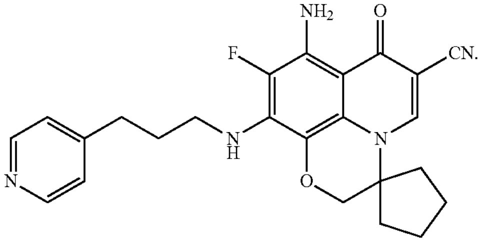
.
27. A pharmaceutical composition comprising a compound of claim 1 and a pharmaceutically acceptable carrier.
* * * * *

UNITED STATES PATENT AND TRADEMARK OFFICE

CERTIFICATE OF CORRECTION

PATENT NO. : 8,476,261 B2
APPLICATION NO. : 12/678120
DATED : July 2, 2013
INVENTOR(S) : Cociorva et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 392 days.

Signed and Sealed this
Eighth Day of September, 2015

Michelle K. Lee
*Director of the United States Patent and Trademark Office*